(12) United States Patent
Sugiyama

(10) Patent No.: US 10,093,977 B2
(45) Date of Patent: Oct. 9, 2018

(54) CANCER ANTIGEN-SPECIFIC T-CELL RECEPTOR GENE, PEPTIDE ENCODED BY THE GENE, AND USE OF THEM

(75) Inventor: Haruo Sugiyama, Minoo (JP)

(73) Assignee: International Institute of Cancer Immunology, Inc., Osaka (JP)

( * ) Notice: Subject to any disclaimer, the term of this patent is extended or adjusted under 35 U.S.C. 154(b) by 0 days.

(21) Appl. No.: 12/529,701

(22) PCT Filed: Feb. 28, 2008

(86) PCT No.: PCT/JP2008/053469
§ 371 (c)(1),
(2), (4) Date: Mar. 26, 2010

(87) PCT Pub. No.: WO2008/108257
PCT Pub. Date: Sep. 12, 2008

(65) Prior Publication Data
US 2010/0190163 A1 Jul. 29, 2010

(30) Foreign Application Priority Data
Mar. 5, 2007 (JP) .................................. 2007-054215

(51) Int. Cl.
| C07H 21/04 | (2006.01) |
| C12Q 1/6881 | (2018.01) |
| C07K 14/725 | (2006.01) |
| C12Q 1/6886 | (2018.01) |
| G01N 33/569 | (2006.01) |
| G01N 33/574 | (2006.01) |

(52) U.S. Cl.
CPC ........ *C12Q 1/6881* (2013.01); *C07K 14/7051* (2013.01); *C12Q 1/6886* (2013.01); *G01N 33/56977* (2013.01); *G01N 33/57492* (2013.01); *C12Q 2600/106* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| 4,923,799 A | 5/1990 | Mak |
| 5,512,478 A | 4/1996 | Orser et al. |
| 6,225,051 B1 | 5/2001 | Sugiyama |
| 6,582,908 B2 * | 6/2003 | Fodor et al. ............ 506/9 |
| 2002/0131960 A1 | 9/2002 | Sadelain et al. |
| 2004/0097703 A1 | 5/2004 | Sugiyama |
| 2004/0247609 A1 | 12/2004 | Sugiyama |
| 2005/0002951 A1 | 1/2005 | Sugiyama et al. |
| 2005/0266014 A1 | 12/2005 | Sugiyama et al. |
| 2006/0035291 A1 | 2/2006 | Itoh et al. |
| 2007/0082860 A1 | 4/2007 | Sugiyama et al. |
| 2007/0238099 A1 | 10/2007 | Cohen et al. |
| 2008/0070835 A1 | 3/2008 | Sugiyama |
| 2008/0152631 A1 | 6/2008 | Sugiyama |
| 2009/0099090 A1 | 4/2009 | Sugiyama et al. |
| 2014/0255941 A1 | 9/2014 | Sugiyama |

FOREIGN PATENT DOCUMENTS

| EP | 1447091 A1 | 8/2001 |
| EP | 1410804 A1 | 4/2004 |
| EP | 1473564 A1 | 11/2004 |
| EP | 1536009 A1 | 6/2005 |
| EP | 1550453 A1 | 7/2005 |
| EP | 1640458 A1 | 3/2006 |
| JP | A2001-517958 | 10/2001 |
| JP | A2002-515243 | 5/2002 |
| JP | 2002-525099 | 8/2002 |
| JP | 2003-500004 | 1/2003 |
| JP | 2009-278927 A | 12/2009 |
| KR | 10-2002-0013503 | 2/2002 |
| WO | WO-93-04695 A1 | 3/1993 |
| WO | WO 1998/054223 A2 | 12/1998 |
| WO | WO 1999/027957 A1 | 6/1999 |
| WO | WO-99-60119 A2 | 11/1999 |
| WO | WO 1999/060119 A2 | 11/1999 |
| WO | WO-00-018795 | 4/2000 |
| WO | WO-00-26249 | 5/2000 |
| WO | WO 00/50641 | 8/2000 |
| WO | WO-02-28414 | 4/2002 |
| WO | WO-02-079253 | 10/2002 |
| WO | WO-03-002142 | 1/2003 |
| WO | WO-03-025569 | 3/2003 |
| WO | WO-03-028757 | 4/2003 |
| WO | WO-03-037060 | 5/2003 |
| WO | WO 2003/059155 A2 | 7/2003 |
| WO | WO-03-106682 | 12/2003 |
| WO | WO-2005-053603 A2 | 6/2005 |
| WO | WO 2005/116074 A2 | 12/2005 |
| WO | WO 2006/064176 A1 | 6/2006 |
| WO | WO 2008/026927 A2 | 3/2008 |

OTHER PUBLICATIONS

Okeefe et al. (The journal of Immunology 2004 Vo. 172 p. 1960).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Ohminami et al. (Blood Jan. 2000 vol. 95 p. 286).*
Tomohiro Kato et al., "Analysis of Accumulated T Cell Clonotypes in Patients With Systemic Lupus Erythematosus," Arthritis & Rhematism, 2000, vol. 43, No. 12, 2712-2721.

(Continued)

*Primary Examiner* — Katherine D Salmon
(74) *Attorney, Agent, or Firm* — Finnegan, Henderson, Farabow, Garrett & Dunner, L.L.P.

(57) ABSTRACT

Disclosed are: a nucleotide sequence and an amino acid sequence for CDR3 region of T-cell receptor (TCR) gene of WT1-specific cytotoxic T-cell (CTL) for WT1 protein; a method for the detection or treatment of cancer using the nucleotide sequence or the amino acid sequence; and a chip, a primer set, a kit, an apparatus and the like for use in the detection of cancer, each of which comprises the nucleotide sequence or the amino acid sequence.

3 Claims, 98 Drawing Sheets

Specification includes a Sequence Listing.

(56) References Cited

OTHER PUBLICATIONS

Christine L. O'Keefe et al., "Molecular Analysis of TCR Clonotypes in LGL: A Clonal Model for Polyclonal Responses[1]," The Journal of Immunology, 2004, vol. 172, No. 3, pp. 1960-1969.
Cinthia Farina et al., "Conserved TCR usage by HLA-Cw*1601-restricted T cell clones recognizing melanoma antigens," International Immunology, 1996, vol. 8, No. 9, pp. 1463-1466.
Yoshihiro Oka et al., "Wilms Tumor Gene Peptide-Based Immunotherapy for Patients with Overt-Leukemia from Myelodysplastic Syndrome (MDS) or MDS with Myelofibrosis," International Journal of Hematology, 2003, vol. 78, No. 1, pp. 56-61.
Yoshiniro Oka et al., "Induction of WT1 (Wilms' tumor gene)—specific cytotoxic T lymphocytes by WT1 peptide vaccine and the resultant cancel regression," Proc. The National Academy of Sciences of the U.S.A., 2004, vol. 101, No. 38, pp. 13885-13890.
Danila Valmori et al, "Vaccination with a Melan-A Peptide Selects an Oligoclonal T Cell Population with Increased Functional Avidity and Tumor Reactivity," The Journal of Immunology, 2002, vol. 168, pp. 4231-4240.
Pierre-Yves Dietrich et al., "Melanoma Patients Respond to a Cytotoxic T Lymphocyte-defined Self-Peptide With Diverse and Nonoverlapping T-Cell Receptor Repertoires[1]," Cancer Research, 2001, vol. 61, pp. 2047-2054.
Pierre G. Coulie et al., "A monoclonal cytolytic T-lymphocyte response observed in a melanoma patient vaccinated with a tumor-specific antigenic peptide encoded by gene MAGE-3," Proc. The National Academy of Sciences of the U.S.A., 2001, vol. 98, No. 18, pp. 10290-10295.
Danièle Godelaine et al, "Polyclonal CTL Responses Observed in Melanoma Patients Vaccinated with Dendritic Cells Pulsed with a MAGE-3 A1 Peptide," The Journal of Immunology, 2003, vol. 171, pp. 4893-4897.
Susanna Mandruzzato et al., "Large and Dissimilar Repertoire of Melan-A/MART-1-Specific CTL in Metastatic Lesions and Blood of a Melanoma Patient," The Journal of Immunology, 2002, vol. 169, pp. 4017-4024.
Office Action dated May 10, 2011 issued in corresponding European application.
Office Action issued in Australian Patent Application No. 2008222061 dated May 31, 2013.
Office Action dated Apr. 16, 2013, issued in Japanese Patent Application No. 2009-502541.
Correspondence dated Nov. 15, 2012, forwarding and describing an Office Action issued in Mexican Patent Application No. MX/a/2009/009589.
Communication pursuant to Article 94(3) EPC dated Oct. 15, 2012, issued in European Patent Application No. 08 720 964.9
Examination Report dated Nov. 27, 2012, issued in Australian Patent Application No. 2008222061.
Xue et al., "Elimination of Human Leukemia Cells NOD/SCID Mice by WT1-TCR Gene-Transduced Human T Cells;" *Blood*, 106, 3062-3067 (2005).
Armstrong et al., "Conformational changes and flexibility in T-cell receptor recognition of peptide-MHC complexes," *Biochem J.*, 415: 183-196 (2008).
Abbey at al., "Expression of T-cell receptor genes during early T-cell development" *Immunology and Cell Biology*, 86:166-174 (2008).
Office Action dated Oct. 23, 2013, issued in Australian Patent Application No. 2008222061.
GenBank accession No. ABF14434.1, T cell receptor beta chain variable region [*Homo sapiens*], submitted Apr. 3, 2006.
GenBank accession No.: BAC01035.1, T cell receptor beta chain [*Homo sapiens*], submitted Dec. 21, 2001.
GenBank accession No. AAP77080.1, AICAR transformylase PurH [*Helicobacter hepaticus* ATCC 51449], submitted May 27, 2003.
GenBank accession No. AF317601.1, *Homo sapiens* T cell receptor beta chain (BV16S1) mRNA, partial CDS, submitted Oct. 29, 2000.
GenBank accession No. CAC06601.1, T-cell receptor beta chain [*Homo sapiens*], submitted Jul. 19, 2000.
GenBank accession No. AAG15764.1, T cell receptor beta chain [*Homo sapiens*], submitted Jul. 31, 2000.
GenBank accession No. AAC52008.1, T cell receptor beta chain, partial [*Homo sapiens*], submitted Jul. 1, 1997.
Office Action dated Dec. 20, 2013, issued in Australian Patent Application No. 2008222061.
Myra Coppage et al., In vitro generation of tumor specific T cells that recognize a shared antigen of AML: Molecular characterization of TCR genes, Leukemia Research, Dec. 6, 2006, vol. 31, No. 2, pp. 195-202, XP-005795007.
J. Zhou et al., "Tumor regression-associated lymphocytes that persist in melanoma patients after adoptive transfer are only minimally present in the original tumors," Database Genbank, Aug. 25, 2003, XP002569162.
Katayoun Rezvani et al., T-Cell Responses Directed against Multiple HLA-A*0201-Restricted Epitopes Derived from Wilms Tumor 1 Protein in Patients with Leukemia and Healthy Donors: Identification, Quantification, and Characterization, Clinical Cancer Research, Dec. 15, 2005, vol. 11, No. 24, pp. 8799-8807, XP-002568654.
Hideki Ohminami et al., "HLA class I-restricted lysis of leukemia cells by a CD8+ cytotoxic T-lymphocyte clone specific for WT1 peptide, "Blood, Jan. 1, 2000, vol. 95, No. 1, pp. 286-293, XP-002190642.
Eva Halapi et al., "T cell receptor usage in malignant diseases, Springer Seminars in Immunopathdogy,", vol. 21, No. 1 pp. 19-35, XP-002568655.
Office Action dated Feb. 4, 2014, issued in Japanese Patent Application No. 2009-502541.
Office Action dated May 6, 2014 issued in European Patent Application No. 08720964.9.
Lefranc et al,. "IMGT unique numbering for immunoglobulin and T cell receptor variable domains and Ig superfamily V-like domains," *Dev. Comp. Immunol.* 27: 55-77 (2003).
English translation of the International Preliminary Report on Patentability with Notification of Transmittal, mailed on Jan. 16, 2014, for International Patent Application No. PCT/JP2012/065707, filed Jun. 20, 2012, by International Institute of Cancer Immunology, Inc. (7 pages).
English translation of the International Search Report, mailed Aug. 7, 2012, for International Patent Application No. PCT/JP2012/065707, filed Jun. 20, 2012, by International Institute of Cancer Immunology, Inc. (2 pages).
Altman, John D., et al., "Phenotypic Analysi of Antigen-Specific T Lymphocytes", *Science*, vol. 274, pp. 94-96, 1996 (3 pages).
Borrello, Ivan M., et al., "Cancer Vaccines for Hematologic Malignancies", *Cancer Control Journal of the Moffitt Cancer Center*, vol. 9, No. 2, Mar./Apr. 2002, pp. 138-151 (14 pages).
Call, Katherine M., et al., "Isolation and Characterization of a Zinc Finger Polypeptide Gene at the Human Chromosome 11 Wilms' Tumor Locus", *Cell*, vol. 60, pp. 509-520, 1990 (12 pages).
Czerkinski, Cecil, et al., "Reverse ELISPOT assay for clonal analysis of cytokine production: I. Enumeration of gamma-interferon-secreting cells", *Journal of Immunological Methods*, vol. 110, pp. 29-36, 1998 (8 pages).
Extended European Search Report issued Jul. 1, 2011 in European Application No. 11154325.2 (11 pages).
Extended European Search Report issued Oct. 31, 2011 in European Application No. 11154327.8 (13 pages).
Extended European Search Report issued Mar. 18, 2015 in European Application No. 14192034.8 (12 pages).
Gessler, Manfred, et al., "Homozygous deletion in Wilms tumours of a zinc-finger gene identified by chromosome jumpking", *Nature*, vol. 343, pp. 774-778, 1990 (5 pages).
Herr, Wolfgang, et al., "Frequency analysis of tumor-reactive cytotoxic T lymphocytes in peripheral blood of a melanoma patient vaccinated with autologous tumor cells", *Cancer Immunology Immunotherapy*, vol. 39, pp. 93-99, 1994 (7 pages).
Kruse, Niels, et al., "Quantificationof cytokine mRNA expression by RT PCR in samples of previously frozen blood", *Journal of Immunological Methods*, vol. 201, pp. 195-203, 1997 (9 pages).

(56) References Cited

OTHER PUBLICATIONS

Lau, Roy, "Phase I Trial of Intravenous Peptide-Pulsed Dendrictic Cells in Patients with Metastatic Melanoma", *Journal of Immunotherapy*, vol. 24, No. 1, pp. 66-78, 2001 (13 pages).

Maeda, Y., et al., "Detection of peptide-specific CTL-precursors in peripheral blood lymphocytes of cancer patients", *British Journal of Cancer*, vol. 87, No. 7, pp. 796-804, 2002 (9 pages).

Menke, A.L., et al., "The Wilms' Tumor 1 Gene: Oncogene or Tumor Suppressor Gene?", *International Review of Cytology*, vol. 181, pp. 151-221, 1998 (32 pages).

Möller, P., et al. "Vaccination with IL-7 gene-modified autologous melanoma cells can enhance the anti-melanoma lytic activity in peripheral blood of patients with a good clinical performance status: a clinical phase I study", *British Journal of Cancer*, vol. 77, No. 11, pp. 1907-1916, 1998 (10 pages).

Nagai, Masahiro, et al., "Increased Activated Human T Cell Lymphotropic Virus Type I (HTLV-I) Tax11-19-Specific Memory and Effector CD8+ Cells in Patients with HTLV-I-Associated Myelopathy/Tropical Spastic Paraparesis: Correlation with HTLV-L Provirus Load", *The Journal of Infectious Diseases*, vol. 183, pp. 197-205, 2001 (9 pages).

Oertil, Daniel, et al. "Rapid Induction of Specific Cytotoxic T Lymphocytes Against Melanoma-Associated Antigens by a Recombinant Vaccinia Virus Vector Expressing Multiple Immunodominant Epitopes and Costimulatory Molecules In Vivo", *Human Gene Therapy*, vol. 13, pp. 569-575, 2002 (7 pages).

Oka, Yoshihiro, et al., "Cancer Immunotherapy Targeting Wilms'Tumor Gene WT1 Product", *Journal of Immunology*, vol. 164, No. 4, pp. 1873-1880, 2000 (8 pages).

Oka, Yoshihiro, et al. "WT1 as a Novel Target Antigen for Cancer Immunotherapy", *Current Cancer Drug Targets*, vol. 2, pp. 45-54, 2002 (10 pages).

Oka, Yoshihiro et al., "Induction of WT1 (Wilms' tumor gene)-specfic cytotoxic T lymphocytes by WT1 peptide vaccine and the resultant cancer regression", *Proceedings of the National Academy of Sciences*, vol. 101, No. 38, Sep. 21, 2004, pp. 13885-13890 (6 pages).

Rezvani, Katayoun, et al. "Functional leukemia-associated antigen-specfic memory CD8+ cells exist in healthy individual and in patients with chronic myelogenous leukemia before and after stem cell transplantation", *Blood*, vol. 102, No. 8, Jun. 26, 2003 (37 pages).

Sugiyama, Haruo, "Wilms'Tumor Gene WT1: Its Oncogenic Function and Clinical Application", *International Journal of Hematology*, vol. 73, pp. 177-187, 2001 (11 pages).

Sugiyama, Haruo, "Cancer Immunotherapy Targeting WT1 Protein", *International Journal of Hematology*, vol. 76, pp. 127-132, 2002 (6 pages).

Tsuboi, Akihiro, "Enhanced induction of human WT1-specific cytotoxic T lymphocytes with a 9-mer WT1 peptide modified at HLA-A*2402-binding residues", *Cancer immunology immunotherapy*, vol. 51, No. 11-12, pp. 614-620, 2002 (7 pages).

Tsuboi, Akihiro, "WT1 Peptide-Based Immunotherapy for Patients with Lung Cancer: Report of Two Cases", *Microbiology and Immunology*, vol. 48, No. 4, pp. 175-184, 2004 (10 pages).

Whiteside, Theresa L., "Monitoring of Antigen-Specific Cytolytic T Lymphocytes in Cancer Patients Receiving Immunotherapy", *Clinical and Diagnostic Laboratory Immunology*, vol. 7, No. 3, pp. 327-332, 2000 (6 pages).

Office Action and Search Report dated Nov. 4, 2014, issued in Chinese Patent Application. No. 201280042412.0 by International Institute of Cancer Immunology, Inc., with English translation (20 pages total).

Partial Supplementary Search Report dated Nov. 27, 2014, issued in European Patent Application No. 12803980.7 by International Institute of Cancer Immunology, Inc. (8 pages).

Partial Supplementary Search Report dated Jan. 5, 2015, issued in European Patent Application No. 12803980.7 by International Institute of Cancer Immunology, Inc. (8 pages).

Ochsenreither, S. et al. (2011) "Wilms Tumor Protein 1' (WT1) Peptide Vaccination-induced Complete Remission in a Patient With Acute Myeloid Leukemia Is Accompanied by the Emergence of a Predominant T-cell Clone Both in Blood and Bone Marrow" *J. Immunother.*, 34(1):85-91.

Ochsenreither, S. et al. (2012) "Wilms' tumor protein 1 (WT1) peptide vaccination in AML patients: predominant TCR CDR3β sequence associated with remission in one patient is detectable in other vaccinated patients" *Cancer Immuncl. Irnmunother*, 61:313-322 (2012).

Genbank Accession No. AAM92197, "T-cell receptor beta chain variable region, partial [*Homo sapiens*]," Published Aug. 10, 2002, (1 page).

Patent Examination Report issued in Australian Patent Application No. 2013206501, dated Jun. 4, 2015 (6 pages).

Patent Examination Report issued in Australian Patent Application No. 2013270605, dated Jun. 4, 2015 (3 pages).

Schumacher, T., "T-Cell-Receptor Gene Therapy," *Nature Reviews Immunology*, vol. 2, Issue 7, Jul. 2002, pp. 512-519 (8 pages).

Willenbrock, K., "Analysis of T-Cell Subpopulations in T-Cell Non-Hodgkin's Lymphoma of Angioimmunoblastic Lymphadenopathy with Dysproteinemia Type by Single Target Gene Amplification of T Cell Receptor-β Gene Rearrangements," *American Journal of Pathology*, vol. 158, No. 5, May 2001, pp. 1851-1857 (7 pages).

Yasukawa, M., *Ketsueki, Shuyou-ka*, vol. 51, No. 3, 2005, pp. 320-326 (11 pages).

European Patent Application No. 12803980.7, filed Jun. 20, 2012, by International Institute of Cancer Immunology, Inc.: Extended European Search Report, including the Supplementary European Search Report and Opinion, dated May 12, 2015.

Office Action mailed May 15, 2015, in U.S. Appl. No. 14/129,695 (19 pages).

Pinilla-Ibarz, J. et al., "Improved human T-cell responses against synthetic HLA-0201 analog peptides derived from the WT1 oncoprotein," *Leukemia*, 20:2025-2033 (2006).

Final Office Action issued in U.S. Appl. No. 14/184,816, dated Aug. 20, 2015 (12 pages).

Kasprowicz, V., "A Highly Restricted T-Cell Receptor Dominates the CD8$_+$T-Cell Response to Parvovirus B19 Infection in HLA-A*2402-Positive Individuals," *Journal of Virology*, Jul. 2006, vol. 80, No. 13 p. 6697-6701 (5 pages).

Eva Halapi et al., "T cell receptor usage in malignant diseases," Springer Seminars in Immunopathology, 1999, vol. 21, No. 1, pp. 19-35, XP-002568655.

U.S. Appl. No. 14/129,695, filed Dec. 27, 2013, by Haruo Sugiyama, entitled "Receptor Gene for Peptide Cancer Antigen-Specific T Cell."

Kruger et al., "Lessons to be learned from primary renal cell carcinomas: novel tumor antigens and HLA ligands for immunotherapy," *Cancer Immunol. Immunother.*, 54: 826-836 (2005).

Robinson et al., "IMGT/HLA Database—a sequence database for the human major histocompatibility complex," *Tissue Antigens*, 55: 280-287 (2000).

U.S. Appl. No. 14/129,695, filed Dec. 27, 2013 by Sugiyama: Final Office Action, dated Jan. 7, 2016, 19 pages.

U.S. Appl. No. 10/562,486, filed Dec. 27, 2005, by Sugiyama: Non-Final Office Action, dated Dec. 2, 2015, with Notice of References Cited (17 pages).

Gotoh, M. et al. (2002) "Development of HLA-A2402/K$^{fi}$ Transgenic Mice" *Int. J. Cancer*, 100:565-570.

U.S. Appl. No. 14/687,628, filed Apr. 15, 2015, by Sugiyama: Office Action, dated Dec. 2, 2016 (21 pages).

Office Action issued in European Patent Application No. 12803980.7 dated Dec. 5, 2016 (5 pages).

Japanese Patent Application No. 2015-151065, filed Jul. 30, 2015, by International Institute of Cancer Immunology Inc: Office Action, dated Jul. 12, 2016 (2 pages), with partial English translation (2 pages).

U.S. Appl. No. 14/184,816, filed Feb. 20, 2014, by Sugiyama: Office Action, dated Nov. 2, 2016 (10 pages).

U.S. Appl. No. 14/687,569, filed Apr. 15, 2015, by Sugiyama: Office Action, dated Aug. 8, 2016 (11 pages).

(56) References Cited

OTHER PUBLICATIONS

Summons to Attend Oral Proceedings pursuant to Rule 115(1) EPC for European Patent Application No. 08720964.9, dated May 2, 2016 (8 pages).
Korean Office Action for Korean Patent Application No. 10-2015-7023123, dated Mar. 24, 2016, with partial English translation (6 pages).
U.S. Appl. No. 14/129,695, filed Dec. 27, 2013, by Sugiyama: Final Office Action, dated Jan. 20, 2017 (14 pages).
U.S. Appl. No. 14/687,569, filed Apr. 15, 2015, by Sugiyama: Office Action, dated Jan. 27, 2017 (13 pages).
Office Action issued in Chinese Patent Application No. 201280042412.0 dated Feb. 9, 2017 (7 pages).
U.S. Appl. No. 14/184,979, filed Feb. 20, 2014, by Sugiyama: Final Office Action, dated Feb. 9, 2017 (15 pages).
Sommer and Tautz, "Minimal homology requirements for PCR primers," *Nucleic Acids Research*, 17(16): 6749 (1989).
Japanese Office Action for Japanese Patent Application No. 2015-151065, dated Jul. 18, 2017, with English translation (5 pages).
U.S. Appl. No. 14/184,816, filed Feb. 20, 2014, by Sugiyama: Final Office Action, dated May 9, 2017 (10 pages).
Office Action dated Mar. 7, 2018, issued by the United States Patent & Trademark Office in U.S. Appl. No. 14/687,569 (6 pages).
Office Action issued in Japanese Patent Application No. 2016-193222 dated Aug. 22, 2017 (13 pages).
U.S. Appl. No. 14/687,628, filed Apr. 15, 2015, by Sugiyama: Non-Final Office Action, dated Aug. 24, 2017 (15 pages).
Office Action issued in Chinese Patent Application No. 201310258589.0 dated Nov. 1, 2017 (19 pages).
Li et al., "The feature of CDR3 sequence of TCR Vβ 21 oligoclonal T cells in CML," Immunological Journal, 16(3): 189-200 (2000).
Toshiro Kurokawa et al.: "Induction and Clonal Expansion of Tumor-Specific Cytotoxic T Lymphocytes from Renal Cell Carcinoma Patients After Stimulation with Autologous Dendritic Cells Loaded with Tumor Cells," *Int. J. Cancer*:91, pp. 749-756 (2001).

E. Hodges et al., "Diagnostic role of test for T cell receptor (TCR) genes," *J. Clin. Pathol.* 56, pp. 1-11 (2003).
Office Action, issued by the Canadian Intellectual Property Office, in corresponding Canadian Patent Application No. 2,679,045, dated Mar. 29, 2018, six (6) pages.
Office Action issued by the Japan Patent Office in corresponding Japan Patent Application No. 2016-193222, dated May 29, 2018, four (4) pages.
Partial English Translation of Office Action issued by the Japan Patent Office in corresponding Japan Patent Application No. 2016-193222, dated May 29, 2018, two (2) pages.
Yutaka Kawakami, "Recent progress in the development of Immunotherapy for melanoma," Skin Cancer, 2004, vol. 19, pp. 25-33.
Non-Final Office Action issued in U.S. Appl. No. 10/562,486, dated Jun. 20, 2018, thirty-five (35) pages.
Brenchley et al., "Expansion of activated human naive T-cells precedes effector function," Clin Exp Immunol, 2002, vol. 130, pp. 431-440.
Pittet et al., "Melan-A/MART-1-specific CD8 T cells: from thymus to tumor," TRENDS in Immunology, vol. 23, No. 7, 2002, pp. 325-328.
Powell et al., "Phenotypic and Functional Maturation of Tumor Antigen-Reactive CD8+ T Lymphocytes in Patients Undergoing Multiple Course Peptide Vaccination," J Immunother, 2004, vol. 27, pp. 36-47.
Lee et al., "Characterization of circulating T cells specific for tumor-associated antigens in melanoma patients," Nature Medicine, 1999, vol. 5, No. 6, pp. 677-85.
Yu et al., "Cancer vaccines: progress reveals new complexities," J Clin Invest. 2002, vol. 110, pp. 289-294.
Meidenbauer et al., "Direct visualization of antigen-specific T cells using peptide-MHC class I tetrameric complexes," Methods, 2003, vol. 31, pp. 160-71.
Andersen et al., "Poor correspondence between predicted and experimental binding of peptides to class I MHC molecules," Tissue Antigens, 2000, vol. 55, pp. 519-531.

\* cited by examiner

Figure 1-1

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 02.01 | TRBV02*01 | TRBJ2-2*01 | TRBD1*01 | 1 | tgtgcc........ | ...ggggc | acccgaata | .aacaccgggagctgttttt | | 1697 | C A G A P R I N T G E L F F |
| 02.02 | TRBV02*01 | TRBJ1-5*01 | | 2 | tgtgcc........ | gggttcgcgcccaacg | | ...agccccagcatttt | | 1698 | C A G F A P N E P Q H F |
| 02.03 | TRBV02*01 | TRBJ1-1*01 | TRBD1*01 | 3 | tgtgcca...... | a ...acag..... | cg | .gaacactgaagcttcttt | | 1699 | C A K Q R N T E A F F |
| 02.04 | TRBV02*01 | TRBJ2-1*01 | TRBD2*01 | 4 | tgtgcc........ | clagagga | .......ggggggg | ...ctacaatgagcagttcttc | | 1700 | C A L E E G G Y N E Q F F |
| 02.05 | TRBV02*01 | TRBJ2-7*01 | TRBD2*01 | 5 | tgtgcca...... | acagtgaagcgcctatc. | .gacta..... | cgac......... | cagtacttc | 1701 | C A N S E A P I D Y D Q Y F |
| 02.06 | TRBV02*01 | TRBJ2-7*01 | TRBD1*01 | 6 | tgtgcca...... | ...acag.... | tgaagcgcctatcga | .ctacgagcagtactc | | 1702 | C A N S E A P I D E Q Y F |
| 02.07 | TRBV02*01 | TRBJ2-3*01 | TRBD2*01 | 7 | tgtgcca...... | acagtatcgactgcgaa | ggggac......... | ...cagatacgcagtatttt | | 1703 | C A N S I D W R K G P D T Q Y F |
| 02.08 | TRBV02*01 | TRBJ1-2*01 | TRBD1*01 | 8 | tgtgcca...... | acgtgttccacga | .....ggggc | ...atggctacacctc | | 1704 | C A N V F H E G H G Y T F |
| 02.09 | TRBV02*01 | TRBJ2-3*01 | TRBD1*01 | 9 | tgtgccagc..... | ..ggaca..... | tt | .acagatacgcagtatttt | | 1705 | C A R D I T D T Q Y F |
| 02.10 | TRBV02*01 | TRBJ2-3*01 | TRBD2*01 | 10 | tgtgccagc..... | gacc...... | cgggg..... | at.....ctatggctacacctc | | 1706 | C A S D P G I Y G Y T F |
| 02.11 | TRBV02*01 | TRBJ2-3*01 | TRBD2*02 | 11 | tgtgccagc..... | ga ...tagcggag... | a | agcacagatacgcagtattt | | 1707 | C A S D S G R S T D T Q Y F |
| 02.12 | TRBV02*01 | TRBJ2-3*01 | TRBD2*02 | 12 | tgtgccagc..... | gggggct | .gactagcgggag... | ccgg......gatacgcagtatttt | | 1708 | C A S G G L T S G S R D T Q Y F |
| 02.13 | TRBV02*01 | TRBJ2-1*01 | TRBD1*01 | 13 | tgtgccagc..... | ggcat ...acagggg... | cg | ...caatgagcagttcttc | | 1709 | C A S G I Q G R N E Q F F |
| 02.14 | TRBV02*01 | TRBJ2-4*01 | TRBD1*01 | 14 | tgtgcagca..... | aggt...gacag..... | aatggtaca | agcaaaacattcagtacttc | | 1710 | C A S K V T E W V Q A K N I Q Y F |
| 02.15 | TRBV02*01 | TRBJ1-5*01 | TRBD1*01 | 15 | tgtgccagca..... | ctgggg ..... | agggggc | gg .......cagccccagcattt | | 1711 | C A S L G R G R Q P Q H F |
| 02.16 | TRBV02*01 | TRBJ1-5*01 | TRBD2*01 | 16 | tgtgcagca..... | atgatgtgtta | ...tagc...... | aatcatcccctg ............attt | | 1712 | C A S N D V V Y S N H P L D F |
| 02.17 | TRBV02*01 | TRBJ2-7*01 | TRBD2*01 | 17 | tgtgcagca..... | atgaagccc... | ctagcg..... | a ...ctacgagcagtactc | | 1713 | C A S N E A P S D Y E Q Y F |
| 02.18 | TRBV02*01 | TRBJ2-7*01 | TRBD2*01 | 18 | tgtgcagca..... | acgaatcc... | actagcg..... | a ...ctacgagcagtactc | | 1714 | C A S N E S T S D Y E Q Y F |
| 02.19 | TRBV02*01 | TRBJ2-7*01 | TRBD1*01 | 19 | tgtgcagca..... | acaggcc | .ggacaca..... | cacgta ...ctacgagcagtactc | | 1715 | C A S N R P D S T Y Y E Q Y F |
| 02.20 | TRBV02*01 | TRBJ2-2*01 | TRBD2*01 | 20 | tgtgcagca..... | ggac | gggact..... | tact ...acaccgggagctgtgtt | | 1716 | C A S R D G T Y Y T G E L F F |
| 02.21 | TRBV02*01 | TRBJ2-2*01 | TRBD1*01 | 21 | tgtgccagcag..... | ggacaggg..... | tg | ...ccggggagctgttttt | | 1717 | C A S R D R G A G E L F F |
| 02.22 | TRBV02*01 | TRBJ2-7*01 | TRBD2*01 | 22 | tgtgccagcag..... | ......ggggc g gac | ...cctacgagcagtactc | | | 1718 | C A S R G G P Y E Q Y F |
| 02.23 | TRBV02*01 | TRBJ2-4*01 | TRBD1*01 | 23 | tgtgccagcag..... | ggt ..gacag..... | aatgggtact | agccaaaaacattcagtacttc | | 1719 | C A S R V T E W V L A K N I Q Y F |
| 02.24 | TRBV02*01 | TRBJ2-5*01 | TRBD2*01 | 24 | tgtgccagcagtg... | cac ..ggacta..... | ccgggggatcaagaa | .....acccagtactc | | 1720 | C A S S A R T T G D Q E T Q Y F |
| 02.25 | TRBV02*01 | TRBJ1-1*01 | TRBD1*01 | 25 | tgtgccagcagtga... | t ..gga..... | Aaggatacgttcatgaacactgaagcttcttt | | | 1721 | C A S S D G K D T F M N T E A F F |
| 02.26 | TRBV02*01 | TRBJ1-1*01 | TRBD1*01 | 26 | tgtgccagcagtga... | tccgcaca gggacag...... | cactgaagcttcttt | | | 1722 | C A S S D P H R D S T E A F F |
| 02.27 | TRBV02*01 | TRBJ1-5*01 | TRBD1*01 | 27 | tgtgccagcagtga... | tgtgggt ta | tagcaatcagccccagcattt | | | 1723 | C A S S D V G Y S N Q P Q H F |
| 02.28 | TRBV02*01 | TRBJ2-7*01 | TRBD2*01 | 28 | tgtgccagcagtgaagc | gc ...ctacgg..... | a | ...ctacgagcagtactc | | 1724 | C A S S E A P S D Y E Q Y F |

Figure 1-2

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 02.29 | TRBV02*01 | TRBJ2-7*01 | TRBD2*01 | 29 | tgtgccagcagtgaagc gc ...ctagc...... aa ..ctacgagcagtactc | | | | | 1725 | C A S S E A P S N Y E Q Y F |
| 02.30 | TRBV02*01 | TRBJ2-3*01 | TRBD2*02 | 30 | tgtgccagcagtgaagc gc ......agcggga... agg ....agatacgcagtatttt | | | | | 1726 | C A S S E A Q R E G D T Q Y F |
| 02.31 | TRBV02*01 | TRBJ2-7*01 | TRBD2*01 | 31 | tgtgccagcagtgaagc ..gactacgg.... a ..ctacgagcagtactc | | | | | 1727 | C A S S E A T S D Y E Q Y F |
| 02.32 | TRBV02*01 | TRBJ1-5*01 | TRBD1*01 | 32 | tgtgccagcagtgaa... ...ggac...... ggcagctcagg ........gcccccagcattt | | | | | 1728 | C A S S E D G S S G P Q H F |
| 02.33 | TRBV02*01 | TRBJ2-5*01 | TRBD2*01 | 33 | tgtgccagcagtgaag..ggg .......gcggggg.. cgcg ....gagaccccagtactc | | | | | 1729 | C A S S E G G G A E T Q Y F |
| 02.34 | TRBV02*01 | TRBJ2-5*01 | TRBD1*01 | 34 | tgtgccagcag...... cgaaggtg ........aggggg ..ccaagagaccagtactc | | | | | 1730 | C A S S E G G G Q E T Q Y F |
| 02.35 | TRBV02*01 | TRBJ2-3*01 | TRBD2*01 | 35 | tgtgccagcagtga... gggactacg...... att ....acagatacgcagtatttt | | | | | 1731 | C A S S E G L A I T D T Q Y F |
| 02.36 | TRBV02*01 | TRBJ2-7*01 | TRBD2*01 | 36 | tgtgccagcagtgaag. ggt ...ctagcgg..... ttt tcctacgagcagtactc | | | | | 1732 | C A S S E G S S G F S Y E Q Y F |
| 02.37 | TRBV02*01 | TRBJ2-7*01 | TRBD2*01 | 37 | tgtgccagcagtgaag. ga ..actacgg...... a tcctacgagcagtactc | | | | | 1733 | C A S S E G T S G S Y E Q Y F |
| 02.38 | TRBV02*01 | TRBJ2-1*01 | TRBD2*02 | 38 | tgtgccagcagtgaa. aacgg ......agcggg... nacatcg......atgagcagttcttc | | | | | 1734 | C A S S E N G A G T S D E Q F F |
| 02.39 | TRBV02*01 | TRBJ2-5*01 | TRBD1*01 | 39 | tgtgccagcagtgaa.. t ...cagg... aacgataatg ....gagaccagtactc | | | | | 1735 | C A S S E S G T I M E T Q Y F |
| 02.40 | TRBV02*01 | TRBJ2-3*01 | TRBD1*01 | 40 | tgtgccagcagtgaa.. ..acagg.... ct ct agcacacagatacgcagtatttt | | | | | 1736 | C A S S E T G S S T D T Q Y F |
| 02.41 | TRBV02*01 | TRBJ2-7*01 | TRBD2*02 | 41 | tgtgccagcagtgaa.. a ......cggga... a .....cctacgagcagtactc | | | | | 1737 | C A S S E T G T Y E Q Y F |
| 02.42 | TRBV02*01 | TRBJ2-5*01 | TRBD2*02 | 42 | tgtgccagcagtg..... gagag ......gcggaggg ggg .....gagaccccagtactc | | | | | 1738 | C A S S G E A G G G E T Q Y F |
| 02.43 | TRBV02*01 | TRBJ2-5*01 | TRBD2*02 | 43 | tgtgccagcagtg..... gaggg ......gcggagg ggggaa......acccagtactc | | | | | 1739 | C A S S G G A G G G E T Q Y F |
| 02.44 | TRBV02*01 | TRBJ2-7*01 | TRBD2*01 | 44 | tgtgccagcag...... cgggggg. aacgagcccatg .............atttt | | | | | 1740 | C A S S G G N E P H D F |
| 02.45 | TRBV02*01 | TRBJ1-5*01 | TRBD1*01 | 45 | tgtgccagcagtg.....ggggag. aacg .....agcccccagcattt | | | | | 1741 | C A S S G G N E P Q H F |
| 02.46 | TRBV02*01 | TRBJ1-5*01 | TRBD1*01 | 46 | tgtgccagcagtg.....ggggg. aaccagcccccatg ................atttt | | | | | 1742 | C A S S G G N Q P H D F |
| 02.47 | TRBV02*01 | TRBJ1-5*01 | TRBD1*01 | 47 | tgtgccagcagtg.....ggggg. aatcagtccatg ..................atttt | | | | | 1743 | C A S S G G N Q S H D F |
| 02.48 | TRBV02*01 | TRBJ2-1*01 | TRBD2*02 | 48 | tgtgccagcag..... cgggacctt ..actacgggag.. ctaggg.......atgagcagttcttc | | | | | 1744 | C A S S G T L L A G A R D E Q F F |
| 02.49 | TRBV02*01 | TRBJ2-1*01 | TRBD2*01 | 49 | tgtgccagcag..... c gggac........ cttactatcccaagctaggg........atgagcagttcttc | | | | | 1745 | C A S S G T L L S Q A R D E Q F F |
| 02.50 | TRBV02*01 | TRBJ2-7*01 | TRBD2*02 | 50 | tgtgccagcagtg..... ggactacgcggggag. cccta tcctacgagcagtactc | | | | | 1746 | C A S S G T S G R P L S Y E Q Y F |
| 02.51 | TRBV02*01 | TRBJ2-7*01 | TRBD1*01 | 51 | tgtgccagcagt...... ttattct .......gggc tccccccg....acgagcagtactc | | | | | 1747 | C A S S L F W A P P D E Q Y F |
| 02.52 | TRBV02*01 | TRBJ2-3*01 | TRBD1*01 | 52 | tgtgccagcag..... cctc..acag... ataccac............tatttt | | | | | 1748 | C A S S L T D T H Y F |
| 02.53 | TRBV02*01 | TRBJ2-3*01 | | 53 | tgtgccagcag..... cct..cacagatacgcagtatttt | | | | | 1749 | C A S S L T D T Q Y F |
| 02.54 | TRBV02*01 | TRBJ2-7*01 | TRBD2*02 | 54 | tgtgccagcagt..... ctggttaa .......cgggag.. agctg...acgagcagtactc | | | | | 1750 | C A S S L V N G R A D E Q Y F |
| 02.55 | TRBV02*01 | TRBJ1-1*01 | TRBD1*01 | 55 | tgtgccagcagt..... at ..gaca..... aggag....cactgaagcttcttt | | | | | 1751 | C A S S M T R S T E A F F |
| 02.56 | TRBV02*01 | TRBJ1-1*01 | TRBD2*01 | 56 | tgtgccagcagt...... aa .......cggggg.. agg .gaacactgaagcttcttt | | | | | 1752 | C A S S N G G N T E A F F |

Figure 1-3

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 02.57 | TRBV02*01 | TRBJ2-3*01 | | 57 | tgtgccagcagt | ccggaaagcctcc | gcacagatacgcagtattt | | | 1753 | C A S S P E S L R T D T Q Y F |
| 02.58 | TRBV02*01 | TRBJ2-7*01 | TRBD2*01 | 58 | tgtgccagcagt | ca | gggact | ggaagcgg | acgagcagtactc | 1754 | C A S S Q G L E A D E Q Y F |
| 02.59 | TRBV02*01 | TRBJ2-1*01 | TRBD2*01 | 59 | tgtgccagcagt | tcc | gggactagc | c | cctacaatgagcagttcttc | 1755 | C A S S S G T S P Y N E Q F F |
| 02.60 | TRBV02*01 | TRBJ2-7*01 | TRBD1*01 | 60 | tgtgccagcagt | tccc | caggg | | tcctacgagcagtactc | 1756 | C A S S S P G S Y E Q Y F |
| 02.61 | TRBV02*01 | TRBJ2-3*01 | TRBD2*02 | 61 | tgtgccagcagt | tcaagt | ggag | | cagatacgcagtattt | 1757 | C A S S S G A D T Q Y F |
| 02.62 | TRBV02*01 | TRBJ2-3*01 | TRBD2*02 | 62 | tgtgccagcag | cact | ctagcggg | t | agcacagatacgcagtattt | 1758 | C A S S T L A G S T D T Q Y F |
| 02.63 | TRBV02*01 | TRBJ1-1*01 | TRBD1*01 | 63 | tgtgccagcagtg | t | acaggg | cct | tgaagcttcttt | 1759 | C A S S V Q G L E A F F |
| 02.64 | TRBV02*01 | TRBJ2-7*01 | TRBD2*01 | 64 | tgtgccagca | ctga | agcg | cctaacga | ctacgagcagtactc | 1760 | C A S T E A P N D Y E Q Y F |
| 02.65 | TRBV02*01 | TRBJ2-3*01 | TRBD2*02 | 65 | tgtgccagca | cgttc | gaggg | agat | acagatacccagtattt | 1761 | C A S T F E G D T D T Q Y F |
| 03.01 | TRBV03-1*01 | TRBJ2-1*01 | TRBD1*01 | 66 | tgtgccagc | | gggc | acctccgt | tcctacaatgagcagttctc | 1762 | C A S G H L R S Y N E Q F F |
| 03.02 | TRBV03-1*01 | TRBJ2-2*01 | TRBD2*01 | 67 | tgtgccagc | cattatagag | ctagcg | t | gaacaccggggagctgttttt | 1763 | C A S H Y R A S V N T G E L F F |
| 03.03 | TRBV03-1*01 | TRBJ1-2*01 | TRBD2*02 | 68 | tgtgccagcagc | | gaggg | tct | ctatgctacacctc | 1764 | C A S S E G L Y G Y T F |
| 03.04 | TRBV03-1*01 | TRBJ2-1*01 | TRBD2*01 | 69 | tgtgccagcagcca | c | ctagcgg | cgag | ctcctacaatgagcagttcttc | 1765 | C A S S H L A A S Y N E Q F F |
| 03.05 | TRBV03-1*01 | TRBJ2-1*01 | TRBD2*02 | 70 | tgtgccagcagcca | tagtatggg | ggggagg | gg | ctacaatgagcagttcttc | 1766 | C A S S H S M G G G G Y N E Q F F |
| 03.06 | TRBV03-1*01 | TRBJ2-1*01 | TRBD2*02 | 71 | tgtgccagcagcca | c | actagcgggaggg | ccgt | aatgagcagttcttc | 1767 | C A S S H T S G R A G N E Q F F |
| 03.07 | TRBV03-1*01 | TRBJ2-3*01 | TRBD2*02 | 72 | tgtgccagcagcc | ttcgatcggt | | ggagg tggg | gatacgcagtattt | 1768 | C A S S L R S G G G G D T Q Y F |
| 03.08 | TRBV03-1*01 | TRBJ1-5*01 | TRBD1*01 | 73 | tgtgccagcagcc | tct | caggg | aaccggtctattcagaccctc | tttt | 1769 | C A S S L S G N R S I Q T P S F |
| 03.09 | TRBV03-1*01 | TRBJ2-7*01 | TRBD2*02 | 74 | tgtgccagcagcc | tat | ctagcggaagg | act | tacgagcagtactc | 1770 | C A S S L S S G R T Y E Q Y F |
| 03.10 | TRBV03-1*01 | TRBJ2-1*01 | TRBD2*01 | 75 | tgtgccagcagcc | ccg cc | gggactag | g | gagcagttcttc | 1771 | C A S S P A G T R E Q F F |
| 03.11 | TRBV03-1*01 | TRBJ2-3*01 | TRBD2*02 | 76 | tgtgccagcagcc | cat | tagcggaa | tt | cacagatacgcagtattt | 1772 | C A S S P L A G F T D T Q Y F |
| 03.12 | TRBV03-1*01 | TRBJ1-6*02 | TRBD2*01 | 77 | tgtgccagcagc | cccga | cggggg | attttt | attcacccctccactt | 1773 | C A S S P P T G D F Y S P L H F |
| 03.13 | TRBV03-1*01 | TRBJ2-1*01 | TRBD2*02 | 78 | tgtgccagcagcc | cacgg | gcgggag | ctggtgg | tgagcagttcttc | 1774 | C A S S P R A G A G G E Q F F |
| 03.14 | TRBV03-1*01 | TRBJ1-4*01 | TRBD1*01 | 79 | tgtgccagcagcc | cacgccccgg | aggg | | gaaaaactgttttt | 1775 | C A S S P R P G G E K L F F |
| 03.15 | TRBV03-1*01 | TRBJ2-3*01 | TRBD2*02 | 80 | tgtgccagcagcc | cc | agcggga | ccttagagcc | tacgcagtattt | 1776 | C A S S P S G T L E A T Q Y F |
| 03.16 | TRBV03-1*01 | TRBJ2-1*01 | TRBD1*01 | 81 | tgtgccagcagcc | ccag | caggggg | g | cctacaatgagcagttctc | 1777 | C A S S P S R G A Y N E Q F F |
| 03.17 | TRBV03-1*01 | TRBJ2-7*01 | TRBD1*01 | 82 | tgtgccagcagcc | ctt | ggaacag | ttcg | tcctacgagcagtactc | 1778 | C A S S P W T G S S Y E Q Y F |
| 03.18 | TRBV03-1*01 | TRBJ2-7*01 | TRBD1*01 | 83 | tgtgccagcagcca | ggc | acaggg | ctcact ctcctacgagcagtactc | TRBJ2-7*01 | 1779 | C A S S Q A Q G G S L S Y E Q Y F |

Figure 1-4

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 03.19 | TRBV03-1*01 | TRBJ1-2*01 | TRBD1*01 | 84 | tgtgccagcagccaaga | cgc | gacaggg | a | atggtacacctc | 1780 | C A S S Q D A T G N G Y T F |
| 03.20 | TRBV03-1*01 | TRBJ1-5*01 | TRBD1*01 | 85 | tgtgccagcagccaaga | cc | ggacaggg | ttggg | aatcagcccagcatttt | 1781 | C A S S Q D R T G V G N Q P Q H F |
| 03.21 | TRBV03-1*01 | TRBJ2-7*01 | TRBD2*01 | 86 | tgtgccagcagccaaga | tagcgg | c | cctacgcagtactc | 1782 | C A S S Q D S G P Y E Q Y F |
| 03.22 | TRBV03-1*01 | TRBJ1-2*01 | | 87 | tgtgccagcagccaaga t | tcaccatct | tatgctcaccttc | | | 1783 | C A S S Q D S P S Y G Y T F |
| 03.23 | TRBV03-1*01 | TRBJ2-1*01 | TRBD1*01 | 88 | tgtgccagcagccaaga | agttcctt | acag | ctcctacaatgagcagttcttc | | 1784 | C A S S Q E G P Y S S Y N E Q F F |
| 03.24 | TRBV03-1*01 | TRBJ1-2*01 | TRBD1*01 | 89 | tgtgccagcagcca | gggg | atgatgctacg | | cctc | 1785 | C A S S Q G M D G Y A F |
| 03.25 | TRBV03-1*01 | TRBJ1-2*01 | TRBD1*01 | 90 | tgtgccagcagccaa | cc | gggacag | cgaaggg | tggctcaccttc | 1786 | C A S S Q P G Q R R G G Y T F |
| 03.26 | TRBV03-1*01 | TRBJ2-1*01 | TRBD2*02 | 91 | tgtgccagcagccaa | cc | gactagcggag | tattt | atgagcagttcttc | 1787 | C A S S Q P T S G S I Y E Q F F |
| 03.27 | TRBV03-1*01 | TRBJ2-7*01 | TRBD2*02 | 92 | tgtgccagcagccaa | caatt | gccggaggg | cg | acgagcagtactc | 1788 | C A S S Q Q L R E G D E Q Y F |
| 03.28 | TRBV03-1*01 | TRBJ2-1*01 | TRBD2*01 | 93 | tgtgccagcagcca | agagta | ggactagc | aac | caatgagcagttcttc | 1789 | C A S S Q R V G L A T N E Q F F |
| 03.29 | TRBV03-1*01 | TRBJ2-7*01 | TRBD2*02 | 94 | tgtgccagcagcca | gtcgg | gccgga | aaa | cctacgagcagtactc | 1790 | C A S S Q S G G K T Y E Q Y F |
| 03.30 | TRBV03-1*01 | TRBJ2-6*01 | TRBD1*01 | 95 | tgtgccagcagccaag | tcatt | gggg | atct ctctgggccaacgtcctgactttc | | 1791 | C A S S Q V I G D L S G A N V L T F |
| 03.31 | TRBV03-1*01 | TRBJ2-1*01 | TRBD2*01 | 96 | tgtgccagcagcc | ggggatt | gactag | | ggaaggcctctccacaatgagcagttcttc | 1792 | C A S S R G L T R E G L S Y N E Q F F |
| 03.32 | TRBV03-1*01 | TRBJ2-6*01 | TRBD2*01 | 97 | tgtgccagcagcc | gacct | gcggg | tgccct | tgggccaacgtcctgactttc | 1793 | C A S S R P A G A L G A N V L T F |
| 03.33 | TRBV03-1*01 | TRBJ1-4*01 | TRBD1*01 | 98 | tgtgccagcagc | gaa | gacag | cag | aatgaaaaactgtttt | 1794 | C A S S R R Q Q N E K L F F |
| 03.34 | TRBV03-1*01 | TRBJ1-2*01 | TRBD1*01 | 99 | tgtgccagcagc | tcccaat | ggac | cgaggaaccgaaggg | ctatgctcaccttc | 1795 | C A S S Q W T E E P K G Y G Y T F |
| 03.35 | TRBV03-1*01 | TRBJ1-1*01 | | 100 | tgtgccagca | cccctcgacga | gaacactgaagcttcttc | | | 1796 | C A S T P S T E N T E A F F |
| 04.001 | TRBV04-2*01 | TRBJ1-3*01 | TRBD1*01 | 101 | tgtgcc | ggcagccaaggatt | ggc cg | tgaaacaccatatttt | | 1797 | C A G S Q G L G R G N T I Y F |
| 04.002 | TRBV04-1*02 | TRBJ2-1*01 | TRBD1*01 | 102 | tgtgccagcag | acaggg | ccc | caatgagcagttcttc | | 1798 | C A S R Q G P N E Q F F |
| 04.003 | TRBV04-1*01 | TRBJ2-2*01 | TRBD1*01 | 103 | tgtgccagcag | aac | gggacaggg | tc | caccgggggagctgttttt | 1799 | C A S R T G Q G S T G E L F F |
| 04.004 | TRBV04-1*01 | TRBJ2-3*01 | TRBD2*01 | 104 | tgtgccagcagc | gat | ggg | t | cgcagtatttt | 1800 | C A S S D G S Q Y F |
| 04.005 | TRBV04-3*01 | TRBJ2-2*01 | TRBD1*01 | 105 | tg | tgccagcagccatcc | cagg | | ccgggggagctgttttt | 1801 | C A S S H P Q A G E L F F |
| 04.006 | TRBV04-1*02 | TRBJ2-1*01 | TRBD2*02 | 106 | tgtgccagcagcca | cccgaggt | tagacggag | acg | acaatgagcagttcttc | 1802 | C A S S H P R L A G D D N E Q F F |
| 04.007 | TRBV04-1*02 | TRBJ2-5*01 | TRBD1*01 | 107 | tgtgccagcagcca | tccga | ggacag | acc | accaagagaccagtactc | 1803 | C A S S H P R T D H Q E T Q Y F |
| 04.008 | TRBV04-1*02 | TRBJ2-7*01 | TRBD2*01 | 108 | tgtgccagcagcca | tccatc | agcgggg | tcggccgg | cgagcagtactc | 1804 | C A S S H P S A G S A G E Q Y F |
| 04.009 | TRBV04-1*01 | TRBJ1-6*01 | TRBD1*01 | 109 | tgtgccagcagca | tagga | gaca | agt | taattcaccctccacttt | 1805 | C A S S H R R Q V N S P L H F |
| 04.010 | TRBV04-1*01 | TRBJ1-3*01 | TRBD2*02 | 110 | tgtgccagcagc | aaag | gggaggg | acggatt | tctgaaacaccatattttt | 1806 | C A S S K G E G R I S G N T I Y F |

Figure 1-5

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 04.011 | TRBV04-3*01 | TRBJ2-2*01 | TRBD1*01 | 111 | tgcgccagcagc... | t ..ggacag..... | aa .cgaacaccgggagctgtttt | | | 1807 | C A S S L D R T N T G E L F F |
| 04.012 | TRBV04-2*01 | TRBJ2-1*01 | TRBD2*01 | 112 | tgtgccagcagcc... | tcggc ..gac.......... | gag .......... | gagcagttcttc | | 1808 | C A S S L G D E E Q F F |
| 04.013 | TRBV04-3*01 | TRBJ2-1*01 | | 113 | tgcgccagcagcc... | taggattgacga ...acaatgagcagttcttc | | | | 1809 | C A S S L G L T N N E Q F F |
| 04.014 | TRBV04-1*02 | TRBJ2-5*01 | TRBD2*02 | 114 | tgcgccagcagcc... | tca ..gactagcgggag.. atgcg .....gagaccagtacttc | | | | 1810 | C A S S L R L A G D A E T Q Y F |
| 04.015 | TRBV04-1*01 | TRBJ2-7*01 | TRBD2*02 | 115 | tgcgccagcagc... | ttgactgtt .......gcgggagg atga... acgagcagtcttc | | | | 1811 | C A S S L T V A G G M N E Q Y F |
| 04.016 | TRBV04-2*01 | TRBJ2-1*01 | TRBD2*01 | 116 | tgtgccagcagcc... | .......tag....... ttggcgaaa .tcctacaatgagcagttcttc | | | | 1812 | C A S S L V A K S Y N E Q F F |
| 04.017 | TRBV04-2*01 | TRBJ1-1*01 | TRBD1*01 | 117 | tgtgccagcagcc... | ttgtccaat ..acag.... tcc ..gaacactgaagcttcttt | | | | 1813 | C A S S L V Q Y S P N T E A F F |
| 04.018 | TRBV04-1*02 | TRBJ1-6*01 | TRBD1*01 | 118 | tgcgccagcagc... | aac ..ggacaggg... acgga ...ataattcaccctccacttt | | | | 1814 | C A S S N G Q G R N N S P L H F |
| 04.019 | TRBV04-1*01 | TRBJ2-2*01 | TRBD2*01 | 119 | tgcgccagcagcc... | cagct gggac....... cct ..gaacaccgggagctgttttt | | | | 1815 | C A S S P A G T L N T G E L F F |
| 04.020 | TRBV04-1*02 | TRBJ1-2*01 | TRBD1*01 | 120 | tgcgccagcagc... | caggggc agc.. aactatgctacacctc | | | | 1816 | C A S S P G G S N Y G Y T F |
| 04.021 | TRBV04-1*01 | TRBJ1-5*01 | TRBD1*01 | 121 | tgcgccagcagcc... | c ..gggacag.... ca tagcaatcagcccagcattt | | | | 1817 | C A S S P G Q H S N Q P Q H F |
| 04.022 | TRBV04-2*01 | TRBJ2-7*01 | TRBD2*01 | 122 | tgtgccagcagcc... | ccttgga .....tagcgg.... agccgggacgaatcaa ........tacttc | | | | 1818 | C A S S P L D S G A G T D Q Y F |
| 04.023 | TRBV04-2*01 | TRBJ2-7*01 | TRBD2*01 | 123 | tgtgccagcagcc... | ccttgga .... tagcgg..... agccgggacg ...... gagcagtactc | | | | 1819 | C A S S P L D S G A G T E Q Y F |
| 04.024 | TRBV04-1*02 | TRBJ2-7*01 | TRBD1*01 | 124 | tgcgccagcagcc... | cactt .....aggg.. tagggc ..cctacgagcagtactc | | | | 1820 | C A S S P L R V G P Y E Q Y F |
| 04.025 | TRBV04-1*02 | TRBJ2-3*01 | TRBD2*02 | 125 | tgcgccagcagcc... | cccc ........ggaggg ..... tacgcagtatttt | | | | 1821 | C A S S P P E G T Q Y F |
| 04.026 | TRBV04-1*01 | TRBJ2-2*01 | TRBD2*02 | 126 | tgcgccagcagcc... | c ........... gagg.. agttt cgaacaccgggagctgtttt | | | | 1822 | C A S S P R S S N T G E L F F |
| 04.027 | TRBV04-1*02 | TRBJ1-2*01 | TRBD2*02 | 127 | tgcgccagcagcc... | cacgtac .......... ggag.. a ctaactatgctacacctc | | | | 1823 | C A S S P R T E T N Y G Y T F |
| 04.028 | TRBV04-3*01 | TRBJ2-5*01 | TRBD2*01 | 128 | tg .......... | tgcagcagcccca ..ggactacgg.... ag ...aagagaccagtacttc | | | | 1824 | C A S S P R T S G E E T Q Y F |
| 04.029 | TRBV04-1*01 | TRBJ2-5*01 | TRBD2*01 | 129 | tgcgccagcagcc... | ......ctacgggggg ccc t .... agagaccagtacttc | | | | 1825 | C A S S P S G G A L E T Q Y F |
| 04.030 | TRBV04-1*01 | TRBJ2-1*01 | TRBD2*02 | 130 | tgcgccagcagcc... | cct c gggacaggg.. agatcgc ........ gttcttc | | | | 1826 | C A S S P S G Q G R S A F F |
| 04.031 | TRBV04-1*01 | TRBJ1-3*01 | TRBD1*01 | 131 | tgcgccagcagcc... | cgagccat ..acaggg... aaca ..ctgaaacaccatatttt | | | | 1827 | C A S S P S H T G N T I Y F |
| 04.032 | TRBV04-1*02 | TRBJ2-1*01 | | 132 | tgcgccagcagcc... | cttcccct ..ctacaatgagcagttcttc | | | | 1828 | C A S S P S L Y N E Q F F |
| 04.033 | TRBV04-1*02 | TRBJ2-7*01 | TRBD2*01 | 133 | tgcgccagcagcc... | cctcc ........cgggg... tcca .tcctacgagcagtacttc | | | | 1829 | C A S S P S R G P S Y E Q Y F |
| 04.034 | TRBV04-1*02 | TRBJ1-3*01 | | 134 | tgcgccagcagcc... | cgtatacg ..ggaaaccacatatttt | | | | 1830 | C A S S P Y T G N T I Y F |
| 04.035 | TRBV04-1*01 | TRBJ1-1*01 | TRBD1*01 | 135 | tgcgccagcagcaag... | catto ....caggg.... atc ..gaacactgaagcttcttt | | | | 1831 | C A S S Q A F Q G S N T E A F F |
| 04.036 | TRBV04-1*02 | TRBJ2-7*01 | TRBD1*01 | 136 | tgcgccagcagccaa gcc ......ggggc cg ..cctacgagcagtacttc | | | | | 1832 | C A S S Q A G A A Y E Q Y F |
| 04.037 | TRBV04-1*01 | TRBJ2-7*01 | TRBD2*02 | 137 | tgcgccagcagcc... | ccagc ..ggactagcgggagg.. a ....tacgagcagtacttc | | | | 1833 | C A S S Q A S G L A G G Y E Q Y F |
| 04.038 | TRBV04-1*01 | TRBJ2-5*01 | TRBD2*02 | 138 | tgcgccagcagcaaga tga ........gaggg taac .....agagaccagtacttc | | | | | 1834 | C A S S Q D E R V T E T Q Y F |

Figure 1-6

| clone # | V name | J name | D name | SEQ ID NO: | V-REGION | N1 | D-REGION | (P) | N2 | J-REGION | SEQ ID NO: | CDR3 amino acid |
|---|---|---|---|---|---|---|---|---|---|---|---|---|
| 04.039 | TRBV04-1*02 | TRBJ2-7*01 | TRBD2*02 | 139 | tgcgccagcagccaa | gattt......cggag... | aac......cgagcagtactc | | | | 1835 | C A S S Q D F G R T E Q Y F |
| 04.040 | TRBV04-3*01 | TRBJ1-2*01 | TRBD1*01 | 140 | tg............... | tgcagcagccaagatgggga....aggggc gc tg...actatgctacacctc | | | | | 1836 | C A S S Q D G E G G A D Y G Y T F |
| 04.041 | TRBV04-2*01 | TRBJ1-1*01 | TRBD1*01 | 141 | tgtgccagcagccaaga | t at c | gggacaggg... | | ccg ...actgaagctttctt | | 1837 | C A S S Q D I G T G P T E A F F |
| 04.042 | TRBV04-1*02 | TRBJ1-3*01 | TRBD1*01 | 142 | tgcgccagcagccaa | gatctg......gggggc ag...tgaaacaccatatattt | | | | | 1838 | C A S S Q D L G G S G N T I Y F |
| 04.043 | TRBV04-3*01 | TRBJ1-1*01 | TRBD1*01 | 143 | tgcgccagcagccaaga | tct a | .......gggc caag | | ...cactgaagcttcttt | | 1839 | C A S S Q D L G P S T E A F F |
| 04.044 | TRBV04-2*01 | TRBJ2-2*01 | TRBD2*02 | 144 | tgcgccagcagccaaga | tcc | ......cggga... tgaag...accgggagctgttttt | | | | 1840 | C A S S Q D P G M E T G E L F F |
| 04.045 | TRBV04-1*01 | TRBJ2-7*01 | TRBD2*01 | 145 | tgcgccagcagccaaga | tc | ......cggg...ctacgagcagtactc | | | | 1841 | C A S S Q D P G Y E Q Y F |
| 04.046 | TRBV04-1*02 | TRBJ1-5*01 | | 146 | tgcgccagcagccaa | gattcagatcagaccac | | | .............cattt | | 1842 | C A S S Q D S D Q T H H F |
| 04.047 | TRBV04-2*01 | TRBJ2-1*01 | TRBD2*02 | 147 | tgtgccagcagccaaga | ......tagcgggag... ctcctacaatgagcagtctc | | | | | 1843 | C A S S Q D S G S S Y N E Q F F |
| 04.048 | TRBV04-3*01 | TRBJ1-5*01 | | 148 | tgcagccagcagccaaga | t | agcggtattgg | | ......tcagcccagcattt | | 1844 | C A S S Q D S G I G Q P Q H F |
| 04.049 | TRBV04-2*01 | TRBJ2-7*01 | TRBD1*01 | 149 | tgcgccagcagccaaga | gatt c gggac... | ...c ctcctacgagcagtactc | | | | 1845 | C A S S Q D S G P S Y E Q Y F |
| 04.050 | TRBV04-1*01 | TRBJ2-2*01 | | 150 | tgcgccagcagcca... | ggattcgc..gcaccgggagctgtttt | | | | | 1846 | C A S S Q D S H T G E L F F |
| 04.051 | TRBV04-1*02 | TRBJ1-5*01 | | 151 | tgcgccagcagccaa | gattca.....aatcagcccagcattt | | | | | 1847 | C A S S Q D S N Q P Q H F |
| 04.052 | TRBV04-1*01 | TRBJ2-7*01 | TRBD1*01 | 152 | tgcgccagcagccaaga | tcccc...actacg... | | | tcc ag ctcctacgagcagtactc | | 1848 | C A S S Q D S P L A S S Y E Q Y F |
| 04.053 | TRBV04-1*01 | TRBJ2-5*01 | | 153 | tgcgccagcagccaaga | cac gt accaagagaccagtactc | | | | | 1849 | C A S S Q D T Y Q E T Q Y F |
| 04.054 | TRBV04-1*01 | TRBJ2-5*01 | TRBD1*01 | 154 | tgtgccagcagccaaga | a | .gacaggg... | | latcc ...gagaccagtactc | | 1850 | C A S S Q E D R V S E T Q Y F |
| 04.055 | TRBV04-1*01 | TRBJ1-5*01 | TRBD1*01 | 155 | tgtgccagcagccaaga | aga ggga... | | | ggtatgat ...caatcagcccagcattt | | 1851 | C A S S Q E E G G M I N Q P Q H F |
| 04.056 | TRBV04-1*01 | TRBJ2-1*01 | TRBD2*01 | 156 | tgcgccagcagccaaga | aittt | ......ggggg... tg | | .......atgagcagttctc | | 1852 | C A S S Q E F G G D E Q F F |
| 04.057 | TRBV04-1*01 | TRBJ2-3*01 | TRBD1*01 | 157 | tgcgccagcagccaaga | agg | ......agcggg... | cit | agcacagatacgcagtattt | | 1853 | C A S S Q E G A G L S T D T Q Y F |
| 04.058 | TRBV04-1*02 | TRBJ1-2*01 | TRBD2*01 | 158 | tgcgccagcagccaaga | agg | ......agggggc ctctc...atggctacacctc | | | | 1854 | C A S S Q E G A S H G Y T F |
| 04.059 | TRBV04-1*01 | TRBJ2-2*01 | TRBD2*01 | 159 | tgtgccagcagccaaga | agggcag...ctagcgg... | | | aggggg.....cggggagctgtttt | | 1855 | C A S S Q E G Q L A E G G G E L F F |
| 04.060 | TRBV04-1*02 | TRBJ2-1*01 | TRBD2*02 | 160 | tgcgccagcagccaaga | gag | .......gggagg g | | ....caatgagcagttctc | | 1856 | C A S S Q E G R G N E Q F F |
| 04.061 | TRBV04-1*01 | TRBJ2-7*01 | TRBD1*01 | 161 | tgcgccagcagccaaga | ac | ...acaggg... atta | | ...tacgagcagtactc | | 1857 | C A S S Q E H R G L Y E Q Y F |
| 04.062 | TRBV04-3*01 | TRBJ2-7*01 | TRBD2*01 | 162 | tgcgccagcagccaaga | aittgggggga gggacta... | | | ag ...tacgagcagtactc | | 1858 | C A S S Q E L G G G T K Y E Q Y F |
| 04.063 | TRBV04-1*02 | TRBJ1-4*01 | TRBD2*01 | 163 | tgcgccagcagccaa | gagcc...cgggggg tcgaaaag | | | ......ctgttttt | | 1859 | C A S S Q E P G G V E K L F F |
| 04.064 | TRBV04-2*01 | TRBJ2-3*01 | TRBD2*02 | 164 | tgcgccagcagccaaga | gca ...agcgggaggg gtgt | | | .......tacgcagtatttt | | 1860 | C A S S Q E Q A G G V V T Q Y F |
| 04.065 | TRBV04-2*01 | TRBJ2-3*01 | TRBD1*01 | 165 | tgtgccagcagccaaga | aaggg ......ggggagg cc gt | | | .....gatacgcagtatttt | | 1861 | C A S S Q E R G E G R D T Q Y F |
| 04.066 | TRBV04-2*01 | TRBJ1-3*01 | TRBD1*01 | 166 | tgtgccagcagccaaga | a | .....agggg. acgaat ctctgaaacaccatatattt | | | | 1862 | C A S S Q E R G R I S G N T I Y F |

Figure 1-7

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 04.067 | TRBV04-2*01 | TRBJ2-7*01 | TRBD2*01 | 167 | tgtgccagcagccaaga | ggtg | gcgggg | tgagg | gagcagtactc | 1863 | C A S S Q E V A G V R E Q Y F |
| 04.068 | TRBV04-1*02 | TRBJ1-3*01 | TRBD2*01 | 168 | tgtgccagcagccaa | gaatggcccgaa | agcgg | to | acaccatatattt | 1864 | C A S S Q E W P E S G H T I Y F |
| 04.069 | TRBV04-1*02 | TRBJ2-7*01 | TRBD2*01 | 169 | tgcgccagcagccaa | cgagc | cgggg | ctacgagcagtactc | | 1865 | C A S S Q G A G G Y E Q Y F |
| 04.070 | TRBV04-1*01 | TRBJ1-6*01 | TRBD1*01 | 170 | tgtgccagcagccaag | gggac | cgaaact | attcaccctccactt | | 1866 | C A S S Q G D R N Y S P L H F |
| 04.071 | TRBV04-1*02 | TRBJ1-1*01 | TRBD1*01 | 171 | tgtgccagcagcagccaa g | gggac | cgctatgt | cactgaagcttctt | | 1867 | C A S S Q G D R Y V V T E A F F |
| 04.072 | TRBV04-1*01 | TRBJ2-7*01 | TRBD1*01 | 172 | tgcgccagcagcagccaag | gggacag | ctcctacgagcagtactc | | | 1868 | C A S S Q G D S S Y E Q Y F |
| 04.073 | TRBV04-2*01 | TRBJ2-7*01 | TRBD2*02 | 173 | tgtgccagcagccaag | ggg | ggaggg g | tacgagcagtactc | | 1869 | C A S S Q G G E G Y E Q Y F |
| 04.074 | TRBV04-1*02 | TRBJ2-7*01 | TRBD2*01 | 174 | tgcgccagcagccaag | g | gcggggggg aaa | cctacgagcagtactc | | 1870 | C A S S Q G G G G E T Y E Q Y F |
| 04.075 | TRBV04-2*01 | TRBJ1-1*01 | TRBD1*01 | 175 | tgtgccagcagccaag | gcgg gggacagg | ttttat | cactgaagcttctt | | 1871 | C A S S Q G G G Q G F I T E A F F |
| 04.076 | TRBV04-3*01 | TRBJ2-2*01 | TRBD1*01 | 176 | tg | tgccagcagcca | agggg to | ccggggagctgttttt | | 1872 | C A S S Q G G P G E L F F |
| 04.077 | TRBV04-1*02 | TRBJ2-5*01 | TRBD2*01 | 177 | tgtgccagcagccaa | ggggg ac | ccaagagaccagtactc | | | 1873 | C A S S Q G G T Q E T Q Y F |
| 04.078 | TRBV04-2*01 | TRBJ2-3*01 | TRBD2*02 | 178 | tgtgccagcagccaag | gactagcgggaggg cc agg | tacgcagtatttt | | | 1874 | C A S S Q G L A G G P G T Q Y F |
| 04.079 | TRBV04-2*01 | TRBJ2-1*01 | TRBD2*02 | 179 | tgtgccagcagccaa | ggat | gaggg c tagttgggttttg | acaatgagcagtcttc | | 1875 | C A S S Q G M R A S W G F D N E Q F F |
| 04.080 | TRBV04-1*01 | TRBJ1-5*01 | TRBD1*01 | 180 | tgcgccagcagccaag | gacgg ta tagcaatcagcccagcatttt | | | | 1876 | C A S S Q G R Y S N Q P Q H F |
| 04.081 | TRBV04-1*02 | TRBJ2-3*01 | TRBD2*01 | 181 | tgtgccagcagccaa | ggggtcgg | gcggg | ctaactatgctacaccttc | | 1877 | C A S S Q G V G R A N Y G Y T F |
| 04.082 | TRBV04-2*01 | TRBJ2-3*01 | TRBD2*02 | 182 | tgtgccagcagccaa | aa | actagccggga at | acagatacgcagtatttt | | 1878 | C A S S Q K L A G D T D T Q Y F |
| 04.083 | TRBV04-2*01 | TRBJ2-1*01 | TRBD2*02 | 183 | tgtgccagcagcca | aaa cc gggactagcggga | ttca | acagagcagtactc | | 1879 | C A S S Q K P G L A G F N E Q Y F |
| 04.084 | TRBV04-1*02 | TRBJ1-5*01 | TRBD1*01 | 184 | tgtgccagcagccaa | aaat | gggg taatcac | ccccagcatttt | | 1880 | C A S S Q K W G N H P Q H F |
| 04.085 | TRBV04-3*01 | TRBJ2-3*01 | TRBD1*01 | 185 | tgtgccagcagccaa | aagt | acaggg | ttctggaactcg gcacagatacgcagtattt | | 1881 | C A S S Q K Y R V L E L G T D T Q Y F |
| 04.086 | TRBV04-1*01 | TRBJ2-3*01 | TRBD2*02 | 186 | tgtgccagcagccaa | ctto | gcgggagg gtag | cagatacgcagtactt | | 1882 | C A S S Q L A G G V A D T Q Y F |
| 04.087 | TRBV04-1*01 | TRBJ2-5*01 | TRBD1*01 | 187 | tgcgccagcagccaa | ct c gggacagggggc gc gggg | gagaccagtactc | | | 1883 | C A S S Q L G T G G A G E T Q Y F |
| 04.088 | TRBV04-1*02 | TRBJ2-7*01 | TRBD2*02 | 188 | tgcgccagcagcca | gcc gggactagcgga | tatg | atgagcagtactc | | 1884 | C A S S Q P G L A G Y D E Q F F |
| 04.089 | TRBV04-1*02 | TRBJ2-5*01 | TRBD1*01 | 189 | tgcgccagcagcca | gcctct gggacag | a | aagagaccagtactc | | 1885 | C A S S Q P L G Q K E T Q Y F |
| 04.090 | TRBV04-1*01 | TRBJ1-2*01 | TRBD1*01 | 190 | tgcgccagcagcca | a | ggc g gttggg | actatgctacacctc | | 1886 | C A S S Q R A V G D Y G Y T F |
| 04.091 | TRBV04-1*02 | TRBJ2-1*01 | TRBD2*02 | 191 | tgcgccagcagccaa cg c gggactagcggga | ag | aatgagcagttcttc | | | 1887 | C A S S Q R G T S G K N E Q F F |
| 04.092 | TRBV04-1*02 | TRBJ2-7*01 | TRBD1*01 | 192 | tgtgccagcagcca | c | gaca | aactgg | ctacgagcagtactc | 1888 | C A S S Q R Q T G Y E Q Y F |
| 04.093 | TRBV04-3*01 | TRBJ1-1*01 | TRBD2*01 | 193 | tgcgccagcagccaa | tcgt | tagc | tgtagctac ctcctacaatgagcagttcttc | | 1889 | C A S S Q S L A V A T S Y N E Q F F |
| 04.094 | TRBV04-1*01 | TRBJ2-7*01 | TRBD2*02 | 194 | tgtgccagcagcca | gac | ccggaggg ggcc ctcctacgagcagtactc | | | 1890 | C A S S Q T G R G P S Y E Q Y F |

Figure 1-8

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 04.095 | TRBV04-1*02 | TRBJ2-7*01 | TRBD2*01 | 195 | tgcgccagcagccaa | a cc gggact | | tcctacgagcagttc | | 1891 | C A S S Q T G T S Y E Q Y F |
| 04.096 | TRBV04-1*01 | TRBJ2-7*01 | TRBD2*01 | 196 | tgggccagcagccaag | tgcga | agcggggg | ag | cctacgagcagtacttc | 1892 | C A S S Q V R S G G A Y E Q Y F |
| 04.097 | TRBV04-1*02 | TRBJ1-2*01 | | 197 | tgcgccagcagccaa | gtatcaga | ag | ctaactatgctacacctc | | 1893 | C A S S Q V S E A N Y G Y T F |
| 04.098 | TRBV04-1*02 | TRBJ1-2*01 | TRBD1*01 | 198 | tgcgccagcagccaa | gt | gacaggggc | tc | ctatgctacacctc | 1894 | C A S S Q V T G G S Y G Y T F |
| 04.099 | TRBV04-1*02 | TRBJ2-7*01 | TRBD1*01 | 199 | tgcgccagcagcca | gtgtaacg | gggacaggg | cga | tacgagcagttc | 1895 | C A S S Q V T G T G R Y E Q Y F |
| 04.100 | TRBV04-1*01 | TRBJ2-7*01 | | 200 | tgcgccagcagccaag | ttaca | tcctacgagcagttc | | | 1896 | C A S S Q V T S Y E Q Y F |
| 04.101 | TRBV04-1*02 | TRBJ2-1*01 | TRBD2*02 | 201 | tgcgccagcagcc | g | gggactagcgggagg | ac | acaatgagcagttctc | 1897 | C A S S R G L A G G H N E Q F F |
| 04.102 | TRBV04-1*01 | TRBJ2-1*01 | TRBD2*02 | 202 | tgcgccagcagc | | tcagac | actacgggag | caccagggg | caatgagcagttcttc | 1898 | C A S S D T S G S T R G N E Q F F |
| 04.103 | TRBV04-1*01 | TRBJ2-5*01 | TRBD1*01 | 203 | tgcgccagcag | | ttc | caggggg | tgga | agaccagtacttc | 1899 | C A S S R G W K T Q Y F |
| 04.104 | TRBV04-2*01 | TRBJ2-1*01 | | 204 | tgtgccagcagc | | acatcgtctgcg | acaatgagcagttcttc | | 1900 | C A S S T S S R D N E Q F F |
| 04.105 | TRBV04-2*01 | TRBJ1-4*01 | TRBD1*01 | 205 | tgccagcagc | | tac | gacaggg | ag | actaatgaaaaactgttttt | 1901 | C A S S Y D R E T N E K L F F |
| 04.106 | TRBV04-1*01 | TRBJ2-7*01 | TRBD1*01 | 206 | tgcgccagcagc | | tactac | caggggg | gcgg | cgagcagtacttc | 1902 | C A S S Y Y Q G G G E Q Y F |
| 05.001 | TRBV05-6*01 | TRBJ2-1*01 | TRBD2*01 | 207 | tgtgcc | | tgcagcttgggaa | | cgggg | ctacaatgg | gcagttcttc | 1903 | C A C S F G E R G Y N G Q F F |
| 05.002 | TRBV05-6*01 | TRBJ2-6*01 | TRBD2*01 | 208 | tgtgcca | | accgccgatcgtggg | agcgg | ttgtg | tctggggccaacgtcctgacttc | 1904 | C A N P P I V G A V V S G A N V L T F |
| 05.003 | TRBV05-6*01 | TRBJ2-1*01 | TRBD1*01 | 209 | tgtgcca | | acagcttg gggac | cgggcoaacaatgaa | cagttcttc | | 1905 | C A N S F G D R A N N E Q F F |
| 05.004 | TRBV05-6*01 | TRBJ2-1*01 | TRBD1*01 | 210 | tgtgcc | | cccagcttg gggacaggg | cctacagtgaca | agttcttc | | 1906 | C A P S F G D R A Y S D K F F |
| 05.005 | TRBV05-8*01 | TRBJ2-1*01 | TRBD1*01 | 211 | tgtgccag | | agaaggg | caggg | c | cctacaatgagcagttcttc | 1907 | C A R E G Q G P Y N E Q F F |
| 05.006 | TRBV05-4*01 | TRBJ2-7*01 | | 212 | tgtgcc | | cgcagcttgcctccggctatgaacaa | | ttcttc | | 1908 | C A R S F A S G Y E Q F F |
| 05.007 | TRBV05-6*01 | TRBJ2-1*01 | TRBD2*02 | 213 | tgtgccag | | tgaa | ggaggg ccc g | | atgagcagttcttc | 1909 | C A S E G G P D E Q F F |
| 05.008 | TRBV05-4*01 | TRBJ2-3*01 | TRBD2*01 | 214 | tgtgccagc | | gggac | actagcg | acc agcacagatacgcagtatttt | | 1910 | C A S G T L A T S T D T Q Y F |
| 05.009 | TRBV05-1*01 | TRBJ1-1*01 | TRBD1*01 | 215 | tgcgccagc | | caccaagcg | gggggc | t | acactgaagcttcttt | 1911 | C A S H Q A G G Y T E A F F |
| 05.010 | TRBV05-1*01 | TRBJ2-5*01 | TRBD2*01 | 216 | tgcgccagca | a | actacgggggg | aac | ccaagagaccagtacttc | | 1912 | C A S K L A G G T Q E T Q Y F |
| 05.011 | TRBV05-1*01 | TRBJ1-1*01 | | 217 | tgcgccagca | | tggt ggga | g | acactgaagcttcttt | | 1913 | C A S M V G D T E A F F |
| 05.012 | TRBV05-5*01 | TRBJ2-1*01 | TRBD1*01 | 218 | tgcgccagca | acctt | ggc ctcaacc | cctacaatgagcagttcttc | | | 1914 | C A S N L G L N P Y N E Q F F |
| 05.013 | TRBV05-6*01 | TRBJ1-1*01 | TRBD1*01 | 219 | tgccagc | cctttg | gggacagg | ccctacc | atgagcagttcttc | | 1915 | C A S P F G D R P Y H E Q F F |
| 05.014 | TRBV05-4*01 | TRBJ2-1*01 | TRBD1*01 | 220 | tgtgccagcag | ggatg | aggg | ttgtgg | aatgagcagttcttc | | 1916 | C A S R D E G L W N E Q F F |
| 05.015 | TRBV05-1*01 | TRBJ2-1*01 | TRBD1*01 | 221 | tgcgccagc | | agggg | gaa tcctacaatgagcagttcttc | | | 1917 | C A S R G E S Y N E Q F F |

Figure 1-9

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 05.016 | TRBV05-4*01 | TRBJ2-7*01 | TRBD1*01 | 222 | tgtgccagcag | gatc | caggg | | ctacgagcagttcttc | 1918 | C A S R I Q G Y E Q Y F |
| 05.017 | TRBV05-1*01 | TRBJ2-1*01 | TRBD2*01 | 223 | tgcgcagcag | att | ggg | tgagagctcctacaatgagcagttcttc | | 1919 | C A S R L G E S S Y N E Q F F |
| 05.018 | TRBV05-6*01 | TRBJ2-1*01 | TRBD2*01 | 224 | tgtgccagcag | gcta | c gggact | tta | cctacaatgagcagttcttc | 1920 | C A S R L R D F T Y N E Q F F |
| 05.019 | TRBV05-8*01 | TRBJ2-1*01 | TRBD2*01 | 225 | tgtgccagcag | accc | ctagc | agagat | ctacaatgagcagttcttc | 1921 | C A S R P L A E I Y N E Q F F |
| 05.020 | TRBV05-5*03 | TRBJ2-3*01 | TRBD1*01 | 226 | tgtgccagcag | gcccctc | gacag | | acagatacgcagtattt | 1922 | C A S R P P P R Q T D T Q Y F |
| 05.021 | TRBV05-1*01 | TRBJ2-1*0 | TRBD2*01 | 227 | tgccgccagcag | acaa | gggacta | ct | aatgagcagttcttc | 1923 | C A S R Q G T T N E Q F F |
| 05.022 | TRBV05-1*01 | TRBJ2-3*01 | TRBD2*02 | 228 | tgcgcagcag | acg | gggga | cga | cacagatacgcagtatttt | 1924 | C A S R R R D D T D T Q Y F |
| 05.023 | TRBV05-6*01 | TRBJ2-7*01 | TRBD2*02 | 229 | tgtgccagcagc | gccgggggtt | tagcgggag | agggct | cgagcagtacttc | 1925 | C A S S A G G F S G R G L E Q Y F |
| 05.024 | TRBV05-1*01 | TRBJ2-3*01 | TRBD2*02 | 230 | tgccgccagcagc | gcctc | agcgggag | ttgaag | cagatacgcagtatttt | 1926 | C A S S A G V E A D T Q Y F |
| 05.025 | TRBV05-1*01 | TRBJ2-1*01 | TRBD1*01 | 231 | tgcgccagcagc | gcgt | caggggg | ctacaatgagcagttct | | 1927 | C A S S A G G Y N E Q F F |
| 05.026 | TRBV05-4*01 | TRBJ2-1*01 | TRBD2*02 | 232 | tgtgccagcagc | gaaaattcccct | ctagccggagg | taga | aatgagcagttcttc | 1928 | C A S S E N S P L A G G R N E Q F F |
| 05.027 | TRBV05-4*01 | TRBJ2-7*01 | TRBD2*01 | 233 | tgtgccagcagctt | c | gcggg | ctcc ag ctcctacgagcagtacttc | | 1929 | C A S S F A G S S Y E Q Y F |
| 05.028 | TRBV05-6*01 | TRBJ2-1*01 | TRBD1*01 | 234 | tgtgccagcagctt | t | gaca | aaaa ctcctacgcagttcttc | | 1930 | C A S S F D K N S Y E Q Y F |
| 05.029 | TRBV05-8*01 | TRBJ2-1*01 | TRBD2*02 | 235 | tgtgccagcagctt | tga | agcgggagg | ctcctacaatgagcagttcttc | | 1931 | C A S S F E A G G S Y N E Q F F |
| 05.030 | TRBV05-1*01 | TRBJ2-1*01 | TRBD1*01 | 236 | tgcgccagcagctt | ttt | caatgagcagttcttc | | | 1932 | C A S S F F N E Q F F |
| 05.031 | TRBV05-8*01 | TRBJ2-7*01 | TRBD2*01 | 237 | tgtgccagcagctt | tgggg | ctaggg | ctacgagcagtactc | | 1933 | C A S S F G A S G G Y E Q Y F |
| 05.032 | TRBV05-4*01 | TRBJ2-7*01 | TRBD2*01 | 238 | tgtgccagcagctt | cg gggaca | tcg g ctcctacgagcagtacttc | | | 1934 | C A S S F G D I G S Y E Q Y F |
| 05.033 | TRBV05-6*01 | TRBJ2-1*01 | TRBD1*01 | 239 | tgtgccagcagctt | tg gggacaggg | cca | acaatgagcagttcttc | | 1935 | C A S S F G D R A N N E Q F F |
| 05.034 | TRBV05-6*01 | TRBJ2-1*01 | TRBD1*01 | 240 | tgtgccagcagctt | tg gggacaggg | cctacaatgagcagttcttc | | | 1936 | C A S S F G D R A Y N E Q F F |
| 05.035 | TRBV05-6*01 | TRBJ2-1*01 | TRBD1*01 | 241 | tgtgccagcagctt | tg gggacaggg | cctact | atgagcagttcttc | | 1937 | C A S S F G D R A Y Y E Q F F |
| 05.036 | TRBV05-6*01 | TRBJ2-1*01 | TRBD1*01 | 242 | tgtgccagcagctt | tg gggacaggg | a | ctacaatgagcagttcttc | | 1938 | C A S S F G D R D Y N E Q F F |
| 05.037 | TRBV05-6*01 | TRBJ2-1*01 | TRBD1*01 | 243 | tgtgccagcagctt | t | ggggc agggcctacaatgagcagtc | cttc | | 1939 | C A S S F G G R A Y N E Q S F |
| 05.038 | TRBV05-1*02 | TRBJ1-2*01 | TRBD1*01 | 244 | tgccgccagc | agctt c gggacag | cgaccgaagg | ctatgctacacctc | | 1940 | C A S S F G T A T E G Y G Y T F |
| 05.039 | TRBV05-4*01 | TRBJ1-1*01 | TRBD1*01 | 245 | tgtgccagcagctt | t gggac | ggaaa | aagcttcttt | | 1941 | C A S S F G T E K A F F |
| 05.040 | TRBV05-5*03 | TRBJ2-7*01 | TRBD1*01 | 246 | tgtgccagcagc tt | c gggacagggg | cccttggg | gagcagtacttc | | 1942 | C A S S F G T G A L G E Q Y F |
| 05.041 | TRBV05-1*01 | TRBJ2-1*01 | TRBD2*01 | 247 | tgccgccagcagc | c | ctagccgg | ttta | tacaatgagcagttcttc | 1943 | C A S S F L A G L Y N E Q F F |
| 05.042 | TRBV05-4*01 | TRBJ2-1*01 | TRBD2*01 | 248 | tgtgccagcagctt | tct gggacta | aga | tacaatgagcagttcttc | | 1944 | C A S S F L G L R Y N E Q F F |
| 05.043 | TRBV05-6*01 | TRBJ2-5*01 | TRBD2*01 | 249 | tgtgccagcagctt | tttgggc | agcggg | gagaccagtacttc | | 1945 | C A S S F L G S G E T Q Y F |

Figure 1-10

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 05.044 | TRBV05-1*01 | TRBJ1-3*01 |  | 250 | tgtgccagcagctt.. | taa | ctctggaaacaccatatattt |  |  | 1946 | C A S S F N S G N T I Y F |
| 05.045 | TRBV05-4*01 | TRBJ2-7*01 | TRBD2*01 | 251 | tgtgccagcagctt.. | ccca ..ggact........ | ta | ....acgagcagtactc |  | 1947 | C A S S F P G L N E Q Y F |
| 05.046 | TRBV05-4*01 | TRBJ2-7*01 | TRBD1*01 | 252 | tgtgccagcagctt.. | c ccc gggacaggggc c | ......acgagcagtactc |  |  | 1948 | C A S S F P G T G G H E Q Y F |
| 05.047 | TRBV05-6*01 | TRBJ2-7*01 |  | 253 | tgtgccagcagctt.. | tccgaaccacct gag ctcctacgagcagtactc |  |  |  | 1949 | C A S S F P N H L S S Y E Q Y F |
| 05.048 | TRBV05-1*01 | TRBJ2-1*01 | TRBD1*01 | 254 | tgtgccagcagctt.. | tccc ...acagggggc aggg | ........atgaacagttcttc |  |  | 1950 | C A S S F P T G G R D E Q F F |
| 05.049 | TRBV05-5*01 | TRBJ2-5*01 | TRBD2*01 | 255 | tgtgccagcagctt.. | cc gggac............ | ggaac ..ccaagagaccagtactc |  |  | 1951 | C A S S F R D G T Q E T Q Y F |
| 05.050 | TRBV05-6*01 | TRBJ2-5*01 | TRBD1*01 | 256 | tgtgccagcagctt.. | cc gggacag..... | accga ..aagagaccagtactc |  |  | 1952 | C A S S F R D R P K E T Q Y F |
| 05.051 | TRBV05-1*01 | TRBJ2-7*01 | TRBD1*01 | 257 | tgtgccagcagctt.. | cc gggacag... | a ag ctcctacgagcagtactc |  |  | 1953 | C A S S F R D R S S Y E Q Y F |
| 05.052 | TRBV05-1*01 | TRBJ2-1*01 | TRBD1*01 | 258 | tgtgccagcagctt.. | cc gggaca........ | ...cctacaatgagcagttcttc |  |  | 1954 | C A S S F R D T Y N E Q F F |
| 05.053 | TRBV05-5*01 | TRBJ1-5*01 | TRBD2*01 | 259 | tgtgccagcagctt.. | .....caggggg tcgg | ...gcaatcagcccagcattt |  |  | 1955 | C A S S F R G S G N Q P Q H F |
| 05.054 | TRBV05-1*01 | TRBJ2-1*01 | TRBD1*01 | 260 | tgtgccagcagctt.. | cc ..gacta........ | .tcctacaatgagcagttcttc |  |  | 1956 | C A S S F R L S Y N E Q F F |
| 05.055 | TRBV05-4*01 | TRBJ2-1*01 | TRBD2*01 | 261 | tgtgccagcagctt.. | .......tagcgggg.... | ...cctacaatgagcagttcttc |  |  | 1957 | C A S S F S G A Y N E Q F F |
| 05.056 | TRBV05-1*01 | TRBJ1-1*01 | TRBD2*01 | 262 | tgtgccagcagctt.. | ......tagcgggg....... | .....tagcgggg........ cctacaatgagcg........... |  | gttcttc | 1958 | C A S S F S G A Y N E R F F |
| 05.057 | TRBV05-1*01 | TRBJ2-1*01 | TRBD1*01 | 263 | tgtgccagcagctt.. | ctca gggac....... | gtccgattt ...tacaatgagcagttcttc |  |  | 1959 | C A S S F S G T S D F Y N E Q F F |
| 05.058 | TRBV05-6*01 | TRBJ1-1*01 |  | 264 | tgtgccagcagctt.. | tagt ..aacactgaagctcttt |  |  |  | 1960 | C A S S F S N T E A F F |
| 05.059 | TRBV05-6*01 | TRBJ2-6*01 | TRBD1*01 | 265 | tgtgccagcagctt.. | ttcgcctgg gggacag..... | cctct ctctgggccaacgtcctgactc |  |  | 1961 | C A S S F S P G G Q P L S G A N V L T F |
| 05.060 | TRBV05-1*01 | TRBJ1-4*01 | TRBD1*01 | 266 | tgtgccagcagctt.. | c ..acaggggc g atgcg | ......gaaaaactgttt |  |  | 1962 | C A S S F T G G D A E K L F F |
| 05.061 | TRBV05-1*02 | TRBJ2-1*01 | TRBD1*01 | 267 | tgtgccagc....... | agcttgt ......gggg. aagc ..cctacaatgagcagttcttc |  |  |  | 1963 | C A S S F V G K P Y N E Q F F |
| 05.062 | TRBV05-4*01 | TRBJ2-7*01 | TRBD1*01 | 268 | tgtgccagcagc.. | gg gggacaggg. accgt ...ctacgagcagtactc |  |  |  | 1964 | C A S S G G Q G T V Y E Q Y F |
| 05.063 | TRBV05-4*01 | TRBJ1-1*01 | TRBD1*01 | 269 | tgtgccagcagc... | .........ggggc cgcactgaat........ | ctttt |  |  | 1965 | C A S S G G R T E S F F |
| 05.064 | TRBV05-1*01 | TRBJ2-7*01 | TRBD2*01 | 270 | tgtgccagcagc... | ..........ggggg ctcctacgagcagtactc |  |  |  | 1966 | C A S S G G S Y E Q Y F |
| 05.065 | TRBV05-1*01 | TRBJ2-3*01 | TRBD2*01 | 271 | tgtgccagcagc.. | gga ..actacgcggag.... | ....agatacgcagtattt |  |  | 1967 | C A S S G T S G R D T Q Y F |
| 05.066 | TRBV05-1*01 | TRBJ2-5*01 | TRBD1*01 | 272 | tgtgccagcagc.. | cacgggtccgac ..ggac..... | ca ..caagagaccagtactc |  |  | 1968 | C A S S H G S D G P Q E T Q Y F |
| 05.067 | TRBV05-1*01 | TRBJ1-2*01 | TRBD1*01 | 273 | tgtgccagcagc.. | cac gggacaggg.... | agcgg | ....tggctacacctc |  | 1969 | C A S S H G T G S G G Y T F |
| 05.068 | TRBV05-1*01 | TRBJ2-5*01 | TRBD2*02 | 274 | tgtgccagcag..... | tatcgggga..... tagcggga.... to ..gagaccagtactc |  |  |  | 1970 | C A S S I G G S G I E T Q Y F |
| 05.069 | TRBV05-4*01 | TRBJ2-5*01 | TRBD2*01 | 275 | tgtgccagcagcttgg..... | cgggggg gag ....gagaccagtactc |  |  |  | 1971 | C A S S L A G G E E T Q Y F |
| 05.070 | TRBV05-1*01 | TRBJ2-1*01 | TRBD2*01 | 276 | tgtgccagcagcttgg | ccg ......gcgg.... | a ..tacaatgagcagttcttc |  |  | 1972 | C A S S L A G G Y N E Q F F |
| 05.071 | TRBV05-1*01 | TRBJ1-1*01 | TRBD1*01 | 277 | tgtgccagcagcttgg | ...caggggc t ..acactgaagctcttt |  |  |  | 1973 | C A S S L A G G Y T E A F F |

Figure 1-11

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 05.072 | TRBV05-1*01 | TRBJ2-1*01 | TRBD2*02 | 278 | tgcgccagcagcttgg | ca | ggaggg tacgt | | tgagcagttcttc | 1974 | C A S S L A G G Y V E Q F F |
| 05.073 | TRBV05-6*01 | TRBJ2-2*01 | TRBD1*01 | 279 | tgtgccagcagctt. | ag | ...cagg... ttgatt | ..aacaccgggagctgttttt | | 1975 | C A S S L A G L I N T G E L F F |
| 05.074 | TRBV05-1*01 | TRBJ1-2*01 | TRBD1*01 | 280 | tgcgccagcagcttgg | ...cagg... | cagtg | ...actatgctacacccttc | | 1976 | C A S S L A G S D Y G Y T F |
| 05.075 | TRBV05-4*01 | TRBJ2-5*01 | TRBD2*02 | 281 | tgtgccagcagcttgg | ccat | gagg. t | accaagagaccccagtactc | | 1977 | C A S S L A M R Y Q E T Q Y F |
| 05.076 | TRBV05-4*01 | TRBJ2-7*01 | | 282 | tgcgccagcagctgg cc ccag | ..cctacgagcagtactc | | | | 1978 | C A S S L A P A Y E Q Y F |
| 05.077 | TRBV05-4*01 | TRBJ2-1*01 | TRBD2*02 | 283 | tgtgccagcagcttgg | ccc | ...cgggag... tgggg | ....aatgagcagttcttc | | 1979 | C A S S L A P G V G N E Q F F |
| 05.078 | TRBV05-1*02 | TRBJ2-1*01 | TRBD2*01 | 284 | tgcgccagc..... | agcttgcgagaggat ..ggactagcggg... cttttccttctcta.....aatgagcagttcttc | | | | 1980 | C A S S L A R G W T S G L F P S L N E Q F F |
| 05.079 | TRBV05-6*01 | TRBJ2-5*01 | TRBD2*01 | 285 | tgtgccagcagctt. | ag | ...ctagcgggg..... | aagagaccccagtactc | | 1981 | C A S S L A S G E E T Q Y F |
| 05.080 | TRBV05-1*01 | TRBJ2-7*01 | TRBD2*01 | 286 | tgcgccagcagcttgg | cgac | gga. | | ...ctacgagcagtactc | 1982 | C A S S L A T D Y E Q Y F |
| 05.081 | TRBV05-1*01 | TRBJ2-7*01 | TRBD1*01 | 287 | tgcgccagcagcttgg | c ..gacagg... | a | .tcctacgagcagtactc | | 1983 | C A S S L A T G S Y E Q Y F |
| 05.082 | TRBV05-4*01 | TRBJ2-3*01 | TRBD2*02 | 288 | tgtgccagcagcttgg | ccgt | ...cgggag... cg | ...cagatacgcagtatttt | | 1984 | C A S S L A V G S A D T Q Y F |
| 05.083 | TRBV05-1*02 | TRBJ2-1*01 | TRBD1*01 | 289 | tgcccagc..... | agcttagcgta cc gggacaggg... tagccctact ...tacaatgagcagttcttc | | | | 1985 | C A S S L A Y R D R V A L T Y N E Q F F |
| 05.084 | TRBV05-1*01 | TRBJ1-2*01 | TRBD2*01 | 290 | tgtgccagcagc ttggcttacgtta ..acta..... tggctact | | | | ...ccttc | 1986 | C A S S L A Y V N Y G Y S F |
| 05.085 | TRBV05-5*03 | TRBJ1-2*01 | | 291 | tgtgccagcagc ttggcttact taaclatgctacacctc | | | | | 1987 | C A S S L A Y V N Y G Y T F |
| 05.086 | TRBV05-1*01 | TRBJ2-4*01 | | 292 | tgcgccagcagcttgg atgatag | ........cattcagtactc | | | | 1988 | C A S S L D D S I Q Y F |
| 05.087 | TRBV05-1*01 | TRBJ2-3*01 | | 293 | tgcgccagcagcttgg atttggaataaccg | ...cagatacgcagtatttt | | | | 1989 | C A S S L D F G I T A D T Q Y F |
| 05.088 | TRBV05-1*02 | TRBJ2-7*01 | TRBD2*01 | 294 | tgcgccagc..... | agcttgg atggc ggac... | | ....cctacgagcagtactc | | 1990 | C A S S L D G G P Y E Q Y F |
| 05.089 | TRBV05-4*01 | TRBJ1-5*01 | TRBD1*01 | 295 | tgtgccagcagc... | ct ..ggac.... | ggaaa | ...caatcagcccagcattt | | 1991 | C A S S L D G N N Q P Q H F |
| 05.090 | TRBV05-1*01 | TRBJ2-6*01 | | 296 | tgtgccagcagcttgg acaaa ctctgggggccaacgtcctgacttc | | | | | 1992 | C A S S L D N S G A N V L T F |
| 05.091 | TRBV05-5*01 | TRBJ2-3*01 | TRBD1*01 | 297 | tgtgccagcagcttgg | ..acaggg... | cctgggaa | ........acgcagtatttt | | 1993 | C A S S L D R A W E T Q Y F |
| 05.092 | TRBV05-5*03 | TRBJ2-5*01 | TRBD1*01 | 298 | tgtgccagcagc tt ggacaggggg | .....gagaccccagtactc | | | | 1994 | C A S S L D R G E T Q Y F |
| 05.093 | TRBV05-1*02 | TRBJ2-1*01 | TRBD2*01 | 299 | tgccagc..... | agctt .ggact..... | cctg | ...caatgagcagttcttc | | 1995 | C A S S L D S C N E Q F F |
| 05.094 | TRBV05-1*02 | TRBJ2-1*01 | | 300 | tgcgccagc..... | agcttgga ctcctacaatgagcagttcttc | | | | 1996 | C A S S L D S Y N E Q F F |
| 05.095 | TRBV05-5*03 | TRBJ2-5*01 | TRBD1*01 | 301 | tgtgccagcagc ttggaagctgg c gggacaggg... t accaagagaccccagtactc | | | | | 1997 | C A S S L E A G G T G Y Q E T Q Y F |
| 05.096 | TRBV05-4*01 | TRBJ2-3*01 | TRBD1*01 | 302 | tgtgccagcagcttgg | ...agggggc aggttga | .....atacgcagtatttt | | | 1998 | C A S S L E G A G L N T Q Y F |
| 05.097 | TRBV05-1*01 | TRBJ1-1*01 | TRBD2*01 | 303 | tgtgccagcagctgg agggac | ...cgggggg..... | acactgaagcttcttt | | | 1999 | C A S S L E G P G D T E A F F |
| 05.098 | TRBV05-1*01 | TRBJ2-5*01 | TRBD2*01 | 304 | tgcgccagcagcttgg aa ..gga | ........caagagaccccagtactc | | | | 2000 | C A S S L E G Q E T Q Y F |
| 05.099 | TRBV05-6*01 | TRBJ2-1*01 | TRBD2*02 | 305 | tgtgccagcagcttgg agggc ..agcggaggg cc tatcga | .......gagcagttcttc | | | | 2001 | C A S S L E G S G R A Y R E Q F F |

Figure 1-12

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 05.100 | TRBV05-5*03 | TRBJ2-3*01 | TRBD2*02 | 306 | tgtgccagcagc tt | | ggag. tctgcctg | ..acagatacgcagtattt | | 2002 | C A S S L E S A L T D T Q Y F |
| 05.101 | TRBV05-1*01 | TRBJ2-7*01 | TRBD1*01 | 307 | tgcgccagcagcttg agtc | | ....cagg...... | acgagcagtactc | | 2003 | C A S S L E S R D E Q Y F |
| 05.102 | TRBV05-6*01 | TRBJ2-7*01 | TRBD2*02 | 308 | tgtgccagcagcttg. tt ...tagcgggag.. | | | t ....tacgagcagtactc | | 2004 | C A S S L F S G S Y E Q Y F |
| 05.103 | TRBV05-6*01 | TRBJ2-1*01 | TRBD2*02 | 309 | tgtgccagcagcttg. tttgt | | ....gcggaggg g | tcctacaatgagcagttcttc | | 2005 | C A S S L F V R E G S Y N E Q F F |
| 05.104 | TRBV05-1*01 | TRBJ2-7*01 | TRBD2*02 | 310 | tgcgccagcagcttgg ggg.... | | gcggaggg cc ttttgg | ...ctacgagcagtactc | | 2006 | C A S S L G A G G P F G Y E Q Y F |
| 05.105 | TRBV05-1*01 | TRBJ2-1*01 | TRBD2*02 | 311 | tgcgccagcagcttgg g | | ...agcggga.. atccaaaaggg | ...tacaatgagcagttcttc | | 2007 | C A S S L G A G I Q K G Y N E Q F F |
| 05.106 | TRBV05-1*01 | TRBJ2-3*01 | TRBD2*02 | 312 | tgcgccagcagcttgg gtga | | .....cggag.. ctc | ..cacagatacgcagtattt | | 2008 | C A S S L G D G S S T D T Q Y F |
| 05.107 | TRBV05-5*01 | TRBJ2-5*01 | TRBD1*01 | 313 | tgtgccagcagcttgg gggacagggggc tggg | | | ...agagaccagtactc | | 2009 | C A S S L G D R G L G E T Q Y F |
| 05.108 | TRBV05-1*02 | TRBJ2-1*01 | TRBD1*01 | 314 | tg........ | tgccagcagcttgg gggacaggg.. | acaactatgatg | | ............agttcttc | 2010 | C A S S L G D R D N Y D E F F |
| 05.109 | TRBV05-4*01 | TRBJ2-2*01 | TRBD2*02 | 315 | tgcgccagcagcttgg ggggg ......clagcgggag.. tt | | | ......cgggagctgttttt | | 2011 | C A S S L G G P S G S S G E L F F |
| 05.110 | TRBV05-4*01 | TRBJ1-1*01 | TRBD1*01 | 316 | tgtgccagcagcttgg g ....gggacaggg.. | | ac | tgaacactgaagcttcttt | | 2012 | C A S S L G G Q G L N T E A F F |
| 05.111 | TRBV05-1*01 | TRBJ2-1*01 | | 317 | tgcgccagcagcttgg gtatcggtg g ctcctacaatgagcagttcttc | | | | | 2013 | C A S S L G I G G S Y N E Q F F |
| 05.112 | TRBV05-1*01 | TRBJ2-2*01 | TRBD2*01 | 318 | tgcgccagcagcttgg | | .........ggc ctgattggc | ..acaccggggagctgtttt | | 2014 | C A S S L G P D W H T G E L F |
| 05.113 | TRBV05-1*01 | TRBJ2-1*01 | TRBD1*01 | 319 | tgcgccagcagcttgg gacc ......ggac.. cgtgggt | | | .....caatgagcagttcttc | | 2015 | C A S S L G P D R G V N E Q F F |
| 05.114 | TRBV05-1*01 | TRBJ1-2*01 | TRBD2*01 | 320 | tgcgccagcagcttgg gacc ..gaca..... | | ctcc | ....atgctacacctc | | 2016 | C A S S L G P T L H G Y T F |
| 05.115 | TRBV05-5*03 | TRBJ1-3*01 | TRBD1*01 | 321 | tgtgccagcagc tta ggacaggg.. ctctggaaacaccatatattt | | | | | 2017 | C A S S L G Q G S G N T I Y F |
| 05.116 | TRBV05-6*01 | TRBJ1-4*01 | TRBD1*01 | 322 | tgtgccagcagcttgg g ....cagggg.. ctac ........gaaaaactgtttt | | | | | 2018 | C A S S L G R G Y E K L F F |
| 05.117 | TRBV05-6*01 | TRBJ2-3*01 | TRBD2*01 | 323 | tgtgccagcagcttgg ggc ..gacta. | | ......tcaactggcg | ...cagatacgcagtattt | | 2019 | C A S S L G R L S H G A D T Q Y F |
| 05.118 | TRBV05-1*01 | TRBJ1-3*01 | TRBD1*01 | 324 | tgcgccagcagcttgg ga ......agcg..... | | ctt ctctggaaacaccatatattt | | | 2020 | C A S S L G S A F S G N T I Y F |
| 05.119 | TRBV05-5*01 | TRBJ1-1*01 | TRBD1*01 | 325 | tgtgccagcagcttgg ggt | | ....cagggg. gttttgt | .....actgaagcttcttt | | 2021 | C A S S L G S G G F G T E A F F |
| 05.120 | TRBV05-1*01 | TRBJ2-6*01 | TRBD1*01 | 326 | tgtgccagcagcttgg gtt | | ...cagggg. gaatccaag ctctgggggccaacgtcctgacttc | | | 2022 | C A S S L G S G G N P S S G A N V L T F |
| 05.121 | TRBV05-1*01 | TRBJ1-1*01 | TRBD1*01 | 327 | tgcgccagcagcttgg gatcgg | | .....ggggc ctt | ..acactgaagcttcttt | | 2023 | C A S S L G S G G P Y T E A F F |
| 05.122 | TRBV05-2*01 | TRBJ2-2*01 | TRBD1*01 | 328 | tgtgccagcagcttgg gttcc | | ......cgg..... ccacgctt. gaacaccggggagctgtttt | | | 2024 | C A S S L G S R P R L N T G E L F F |
| 05.123 | TRBV05-6*01 | TRBJ1-1*01 | TRBD1*01 | 329 | tgtgccagcagcttgg | | ggacaggggc ttgt | ..acactgaagcttcttt | | 2025 | C A S S L G T G G L Y T E A F F |
| 05.124 | TRBV05-1*02 | TRBJ1-2*01 | TRBD1*01 | 330 | tgggccagc...... agcttg gggacaggg.. | | ....ctatgctacacctc | | | 2026 | C A S S L G T G G Y G Y T F |
| 05.125 | TRBV05-1*01 | TRBJ2-3*01 | TRBD1*01 | 331 | tgcgccagcagc... ctc gggacaggg.. aggg | | | ....cagatacgcagtattt | | 2027 | C A S S L G T G R A D T Q Y F |
| 05.126 | TRBV05-1*01 | TRBJ2-1*01 | TRBD2*02 | 332 | tgcgccagcagcttgg gtacagg ....cggga.. | | cg | ....atgagcagttcttc | | 2028 | C A S S L G T G R D D E Q F F |
| 05.127 | TRBV05-1*01 | TRBJ1-1*01 | TRBD2*01 | 333 | tgcgccagcagcttgg ggaccaccga | | ..actagacgggg...... | ...........agttcttc | | 2029 | C A S S L G T T E L A G E F F |

Figure 1-13

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 05.128 | TRBV05-6*01 | TRBJ2-7*01 | TRBD2*01 | 334 | tgtgccagcagc.... | ctt | gggac........... | gtggaa ...ctacgagcagtacttc | | 2030 | C A S S L G T W N Y E Q Y F |
| 05.129 | TRBV05-6*01 | TRBJ2-7*01 | TRBD2*02 | 335 | tgtgccagcagcttgg | ggg | ...tagcggagg. | tttga | .....acgagcagtacttc | 2031 | C A S S L G V A G G L N E Q Y F |
| 05.130 | TRBV05-6*01 | TRBJ2-5*01 | TRBD1*01 | 336 | tgtgccagcagcttgg | gtgttt | ...cagg.. | ttga | ....agacccagtacttc | 2032 | C A S S L G V S G L K T Q Y F |
| 05.131 | TRBV05-4*01 | TRBJ2-7*01 | TRBD2*02 | 337 | tgtgccagcagctt.. | aggcgt | ....tacgggag. | | ......cgagcagtacttc | 2033 | C A S S L G V S G S E Q Y F |
| 05.132 | TRBV05-6*01 | TRBJ1-1*01 | | 338 | tgtgccagcagcttgg | gtgtgagtt | ...acactgaagcttcttt | | | 2034 | C A S S L G V S Y T E A F F |
| 05.133 | TRBV05-1*02 | TRBJ2-1*01 | TRBD2*02 | 339 | tgtgccagc........ | agcttgggtg | .......gcgggag.. | acttacgatgagcac .......tcttc | | 2035 | C A S S L G W R E T Y D E H F F |
| 05.134 | TRBV05-1*02 | TRBJ2-1*01 | TRBD2*02 | 340 | tgcgccagc....... | agcttgggtg | .......gcgggag.. | acttacg | .......atgagcagttcttc | 2036 | C A S S L G W R E T Y D E Q F F |
| 05.135 | TRBV05-1*01 | TRBJ2-1*01 | TRBD2*02 | 341 | tgcgccagc........ | agcttgggtg | .......gcgggag.. | gcc.act... | tacaatgagcagttcttc | 2037 | C A S S L G W R E T Y N E Q F F |
| 05.136 | TRBV05-5*03 | TRBJ1-1*01 | TRBD1*01 | 342 | tgtgccagcagc | ctcattccgt | ......gggag. | taacgagtatc | .......atgagcagttcttc | 2038 | C A S S L I P V G V T S Y H E Q F F |
| 05.137 | TRBV05-5*03 | TRBJ1-2*01 | TRBD1*01 | 343 | tgtgccagcagc | ttgttag | ...caggggtg | a ..aactatgctacacctc | | 2039 | C A S S L L A G G N Y G Y T F |
| 05.138 | TRBV05-1*01 | TRBJ1-1*01 | TRBD1*01 | 344 | tgtgccagcagcttgg | ttg | .......ggggc | ttggg ....cactgaagcttcttt | | 2040 | C A S S L L G G L G T E A F F |
| 05.139 | TRBV05-5*03 | TRBJ2-1*01 | TRBD2*02 | 345 | tgcgccagcagc.... | ctcttg | .........gggag.. | cgccaaa.... | tacaatgagcagttcttc | 2041 | C A S S L L G S A K Y N E Q F F |
| 05.140 | TRBV05-1*02 | TRBJ2-3*01 | TRBD2*02 | 346 | tgcgccagc........ | agcctcttgaa | ......ggag.. | aagg | ....cagatacgcagtattt | 2042 | C A S S L L K E K A D T Q Y F |
| 05.141 | TRBV05-1*01 | TRBJ2-3*01 | TRBD2*02 | 347 | tgcgccagcagctg.. | tta | ....cgggag.. | catca | .....agatacgcagtattt | 2043 | C A S S L L R E H Q D T Q Y F |
| 05.142 | TRBV05-1*01 | TRBJ2-3*01 | TRBD2*02 | 348 | tgcgccagcagcttg. | tta | ....cgggag.. | catcg | ....agatacgcagtattt | 2044 | C A S S L L R E H R D T Q Y F |
| 05.143 | TRBV05-1*01 | TRBJ2-3*01 | TRBD2*02 | 349 | tgcgccagcagc.... | ctctt | .........gaggg | agaagg | ...cagatacgcagtattt | 2045 | C A S S L L R E K A D T Q Y F |
| 05.144 | TRBV05-1*01 | TRBJ2-3*01 | TRBD2*02 | 350 | tgcgccagcagcttg. | tt | .......gcggga.. | a | agcacagatacgcagtattt | 2046 | C A S S L L R E S T D T Q Y F |
| 05.145 | TRBV05-5*01 | TRBJ2-5*01 | TRBD2*02 | 351 | tgtgccagcagcttg. | ctat | .......cggagg | ggg | ....gagaccagtacttc | 2047 | C A S S L L S G G G E T Q Y F |
| 05.146 | TRBV05-6*01 | TRBJ1-2*01 | TRBD1*01 | 352 | tgtgccagcagc.... | ctgatcg | .......aggg.. | tag | ....ctatgctacacctc | 2048 | C A S S L M E G S Y G Y T F |
| 05.147 | TRBV05-1*01 | TRBJ2-1*01 | TRBD1*01 | 353 | tgcgccagcagcttg. | aatgc | ..actacgcg | tg | .....aatgagcagttcttc | 2049 | C A S S L N A L A V N E Q F F |
| 05.148 | TRBV05-6*01 | TRBJ2-5*01 | | 354 | tgtgccagcagcttg. | aatgaagg | ...aagagaccagtacttc | | | 2050 | C A S S L N E E E T Q Y F |
| 05.149 | TRBV05-6*01 | TRBJ2-3*01 | TRBD2*01 | 355 | tgtgccagcagcttg. | cg | ......agcgggg.. | tgggaagaaga | ..cacagatacgcagtattt | 2051 | C A S S L R A G W E E D T D T Q Y F |
| 05.150 | TRBV05-5*03 | TRBJ2-7*01 | TRBD2*02 | 356 | tgtgccagcagc | ttacgg | .....gcgggaggg | c tag | ....acgagcagtacttc | 2052 | C A S S L R A G G L D E Q Y F |
| 05.151 | TRBV05-1*01 | TRBJ1-1*01 | TRBD1*01 | 357 | tgcgccagcagcttg. | cgattat | ..acag.... | ccat | ..aacactgaagcttcttt | 2053 | C A S S L R L Y S H N T E A F F |
| 05.152 | TRBV05-6*01 | TRBJ2-7*01 | TRBD1*01 | 358 | tgtgccagcagc.... | ctac | ..gacag..... | tcccc | ....cgagcagtacttc | 2054 | C A S S L R Q S P E Q Y F |
| 05.153 | TRBV05-6*01 | TRBJ2-1*01 | TRBD1*01 | 359 | tgtgccagcagcttg. | cg | ....cagg..... | | ....gagcagttcttc | 2055 | C A S S L R R E Q F F |
| 05.154 | TRBV05-1*01 | TRBJ2-1*01 | TRBD1*01 | 360 | tgcgccagcagcttg. | t | ....caggggg | | ...ctacaatgagcagttcttc | 2056 | C A S S L S G G Y N E Q F F |
| 05.155 | TRBV05-4*01 | TRBJ2-1*01 | TRBD2*02 | 361 | tgtgccagcagctt.. | at c | gggactagcgggag.. | ttcg... | ...tgagcagttcttc | 2057 | C A S S L S G L A G V R E Q F F |

Figure 1-14

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 05.156 | TRBV05-1*01 | TRBJ2-7*01 | TRBD1*01 | 362 | tgcgccagcagcttg | tc | gggc aggaagcta | tcctacgagcagtactc | | 2058 | C A S S L S G R K V S Y E Q Y F |
| 05.157 | TRBV05-6*01 | TRBJ1-1*01 | TRBD1*01 | 363 | tgtgccagcagcttt | aag | caggggc | g | agcttcttt | 2059 | C A S S L S R G R A F F |
| 05.158 | TRBV05-1*01 | TRBJ2-5*01 | TRBD2*01 | 364 | tgcgccagcagcttg | tcg | agcg | atatctc | ccaagagaccagtactc | 2060 | C A S S S D I S Q E T Q Y F |
| 05.159 | TRBV05-5*03 | TRBJ2-7*01 | | 365 | tgtgccagcagc | ttaactg | cctacgagcagtactc | | | 2061 | C A S S L T A Y E Q Y F |
| 05.160 | TRBV05-1*01 | TRBJ2-1*01 | TRBD2*01 | 366 | tgcgccagcagc | ac | cgggg | ctcctacaatgagcagttctc | | 2062 | C A S S L T G G S Y N E Q F F |
| 05.161 | TRBV05-6*01 | TRBJ2-1*01 | TRBD1*01 | 367 | tgtgccagcagcttgg | t | ggggg | aaagg | gagcagttctc | 2063 | C A S S L V G E R E Q F F |
| 05.162 | TRBV05-1*02 | TRBJ2-5*01 | TRBD2*02 | 368 | tgcgccagc | agcttgttg | gcgggag | attc | gagaccagtactc | 2064 | C A S S L V G G R F E T Q Y F |
| 05.163 | TRBV05-1*01 | TRBJ2-5*01 | TRBD2*01 | 369 | tgtgccagcagcttgg | tg | ggga | tc | gagaccagtactc | 2065 | C A S S L V G I E T Q Y F |
| 05.164 | TRBV05-8*01 | TRBJ2-1*01 | | 370 | tgtgccagcagctgg | tact | tgagcagttctc | | | 2066 | C A S S L V L E Q F F |
| 05.165 | TRBV05-5*01 | TRBJ2-5*01 | TRBD1*01 | 371 | tgcgccagcagcttc | t | gggac | gcggtg | aagagaccagtactc | 2067 | C A S S L W D G G E E T Q Y F |
| 05.166 | TRBV05-1*01 | TRBJ2-5*01 | TRBD1*01 | 372 | tgcgccagc | agcttgt | ggac | ccgtatt | accaagagaccagtactc | 2068 | C A S S L W T R I Y Q E T Q Y F |
| 05.167 | TRBV05-1*01 | TRBJ2-1*01 | TRBD2*01 | 373 | tgcgccagcagcttg | tatttggggttgag | gggac | | atgagcagttctc | 2069 | C A S S L Y L G V R G H E Q F F |
| 05.168 | TRBV05-1*01 | TRBJ2-1*01 | TRBD2*02 | 374 | tgtgccagcagcttg | tatcttt | gag | ctcctacaat | gagcagttctc | 2070 | C A S S L Y P L S S Y N E Q F F |
| 05.169 | TRBV05-6*01 | TRBJ2-5*01 | TRBD1*01 | 375 | tgtgccagcagc | atgtttgt | ggggc | t | gagaccagtactc | 2071 | C A S S M F L V G A E T Q Y F |
| 05.170 | TRBV05-1*01 | TRBJ1-1*01 | TRBD2*01 | 376 | tgcgccagcag | taat | gact | t | cactgaagcttctt | 2072 | C A S S N D F T E A F F |
| 05.171 | TRBV05-1*01 | TRBJ2-7*01 | TRBD2*01 | 377 | tgcgccagcagc | c | ogg | ccga | ctacgagcagtactc | 2073 | C A S S P A D Y E Q Y F |
| 05.172 | TRBV05-8*01 | TRBJ2-7*01 | TRBD2*01 | 378 | tgcgccagcagc | cccg | c gggactagcgg | a | ctacgagcagtactc | 2074 | C A S S P A G L A D Y E Q Y F |
| 05.173 | TRBV05-4*01 | TRBJ2-1*01 | TRBD2*01 | 379 | tgtgccagcagc | cccgagcgcca | gggac | g | atgagcagttctc | 2075 | C A S S P D A R D D E Q F F |
| 05.174 | TRBV05-1*01 | TRBJ1-1*01 | | 380 | tgtgccagcagc | cctttac | aacactgaagcttctt | | | 2076 | C A S S P F Y N T E A F F |
| 05.175 | TRBV05-5*01 | TRBJ2-1*01 | TRBD1*01 | 381 | tgtgccagcagc | ccc | ggacagg | tctggt | caatgagcagttctc | 2077 | C A S S P G Q G L V N E Q F F |
| 05.176 | TRBV05-1*01 | TRBJ2-2*01 | TRBD2*02 | 382 | tgcgccagcagc | cccgga | ccgga | gaacaccgggagctgttttt | | 2078 | C A S S P G R E N T G E L F F |
| 05.177 | TRBV05-1*02 | TRBJ2-7*01 | TRBD1*01 | 383 | tgcgccagc | agccct | gggacagggg | tagc | ggagcagtactc | 2079 | C A S S P G T G V A E Q Y F |
| 05.178 | TRBV05-6*01 | TRBJ2-7*01 | TRBD2*01 | 384 | tgtgccagcagc | ccaggt | ggggg | cctacgagcagtactc | | 2080 | C A S S P G W G A Y E Q Y F |
| 05.179 | TRBV05-8*01 | TRBJ2-1*01 | TRBD1*01 | 385 | tgtgccagcagc | ccgtagt | aggggg | aa | cctacaatgagcagttctc | 2081 | C A S S P L V G G T Y N E Q F F |
| 05.180 | TRBV05-6*01 | TRBJ2-2*01 | TRBD1*01 | 386 | tgtgccagcagc | ccccc | gacaggg | aggg | ccgggagctgttttt | 2082 | C A S S P P T G R A G E L F F |
| 05.181 | TRBV05-1*01 | TRBD2*01 | TRBD2*01 | 387 | tgcgccagcag | tc | ctagcggggg | t | tacaatgagcagttctc | 2083 | C A S S P S G G Y N E Q F F |
| 05.182 | TRBV05-1*02 | TRBJ2-5*01 | TRBD1*01 | 388 | tgtgccagc | agcccgtctccctac | cagg | gagaccagtactc | | 2084 | C A S S P V S P T R E T Q Y F |
| 05.183 | TRBV05-4*01 | TRBJ2-2*01 | TRBD2*01 | 389 | tgtgccagcagc | ccttggg | gcggggg | cgag | ccggggagctgttttt | 2085 | C A S S P W G G G R A G E L F F |

Figure 1-15

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 05.184 | TRBV05-1*01 | TRBJ2-1*01 | TRBD2*02 | 390 | tgtgccagcagc.... | ccgt. | ggactagcgggaggg | ccgg | ......gttcttc | 2086 | C A S S P W T S G R A G F F |
| 05.185 | TRBV05-4*01 | TRBJ2-1*01 | TRBD1*01 | 391 | tgtgccagcagc.. | ca gggaca..... | cc g ctcctacaatgagcagttcttc | | | 2087 | C A S S Q G H R S Y N E Q F F |
| 05.186 | TRBV05-5*01 | TRBJ2-1*01 | TRBD2*01 | 392 | tgtgccagcagc.... | ca gggactagcggg... | cc ...cctacaatgagcagttcttc | | | 2088 | C A S S Q G L A G P Y N E Q F F |
| 05.187 | TRBV05-5*03 | TRBJ2-3*01 | TRBD1*01 | 393 | tgtgccagcagc cgcat | .....aggggg. | tt ...cagatacgcagtattt | | | 2089 | C A S S R I G G S D T Q Y F |
| 05.188 | TRBV05-1*01 | TRBJ2-7*01 | TRBD2*02 | 394 | tgtgccagcagc.... | cgaataccactaaca | .....agcgggaggg cc gattgg | .......gagcagtactc | | 2090 | C A S S R I P L T S G R A D W E Q Y F |
| 05.189 | TRBV05-1*01 | TRBJ1-1*01 | TRBD1*01 | 395 | tgtgccagcagc..... | ccpaat gggacaggg... | acg .....actgaagcttctc | | | 2091 | C A S S R M G Q G R T E A F F |
| 05.190 | TRBV05-1*01 | TRBJ2-1*01 | TRBD2*02 | 396 | tgtgccagcagc.... | a ....... | ggaggg gtcgccgaccgt | .....aatgagcagttcttc | | 2092 | C A S S R R G A D R N E Q F F |
| 05.191 | TRBV05-1*01 | TRBJ2-1*01 | TRBD2*02 | 397 | tgtgccagcagct... | c ........ | agcgggagg... | .ctacaatgagcagttcttc | | 2093 | C A S S A G G Y N E Q F F |
| 05.192 | TRBV05-6*01 | TRBJ2-6*01 | TRBD2*02 | 398 | tgtgccagcagct... | cc .......... | gaggg cc t ctctgggggccaaacgtcctgactctc | | | 2094 | C A S S E G L S G A N V L T F |
| 05.193 | TRBV05-1*01 | TRBJ2-7*01 | TRBD1*01 | 399 | tgtgccagcagct... | c gggacaggg... | ta ...cctacgagcagtactc | | | 2095 | C A S S G Q G T Y E Q Y F |
| 05.194 | TRBV05-6*01 | TRBJ2-3*01 | TRBD1*01 | 400 | tgtgccagcagct... | ca gggacag.... | acttc ..cacagatacgcagtattt | | | 2096 | C A S S G T D F S T D T Q Y F |
| 05.195 | TRBV05-6*01 | TRBJ2-1*01 | TRBD2*02 | 401 | tgtgccagcagct... | cta ...tagcgggag. | cttgg ......caatgagcagttcttc | | | 2097 | C A S S I A G A G N E Q F F |
| 05.196 | TRBV05-5*01 | TRBJ2-5*01 | | 402 | tgtgccagcagct..... | ccatatcc ...gagaccagtactc | | | | 2098 | C A S S I S E T Q Y F |
| 05.197 | TRBV05-4*01 | TRBJ2-3*01 | | 403 | tgtgccagcag..... | ttctatgtctcgcgcc ct agcacagatacgcagtattt | | | | 2099 | C A S S I V S R P S T D T Q Y F |
| 05.198 | TRBV05-2*01 | TRBJ2-2*01 | TRBD1*01 | 404 | tgtgccagcagct.... | ccctg ...ctagcgggg... | atag ..acaccgggagctgttttt | | | 2100 | C A S S L L A G I D T G E L F F |
| 05.199 | TRBV05-4*01 | TRBJ2-7*01 | TRBD1*01 | 405 | tgtgccagcagct... | cccca ..ggacaggga... | a ...cctacgagcagtactc | | | 2101 | C A S S P G Q G T Y E Q Y F |
| 05.200 | TRBV05-4*01 | TRBJ2-1*01 | TRBD2*01 | 406 | tgtgccagcagct... | cccccc ...ctag...... | t ......aatgagcagttcttc | | | 2102 | C A S S P P P S N E Q F F |
| 05.201 | TRBV05-4*01 | TRBJ2-7*01 | TRBD2*02 | 407 | tgtgccagcagct... | cccc ..gactagcgga... | c ctcctacgagcagtactc | | | 2103 | C A S S P T S G T S Y E Q Y F |
| 05.202 | TRBV05-6*01 | TRBJ2-7*01 | TRBD2*02 | 408 | tgtgccagcag..... | ttctc ......agcgggaggg cc t ...ctacgagcagtactc | | | | 2104 | C A S S Q R E G L Y E Q Y F |
| 05.203 | TRBV05-4*01 | TRBJ2-7*01 | TRBD2*01 | 409 | tgtgccagcagct..... | ctagcg... | agg ..cctacgagcagtactc | | | 2105 | C A S S S E A Y E Q Y F |
| 05.204 | TRBV05-1*01 | TRBJ2-1*01 | TRBD2*01 | 410 | tgtgccagcagct.... | .....ctagcgggg... | .ctacaatgagcagttcttc | | | 2106 | C A S S S G A Y N E Q F F |
| 05.205 | TRBV05-6*01 | TRBJ1-1*01 | TRBD1*01 | 411 | tgtgccagcagct.... | cctcaaaaa gga....... | tat tgaacactgaagcttctt | | | 2107 | C A S S S K R I L N T E A F F |
| 05.206 | TRBV05-1*01 | TRBJ2-3*01 | TRBD2*02 | 412 | tgtgccagcagct.. | c ..gactacgga... | to ....cagatacgcagtatttt | | | 2108 | C A S S S P D T Q Y F |
| 05.207 | TRBV05-6*01 | TRBJ2-1*01 | TRBD2*01 | 413 | tgtgccagcagct.. | c ..gactacg... | tgag ctcctacaatgagcagttcttc | | | 2109 | C A S S T S V S S Y N E Q F F |
| 05.208 | TRBV05-8*01 | TRBJ2-5*01 | TRBD1*01 | 414 | tgtgccagcagc.... | acga .ggac..... | ggag ....gagaccagtactc | | | 2110 | C A S S T R T E E T Q Y F |
| 05.209 | TRBV05-1*01 | TRBJ2-1*01 | TRBD2*01 | 415 | tgtgccagcag..... | tactc ...... | ccgggg ....cctacaatgagcagttcttc | | | 2111 | C A S S T S G A Y N E Q F F |
| 05.210 | TRBV05-1*01 | TRBJ2-2*01 | TRBD2*02 | 416 | tgtgccagcag..... | ac ..gactagcgggag... | gaacaccgggagctgttttt | | | 2112 | C A S S T T S G R N T G E L F F |
| 05.211 | TRBV05-1*01 | TRBJ2-3*01 | TRBD2*02 | 417 | tgtgccagcagc..... | gtc ....gccggga... | tc ..cacagatacgcagtatttt | | | 2113 | C A S S V A G S T D T Q Y F |

Figure 1-16

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 05.212 | TRBV05-1*01 | TRBJ2-7*01 | TRBD2*01 | 418 | tgcgccagcagc... | gt | ...cgt...... | tgag | ......gagcagtactlc | 2114 | C A S S V G E E Q Y F |
| 05.213 | TRBV05-1*01 | TRBJ1-2*01 | TRBD1*01 | 419 | tgcgccagcagct... | ggg | cc gggacaggggg. | ...clatggctacacctlc | 2115 | C A S S W A G T G G Y G Y T F |
| 05.214 | TRBV05-1*01 | TRBJ2-1*01 | TRBD1*01 | 420 | tgcgccagcagct... | gggacagg... | tct | .......atgagcagttcttc | 2116 | C A S S W D R V Y E Q F F |
| 05.215 | TRBV05-1*01 | TRBJ2-5*01 | TRBD2*01 | 421 | tgcgccagcagt... | ........ggggggg | ggcctactcatc. | ccaagagaccagtactlc | 2117 | C A S S W G G A Y S S Q E T Q Y F |
| 05.216 | TRBV05-1*01 | TRBJ2-1*01 | TRBD2*01 | 422 | tgcgccagcagct... | ....... | ggggggg gcgggaaact. | ..tacaatgagcagttcttc | 2118 | C A S S W G G R E T Y N E Q F F |
| 05.217 | TRBV05-1*01 | TRBJ2-1*01 | TRBD1*01 | 423 | tgcgccagcagt... | gg | gggacagggg. | ccggg | ........gagcagttcttc | 2119 | C A S S W G T G A G E Q F F |
| 05.218 | TRBV05-1*01 | TRBJ2-1*01 | TRBD1*01 | 424 | tgcgccagcagct... | gg | gggacagg... | ffccgtgac. | ........cagtlcttc | 2120 | C A S S W G T G S G D Q F F |
| 05.219 | TRBV05-1*01 | TRBJ2-1*01 | TRBD1*01 | 425 | tgcgccagcagt... | gg | gggacaggg... | tccgg | ........tgagcagttcttc | 2121 | C A S S W G T G S G E Q F F |
| 05.220 | TRBV05-6*01 | TRBJ2-3*01 | TRBD2*01 | 426 | tgcgccagcagt... | ggaa | ggac...... | gccgcc | .gcagagatacgcagtattt | 2122 | C A S S W K G R R R T D T Q Y F |
| 05.221 | TRBV05-6*01 | TRBJ1-2*01 | TRBD1*01 | 427 | tgtgccagcagt... | ggtcagcc | g ctaactatggctacacctlc | | | 2123 | C A S S W S A A N Y G Y T F |
| 05.222 | TRBV05-6*01 | TRBJ2-7*01 | TRBD1*01 | 428 | tgtgccagcagt... | at | .......ggggg | tt | ..ctacgagcagtactlc | 2124 | C A S S Y G G F Y E Q Y F |
| 05.223 | TRBV05-8*01 | TRBJ1-1*01 | TRBD2*01 | 429 | tgtgccagcagct... | a | c gggact........ | gc | ...cactgaagcttcttt | 2125 | C A S S Y G T A T E A F F |
| 05.224 | TRBV05-1*01 | TRBJ1-1*01 | TRBD1*01 | 430 | tgcgccagcagt... | ac | gggacagg... | to | ...cactgaagcttcttt | 2126 | C A S S Y G T G S T E A F F |
| 05.225 | TRBV05-4*01 | TRBJ1-5*01 | | 431 | tgtgccagcagct... | acct | ..caatcagcccagcattt | | | 2127 | C A S S Y L N Q P Q H F |
| 05.226 | TRBV05-6*01 | TRBJ2-5*01 | TRBD1*01 | 432 | tgtgccagca...... | ccaa | .gacagg...... | cctlaaggg... | gagaccagtactlc | 2128 | C A S T K T G L K G E T Q Y F |
| 05.227 | TRBV05-1*01 | TRBJ2-1*01 | TRBD2*02 | 433 | tgcgccagca...... | cctgcc | ...... | ggag. | ...cctacaatgagcagtlcttc | 2129 | C A S T L A G A Y N E Q F F |
| 05.228 | TRBV05-1*01 | TRBJ2-1*01 | TRBD2*01 | 434 | tgcgccagca...... | ctccgg | ......gcggggg. | ... | ...tacaatgagcagttcttc | 2130 | C A S T P G G G Y N E Q F F |
| 05.229 | TRBV05-4*01 | TRBJ2-2*01 | TRBD2*01 | 435 | tgtgccagca...... | cccco | ...... | cggga... | atcccta | ........ggggagclgttttt | 2131 | C A S T P R G S L G E L F F |
| 05.230 | TRBV05-6*01 | TRBJ2-1*01 | TRBD1*01 | 436 | tgtgcca......... | cctcctttg gggac... | cgggcctacaatgac | ............cagtlcttc | 2132 | C A T S F G D R A Y N D Q F F |
| 05.231 | TRBV05-6*01 | TRBJ2-1*01 | TRBD1*01 | 437 | tgtgcca......... | ccagcttg gggacaggg... | cctacaatgagcagttcttc | | 2133 | C A T S F G D R A Y N E Q F F |
| 05.232 | TRBV05-4*01 | TRBJ2-1*01 | TRBD1*01 | 438 | tgtgcc.......... | gtaaggaccg | ...agggggg gat | ....caatgagcagttcttc | 2134 | C A V R T E G A I N E Q F F |
| 06.001 | TRBV06-1*01 | TRBJ1-1*01 | TRBD2*01 | 439 | tgtgcc.......... | ggcagtggt...acag... | a .gaacactgaagcttcttt | | 2135 | C A G S G T E N T E A F F |
| 06.002 | TRBV06-1*01 | TRBJ2-7*01 | TRBD1*01 | 440 | tgtgcca......... | ttc | .......gaggg gata | ...cctacgagcagtactlc | 2136 | C A I R G D T Y E Q Y F |
| 06.003 | TRBV06-6*01 | TRBJ2-7*01 | TRBD1*01 | 441 | tgtgcca......... | tctcgtct ...cagg... | ttttgaaa | .....acgagcagtactlc | 2137 | C A I S S Q G L E N E Q Y F |
| 06.004 | TRBV06-3*01 | TRBJ2-1*01 | TRBD2*02 | 442 | tgtgcca......... | gcga | ....tagcgggaggg ata | .......aatgagcagttcttc | 2138 | C A S A I A G G I N E Q F F |
| 06.005 | TRBV06-1*01 | TRBJ2-1*01 | TRBD2*01 | 443 | tgtgccagc....... | gcaaagcgtgt gggactacgcgg..... | a | ...ctacaatgagcagtlcttc | 2139 | C A S A K R V G L A D Y N E Q F F |
| 06.006 | TRBV06-1*01 | TRBJ2-7*01 | TRBD2*01 | 444 | tgtgccagc....... | gctt | ....cggggggg | gac | ag ctcctacgagcagtactlc | 2140 | C A S A S G G D S S Y E Q Y F |

Figure 1-17

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 06.007 | TRBV06-6*01 | TRBJ1-1*01 | | 445 | tgtgccagc | | tgaagcttcttt | | | 2141 | C A S E A F F |
| 06.008 | TRBV06-1*01 | TRBJ1-4*01 | TRBD2*02 | 446 | tgtgccagc | | gagg..cagt | ..taatgaaaactgttttt | | 2142 | C A S E A V N E K L F F |
| 06.009 | TRBV06-5*01 | TRBJ2-5*01 | TRBD1*01 | 447 | tgtgccagc | ggagcc | ......gggc.tgat | ....gacccagtacttc | | 2143 | C A S G A G L M T Q Y F |
| 06.010 | TRBV06-5*01 | TRBJ2-7*01 | TRBD1*01 | 448 | tgtgccag | tg.gggacaggg | ...caa | ...acgagcagtacttc | | 2144 | C A S G D R A N E Q Y F |
| 06.011 | TRBV06-5*01 | TRBJ1-2*01 | TRBD1*01 | 449 | tgtgccagc | gg c gggacaggggg | a | ...tatggctacacctc | | 2145 | C A S G G G T G G Y G Y T F |
| 06.012 | TRBV06-1*01 | TRBJ2-1*01 | TRBD2*01 | 450 | tgtgccagc | ggcagc ccc | gggactagcgg | ...cgga ........aatgagcagttcttc | | 2146 | C A S G S P G T S G G N E Q F F |
| 06.013 | TRBV06-5*01 | TRBJ2-5*01 | TRBD1*01 | 451 | tgtgccagca | togacc | ..ggacaggg | ... cccggg.....gagaccagtacttc | | 2147 | C A S I D R T G P G E T Q Y F |
| 06.014 | TRBV06-5*01 | TRBJ2-3*01 | TRBD2*02 | 452 | tgtgccagca | to | .ggactagcggagg. | tat .....agatacgcagtattt | | 2148 | C A S I G L A G G I D T Q Y F |
| 06.015 | TRBV06-5*01 | TRBJ2-5*01 | TRBD1*01 | 453 | tgtgccagca | agggac | ...cagggg | ...cagagccccat ........tacttc | | 2149 | C A S K G P G A E A H Y F |
| 06.016 | TRBV06-6*04 | TRBJ2-5*01 | TRBD1*01 | 454 | tgtgccagca | agggac | ...cagggg | ..cagagg ......cccagtacttc | | 2150 | C A S K G P G A E A Q Y F |
| 06.017 | TRBV06-5*01 | TRBJ1-5*01 | TRBD1*01 | 455 | tgtgccagca | aactc | .ggacaggg | ...ttccggg ...tcagcccagcatttt | | 2151 | C A S K L G Q V P G Q P Q H F |
| 06.018 | TRBV06-5*01 | TRBJ2-7*01 | TRBD1*01 | 456 | tgtgccagca | aattaac | .gacag | ....cca ...cctacgagcagtacttc | | 2152 | C A S K L T T A T Y E Q Y F |
| 06.019 | TRBV06-2*01 | TRBJ2-2*01 | TRBD2*01 | 457 | tgtgccagca | aatcttatc | ......gcgg | .....gaacaccgggagctgtttt | | 2153 | C A S K S Y R G N T G E L F F |
| 06.020 | TRBV06-1*01 | TRBJ2-7*01 | TRBD1*01 | 458 | tgtgccagca | agt | ..acaggggc.cta | ..cctacgagcagtacttc | | 2154 | C A S K Y R G P T Y E Q Y F |
| 06.021 | TRBV06-2*01 | TRBJ2-2*01 | TRBD1*01 | 459 | tgtgccagca | ctg | ...cagggg | .. aaca ...cctacgagcagtacttc | | 2155 | C A S L Q G N T Y E Q Y F |
| 06.022 | TRBV06-3*01 | TRBJ2-2*01 | TRBD2*01 | 460 | tgtgccagca | ttgagtta cc | oggacta | ..........cggggagctgtttt | | 2156 | C A S L S Y R D Y G E L F F |
| 06.023 | TRBV06-6*01 | TRBJ2-2*01 | TRBD1*01 | 461 | tgtgccagca | tgtc | .....ggggc.ctttgagct | ..acaccgggagctgtttt | | 2157 | C A S M S G P L S Y T G E L F F |
| 06.024 | TRBV06-6*01 | TRBJ2-2*01 | TRBD1*01 | 462 | tgtgccagca | tgtcc | ......gggc.ctatgacctacacctteqacctqtq.... | ttt | | 2158 | C A S M S G P M T Y T F E L C F |
| 06.025 | TRBV06-5*01 | TRBJ2-5*01 | TRBD2*01 | 463 | tgtgccagca | atccgct | ......gggggg | aggagtg....gagaccagtacttc | | 2159 | C A S N P L G G G V E T Q Y F |
| 06.026 | TRBV06-1*01 | TRBJ1-5*01 | TRBD1*01 | 464 | tgtgccagcag | agc | ..gacagggg | .. tcgg .....cagcccagcattt | | 2160 | C A S R A T G G R Q P Q H F |
| 06.027 | TRBV06-5*01 | TRBJ2-3*01 | TRBD1*01 | 465 | tgtgccagcag | ag | ...agggggg | .gccaaccgctc | .....gatacgcagtattt | 2161 | C A S R E G G Q P L D I Q Y F |
| 06.028 | TRBV06-5*01 | TRBJ1-2*01 | TRBD1*01 | 466 | tgtgccagcag | | | ...gggc g gaat | ....ctatggctacacctc | 2162 | C A S R G G I Y G Y T F |
| 06.029 | TRBV06-6*01 | TRBJ2-5*01 | | 467 | tgtgccagcag | act | ...agagaccagtacttc | | | 2163 | C A S R L E T Q Y F |
| 06.030 | TRBV06-3*01 | TRBJ2-1*01 | TRBD2*01 | 468 | tgtgccagcag | att | ...actagc | ......tggtacaatgac | ...........cagttcttc | 2164 | C A S R L L A G Y N D Q F F |
| 06.031 | TRBV06-1*01 | TRBJ2-3*01 | TRBD2*02 | 469 | tgtgccagcag | ..... | acccgacga | ......gagg | ....gatacgcagtatttt | 2165 | C A S R P D E R D T Q Y F |
| 06.032 | TRBV06-5*01 | TRBJ1-4*01 | TRBD1*01 | 470 | tgtgccagcag | ac | ...cagggg | ....cccccttg | ......aacattoagtacttc | 2166 | C A S R P G A P L N I Q Y F |
| 06.033 | TRBV06-1*01 | TRBJ2-1*01 | TRBD2*02 | 471 | tgtgccagcag | acaagcgt | ..tagccgagggg c | ttaccg | ........atgagcagttcttc | 2167 | C A S R Q A L A G G L T D E Q F F |
| 06.034 | TRBV06-1*01 | TRBJ2-1*01 | TRBD2*02 | 472 | tgtgccagcag | c | | .....ggaggg acc | ..cctacaatgagcagttcttc | 2168 | C A S R R D P Y N E Q F F |

Figure 1-18

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 06.035 | TRBV06-1*01 | TRBJ2-2*01 | TRBD2*02 | 473 | tgtgccagcag | gatgatc | gaggg | caccgggagctgttttt | | 2169 | C A S R R I E G T G E L F F |
| 06.036 | TRBV06-1*01 | TRBJ2-7*01 | TRBD2*02 | 474 | tgtgc | aagcaggtc | gaggg c g | tcctacagcagtacttc | | 2170 | C A S R S R A S Y E Q Y F |
| 06.037 | TRBV06-6*01 | TRBJ2-1*01 | TRBD2*02 | 475 | tgtgccagcag | gagt | actacggagg | ctcctacaatgagcagttcttc | | 2171 | C A S R S T S G G S S Y N E Q F F |
| 06.038 | TRBV06-3*01 | TRBJ2-3*01 | TRBD1*01 | 476 | tgtgccagcag | aaccct c gggacaggg | t | cagatacgcagtattt | | 2172 | C A S R T L G T G S D T Q Y F |
| 06.039 | TRBV06-6*01 | TRBJ2-3*01 | TRBD2*01 | 477 | tgtgccagcag | agttaagaga ggactagc | aga | agatacgcagtattt | | 2173 | C A S R V K R G L A E D T Q Y F |
| 06.040 | TRBV06-1*01 | TRBJ1-2*01 | TRBD1*01 | 478 | tgtgccagcag | ggtaaacc | gggc tgag | tatgctacacctc | | 2174 | C A S R V N R A E Y G Y T F |
| 06.041 | TRBV06-1*01 | TRBJ2-7*01 | TRBD1*01 | 479 | tgtgccagc | tcagc ggacaggg | aa | tacgagcagtacttc | | 2175 | C A S S A D R E Y E Q Y F |
| 06.042 | TRBV06-1*01 | TRBJ2-1*01 | TRBD2*02 | 480 | tgtgccagcagtg | ccctcga | gagg | tacaatgagcagttcttc | | 2176 | C A S S A L E R Y N E Q F F |
| 06.043 | TRBV06-1*01 | TRBJ2-7*01 | TRBD1*01 | 481 | tgtgccagcagtg | c | caggg | acgagcagtacttc | | 2177 | C A S S A R D E Q Y F |
| 06.044 | TRBV06-1*01 | TRBJ2-7*01 | TRBD1*01 | 482 | tgtgccagcagtg | ccc gggac | ggag | cctacgagcagtacttc | | 2178 | C A S S A R D G A Y E Q Y F |
| 06.045 | TRBV06-5*01 | TRBJ2-3*01 | TRBD2*01 | 483 | tgtgccagcagtt | gca | cgggg | cthagagatacc | cagtatttt | 2179 | C A S S C T G L R D T Q Y F |
| 06.046 | TRBV06-5*01 | TRBJ2-7*01 | TRBD2*01 | 484 | tgtgccagcagt | gac | gcgg | aaagcgcgaccagcac | tacttc | 2180 | C A S S D A E S A D Q H Y F |
| 06.047 | TRBV06-1*01 | TRBJ2-7*01 | TRBD1*01 | 485 | tgtgccagcagtga | cga ggacag | cgccgaccagcac | | tacttc | 2181 | C A S S D E D S A D Q H Y F |
| 06.048 | TRBV06-1*01 | TRBJ2-7*01 | TRBD2*01 | 486 | tgtgccagcagtga | cgaggga | agcg | ccgaccagcagtacttt | | 2182 | C A S S D E E S A D Q Q Y F |
| 06.049 | TRBV06-1*01 | TRBJ2-6*01 | TRBD2*01 | 487 | tgtgccagcagtga | ttt | cgggga | a | ggggccaacgtcctgacttc | 2183 | C A S S D F G G G A N V L T F |
| 06.050 | TRBV06-1*01 | TRBJ2-7*01 | TRBD1*01 | 488 | tgtgccagcagtga | cg gggacagg | acctaccac | | cagtacttc | 2184 | C A S S D G D R T Y H Q Y F |
| 06.051 | TRBV06-1*01 | TRBJ2-1*01 | TRBD2*02 | 489 | tgtgccagcagtga | t | ggaggg tggggg | tcctacaatgagcagttcttc | | 2185 | C A S S D G G W G S Y N E Q F F |
| 06.052 | TRBV06-1*01 | TRBJ1-4*01 | | 490 | tgtgccagcagt | cctctt | | tgaaaaactgtttt | | 2186 | C A S S D L F E K L F F |
| 06.053 | TRBV06-6*01 | TRBJ2-4*01 | TRBD1*01 | 491 | tgtgccagcag | cgacccccccg | caggg | ttcg | acattcagtacttc | 2187 | C A S S D P P A G F D I Q Y F |
| 06.054 | TRBV06-1*01 | TRBJ2-6*01 | TRBD2*01 | 492 | tgtgccagcagtga | caggg | ccctat ctctgggggccaacgtcctgacttc | | | 2188 | C A S S D R G P I S G A N V L T F |
| 06.055 | TRBV06-1*01 | TRBJ2-1*01 | TRBD2*01 | 493 | tgtgccagcagtga | tacg | c | caatgagcagttcttc | | 2189 | C A S S D S A N E Q F F |
| 06.056 | TRBV06-1*01 | TRBJ2-2*01 | TRBD2*01 | 494 | tgtgccagcagtga | ct | ctagc | cca | aacaccgggagctgttttt | 2190 | C A S S D S S P N T G E L F F |
| 06.057 | TRBV06-1*01 | TRBJ1-1*01 | TRBD2*01 | 495 | tgtgccagcagtga | t | acag | agaacactgaaga | ttcttt | 2191 | C A S S D T E N T E D F F |
| 06.058 | TRBV06-1*01 | TRBJ2-7*01 | TRBD1*01 | 496 | tgtgccagcagtga | ggctg | aggggc t | tcctacgagcagt | | 2192 | C A S S E A E G A S Y E Q Y F |
| 06.059 | TRBV06-1*01 | TRBJ1-5*01 | TRBD1*01 | 497 | tgtgccagcagtgaagc | cttcggtggtgccct ggga | | | cagcccccagcatttt | 2193 | C A S S E A F G G A L G Q P Q H F |
| 06.060 | TRBV06-1*01 | TRBJ2-2*01 | TRBD1*01 | 498 | tgtgccagcagtgaagc | gggc gt | | ggagctgttttt | | 2194 | C A S S E A G V E L F F |
| 06.061 | TRBV06-1*01 | TRBJ2-3*01 | TRBD1*01 | 499 | tgtgccagcagtgaagc g | cagggg gccc | cacagatacgcagtattt | | | 2195 | C A S S E A Q G G P T D T Q Y F |
| 06.062 | TRBV06-1*01 | TRBJ2-3*01 | TRBD1*01 | 500 | tgtgccagcagtgaagc g | cagggg | gccgcaccacggcgatacgcagtt | | ttt | 2196 | C A S S E A Q G G R T D T Q F F |

Figure 1-19

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 06.063 | TRBV06-1*01 | TRBJ1-2*01 | TRBD1*01 | 501 | tgtgccagcagtgaagc | cc | gggac... | cgtctgcgt | ...ctatgctacacttc | 2197 | C A S S E A R D R L A V Y G Y T F |
| 06.064 | TRBV06-1*01 | TRBJ2-7*01 | TRBD2*02 | 502 | tgtgccagcagtgaagc | ... | tagcgggag. | ctcctacgagcagtacttc | | 2198 | C A S S E A S G S S Y E Q Y F |
| 06.065 | TRBV06-6*01 | TRBJ2-7*01 | TRBD2*01 | 503 | tgtgccagcagt... | gaagatcc | ccc gggactagcgg | c | ...cgagcagtacttc | 2199 | C A S S E D P P G L A A E Q Y F |
| 06.066 | TRBV06-1*01 | TRBJ2-1*01 | TRBD2*01 | 504 | tgtgccagcagtgaag. | atagt | ...ctagcgggg... | caga... | acaatgagcagttcttc | 2200 | C A S S E D S L A G Q N N E Q F F |
| 06.067 | TRBV06-1*01 | TRBJ2-7*01 | TRBD1*01 | 505 | tgtgccagcagtgaag. | ata cc | gggacagg... | a | .tcctacgagcagtactc | 2201 | C A S S E D T G T G S Y E Q Y F |
| 06.068 | TRBV06-1*01 | TRBJ2-7*01 | TRBD1*01 | 506 | tgtgccagcagtgaag. | aga | gggacagggggc | aggacgagtac | ...........tacttc | 2202 | C A S S E E R D R G Q D E Y Y F |
| 06.069 | TRBV06-1*01 | TRBJ2-6*01 | TRBD2*02 | 507 | tgtgccagcagtgaag. | ......... | agg. | tcaacc | .ctggggccaacgtcctgacttc | 2203 | C A S S E E V N P G A N V L T F |
| 06.070 | TRBV06-1*01 | TRBJ1-2*01 | TRBD2*01 | 508 | tgtgccagcagtgaa.. | tttcgt | ...cggggg. | caagc | ......atgctacacttc | 2204 | C A S S E F S S G G K H G Y T F |
| 06.071 | TRBV06-1*01 | TRBJ2-6*01 | TRBD1*01 | 509 | tgtgccagcagtgaag. | ga | .gacag... | ctctgggccaacgtcctgacttc | | 2205 | C A S S E G D S S G A N V L T F |
| 06.072 | TRBV06-1*01 | TRBJ2-7*01 | TRBD1*01 | 510 | tgtgccagcagtga... | gg | gggacag... | cc | ..cctacgagcagtacttc | 2206 | C A S S E G D S P Y E Q Y F |
| 06.073 | TRBV06-1*01 | TRBJ2-4*01 | TRBD2*01 | 511 | tgtgccagcagtga... | ......... | gggggg | gctagtcaagtgtcgggt | ...caaaacattcagtacttc | 2207 | C A S S E G G A S Q V S G V K N I Q Y F |
| 06.074 | TRBV06-1*01 | TRBJ2-5*01 | TRBD1*01 | 512 | tgtgccagcagtgaag. | gg | ...cagg... | tgtc | .ccaagagaccagtacttc | 2208 | C A S S E G Q V S Q E T Q Y F |
| 06.075 | TRBV06-1*01 | TRBJ2-3*01 | TRBD2*02 | 513 | tgtgccagcagtgaa.. | ......... | ctagcgggag... | a | .cacagatacgcagtatttt | 2209 | C A S S E L A G D T D T Q Y F |
| 06.076 | TRBV06-1*01 | TRBJ2-5*01 | TRBD2*02 | 514 | tgtgccagcagtgaa.. | ......... | ctagcgggaggg | cc | .ccaagagaccagtcagc | 2210 | C A S S E L A G G P Q E T Q Y F |
| 06.077 | TRBV06-1*01 | TRBJ2-6*01 | TRBD2*01 | 515 | tgtgccagcagtgaa.. | ......... | ctag... | gacgctt | ctctgggccaacgtcctgacttc | 2211 | C A S S E L G R F S G A N V L T F |
| 06.078 | TRBV06-1*01 | TRBJ2-5*01 | TRBD2*02 | 516 | tgtgccagcagtgaa.. | cgggcc | ...ggagg. | atcg | ....gagaccagtacttc | 2212 | C A S S E R A G G S E T Q Y F |
| 06.079 | TRBV06-1*01 | TRBJ1-5*01 | TRBD1*01 | 517 | tgtgccagcagtga.. | gcg | ...aggg... | cc | ...caatcagcccagcattt | 2213 | C A S S E R G P N Q P Q H F |
| 06.080 | TRBV06-1*01 | TRBJ1-1*01 | TRBD1*01 | 518 | tgtgccagcagtgaa.. | a | .ggacagg... | tgg | .gaacactgaagcttcttt | 2214 | C A S S E R T G G N T E A F F |
| 06.081 | TRBV06-1*01 | TRBJ1-1*01 | TRBD1*01 | 519 | tgtgccagcagtgaa.. | ......... | acag... | ac | .aacactgaagcttcttt | 2215 | C A S S E T D N T E A F F |
| 06.082 | TRBV06-1*01 | TRBJ2-7*01 | TRBD1*01 | 520 | tgtgccagcagtgaa.. | ac. | ggacaggg... | tc | ...acgagcagtacttc | 2216 | C A S S E T D R G H E Q Y F |
| 06.083 | TRBV06-1*01 | TRBJ2-7*01 | TRBD2*02 | 521 | tgtgccagcagtga... | ga | ...cgggaggg | tatgg | .....cgagcagtacttc | 2217 | C A S S E T G G Y G E Q Y F |
| 06.084 | TRBV06-1*01 | TRBJ2-7*01 | | 522 | tgtgccagcagtga... | gaccat | ctcctacgagcagtactt | | | 2218 | C A S S E T I S Y E Q Y F |
| 06.085 | TRBV06-1*01 | TRBJ2-1*01 | TRBD2*02 | 523 | tgtgccagcagtga... | gactagcgggaggg | agactgac | ............ttcttc | | 2219 | C A S S E T S G R E T D F F |
| 06.086 | TRBV06-1*01 | TRBJ1-3*01 | TRBD2*01 | 524 | tgtgccagcagtgaag. | tat | ...cggg. | tag | ...tggaaacaccatatattt | 2220 | C A S S E V S G G N T I Y F |
| 06.087 | TRBV06-6*01 | TRBJ2-5*01 | TRBD1*01 | 525 | tgtgccagcag...... | cttcta | ..acag... | actt | .ccaagagaccagtacttc | 2221 | C A S S F L T D F Q E T Q Y F |
| 06.088 | TRBV06-3*01 | TRBJ2-7*01 | | 526 | tgtgccagcagtt... | ttcccgtgtagt | .....agagaccagtacttc | | | 2222 | C A S S F P G V V E T Q Y F |
| 06.089 | TRBV06-5*01 | TRBJ2-7*01 | TRBD2*02 | 527 | tgtgccagcagt..... | gggg | ......agcgggaggg | gagg | ....tacgagcagtacttc | 2223 | C A S S G E R E G R Y E Q Y F |

Figure 1-20

| clone # | V name | J name | D name | SEQ ID NO: | V-REGION | N1 | D-REGION | (P) | N2 | J-REGION | SEQ ID NO: | CDR3 amino acid |
|---|---|---|---|---|---|---|---|---|---|---|---|---|
| 06.090 | TRBV06-1*01 | TRBJ2-1*01 | TRBD2*01 | 528 | tgtgccagcagtg | gactagcgg | at | | tacaatgagcagttcttc | | 2224 | C A S S G L A D Y N E Q F F |
| 06.091 | TRBV06-6*01 | TRBJ1-1*01 | TRBD1*01 | 529 | tgtgccagcagt | ggacag | ccca | | tgaacactgaagcttcttt | | 2225 | C A S S G Q P M N T E A F F |
| 06.092 | TRBV06-6*01 | TRBJ2-7*01 | TRBD1*01 | 530 | tgtgccagcagt | gg cc gggaca | cagctg | | cctacgagcagtactc | | 2226 | C A S S G R D T A A Y E Q Y F |
| 06.093 | TRBV06-1*01 | TRBJ1-1*01 | TRBD1*01 | 531 | tgtgccagcagtg | gt acag | a | | gaacactgaagcttctt | | 2227 | C A S S G T E N T E A F F |
| 06.094 | TRBV06-1*01 | TRBJ2-3*01 | TRBD2*02 | 532 | tgtgccagcag | ccacgctcat | gaggg agcg | | gatacgcagtattt | | 2228 | C A S S H A H E G A D T Q Y F |
| 06.095 | TRBV06-5*01 | TRBJ2-3*01 | TRBD2*01 | 533 | tgtgccagcagt | cacctcg gggac | gga | | acagatacgcagtatttt | | 2229 | C A S S H L G D T D T Q Y F |
| 06.096 | TRBV06-5*01 | TRBJ1-2*01 | | 534 | tgtgccagcagt | ccataacc | ctaactatgctacacctc | | | | 2230 | C A S S H N P N Y G Y T F |
| 06.097 | TRBV06-6*04 | TRBJ1-1*01 | TRBD1*01 | 535 | tgtgccagcagc | ccacc | ggggtc | | ggggggaccccacacttcggtttt | ttt | 2231 | C A S S H R G R G D P H T F G F F |
| 06.098 | TRBV06-5*01 | TRBJ2-2*01 | TRBD2*01 | 536 | tgtgccagcagt | cactcaagg | agcgggg | | accatttatc | cttc | 2232 | C A S S H S R S G D H L S F |
| 06.099 | TRBV06-2*01 | TRBJ2-2*01 | TRBD2*01 | 537 | tgtgccagcagt | att gact | ctcaag | | ccggggagctgttttt | | 2233 | C A S S I D S Q A G E L F F |
| 06.100 | TRBV06-5*01 | TRBJ2-7*01 | TRBD2*02 | 538 | tgtgccagcag | cat tagcgggag | cca ctcctacgagcagtactc | | | | 2234 | C A S S I S G S H S Y E Q Y F |
| 06.101 | TRBV06-5*01 | TRBJ2-7*01 | TRBD1*01 | 539 | tgtgccagcagt | atctcaaggatcg | gggaca | atct | | gtactc | 2235 | C A S S I S R I G D N L Y F |
| 06.102 | TRBV06-5*01 | TRBJ2-7*01 | TRBD1*01 | 540 | tgtgccagcagt | atctcaaggaccg | gggaca | atct | | gtactc | 2236 | C A S S I S R T G D N L Y F |
| 06.103 | TRBV06-6*01 | TRBJ2-7*01 | TRBD1*01 | 541 | tgtgccagcagt | a | agggggc agggggccgcctac | | ggctacaccttc | | 2237 | C A S S K G A G A A Y G Y T F |
| 06.104 | TRBV06-5*01 | TRBJ1-3*01 | TRBD2*01 | 542 | tgtgccagcagt | aaataccct | ggggc a | | gaaacaccatatatttt | | 2238 | C A S S K Y P G G R N T I Y F |
| 06.105 | TRBV06-6*01 | TRBJ2-7*01 | TRBD2*02 | 543 | tgtgccagcag | c | ctagcgggag tt | | tacgagcagtactc | | 2239 | C A S S L A G V Y E Q Y F |
| 06.106 | TRBV06-5*01 | TRBJ2-1*01 | TRBD2*01 | 544 | tgtgccagcagtt | t gggactagcgggg | a | | acaatgagcagttctc | | 2240 | C A S S L G L A G N N E Q F F |
| 06.107 | TRBV06-5*01 | TRBJ1-3*01 | TRBD1*01 | 545 | tgtgccagcagt | t gggacagggggc | | | aaacaccatatattt | | 2241 | C A S S L G Q G A N T I Y F |
| 06.108 | TRBV06-6*01 | TRBJ2-5*01 | TRBD1*01 | 546 | tgtgccagcag | cct gggacag | c | | accaagagaccagtactc | | 2242 | C A S S L G Q H Q E T Q Y F |
| 06.109 | TRBV06-5*01 | TRBJ2-1*01 | TRBD2*01 | 547 | tgtgccagcagt | ct c gggact | cccgg | | atgagcagttctc | | 2243 | C A S S L G T P R D E Q F F |
| 06.110 | TRBV06-3*01 | TRBJ1-2*01 | TRBD1*01 | 548 | tgtgccagcagtt | taatcc gacaggg | ttgggg | | ctatgctacacctc | | 2244 | C A S S L I R Q G W G Y G Y T F |
| 06.111 | TRBV06-1*01 | TRBJ2-1*01 | TRBD2*02 | 549 | tgtgccagcagt | ttg ctagcggag | aaaacg | | acgagcagtactc | | 2245 | C A S S L L A G E N D E Q Y F |
| 06.112 | TRBV06-9*01 | TRBJ1-5*01 | TRBD1*01 | 550 | tgtgccagcagt | ct cagg | a | | cccagcattt | | 2246 | C A S S L R T Q H F |
| 06.113 | TRBV06-5*01 | TRBJ1-1*01 | TRBD1*01 | 551 | tgtgccagcagt | ctctccggaccg | gggaca | atctgtc | | cttc | 2247 | C A S S L S G T G D N L S F |
| 06.114 | TRBV06-5*01 | TRBJ2-1*01 | TRBD2*01 | 552 | tgtgccagcagt | cta | ag ctcctacaatgagcagttcttc | | | | 2248 | C A S S L S S Y N E Q F F |
| 06.115 | TRBV06-3*01 | TRBJ1-5*01 | TRBD1*01 | 553 | tgtgccagcgc | tcca acaggggc cg | aatcagcccagcattt | | | | 2249 | C A S S N R G P N Q P Q H F |
| 06.116 | TRBV06-3*01 | TRBJ2-7*01 | TRBD2*02 | 554 | tgtgccagcagt | cc | agcgggag agggg | | tacgagcagtactc | | 2250 | C A S S P A G E G Y E Q Y F |

Figure 1-21

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 06.117 | TRBV06-5*01 | TRBJ2-5*01 | TRBD1*01 | 555 | tgtgccagcagt | cca..gacag...agc | agagaccagtactc | | | 2251 | C A S S P D R A E T Q Y F |
| 06.118 | TRBV06-5*01 | TRBJ1-3*01 | TRBD1*01 | 556 | tgtgccagcag | ccc..gga | gtccgtccgagga | ggaaaacaccatatttt | | 2252 | C A S S P E S V R G G N T I Y F |
| 06.119 | TRBV06-5*01 | TRBJ2-6*01 | | 557 | tgtgccagcagt | c..ctgggcaacgtcctgacttc | | | | 2253 | C A S S P G A N V L T F |
| 06.120 | TRBV06-5*01 | TRBJ2-7*01 | TRBD2*01 | 558 | tgtgccagcagt | cc | cgggggg gggacgactat | | cagtacttc | 2254 | C A S S P G G G D D Y Q Y F |
| 06.121 | TRBV06-5*01 | TRBJ1-4*01 | TRBD2*01 | 559 | tgtgccagcag | ccc | cgggggg g | aaaactgttttt | | 2255 | C A S S P G G G K L F F |
| 06.122 | TRBV06-5*01 | TRBJ2-7*01 | TRBD2*01 | 560 | tgtgccagcagt | cc | cgggggg ggaacgaccac | | cagtacttc | 2256 | C A S S P G G G N D H Q Y F |
| 06.123 | TRBV06-5*01 | TRBJ2-7*01 | TRBD2*01 | 561 | tgtgccagcagt | cc | cgggggg ggaactacc | | agcagtacttc | 2257 | C A S S P G G G N Y Q Q Y F |
| 06.124 | TRBV06-5*01 | TRBJ2-1*01 | TRBD2*01 | 562 | tgtgccagcag | ccccgggc | cgggg..ccggg | | aatgagcagttcttc | 2258 | C A S S P G P G P G N E Q F F |
| 06.125 | TRBV06-6*01 | TRBJ2-1*01 | TRBD1*01 | 563 | tgtgccagcagt | cc gggacagggg | ggat | caatgagcagttcttc | | 2259 | C A S S P G Q G G I N E Q F F |
| 06.126 | TRBV06-5*01 | TRBJ2-7*01 | TRBD1*01 | 564 | tgtgccagcagt | cc gggacaggg | caa | ctacgagcagttctc | | 2260 | C A S S P G Q G N Y E Q Y F |
| 06.127 | TRBV06-5*01 | TRBJ2-7*01 | TRBD1*01 | 565 | tgtgccagcagt | cc gggacaggg | caactaca | agcagtacttc | | 2261 | C A S S P G Q G N Y K Q Y F |
| 06.128 | TRBV06-6*01 | TRBJ2-1*01 | TRBD1*01 | 566 | tgtgccagcagt | cca gggacagg | at | ctacaatgagcagttctc | | 2262 | C A S S P G T G I Y N E Q F F |
| 06.129 | TRBV06-5*01 | TRBJ2-3*01 | TRBD2*02 | 567 | tgtgccagcagt | ccaa | tagcaggaggg cc tggg | gatacgcagtattt | | 2263 | C A S S P I A G G P G D T Q Y F |
| 06.130 | TRBV06-6*01 | TRBJ2-5*01 | TRBD1*01 | 568 | tgtgccagcag | ccogatta | acagggggc accaagagaccagtacttc | | | 2264 | C A S S P I N R G H Q E T Q Y F |
| 06.131 | TRBV06-2*01 | TRBJ1-4*01 | TRBD1*01 | 569 | tgtgccagcagt | cccaaggcggcg ggga | tc | aatgaaaactgttttt | | 2265 | C A S S P K A A G I N E K L F F |
| 06.132 | TRBV06-6*01 | TRBJ2-3*01 | TRBD2*01 | 570 | tgtgccagcagt | ccc | actagcg | aaccg | acagatacgcagtatttt | 2266 | C A S S P L A E P T D T Q Y F |
| 06.133 | TRBV06-3*01 | TRBJ2-3*01 | TRBD2*02 | 571 | tgtgccagcagt | ccctg | agcggagg cacgcg | gatacgcagtatttt | | 2267 | C A S S P L S G R H A D T Q Y F |
| 06.134 | TRBV06-6*01 | TRBJ2-3*01 | TRBD1*01 | 572 | tgtgccagcagt | cct cc gggac | ctaagat | agatacgcagtatttt | | 2268 | C A S S P P G P K I D T Q Y F |
| 06.135 | TRBV06-5*01 | TRBJ1-5*01 | TRBD1*01 | 573 | tgtgccagcagt | ccct | cagggctcctcgc | gccccagccatttt | | 2269 | C A S S P S G L L A P Q H F |
| 06.136 | TRBV06-5*01 | TRBJ2-7*01 | TRBD1*01 | 574 | tgtgccagcag | ccccctc | gacaggg | agtctggg | cgagcagtacttc | 2270 | C A S S P S T G S L G E Q Y F |
| 06.137 | TRBV06-5*01 | TRBJ2-3*01 | TRBD1*01 | 575 | tgtgccagcagt | ccta cc gggacaggggg | cggga | gagcagtacttc | | 2271 | C A S S P T G T G A G E Q Y F |
| 06.138 | TRBV06-6*01 | TRBJ2-3*01 | TRBD2*01 | 576 | tgtgccagcag | caa ggacaggggg | aggttg | acagatacgcagtatttt | | 2272 | C A S S Q G Q G R L T D T Q Y F |
| 06.139 | TRBV06-2*01 | TRBJ1-2*01 | TRBD1*01 | 577 | tgtgccagcag | ccaaaaaccccggccct | ggga | agtggag | accttc | 2273 | C A S S Q K P G P W E V E T F |
| 06.140 | TRBV06-1*01 | TRBJ2-1*01 | TRBD2*01 | 578 | tgtgccagcag | ccgattga gggact | ctacaatgagcagttcttc | | | 2274 | C A S S R L E G L Y N E Q F F |
| 06.141 | TRBV06-6*01 | TRBJ2-7*01 | TRBD2*01 | 579 | tgtgccagcag | cc ggactag | tatcc | atgagcagttcttc | | 2275 | C A S S R T S I H E Q F F |
| 06.142 | TRBV06-2*01 | TRBJ2-1*01 | TRBD2*01 | 580 | tgtgccagcag | ccgt actag | tgtgaggccc | tcttc | | 2276 | C A S S R T S V R A L F |
| 06.143 | TRBV06-1*01 | TRBJ2-7*01 | | 581 | tgtgccagcag | ctccgcatgg | gagcagtacttc | | | 2277 | C A S S S A W E Q Y F |
| 06.144 | TRBV06-5*01 | TRBJ2-7*01 | TRBD2*01 | 582 | tgtgccagcagtt | ccgaa | cggg | ccaggtgcaacaa | tacttc | 2278 | C A S S S E R A R C Q Q Y F |

Figure 1-22

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 06.145 | TRBV06-5*01 | TRBJ2-7*01 | TRBD2*01 | 583 | tgtgccagcagtt... | c | .......cgggg... | caa | ..cctacgagcagtactto | 2279 | C A S S S G A T Y E Q Y F |
| 06.146 | TRBV06-5*01 | TRBJ2-7*01 | TRBD2*01 | 584 | tgtgccagcagtt... | c | ......cgggggg... | aa | ..cctacgagcagtactto | 2280 | C A S S S G G T Y E Q Y F |
| 06.147 | TRBV06-5*01 | TRBJ1-1*01 | TRBD1*01 | 585 | tgtgccagcagtt... | ca | ..ggaca..... | ca | tgaacactgaagcttcttt | 2281 | C A S S S G H M N T E A F F |
| 06.148 | TRBV06-2*01 | TRBJ2-1*01 | TRBD2*01 | 586 | tgtgccagcagtt... | c | gggactag..... | gttt | ......caatgagcagttcttc | 2282 | C A S S S G L G F N E Q F F |
| 06.149 | TRBV06-6*01 | TRBJ2-1*01 | TRBD1*01 | 587 | tgtgccagcag..... | ctca ..ggacaggg... | aggatcctacaatgat | ........cagttcttc | | 2283 | C A S S S G Q G G S Y N D Q F F |
| 06.150 | TRBV06-6*01 | TRBJ2-5*01 | TRBD1*01 | 588 | tgtgccagcag..... | ct cc gggacaggg... | cggg | ..agagaccagtactto | | 2284 | C A S S S G T G A G E T Q Y F |
| 06.151 | TRBV06-5*01 | TRBJ2-1*01 | TRBD2*02 | 589 | tgtgccagcagtt... | cc gggactacgcggg... | attttt | ..tacaatgagcagttcttc | | 2285 | C A S S S G T S G D F Y N E Q F F |
| 06.152 | TRBV06-5*01 | TRBJ2-3*01 | | 590 | tgtgccagcagtt... | ccctccctctg ..cagatacgcagtattt | | | | 2286 | C A S S S L P L A D T Q Y F |
| 06.153 | TRBV06-5*01 | TRBJ2-7*01 | TRBD2*02 | 591 | tgtgccagcagtt... | ctctct cc gggactagcggga... | aaacaggg ...tacgagcagtactto | | | 2287 | C A S S S L S G T S G K T G Y E Q Y F |
| 06.154 | TRBV06-5*01 | TRBJ1-3*01 | | 592 | tgtgccagcagtt... | cctcggtgaa ..tgaaacaccatatattt | | | | 2288 | C A S S S V N G N T I Y F |
| 06.155 | TRBV06-5*01 | TRBJ1-1*01 | TRBD1*01 | 593 | tgtgccagcag..... | ctca ..acaggg... | ..acactgaagcttcttt | | | 2289 | C A S S S T G D T E A F F |
| 06.156 | TRBV06-1*01 | TRBJ2-3*01 | TRBD1*01 | 594 | tgtgccagcagt.... | ..acaggg... | ttccg | ...agatacgcagtattt | | 2290 | C A S S T G F R D T Q Y F |
| 06.157 | TRBV06-5*01 | TRBJ1-2*01 | TRBD1*01 | 595 | tgtgccagcagt.... | act ..acaggggg... | aaag | ...ggctacacctto | | 2291 | C A S S T T G G K G Y T F |
| 06.158 | TRBV06-1*01 | TRBJ2-1*01 | TRBD1*01 | 596 | tgtgccagcagtg... | tcaa .........gggc tagttagggag... | tacaatgagcagttcttc | | | 2292 | C A S S V K G L V R E Y N E Q F F |
| 06.159 | TRBV06-5*01 | TRBJ2-5*01 | TRBD2*02 | 597 | tgtgccagcagt.... | gtcc gggactagcgga... | ........gagcagttcttc | | | 2293 | C A S S V P G L A G E Q F F |
| 06.160 | TRBV06-6*01 | TRBJ2-1*01 | TRBD1*01 | 598 | tgtgccagcagt.... | gt ..aca..... | aaa ctctacaatgagcagttcttc | | | 2294 | C A S S V Q N S Y N E Q F F |
| 06.161 | TRBV06-6*01 | TRBJ1-1*01 | TRBD1*01 | 599 | tgtgccagcagtg... | tga ggga......... | gaacactgaagcttcttt | | | 2295 | C A S S V R E N T E A F F |
| 06.162 | TRBV06-3*01 | TRBJ2-1*01 | TRBD2*01 | 600 | tgtgccagcagtt... | ggg cc gggacta........ | cg | ......aatgagcagttcttc | | 2296 | C A S S W A G T T N E Q F F |
| 06.163 | TRBV06-3*01 | TRBJ2-5*01 | TRBD1*01 | 601 | tgtgccagcagtt... | ........ggggg. atggg ...agagaccagtactto | | | | 2297 | C A S S W G M G E T Q Y F |
| 06.164 | TRBV06-5*01 | TRBJ2-7*01 | TRBD2*01 | 602 | tgtgccagcagtt... | gga ..ggactagcgg..... | t | ...tacgagcagtactto | | 2298 | C A S S W R T S G Y E Q Y F |
| 06.165 | TRBV06-6*01 | TRBJ2-3*01 | TRBD1*01 | 603 | tgtgccagcagtt... | ggacaggg... | ct ..acagatacgcagtattt | | | 2299 | C A S S W T G L T D T Q Y F |
| 06.166 | TRBV06-3*01 | TRBJ1-5*01 | TRBD1*01 | 604 | tgtgccagcagttac... | gcc ..gacaggg... | aagta | ......cagcccccagcatttt | | 2300 | C A S S Y A D R E V Q P Q H F |
| 06.167 | TRBV06-3*01 | TRBJ2-1*01 | TRBD1*01 | 605 | tgtgccagcagttac... | gc ..ggaca...... | ctttt ctcctacaatgagcagttcttc | | | 2301 | C A S S Y A D T F S Y N E Q F F |
| 06.168 | TRBV06-3*01 | TRBJ2-1*01 | TRBD1*01 | 606 | tgtgccagcagttac... | g ..caggg... | c | ........tgagcagttcttc | | 2302 | C A S S Y A G A E Q F F |
| 06.169 | TRBV06-5*01 | TRBJ1-6*01 | TRBD1*01 | 607 | tgtgccagcagttac... | gc ..gacaggggg... | agggg | ........tcaccctccactttt | | 2303 | C A S S Y A T G E G S P L H F |
| 06.170 | TRBV06-6*01 | TRBJ1-4*01 | TRBD1*01 | 608 | tgtgccagcagttac... | gcct... .acaggg... | aga caactaatgaaaaactgttttt | | | 2304 | C A S S Y A Y R E T T N E K L F F |
| 06.171 | TRBV06-6*01 | TRBJ2-5*01 | | 609 | tgtgccagcagtact... | ttgagatg ..aagagaccagtactto | | | | 2305 | C A S S Y F E M E E T Q Y F |
| 06.172 | TRBV06-5*01 | TRBJ1-1*01 | | 610 | tgtgccagcagtta... | tttcc tgaacactgaagcttcttt | | | | 2306 | C A S S Y F L N T E A F F |

Figure 1-23

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 06.173 | TRBV06-3*01 | TRBJ2-5*01 | TRBD2*02 | 611 | tgtgccagcagttact. | tctccccc. | ggactagcgggag. | ...aagagacccagtactic | | 2307 | C A S S Y F S P G L A G E E T Q Y F |
| 06.174 | TRBV06-5*01 | TRBJ2-7*01 | TRBD2*01 | 612 | tgtgccagcagttac. | ggg | ...gcggggggg. | a | ...tacgagcagtactic | 2308 | C A S S Y G A G G G Y E Q Y F |
| 06.175 | TRBV06-5*01 | TRBJ2-1*01 | TRBD1*01 | 613 | tgtgccagcagttac. | | ...ggggc cccacccag | ... | tacaatgagcagttctc | 2309 | C A S S Y G A P P Q Y N E Q F F |
| 06.176 | TRBV06-2*01 | TRBJ2-3*01 | TRBD2*01 | 614 | tgtgccagcagttac. | gggg | ...ctagcgg. | ... | ttcagatacctac. | ...tatttt | 2310 | C A S S Y G A S G S D T Y Y F |
| 06.177 | TRBV06-5*01 | TRBJ2-7*01 | TRBD2*01 | 615 | tgtgccagcagttac. | g | gggacta. | ... | ctcctacgagcagtactic | 2311 | C A S S Y G D Y S Y E Q Y F |
| 06.178 | TRBV06-1*01 | TRBJ2-7*01 | TRBD2*01 | 616 | tgtgccagcagt. | tacg | gggacta. | ...ctcctacc. | ...agcagtactic | 2312 | C A S S Y G D Y S Y Q Q Y F |
| 06.179 | TRBV06-5*01 | TRBJ2-2*01 | TRBD2*01 | 617 | tgtgccagcagttac. | ggactagcgg. | ...ta. | ..aacaccggggagctgttttt | | 2313 | C A S S Y G L A V N T G E L F F |
| 06.180 | TRBV06-5*01 | TRBJ1-2*01 | TRBD1*01 | 618 | tgtgccagcagttac. | | ...gggc aaacgat. | taactatggctacacctc | | 2314 | C A S S Y G Q T I N Y G Y T F |
| 06.181 | TRBV06-6*01 | TRBJ2-7*01 | TRBD2*02 | 619 | tgtgccagcagttac. | ggccgcgc | ...gcgggag. | ccctatgg | tg. | ...gtacttc | 2315 | C A S S Y G R A R E P L W W Y F |
| 06.182 | TRBV06-5*01 | TRBJ1-2*01 | TRBD1*01 | 620 | tgtgccagcagttac. | gg | ...cagg. | ...ag | taactatggctacacctc | 2316 | C A S S Y G R S N Y G Y T F |
| 06.183 | TRBV06-5*01 | TRBJ2-1*01 | TRBD1*01 | 621 | tgtgccagcagttac. | | ...ggac. | ...gggt | ...caatgagcagtactic | 2317 | C A S S Y G R V N E Q F F |
| 06.184 | TRBV06-5*01 | TRBJ2-7*01 | | 622 | tgtgccagcagttac. | | agcagca | ..cctacgagcagtactic | | 2318 | C A S S Y G S T Y E Q Y F |
| 06.185 | TRBV06-5*01 | TRBJ2-2*01 | TRBD1*01 | 623 | tgtgccagcagttac. | gggacaggg. | aagt | ...caccggggagctgttttt | | 2319 | C A S S Y G T G E V T G E L F F |
| 06.186 | TRBV06-5*01 | TRBJ1-6*01 | TRBD1*01 | 624 | tgtgccagcagttac. | ggt | ...acaggg. | acgattc | ...attcaccctccacttt | 2320 | C A S S Y G T I H S P L H F |
| 06.187 | TRBV06-2*01 | TRBJ2-3*01 | TRBD2*01 | 625 | tgtgccagcagttac. | gggac. | | cagcgcctccatacgcactt. | ...tttt | 2321 | C A S S Y G T S A S H T H F F |
| 06.188 | TRBV06-2*01 | TRBJ2-3*01 | TRBD2*01 | 626 | tgtgccagcagttac. | gggactagcgg. | ...tt | ...cagatacgcagtattt | | 2322 | C A S S Y G T S G S D T Q Y F |
| 06.189 | TRBV06-2*01 | TRBJ2-7*01 | TRBD1*01 | 627 | tgtgccagcagttac. | g | ...gcg. | ...t | ...ctacgagcagtactic | 2323 | C A S S Y G V Y E Q Y F |
| 06.190 | TRBV06-5*01 | TRBJ1-6*01 | TRBD1*01 | 628 | tgtgccagcagttac. | at | ...acag. | | aattcaccctccactt | 2324 | C A S S Y I Q N S P L H F |
| 06.191 | TRBV06-6*01 | TRBJ2-3*01 | TRBD2*02 | 629 | tgtgccagcagtta. | t | ...ctagcggga. | aa | ..cacagatacgcagtatttt | 2325 | C A S S Y L A G N T D T Q Y F |
| 06.192 | TRBV06-5*01 | TRBJ1-1*01 | TRBD1*01 | 630 | tgtgccagcagttac. | ctc | ...gggg. | gtc | gaacactgaagcttcttc | 2326 | C A S S Y L G G S N T E A F F |
| 06.193 | TRBV06-6*01 | TRBJ2-7*01 | TRBD1*01 | 631 | tgtgccagcagttact. | t | gggacagg. | a | ...gagcagtactic | 2327 | C A S S Y L G Q G E Q Y F |
| 06.194 | TRBV06-6*01 | TRBJ2-5*01 | TRBD2*02 | 632 | tgtgccagcagttac. | ctgact | ...ctagcgggaggg | cc | ccaagagacccagtactic | 2328 | C A S S Y L T L A G G P Q E T Q Y F |
| 06.195 | TRBV06-3*01 | TRBJ2-4*01 | TRBD1*01 | 633 | tgtgccagcagttac. | aaccc. | .gaca. | ...tcagg | agccaaaaacattcagtactic | 2329 | C A S S Y N P T S G A K N I Q Y F |
| 06.196 | TRBV06-2*01 | TRBJ2-2*01 | TRBD1*01 | 634 | tgtgccagcagttac. | ccc | ggacaggggc | cc | ..acaccggggagctgttttt | 2330 | C A S S Y P G Q G A H T G E L F F |
| 06.197 | TRBV06-5*01 | TRBJ2-7*01 | TRBD1*01 | 635 | tgtgccagcagttac. | ca | ggacaggg. | | ...tacgagcagtactic | 2331 | C A S S Y Q D R G Y E Q Y F |
| 06.198 | TRBV06-3*01 | TRBJ1-5*01 | TRBD1*01 | 636 | tgtgccagcagttac. | | ...cagggg. | tggggcc | ..caatcagcccagcatttt | 2332 | C A S S Y Q Q G W G P N Q P Q H F |
| 06.199 | TRBV06-5*01 | TRBJ2-1*01 | TRBD2*02 | 637 | tgtgccagcagttac. | | | aggg | ...atgag | 2333 | C A S S Y R D E Q F F |
| 06.200 | TRBV06-5*01 | TRBJ2-7*01 | TRBD2*01 | 638 | tgtgccagcagtta. | ta | gggac. | | ctcccctaccaacaa. | ...tacttc | 2334 | C A S S Y R D L P Y Q Q Y F |

Figure 1-24

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 06.201 | TRBV06-2*01 | TRBJ2-1*01 | TRBD2*01 | 639 | tgtgccagcagtta... | tc | gggact......cgta | ...ctacaatgagcagttcttc | | 2335 | C A S S Y R D S Y Y N E Q F F |
| 06.202 | TRBV06-5*01 | TRBJ2-7*01 | TRBD2*01 | 640 | tgtgccagcagtta... | ta | gggac............ | gtcg ...cctacgagcagtacttc | | 2336 | C A S S Y R D V A Y E Q Y F |
| 06.203 | TRBV06-5*01 | TRBJ2-7*01 | TRBD2*01 | 641 | tgtgccagcagtta... | ta | gggac............ | gttc ...cctacgagcagtacttc | | 2337 | C A S S Y R D V P Y E Q Y F |
| 06.204 | TRBV06-5*01 | TRBJ2-7*01 | TRBD2*01 | 642 | tgtgccagcagtta... | ta | gggac............ | gtccctaccaa........cagtacttc | | 2338 | C A S S Y R D V P Y Q Q Y F |
| 06.205 | TRBV06-5*01 | TRBJ2-7*01 | TRBD1*01 | 643 | tgtgccagcagttac. | cgt | ggacaggg. | a .....acgagcagtacttc | | 2339 | C A S S Y R G Q G N E Q Y F |
| 06.206 | TRBV06-5*01 | TRBJ2-7*01 | TRBD1*01 | 644 | tgtgccagcagtac. | cgcgg | ...cagg... | ttttgg ...acgagcagtacttc | | 2340 | C A S S Y R G R V L D E Q Y F |
| 06.207 | TRBV06-6*01 | TRBJ1-5*01 | TRBD1*01 | 645 | tgtgccagcagtac. | c ..gaca..... | ag | a tagcaatcagcccagcattc | | 2341 | C A S S Y R Q D S N Q P Q H F |
| 06.208 | TRBV06-5*01 | TRBJ2-7*01 | TRBD1*01 | 646 | tgtgccagcagtac. | c ..gacaggg. | a ...cctacgagcagtacttc | | | 2342 | C A S S Y R Q G T Y E Q Y F |
| 06.209 | TRBV06-6*01 | TRBJ2-7*01 | TRBD2*01 | 647 | tgtgccagcagtta. | cgccaatacacatcc ..gac. | ........gg t | ...tacgagcagtacttc | | 2343 | C A S S Y R Q Y T S D G Y E Q Y F |
| 06.210 | TRBV06-3*01 | TRBJ2-3*01 | TRBD1*01 | 648 | tgtgccagcagttac. | cggt ......gggg. tgtgatacc | ...... | cagtatttt | | 2344 | C A S S Y R W G V D T Q Y F |
| 06.211 | TRBV06-5*01 | TRBJ2-1*01 | TRBD2*01 | 649 | tgtgccagcagtactc | g ......gccggg. | ........ | gagcagttcttc | | 2345 | C A S S Y S A G E Q F F |
| 06.212 | TRBV06-6*01 | TRBJ2-5*01 | TRBD1*01 | 650 | tgtgccagcagtactc | .ggac........... | gagaccagtacttc | | | 2346 | C A S S Y S D E T Q Y F |
| 06.213 | TRBV06-5*01 | TRBJ1-6*01 | TRBD1*01 | 651 | tgtgccagcagtactc | tg gggacag.... | tcaggta ......tcacccctccactt | | | 2347 | C A S S Y S G D S Q V S P L H F |
| 06.214 | TRBV06-5*01 | TRBJ2-1*01 | TRBD2*02 | 652 | tgtgccagcagtactc | gggcggag ......agcgggaggg. ccggg......atgagcagttcttc | | | | 2348 | C A S S Y S G G E R E G R D E Q F F |
| 06.215 | TRBV06-5*01 | TRBJ1-3*01 | TRBD2*02 | 653 | tgtgccagcagtactc | ........gggagg. aaa ..tgaaacaccatatatttt | | | | 2349 | C A S S Y S G G N G N T I Y F |
| 06.216 | TRBV06-5*01 | TRBJ2-7*01 | TRBD1*01 | 654 | tgtgccagcagtactc | t .......gggc ccctt ...tacgagcagtacttc | | | | 2350 | C A S S Y S G P L Y E Q Y F |
| 06.217 | TRBV06-5*01 | TRBJ2-7*01 | TRBD2*02 | 655 | tgtgccagcagtactc | a ........gggaggg gctatgattacto .........cttc | | | | 2351 | C A S S Y S G R G Y D Y S F |
| 06.218 | TRBV06-5*01 | TRBJ2-7*01 | TRBD1*01 | 656 | tgtgccagcagtactc | .......gggc cgacggcccctgg ...acgagcagtacttc | | | | 2352 | C A S S Y S G R R P L D E Q Y F |
| 06.219 | TRBV06-6*01 | TRBJ1-3*01 | TRBD1*01 | 657 | tgtgccagcagtactc | gaagg ...cagggg. gaga ...ggaaaccatatatttt | | | | 2353 | C A S S Y S K A G G R G N T I Y F |
| 06.220 | TRBV06-5*01 | TRBJ1-1*01 | TRBD1*01 | 658 | tgtgccagcagtactc | ctt ....agggg. aag ...cactgaagcttcttt | | | | 2354 | C A S S Y S L G G S T E A F F |
| 06.221 | TRBV06-5*01 | TRBJ2-3*01 | | 659 | tgtgccagcagtactc | g ccaga ..cacagatacgcagtattc | | | | 2355 | C A S S Y S P D T D T Q Y F |
| 06.222 | TRBV06-3*01 | TRBJ2-7*01 | TRBD2*01 | 660 | tgtgccagcagtactc | ccc ..gactacgg.... ccctg ......gagcagtacttc | | | | 2356 | C A S S Y S P T S G P W E Q Y F |
| 06.223 | TRBV06-5*01 | TRBJ2-1*01 | TRBD1*01 | 661 | tgtgccagcagtactc | t ...cagggggg. ag ......aatgagcagttcttc | | | | 2357 | C A S S Y S Q G E N E Q F F |
| 06.224 | TRBV06-6*01 | TRBJ1-2*01 | TRBD1*01 | 662 | tgtgccagcagtactc | t .....cag..... ctag ctaactatgctacacctc | | | | 2358 | C A S S Y S Q L A N Y G Y T F |
| 06.225 | TRBV06-3*01 | TRBJ2-7*01 | TRBD1*01 | 663 | tgtgccagcagtactc | ccaa c gggac....... gatc ...cctacgagcagtacttc | | | | 2359 | C A S S Y S Q R D D P Y E Q Y F |
| 06.226 | TRBV06-6*01 | TRBJ2-1*01 | TRBD1*01 | 664 | tgtgccagcagtactc | gag a ..gacagg.... cc ctcctacaatgagcagttcttc | | | | 2360 | C A S S Y S R D R P S Y N E Q F |
| 06.227 | TRBV06-5*01 | TRBJ2-2*01 | | 665 | tgtgccagcagtactc | tcgtgaa ..aacaccgggagctgttttt | | | | 2361 | C A S S Y S R E N T G E L F F |
| 06.228 | TRBV06-2*01 | TRBJ2-4*01 | TRBD1*01 | 666 | tgtgccagcagtactc | aagg ....caggg... tg ....aaaacattcagtacttc | | | | 2362 | C A S S Y S R Q G E N I Q Y F |

Figure 1-25

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 06.229 | TRBV06-6*01 | TRBJ1-5*01 | TRBD1*01 | 667 | tgtgccagcagttactc | ga..gacaggg.. | tggg | ......cagcccagcattt | | 2363 | C A S S Y S R Q G G Q P Q H F |
| 06.230 | TRBV06-2*01 | TRBJ2-1*01 | TRBD2*02 | 668 | tgtgccagcagtta.. | ttctcgag.. | tagcggga.. | tt.. ..caatgagcagttcttc | | 2364 | C A S S Y S R V A G F N E Q F |
| 06.231 | TRBV06-5*01 | TRBJ2-1*01 | | 669 | tgtgccagcagttactc | tcg ..ctacaatgagcagttcttc | | | | 2365 | C A S S Y S R Y N E Q F F |
| 06.232 | TRBV06-5*01 | TRBJ1-1*01 | TRBD1*01 | 670 | tgtgccagcagttactc | g t | ......cggg.. | ......cactgaagctttctt | | 2366 | C A S S Y S S G T E A F F |
| 06.233 | TRBV06-6*01 | TRBJ2-7*01 | TRBD2*01 | 671 | tgtgccagcagttactc | tt ..ctagcg.. | ..at ag | ctcctacgagcagtactc | | 2367 | C A S S Y S S S D S S Y E Q Y F |
| 06.234 | TRBV06-5*01 | TRBJ1-2*01 | TRBD1*01 | 672 | tgtgccagcagttactc | ctcggttcc ..gacaggg.. | ttatc | ..ctatggctacacctttc | | 2368 | C A S S Y S S V P T G L S Y G Y T F |
| 06.235 | TRBV06-6*01 | TRBJ2-7*01 | TRBD1*01 | 673 | tgtgccagcagttactc | ..gacag.. | agtctcg | ......cgagcagtactc | | 2369 | C A S S Y S T E S R E Q Y F |
| 06.236 | TRBV06-5*01 | TRBJ1-6*01 | TRBD1*01 | 674 | tgtgccagcagttactc | g gta gggacag.. | ag | ......tcacccctccacttt | | 2370 | C A S S Y S V G T E S P L H F |
| 06.237 | TRBV06-7*01 | TRBJ1-5*01 | | 675 | tgtgccagcagttactc | g gtc agcaatcagcccagcattt | | | | 2371 | C A S S Y S V S N Q P Q H F |
| 06.238 | TRBV06-6*01 | TRBJ2-1*01 | TRBD2*02 | 676 | tgtgccagcagtac.. | actccacgag.. | ..tagcgggag.. | tccgg ........tgagcagttcttc | | 2372 | C A S S Y T P Q S S G R S G E Q F F |
| 06.239 | TRBV06-5*01 | TRBJ1-1*01 | TRBD1*01 | 677 | tgtgccagcagttac.. | gt ......agggg.. | | ......cactgaagctttctt | | 2373 | C A S S Y V G G T E A F F |
| 06.240 | TRBV06-3*01 | TRBJ2-5*01 | TRBD2*01 | 678 | tgtgccagcagttac.. | gta ..acta.. | .......caa ..aagagaccagtactc | | | 2374 | C A S S Y V T T K E T Q Y F |
| 06.241 | TRBV06-5*01 | TRBJ2-7*01 | TRBD2*02 | 679 | tgtgccagcagttact | .........gggaggg ggct | ..tacgagcagtactc | | | 2375 | C A S S Y W E G A Y E Q Y F |
| 06.242 | TRBV06-6*01 | TRBJ2-2*01 | TRBD2*02 | 680 | tgtgccagcagttact | at ......gggaggg aa ..accggggagctgttttt | | | | 2376 | C A S S Y Y G R E T G E L F F |
| 06.243 | TRBV06-6*01 | TRBJ2-1*01 | TRBD2*02 | 681 | tgtgccagca.. | cg ......gcggga.. | a ..cctacaatgagcagttcttc | | | 2377 | C A S T A G T Y N E Q F F |
| 06.244 | TRBV06-5*01 | TRBJ1-2*01 | TRBD2*02 | 682 | tgtgccagca.. | ctgatttttacg ......gcggggag.. | c | ......atggctacacctttc | | 2378 | C A S T D F Y G G R H G Y T F |
| 06.245 | TRBV06-1*01 | TRBJ1-1*01 | TRBD1*01 | 683 | tgtgccagca.. | ccgatccttt ..gacagg.. | catgaacactgaagcttcttt | | | 2379 | C A S T D P L T G M N T E A F F |
| 06.246 | TRBV06-6*01 | TRBJ1-5*01 | TRBD1*01 | 684 | tgtgccagca.. | ccga ..ggac.. | ccgaggg | ......agcccagcattt | | 2380 | C A S T E D P R E P Q H F |
| 06.247 | TRBV06-5*01 | TRBJ1-1*01 | TRBD1*01 | 685 | tgtgccagca.. | cccaccggggaa ......agggg.. | attctgacacttttagg.......... | tttcttt | | 2381 | C A S T H R G K G D S D T L G F F |
| 06.248 | TRBV06-5*01 | TRBJ1-2*01 | TRBD1*01 | 686 | tgtgccagca.. | ccct ..gacagg.. | t ..tatgctacacctc | | | 2382 | C A S T L T G Y G Y T F |
| 06.249 | TRBV06-5*01 | TRBJ2-1*01 | TRBD2*02 | 687 | tgtgccagca.. | coatg ..ctagccgggag.. | ttgaa.. ..accgggggagctgttttt | | | 2383 | C A S T M L A G V E T G E L F F |
| 06.250 | TRBV06-5*01 | TRBJ2-1*01 | TRBD2*01 | 688 | tgtgccagca.. | cccctctg gggactagcgg.... | c ......gagcagttcttc | | | 2384 | C A S T P L G T S G E Q F F |
| 06.251 | TRBV06-2*01 | TRBJ2-7*01 | TRBD2*02 | 689 | tgtgccagca.. | ccca ......cgggag.. | cgcccctc.. ..cgagcagtactc | | | 2385 | C A S T P R E R P S E Q Y F |
| 06.252 | TRBV06-5*01 | TRBJ2-5*01 | TRBD2*01 | 690 | tgtgccagca.. | cccgtc ......cgggg.. | cctgg.. ccaagaaccaccagtactc | | | 2386 | C A S T P S G A W Q E T Q Y F |
| 06.253 | TRBV06-2*01 | TRBJ2-2*01 | TRBD2*01 | 691 | tgtgccagca.. | cc ......cagg.. | tgggcc ......gagctgttttt | | | 2387 | C A S T Q G G A E L F F |
| 06.254 | TRBV06-5*01 | TRBJ2-3*01 | TRBD2*01 | 692 | tgtgccagca.. | cac gggact.. | ct agcacagatacagcagtatttt | | | 2388 | C A S T R D S S T D T Q Y F |
| 06.255 | TRBV06-1*01 | TRBJ1-1*01 | TRBD1*01 | 693 | tgtgccagca.. | cccgt cc gggacaggggc ttctg.. ..acactgaagcttcttt | | | | 2389 | C A S T R P G Q G A S D T E A F F |

Figure 1-26

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 06.256 | TRBV06-5*01 | TRBJ2-2*01 | | 694 | tgtgccagca | cttccgcctcc | | gggagctgttt | | 2390 | C A S T S G L R E L F F |
| 06.257 | TRBV06-6*01 | TRBJ1-1*01 | TRBD2*01 | 695 | tgtgccagca | cca | cgggg | t | tgaacactgaagcttctt | 2391 | C A S T T G L N T E A F F |
| 06.258 | TRBV06-1*01 | TRBJ2-7*01 | TRBD1*01 | 696 | tgtgccagca | ccgt | gggacaggggc | g tgg | gagcagtactc | 2392 | C A S T V G Q G A W E Q Y F |
| 06.259 | TRBV06-1*01 | TRBJ2-3*01 | TRBD2*01 | 697 | tgtgccagc | t | gggac | ccctgaacc | cagatacgcagtatttt | 2393 | C A S W D A L P D T Q Y F |
| 06.260 | TRBV06-3*01 | TRBJ1-1*01 | TRBD1*01 | 698 | tgtgcca | ctga | gggc g tttgg | tgaacactgaagcttctt | | 2394 | C A T E G R L V N T E A F F |
| 07.01 | TRBV07-3*01 | TRBJ2-3*01 | TRBD2*02 | 699 | tgtgcca | teagcatatcgc | cgggag | cccagataccoaa | tatttt | 2395 | C A I S I A G S P D T Q Y F |
| 07.02 | TRBV07-2*01 | TRBJ2-7*01 | TRBD1*01 | 700 | tgtgcc | coaaggaacc | ggacaggggg | agatctcc | acgagcagtactc | 2396 | C A P R N R T G G D L H E Q Y F |
| 07.03 | TRBV07-6*01 | TRBJ2-1*01 | TRBD1*01 | 701 | tgtgcc | tcc ggac | ggag ctcctacaatgagcagttctc | | | 2397 | C A S G R S S Y N E Q F F |
| 07.04 | TRBV07-9*01 | TRBJ2-5*01 | TRBD2*02 | 702 | tgtgccagcag | gttc | gaggg cgg | agagaccagtactc | | 2398 | C A S R F E G G E T Q Y F |
| 07.05 | TRBV07-9*01 | TRBJ2-2*01 | TRBD1*01 | 703 | tgtgccagcag | a | ggacaggg | gaacaaccgggagctgtttt | | 2399 | C A S R G Q G N T G E L F F |
| 07.06 | TRBV07-9*01 | TRBJ2-5*01 | TRBD2*02 | 704 | tgtgccagcag | aac | cggga | actag | gagaccccagtactc | 2400 | C A S R T G N W E T Q Y F |
| 07.07 | TRBV07-8*01 | TRBJ2-7*01 | TRBD1*01 | 705 | tgtgccagcagc | g | agggggc g g | cctacgagcagtactc | | 2401 | C A S S E G A A Y E Q Y F |
| 07.08 | TRBV07-3*01 | TRBJ2-1*01 | TRBD2*01 | 706 | tgtgccagcagctt | c | ctagcgggg | ttttg | aatgagcagttcttc | 2402 | C A S S F L A G V L N E Q F F |
| 07.09 | TRBV07-3*01 | TRBJ2-1*01 | | 707 | tgtgccagcagctt | tatgcc gag ctcctacaatgagcagttcttc | | | | 2403 | C A S S F M A S S Y N E Q F F |
| 07.10 | TRBV07-3*01 | TRBJ2-2*01 | TRBD2*02 | 708 | tgtgccagcagctt | caa | cgggag | a | accgggagctgtttt | 2404 | C A S S F N G R T G E L F F |
| 07.11 | TRBV07-9*01 | TRBJ2-2*01 | TRBD1*01 | 709 | tgtgccagcagctt | cc | gacagg | cagtg | acaccgggagctgtttt | 2405 | C A S S F R Q G S D T G E L F F |
| 07.12 | TRBV07-6*01 | TRBJ2-3*01 | TRBD1*01 | 710 | tgtgccagcagc | gggg tgttggtt | gatacgcagtattt | | | 2406 | C A S S G V L V D T Q Y F |
| 07.13 | TRBV07-3*01 | TRBJ2-3*01 | TRBD2*02 | 711 | tgtgccagcagc | ca | cgggggg | t | cagatacgcagtattt | 2407 | C A S S H G G S D T Q Y F |
| 07.14 | TRBV07-3*01 | TRBJ2-1*01 | TRBD2*02 | 712 | tgtgccagcagc | caca | tagccggaggg | tcctacaatgagcagttcttc | | 2408 | C A S S H I A G G S Y N E Q F F |
| 07.15 | TRBV07-9*03 | TRBJ1-2*01 | TRBD2*01 | 713 | tgtgccagcagc | t | tagccggg | cgggcac | ggctacacctc | 2409 | C A S S L A G G H G Y T F |
| 07.16 | TRBV07-2*02 | TRBJ2-7*01 | TRBD2*01 | 714 | tgtgccagcagctagc | gcta | gggggg | cca | gagcagtactc | 2410 | C A S S L A L G G P E Q Y F |
| 07.17 | TRBV07-6*01 | TRBJ2-3*01 | TRBD2*02 | 715 | tgtgccagcagcttag | g tt | gggactagcgggaggg | cc | cacagatacgcagtattt | 2411 | C A S S L A L G L A G G P T D T Q Y F |
| 07.18 | TRBV07-9*01 | TRBJ2-1*01 | TRBD1*01 | 716 | tgtgccagcagcttagc | ctc | ggacagg | ccccgag | aatgagcagttcttc | 2412 | C A S S L A S D R A P E N E Q F F |
| 07.19 | TRBV07-6*01 | TRBJ1-2*01 | TRBD1*01 | 717 | tgtgccagcagctag | ac | ggggg | aggaggg | ggctacacctc | 2413 | C A S S L D G G G G G Y T F |
| 07.20 | TRBV07-3*01 | TRBJ2-3*01 | TRBD2*02 | 718 | tgtgccagcagctta | gacgg | gcggga | tgt | agatacgcagtattt | 2414 | C A S S L D G R D V D T Q Y F |
| 07.21 | TRBV07-9*01 | TRBJ2-5*01 | | 719 | tgtgccagcagcttag | atccg | caagagacccagtactc | | | 2415 | C A S S L D P Q E T Q Y F |
| 07.22 | TRBV07-9*01 | TRBJ2-2*01 | TRBD1*01 | 720 | tgtgccagcagctag | acag | a | aacaccgggagctgtttt | | 2416 | C A S S L D R N T G E L F F |

Figure 1-27

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 07.23 | TRBV07-2*02 | TRBJ2-3*01 | TRBD2*01 | 721 | tgtgccagcagcttag. | accggt. | ggga. | tgggagcaacagatacgcagtatttt | | 2417 | C A S S L D R W D G S T D T Q Y F |
| 07.24 | TRBV07-9*01 | TRBJ1-5*01 | | 722 | tgtgccagcagcttag. | actgg. | ...aatcagcccagcattt | | | 2418 | C A S S L D W N Q P Q H F |
| 07.25 | TRBV07-9*01 | TRBJ2-1*01 | TRBD2*01 | 723 | tgtgccagcagcttag. | a | gga. | ctcctacaatgagcagttctc | | 2419 | C A S S L E D S Y N E Q F F |
| 07.26 | TRBV07-9*01 | TRBJ2-5*01 | TRBD2*01 | 724 | tgtgccagcagcttag. | a | ...acta. | atcgttg. | ..aagagaccagtactc | 2420 | C A S S L E L I V E E T Q Y F |
| 07.27 | TRBV07-9*01 | TRBJ2-5*01 | TRBD2*01 | 725 | tgtgccagcagcttag. | a | ...acta. | agcgttg. | ...aagagaccagtactc | 2421 | C A S S L E L S V E E T Q Y F |
| 07.28 | TRBV07-2*03 | TRBJ2-7*01 | | 726 | tgt. | gccagcagcttagaaagtgcgttgga. | ...ctacgagcagtactc | | | 2422 | C A S S L E V A L D Y E Q Y F |
| 07.29 | TRBV07-6*01 | TRBJ2-3*01 | TRBD2*02 | 727 | tgtgccagcagcta. | ttt. | ...gcggag. | ...cagatacgcagtatttt | | 2423 | C A S S L F A G A D T Q Y F |
| 07.30 | TRBV07-2*03 | TRBJ2-1*01 | TRBD2*01 | 728 | tgt. | gccagcagcctcttcc. | ...ctagcg. | a | ...ctacaatgagcagttctc | 2424 | C A S S L F P S D Y N E Q F F |
| 07.31 | TRBV07-6*01 | TRBJ1-4*01 | TRBD2*01 | 729 | tgtgccagcagctt. | gggggg gg. | ...tgaaaaactgtttt | | | 2425 | C A S S L G G G E K L F F |
| 07.32 | TRBV07-9*01 | TRBJ2-1*01 | TRBD2*01 | 730 | tgtgccagcagcta. | ...ggggg. | ...aatgagcagttctc | | | 2426 | C A S S L G G N E Q F F |
| 07.33 | TRBV07-9*01 | TRBJ1-1*01 | TRBD1*01 | 731 | tgtgccagcagc. | ctt. | ...ggggg. | ...cactgaagcttcttt | | 2427 | C A S S L G G T E A F F |
| 07.34 | TRBV07-8*01 | TRBJ2-7*01 | TRBD1*01 | 732 | tgtgccagcagctt. | gggacagggggc. | ca | ...acgagcagtactc | | 2428 | C A S S L G Q G A N E Q Y F |
| 07.35 | TRBV07-9*01 | TRBJ1-2*01 | TRBD1*01 | 733 | tgtgccagcagcttag. | ggcgtga. | .gacagggg. | aagt. | ...ctatgctgcacctc | 2429 | C A S S L G R E T G E V Y G Y T F |
| 07.36 | TRBV07-9*01 | TRBJ2-1*01 | TRBD2*01 | 734 | tgtgccagcagctt. | g | gggactagcg. | | ...atgagcagttctc | 2430 | C A S S L G T S D E Q F F |
| 07.37 | TRBV07-2*03 | TRBJ2-7*01 | TRBD1*01 | 735 | tgt. | gccagcagctt. | ...aggg. | tacgtcag. | ...cgagcagtactc | 2431 | C A S S L G Y V S E Q Y F |
| 07.38 | TRBV07-9*01 | TRBJ2-1*01 | TRBD1*01 | 736 | tgtgccagcagctta. | att. | ...ggggg. | tttcggt. | .ctacaatgagcagttctc | 2432 | C A S S L I G V S V Y N E Q F F |
| 07.39 | TRBV07-2*02 | TRBJ1-1*01 | TRBD1*01 | 737 | tgtgccagcagctta. | aaagtact. | ggga. | | ...gaagctttttt | 2433 | C A S S L K V L G E A F F |
| 07.40 | TRBV07-2*01 | TRBJ1-3*01 | TRBD1*01 | 738 | tgtgccagcagctta. | cto. | ...ggggg. | atac. | ...ggaaacaccatatttt | 2434 | C A S S L L G G Y G N T I Y F |
| 07.41 | TRBV07-9*01 | TRBJ2-3*01 | TRBD2*02 | 739 | tgtgccagcagctt. | gatggagt. | ...cggga. | ttgggggag. | ...agatacgcagtatttt | 2435 | C A S S L M E S G L V G R D T Q Y F |
| 07.42 | TRBV07-9*01 | TRBJ2-1*01 | TRBD2*01 | 740 | tgtgccagcagcta. | atgggc. | ggac. | | ...atgagcagttctc | 2436 | C A S S L M G G H E Q F F |
| 07.43 | TRBV07-2*03 | TRBJ1-4*01 | TRBD1*01 | 741 | tgt. | gccagcagcttaatggg. | gggacagg. | c | ...aatgaaaaactgtttt | 2437 | C A S S L M G G T G N E K L F F |
| 07.44 | TRBV07-2*01 | TRBJ2-5*01 | TRBD2*01 | 742 | tgtgccagcagcttaa. | aat cc gggactagcg. | | ...aagagaccagtactc | | 2438 | C A S S L N P G L A E E T Q Y F |
| 07.45 | TRBV07-9*01 | TRBJ2-1*01 | TRBD1*01 | 743 | tgtgccagcagcttaa. | accccctcgcccg. | c gggacag. | | ...acaatgagcagttctc | 2439 | C A S S L N P L A R G T D N E Q F F |
| 07.46 | TRBV07-3*01 | TRBJ2-3*01 | TRBD2*01 | 744 | tgtgccagcagcttaa. | gaggtt. | .ggactagcg. | a | ..cacagatacgcagtatttt | 2440 | C A S S L R G W T S D T D T Q Y F |
| 07.47 | TRBV07-3*01 | TRBJ2-6*01 | TRBD2*01 | 745 | tgtgccagcagcttaa. | gt. | ...gcgg. | ...ctggggccaacgtcctgacttc | | 2441 | C A S S L S A A G A N V L T F |
| 07.48 | TRBV07-3*01 | TRBJ2-3*01 | TRBD2*02 | 746 | tgtgccagcagcta. | tccgc. | ...cgggag. | cc. | ...cagatacgcagtatttt | 2442 | C A S S L S A G S P D T Q Y F |
| 07.49 | TRBV07-3*01 | TRBJ2-1*01 | TRBD2*02 | 747 | tgtgccagcagctta. | g. | ...tagcgggag. | cattg. | ...atgagcagttctc | 2443 | C A S S L S S G S I D E Q F F |
| 07.50 | TRBV07-2*03 | TRBJ2-3*01 | TRBD2*02 | 748 | tgt. | gccagcagctgacgg. | ...gcgggaggg. | | ...cagatacgcgcagtatttt | 2444 | C A S S L T G G R A D T Q Y F |

Figure 1-28

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 07.51 | TRBV07-3*01 | TRBJ2-7*01 | TRBD1*01 | 749 | tgtgccagcagcttaac | a | gggacagg | agtg | tacgagcagtacttc | 2445 | C A S S L T G T G V Y E Q Y F |
| 07.52 | TRBV07-3*01 | TRBJ2-1*01 | TRBD2*02 | 750 | tgtgccagcagctt | gactagcgggag | ctcctacaatgagcagttctc | | | 2446 | C A S S L T S G S S Y N E Q F F |
| 07.53 | TRBV07-9*01 | TRBJ2-7*01 | TRBD2*01 | 751 | tgtgccagcagcttag | tag | acggaa | cctacgagcagtactc | | 2447 | C A S S L V D G T Y E Q Y F |
| 07.54 | TRBV07-8*01 | TRBJ2-7*01 | TRBD2*02 | 752 | tgtgccagcagcttag | ttcctcct | ggactagcgggag | tcgaagga | tacgagcagtactc | 2448 | C A S S L V P P G L A G V E G Y E Q Y F |
| 07.55 | TRBV07-9*01 | TRBJ2-5*01 | TRBD1*01 | 753 | tgtgccagcagcttag | tt | cagg | c | ccaagagaccagtactc | 2449 | C A S S L V Q A Q E T Q Y F |
| 07.56 | TRBV07-9*01 | TRBJ2-2*01 | TRBD1*01 | 754 | tgtgccagcagctta | tggga | gacaggg | aaatcgac | caccgggagctgttttt | 2450 | C A S S L W E T G K S T T G E L F F |
| 07.57 | TRBV07-9*01 | TRBJ2-2*01 | TRBD2*02 | 755 | tgtgccagcagctta | tactttgt | ggactagcggga | c | ccggggagctgtttt | 2451 | C A S S L Y F G G L A G P G E L F F |
| 07.58 | TRBV07-8*01 | TRBJ2-7*01 | TRBD2*01 | 756 | tgtgccagcagc | at | gggactagcgg | agaccta | tacgagcagtactc | 2452 | C A S S M G L A E T L Y E Q Y F |
| 07.59 | TRBV07-3*01 | TRBJ2-1*01 | TRBD1*01 | 757 | tgtgccagcagc | cccgaccccat | agggg | atcc | acgagcagttctc | 2453 | C A S S P D P H R G I H E Q F F |
| 07.60 | TRBV07-2*03 | TRBJ2-1*01 | | 758 | tgt | gccagcagccga | ctacacagcagttctc | | | 2454 | C A S S P D Y N E Q F F |
| 07.61 | TRBV07-9*01 | TRBJ2-1*01 | TRBD2*02 | 759 | tgtgccagcagc | ccc | gggactagccgggaggg | t | caatgagcagttctc | 2455 | C A S S P G T S G R V N E Q F F |
| 07.62 | TRBV07-2*03 | TRBJ1-3*01 | | 760 | tgt | gccagcagccaattgggtctgag | tctggaaacaccatatatt | | | 2456 | C A S S P I G S E S G N T I Y F |
| 07.63 | TRBV07-9*01 | TRBJ2-1*01 | TRBD1*01 | 761 | tgtgccagcagc | cccggg | caggggc | g atat | caatgagcagttctc | 2457 | C A S S P R A G G D I N E Q F F |
| 07.64 | TRBV07-9*01 | TRBJ2-7*01 | TRBD2*02 | 762 | tgtgccagcagc | cct | cggga | gaacaccgggagcgtttt | | 2458 | C A S S P R E N T G E L F F |
| 07.65 | TRBV07-9*01 | TRBJ2-1*01 | TRBD2*01 | 763 | tgtgccagcagc | cca | cgggg | a | acgagcagtactc | 2459 | C A S S P R G N E Q Y F |
| 07.66 | TRBV07-2*03 | TRBJ2-7*01 | TRBD2*01 | 764 | tgt | gccagcagccc | ggactagcg | agtg | gttcttc | 2460 | C A S S P R T S E W F F |
| 07.67 | TRBV07-2*02 | TRBJ2-2*01 | TRBD2*01 | 765 | tgtgccagcagc | ccaa | ggact | | acggggagctgtttt | 2461 | C A S S P R T T G E L F F |
| 07.68 | TRBV07-9*01 | TRBJ2-2*01 | TRBD1*01 | 766 | tgtgccagcagc | cc | gacagggc | gcagg | cgggggagctgtttt | 2462 | C A S S P T G G A G G E L F F |
| 07.69 | TRBV07-3*01 | TRBJ2-1*01 | TRBD1*01 | 767 | tgtgccagcagc | cccta ccc gggaca | aaa | ctacaatgagcagttctc | | 2463 | C A S S P Y P G Q N Y N E Q F F |
| 07.70 | TRBV07-3*01 | TRBJ2-1*01 | TRBD2*01 | 768 | tgtgccagcagc | ccgtataggt | cta | ata | acaatgagcagttctc | 2464 | C A S S P Y R S N N N E Q F F |
| 07.71 | TRBV07-9*01 | TRBJ2-6*01 | TRBD1*01 | 769 | tgtgccagcagc | caggg | tccc | ctggggccaacgtcctgacttc | | 2465 | C A S S Q G P P G A N V L T F |
| 07.72 | TRBV07-9*01 | TRBJ2-7*01 | | 770 | tgtgccagcagc | cgtgatctccc ctctacgagcagtactc | | | | 2466 | C A S S R D L P S Y E Q Y F |
| 07.73 | TRBV07-9*01 | TRBJ2-3*01 | | 771 | tgtgccagcagc | cgtcccg | gcacagatacgcagtttt | | | 2467 | C A S S R P G T D T Q Y F |
| 07.74 | TRBV07-8*01 | TRBJ1-2*01 | TRBD1*01 | 772 | tgtgccagcagc | cggactatacgtact | cc gggacag | ctaactatgctacacctc | | 2468 | C A S S R T Y T Y S G T A N Y G Y T F |
| 07.75 | TRBV07-2*03 | TRBJ2-7*01 | TRBD1*01 | 773 | tgt | gccagcagcagat gggacag | c ag ctcctacgagcagtactc | | | 2469 | C A S S R W D S S Y E Q Y F |
| 07.76 | TRBV07-6*01 | TRBJ2-5*01 | TRBD2*02 | 774 | tgtgccagcagct | ccga | agcgggag | ca caagagaccagtactc | | 2470 | C A S S E A G A Q E T Q Y F |
| 07.77 | TRBV07-9*01 | TRBJ1-1*01 | | 775 | tgtgccagcagct | ccgag a tgaacactgaagcttctt | | | | 2471 | C A S S E M N T E A F F |
| 07.78 | TRBV07-7*01 | TRBJ2-2*01 | TRBD2*01 | 776 | tgtgc | tagc | agcagcggagat | gaacaccgggagctgtttt | | 2472 | C A S S E M N T G E L F F |

Figure 1-29

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 07.79 | TRBV07-9*01 | TRBJ2-7*01 | TRBD2*02 | 777 | tgtgccagcagct... | ct..ggactagcggagg. | tgc.gag | ctccacgagcagtacttc | | 2473 | C A S S G L A G G A S S Y E Q Y F |
| 07.80 | TRBV07-2*03 | TRBJ2-1*01 | TRBD2*01 | 778 | tgt... | ...gccagcagctc | ....cggg.. | tcctacaatgagcagttctc | | 2474 | C A S S G S Y N E Q F F |
| 07.81 | TRBV07-9*01 | TRBJ2-1*01 | TRBD2*01 | 779 | tgtgccagcagct... | caatta..gactagc....... | cg ... | acaatgagcagttcttc | | 2475 | C A S S I R L A D N E Q F F |
| 07.82 | TRBV07-9*01 | TRBJ1-2*01 | | 780 | tgtgccagcagct... | ccctattatc ... | ctatgctacacttc | | | 2476 | C A S S L L S Y G Y T F |
| 07.83 | TRBV07-9*01 | TRBJ1-2*01 | TRBD1*01 | 781 | tgtgccagcagct... | caaact.ggga.. | ......to..acatgctacacctc | | | 2477 | C A S S N W D H Y G Y T F |
| 07.84 | TRBV07-3*01 | TRBJ2-2*01 | TRBD1*01 | 782 | tgtgccagcagc... | agct.cc.gggacaggg... | t ... | acaccgggagctgtttt | | 2478 | C A S S G T G Y T G E L F F |
| 07.85 | TRBV07-9*01 | TRBJ2-7*01 | TRBD2*01 | 783 | tgtgccagcagct... | cc...actagcgggg.. | ctcctacgagcagtactc | | | 2479 | C A S S T S G G S Y E Q Y F |
| 07.86 | TRBV07-8*01 | TRBJ2-3*01 | | 784 | tgtgccagcagct... | catacgacg. | ...cagatacgcagtattt | | | 2480 | C A S S Y D A D T Q Y F |
| 07.87 | TRBV07-9*01 | TRBJ2-1*01 | TRBD2*01 | 785 | tgtgccagcag... | ta.cc.gggactagcg... | ..at... | tacaatgagcagttctc | | 2481 | C A S S T G T S D Y N E Q F F |
| 07.88 | TRBV07-2*02 | TRBJ2-1*01 | TRBD2*02 | 786 | tgtgccagcagct... | gggcgg. | .....agcgggaggg..ggct..... | ..atgagcagttcttc | | 2482 | C A S S W G G A G G G Y E Q F F |
| 07.89 | TRBV07-6*01 | TRBJ1-3*01 | TRBD1*01 | 787 | tgtgccagcagct... | g.gggact... | gaa.ctctgaaacacatatattt | | | 2483 | C A S S W G L N S G N T I Y F |
| 07.90 | TRBV07-9*01 | TRBJ2-1*01 | TRBD2*01 | 788 | tgtgccagcagct... | accct ...acaggg... | tcctacaatgagcagttctc | | | 2484 | C A S S Y P T G S Y N E Q F F |
| 07.91 | TRBV07-9*01 | TRBJ2-1*01 | TRBD1*01 | 789 | tgt gcc agc acc gaa ctt acg gga ccc cgg gca aac gag ttc ttc | | | | | 2485 | C A S T E L T G P R A N E Q F F |
| 07.92 | TRBV07-3*01 | TRBJ2-1*01 | TRBD2*02 | 790 | tgtgccagca... | .....cct ...tagcggaggg..gt | .....caatgagcagttctc | | | 2486 | C A S T L A G G V N E Q F F |
| 09.01 | TRBV09*01 | TRBJ1-2*01 | TRBD1*01 | 791 | tgtgccagcagcg... | cc.gggac... | g.g.ctaactatgctacacctc | | | 2487 | C A S S A G T A N Y G Y T F |
| 09.02 | TRBV09*01 | TRBJ1-2*01 | TRBD1*01 | 792 | tgtgccagcagcg... | .....caggg... | tatcgcgg | ....ggctacacctc | | 2488 | C A S S A G V S R G Y T F |
| 09.03 | TRBV09*01 | TRBJ2-3*01 | TRBD1*01 | 793 | tgtgccagcagcg... | cccacca.gggactag... | atcttgg... | agatacgcagtatttt | | 2489 | C A S S A H Q G L D L G D T Q Y F |
| 09.04 | TRBV09*01 | TRBJ2-3*01 | TRBD2*02 | 794 | tgtgccagcagcg... | ccctcac..... | ..cggga.. | accc ..cacagatacgcagtattt | | 2490 | C A S S A L T G N P T D T Q Y F |
| 09.05 | TRBV09*01 | TRBJ1-1*01 | TRBD1*01 | 795 | tgtgccagcagcg... | ctt cc.gggacag... | c ... | gaacactgaagcttctt | | 2491 | C A S S A S G T A N T E A F F |
| 09.06 | TRBV09*01 | TRBJ1-1*01 | TRBD2*01 | 796 | tgtgccagcagcg... | cctcacagg.. | ...gcggggg... | cactgaagcttctt | | 2492 | C A S S A S Q G G G T E A F F |
| 09.07 | TRBV09*01 | TRBJ1-1*01 | TRBD1*01 | 797 | tgtgccagcagcg... | cca.cc.gggac.. | ......tggagg | ...cactgaagcagtactc | | 2493 | C A S S A T G T G G T E A F F |
| 09.08 | TRBV09*01 | TRBJ2-7*01 | TRBD1*01 | 798 | tgtgccagcagcg... | c..gactagcgg... | cgacct..ctacgagcagtactc | | | 2494 | C A S S A T S G D L Y E Q Y F |
| 09.09 | TRBV09*01 | TRBJ2-7*01 | TRBD1*01 | 799 | tgtgccagcagcg... | ccacta cc.gggaca... | ...att ... | tacgagcagtactc | | 2495 | C A S S A T T G T I Y E Q Y F |
| 09.10 | TRBV09*01 | TRBJ1-1*01 | TRBD1*01 | 800 | tgtgccagcagcg... | catat ..ggacagg... | ...cactgaagcttctt | | | 2496 | C A S S A Y G Q G T E A F F |
| 09.11 | TRBV09*01 | TRBJ2-5*01 | TRBD1*01 | 801 | tgtgccagcagcg... | cctatcctgaa.ggacagg... | ccaaga ... | ....ccagtacttc | | 2497 | C A S S A Y P E G T G Q D Q Y F |
| 09.12 | TRBV09*01 | TRBJ2-3*01 | TRBD2*01 | 802 | tgtgccagcagcg... | a c.gggactagccg... | aagaggg ... | gatacgcagtatttt | | 2498 | C A S S D G T S G R G D T Q Y F |
| 09.13 | TRBV09*01 | TRBJ2-6*01 | TRBD2*01 | 803 | tgtgccagcg... | agca.. | ....cgggg... | ctggggccaactgctgacttc | | 2499 | C A S S E H G A G A N V L T F |

Figure 1-30

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 09.14 | TRBV09*01 | TRBJ2-3*01 | TRBD2*01 | 804 | tgtgccagcagcg... | aat cc | gggacta... | c | ...cacagatacgcagtattt | 2500 | C A S S E S G T T T D T Q Y F |
| 09.15 | TRBV09*01 | TRBJ2-3*01 | TRBD1*01 | 805 | tgtgccagcagcg... | aat .ggacag.... | ct agcacagatacgcagtattt | | | 2501 | C A S S E W T A S T D T Q Y F |
| 09.16 | TRBV09*01 | TRBJ1-4*01 | TRBD1*01 | 806 | tgtgccagcagcg... | agt ...acaggg. | agtgggg ......gaaaaactgttttt | | | 2502 | C A S S E Y R G V G E K L F F |
| 09.17 | TRBV09*01 | TRBJ2-7*01 | TRBD2*01 | 807 | tgtgccagcagc.... | ttc .ggactag... | ...ngggaccccagcctacnagcan | ...........tactc | | 2503 | C A S S F G L G G P P A Y E H Y F |
| 09.18 | TRBV09*01 | TRBJ1-4*01 | TRBD1*01 | 808 | tgtgccagcagcg... | gggatt ...caggg.. | taacag.........aactgttttt | | | 2504 | C A S S G D S G V T E L F F |
| 09.19 | TRBV09*01 | TRBJ2-7*01 | | 809 | tgtgccagcagcg... | gaga ctcctacgagcagttcttc | | | | 2505 | C A S S G D S Y E Q Y F |
| 09.20 | TRBV09*01 | TRBJ2-7*01 | TRBD1*01 | 810 | tgtgccagcagcg... | gcgaa .gacag... | ctcctacgagcagttcttc | | | 2506 | C A S S G E D S S Y E Q Y F |
| 09.21 | TRBV09*01 | TRBJ2-7*01 | TRBD2*01 | 811 | tgtgccagcagcg... | gggggg ... | agcgga... | ta .cctacgagcagttcttc | | 2507 | C A S S G G E R G T Y E Q Y F |
| 09.22 | TRBV09*01 | TRBJ2-6*01 | TRBD1*01 | 812 | tgtgccagcagcg... | ...gacagggg... | ttat ctctgggccaactgcctgacttc | | | 2508 | C A S S G Q G V I S G A N V L T F |
| 09.23 | TRBV09*01 | TRBJ2-5*01 | TRBD2*01 | 813 | tgtgccagcagcg... | gtt ...ctagcgggg.. | t ....gagaccagtactc | | | 2509 | C A S S G S S G G E T Q Y F |
| 09.24 | TRBV09*01 | TRBJ2-3*01 | TRBD1*01 | 814 | tgtgccagcagc.... | ttaga ...agggg.. | tatc ..cacagatacgcagtattt | | | 2510 | C A S S L E G V S T D T Q Y F |
| 09.25 | TRBV09*01 | TRBJ1-6*01 | TRBD1*01 | 815 | tgtgccagcagc.... | ttaggag c gggacagg... | aa ........taccccctccacttt | | | 2511 | C A S S L G A G Q E S P L H F |
| 09.26 | TRBV09*01 | TRBJ2-3*01 | TRBD1*01 | 816 | tgtgccagcagc.... | tta .....ggggc t | agcacagatacgcagtattt | | | 2512 | C A S S L G A S T D T Q Y F |
| 09.27 | TRBV09*01 | TRBJ1-5*01 | TRBD1*01 | 817 | tgtgccagcagc.... | ctcg gggac..... | ggatt ...caatcagccccagcattt | | | 2513 | C A S S L G D G F N Q P Q H F |
| 09.28 | TRBV09*01 | TRBJ2-7*01 | TRBD2*01 | 818 | tgtgccagcagc.... | tt gggactag..... | ggggatcccccagcctactac... | ......cagtactc | | 2514 | C A S S L G L G G S P A Y Y Q Y F |
| 09.29 | TRBV09*01 | TRBJ1-5*01 | TRBD2*01 | 819 | tgtgccagcagc.... | ct c gggaca..... | aac agcaatcagcccccagcagtcttc | | | 2515 | C A S S L G T N S N Q P Q H F |
| 09.30 | TRBV09*01 | TRBJ2-1*01 | TRBD1*01 | 820 | tgtgccagcagc.... | ct ..acaggggg... | g ctcctacaatgagcagttctc | | | 2516 | C A S S L Q G G S Y N E Q F F |
| 09.31 | TRBV09*01 | TRBJ2-2*01 | TRBD2*01 | 821 | tgtgccagcagc.... | ctccgggg..... | tagcgggg... | tcg ....ccggggagctgtttt | | 2517 | C A S S L R G S G V A G E L F |
| 09.32 | TRBV09*01 | TRBJ2-7*01 | TRBD1*01 | 822 | tgtgccagcagc.... | cc gggacaggg... | ctcctacgagcagtactc | | | 2518 | C A S S P G Q G S Y E Q Y F |
| 09.33 | TRBV09*01 | TRBJ1-5*01 | | 823 | tgtgccagcagc.... | ccccattggtctgt | ......tcagcccccagcattt | | | 2519 | C A S S P H W S V Q P Q H F |
| 09.34 | TRBV09*01 | TRBJ2-1*01 | | 824 | tgtgccagcagc.... | cccccctgccgtcc ctcctacaatgagcagttcttc | | | | 2520 | C A S S P P A G P S Y N E Q F F |
| 09.35 | TRBV09*01 | TRBJ2-1*01 | TRBD2*01 | 825 | tgtgccagcagc.... | ccaca .....acg..... | agt .tcctacaatgagcagttcttc | | | 2521 | C A S S P Q A S S Y N E Q F F |
| 09.36 | TRBV09*01 | TRBJ1-5*01 | TRBD1*01 | 826 | tgtgccagcagc.... | cccac .ggacag.... | cgg .....atcagcccccagcattt | | | 2522 | C A S S P T D R A D Q P Q H F |
| 09.37 | TRBV09*01 | TRBJ2-1*01 | TRBD2*01 | 827 | tgtgccagcagc.... | c .......gcgg..... | a tgaacactgaagcttctt | | | 2523 | C A S S R G M N T E A F F |
| 09.38 | TRBV09*01 | TRBJ2-5*01 | TRBD1*01 | 828 | tgtgccagcag..... | tcgtt .ggac..... | cgctcc ..ccaagagaccagtactc | | | 2524 | C A S S R W T A P Q E T Q Y F |
| 09.39 | TRBV09*01 | TRBJ2-1*01 | TRBD2*02 | 829 | tgtgccacag...... | tctaa .....agcggagg... | Ctcctacaatgagcagttcttc | | | 2525 | C A S S S K A G G S Y N E Q F F |
| 09.40 | TRBV09*01 | TRBJ2-5*01 | TRBD2*01 | 830 | tgtgccagcagc.... | tccc .......gcggggagg | gg ..caagagaccagtactc | | | 2526 | C A S S S R G R G Q E T Q Y F |
| 09.41 | TRBV09*01 | TRBJ2-1*01 | TRBD2*01 | 831 | tgtgccagcagc.... | ag .....tagcggggg. | cgga ....aatgagcagttcttc | | | 2527 | C A S S S R G R G G G N E Q F F |

Figure 1-31

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 09.42 | TRBV09*01 | TRBJ2-2*01 | TRBD1*01 | 832 | tgtgccagcagcgtag | cagg | ...t | ...cggggagctgtttt | | 2528 | C A S S V A G S G E L F F |
| 09.43 | TRBV09*01 | TRBJ1-1*01 | TRBD1*01 | 833 | tgtgccagcagcgtag | ct t | ...acaggg... | cgg.......tgaagctttctt | | 2529 | C A S S V A Y R G G E A F F |
| 09.44 | TRBV09*01 | TRBJ1-2*01 | | 834 | tgtgccagcagcgtag | atg | ...agggg... | acccc.......ctacacctc | | 2530 | C A S S V D E G T P Y T F |
| 09.45 | TRBV09*01 | TRBJ2-7*01 | TRBD1*01 | 835 | tgtgccagcagcgtag | atg | ...gggggc attc | ctcctacgagcagtactc | | 2531 | C A S S V D G G H S S Y E Q Y F |
| 09.46 | TRBV09*01 | TRBJ1-5*01 | TRBD2*02 | 836 | tgtgccagcagcgtag | a | ...cggga... | a tagcaatcagcccagcagatttt | | 2532 | C A S S V D G N S N Q P Q H F |
| 09.47 | TRBV09*01 | TRBJ2-1*01 | TRBD2*01 | 837 | tgtgccagcagcgtag | accttgtg | ggga......... | ...acaatgagcagttcttc | | 2533 | C A S S V D L V G N N E Q F F |
| 09.48 | TRBV09*02 | TRBJ2-1*01 | TRBD2*01 | 838 | tgtgccagcagcgtag | ac | ...agcgggg... | aa ...tacaatgagcagttcttc | | 2534 | C A S S V D S G E Y N E Q F F |
| 09.49 | TRBV09*01 | TRBJ2-1*01 | TRBD1*01 | 839 | tgtgccagcagcgtag | agg | ...ctagcgg... | ...ctacaatgagcagttcttc | | 2535 | C A S S V E A S G Y N E Q F F |
| 09.50 | TRBV09*01 | TRBJ2-3*01 | TRBD1*01 | 840 | tgtgccagcagcgtag | a | ......gggc agg | agcacagatacgcagtattt | | 2536 | C A S S V E G R S T D T Q Y F |
| 09.51 | TRBV09*01 | TRBJ2-1*01 | TRBD1*01 | 841 | tgtgccagcagcgtag | agtat | ....agggg... | ......aatgagcagttcttc | | 2537 | C A S S V E Y R G N E Q F F |
| 09.52 | TRBV09*01 | TRBJ2-1*01 | TRBD1*01 | 842 | tgtgccagcagcgtag | | ...gggc atttgacgg | ....tgagcagttcttc | | 2538 | C A S S V G A F D G E Q F F |
| 09.53 | TRBV09*01 | TRBJ2-4*01 | TRBD1*01 | 843 | tgtgccagcagcgtag | gg | ......gcggg... | agccaaaaacattcagtactc | | 2539 | C A S S V G A G A K N I Q Y F |
| 09.54 | TRBV09*01 | TRBJ2-1*01 | TRBD2*02 | 844 | tgtgccagcagcgtag | g | ...agcgggaggg cc | ...caatgagcagttcttc | | 2540 | C A S S V G A G G P N E Q F F |
| 09.55 | TRBV09*01 | TRBJ2-5*01 | TRBD2*01 | 845 | tgtgccagcagcgt. | t | ......ggggg... | ......agagaccagtactc | | 2541 | C A S S V G G E T Q Y F |
| 09.56 | TRBV09*01 | TRBJ2-1*01 | TRBD2*02 | 846 | tgtgccagcagcgtag | ga | ......ggaggg c tgg | ....acaatgagcagttcttc | | 2542 | C A S S V G G G L D N E Q F F |
| 09.57 | TRBV09*01 | TRBJ2-3*01 | TRBD1*01 | 847 | tgtgccagcagcgtag | | ......ggggc aggg | gcacagatacgcagtattt | | 2543 | C A S S V G G R G T D T Q Y F |
| 09.58 | TRBV09*01 | TRBJ2-1*01 | TRBD2*02 | 848 | tgtgccagcagcgtag | | ...gccggag... cg | ...cctacaatgagcagttcttc | | 2544 | C A S S V G G S A Y N E Q F F |
| 09.59 | TRBV09*01 | TRBJ2-6*01 | TRBD2*02 | 849 | tgtgccagcagcgtag | ggcat ggg | ............ | ...tctggggcaacgtcctgactttt | | 2545 | C A S S V G H G S G A N V L T F |
| 09.60 | TRBV09*01 | TRBJ2-2*01 | TRBD1*01 | 850 | tgtgccagcagcgt. | gggaca..... | cctcctg | ....accgggggagctgtttt | | 2546 | C A S S V G H L L T G E L F F |
| 09.61 | TRBV09*01 | TRBJ2-7*01 | TRBD2*02 | 851 | tgtgccagcagcgt. | c | ...ggactagcggga... | cccccag ...cctacgagcagtactc | | 2547 | C A S S V G L A G P P A Y E Q Y F |
| 09.62 | TRBV09*01 | TRBJ2-7*01 | TRBD2*02 | 852 | tgtgccagcagcgt. | c | ...ggactagcggga... | ccccccagcctacgt.......gcagtactc | | 2548 | C A S S V G L A G P P A Y V Q Y F |
| 09.63 | TRBV09*01 | TRBJ2-7*01 | TRBD2*01 | 853 | tgtgccagcagcgt. | c | ...ggacta...... | ccggaccccag ...cctacgagcagtactc | | 2549 | C A S S V G L P G P P A Y E Q Y F |
| 09.64 | TRBV09*01 | TRBJ2-5*01 | TRBD2*02 | 854 | tgtgccagcagcgtag | gcaa | ...tagcggga... | ...aagagaccagtactc | | 2550 | C A S S V G N S G K E T Q Y F |
| 09.65 | TRBV09*01 | TRBJ1-6*01 | TRBD2*01 | 855 | tgtgccagcagcgtag | gg | ......agcgg... | tacggga........tcaccctccactt | | 2551 | C A S S V G S G T G S P L H F |
| 09.66 | TRBV09*01 | TRBJ2-7*01 | TRBD1*01 | 856 | tgtgccagcagcgt. | c | gggacaggggg | gatgtgg ......gagcagtactc | | 2552 | C A S S V G T G G M W E Q Y F |
| 09.67 | TRBV09*01 | TRBJ1-6*01 | TRBD1*01 | 857 | tgtgccagcagcgtag | gggtgg | ....agggg... tc | ......aattcacccctccactt | | 2553 | C A S S V G V E G V N S P L H F |
| 09.68 | TRBV09*01 | TRBJ2-1*01 | TRBD2*02 | 858 | tgtgccagcagcgt. | cccctc | ...gactagcggagg... | to ...acaatgagcagttcttc | | 2554 | C A S S V P R L A G G H N E Q F F |
| 09.69 | TRBV09*01 | TRBJ2-1*01 | TRBD2*02 | 859 | tgtgccagcagcgta. | ccttatcg | ......gggaag... | .......tgagcagttcttc | | 2555 | C A S S V P Y R G G E Q F F |

Figure 1-32

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 09.70 | TRBV09*01 | TRBJ2-7*01 | TRBD2*02 | 860 | tgtgccagcagcgt..cc | ......agcggaggg | cggt | ......gagcagtactc | | 2556 | C A S S V Q R E G G E Q Y F |
| 09.71 | TRBV09*01 | TRBJ2-7*01 | TRBD2*02 | 861 | tgtgccagcagcgta. agt | ......gggagg | ..ctacgagcagtactc | | | 2557 | C A S S V R W E G Y E Q Y F |
| 09.72 | TRBV09*01 | TRBJ2-1*01 | TRBD1*01 | 862 | tgtgccagcagcgta. to | .......gggc g | ..cctacaatgagcagttcttc | | | 2558 | C A S S V S G A Y N E Q F F |
| 09.73 | TRBV09*01 | TRBJ2-1*01 | TRBD2*02 | 863 | tgtgccagcagcgta. t | .......cgggag. | a ...ctacaatgagcagttcttc | | | 2559 | C A S S V S G D Y N E Q F F |
| 09.74 | TRBV09*01 | TRBJ1-5*01 | TRBD1*01 | 864 | tgtgccagcagcgta. tcc | ......ggggg. | ..gcaatcagcccagcattt | | | 2560 | C A S S V S G G N Q P Q H F |
| 09.75 | TRBV09*01 | TRBJ2-2*01 | TRBD2*01 | 865 | tgtgccagcagcgta. tct gggact. | .......caaccg. | ...acaccgggagcgtgtttt | | | 2561 | C A S S V S G T Q P D T G E L F F |
| 09.76 | TRBV09*01 | TRBJ2-3*01 | TRBD1*01 | 866 | tgtgccagcagcgt..ca cc gggaca.... | ac ..cacagatacgcagtattt | | | | 2562 | C A S S V T G T T T D T Q Y F |
| 09.77 | TRBV09*01 | TRBJ1-3*01 | TRBD2*01 | 867 | tgtgccagcagcgta. accact | ........gggggg | ....ggaaacaccatatattt | | | 2563 | C A S S V T T G G G N T I Y F |
| 09.78 | TRBV09*01 | TRBJ2-1*01 | TRBD2*02 | 868 | tgtgccagcagcgtag ttccc | .......agcgga... | tgtatgg ........tgagcagttcttc | | | 2564 | C A S S V V P S G M Y G E Q F F |
| 09.79 | TRBV09*01 | TRBJ2-1*01 | TRBD2*02 | 869 | tgtgccagcagcgtag t ..gactagcgggagg. agg .tcctacaatgagcagttcttc | | | | | 2565 | C A S S V V T S G R R S Y N E Q F F |
| 09.80 | TRBV09*01 | TRBJ2-3*01 | | 870 | tgtgccagcagcgt..ctacgacg ..gcacagatacgcagtattt | | | | | 2566 | C A S S V Y D G T D T Q Y F |
| 09.81 | TRBV09*01 | TRBJ2-6*01 | TRBD2*01 | 871 | tgtgccagca......ccgccaa ...tagcg..... aaggctctac.... ..gggccaacgtcctgactttc | | | | | 2567 | C A S T A N S E G S Y G A N V L T F |
| 10.01 | TRBV10-3*01 | TRBJ2-1*01 | TRBD2*01 | 872 | tgtgccatcagtg....cc ..gacta....... ttcc ag ctcctacaatgagcagttcttc | | | | | 2568 | C A I S A D Y S S S Y N E Q F F |
| 10.02 | TRBV10-3*01 | TRBJ2-7*01 | TRBD2*02 | 873 | tgtgccatcagtgagtc a | ......gggag. ctcctacgagcagtactc | | | | 2569 | C A I S E G G S S Y E Q Y F |
| 10.03 | TRBV10-3*01 | TRBJ2-1*01 | TRBD1*01 | 874 | tgtgccatcagtgagtc ga | .....tagcgggg. t | .......caatgagcagttcttc | | | 2570 | C A I S E S I A G V N E Q F F |
| 10.04 | TRBV10-3*01 | TRBJ2-3*01 | TRBD2*01 | 875 | tgtgccatcagtgagtc acct | ........gggggg | ctcgaa. cacagatacgcagtattt | | | 2571 | C A I S E S P G G A R N T D T Q Y F |
| 10.05 | TRBV10-3*01 | TRBJ2-1*01 | TRBD1*01 | 876 | tgtgccatcagtg.... ggga..... tgtcga gaag ctcctacaatgagcagttcttc | | | | | 2572 | C A I S G D V E S S Y N E Q F F |
| 10.06 | TRBV10-3*01 | TRBJ2-1*01 | TRBD1*01 | 877 | tgtgccatcagtg.... gatcgc ..gacagc.... ag ......aatgagcagttcttc | | | | | 2573 | C A I S G S R Q E N E Q F F |
| 10.07 | TRBV10-3*01 | TRBJ2-3*01 | TRBD2*02 | 878 | tgtgccatcagt.... agc ...ctagcggag. a .....agatacgcagtattt | | | | | 2574 | C A I S L A G E D T Q Y F |
| 10.08 | TRBV10-1*01 | TRBJ2-7*01 | TRBD2*02 | 879 | tgcgccagcagtg... g gggactagcggga.... ..tacgagcagtactc | | | | | 2575 | C A S S G G L A G Y E Q Y F |
| 10.09 | TRBV10-3*02 | TRBJ2-7*01 | TRBD2*01 | 880 | tgtgcca....... caaagga ....cgggg... at tcctacgagcagtactc TRBJ2 | | | | | 2576 | C A T K D G D S Y E Q Y F |
| 10.10 | TRBV10-3*01 | TRBJ1-1*01 | TRBD1*01 | 881 | tgtgcca........ cc ...caggg ....cgggggag tgaacactgaagcttcttt | | | | | 2577 | C A T Q G G G V N T E A F F |
| 10.11 | TRBV10-3*01 | TRBJ2-1*01 | TRBD2*01 | 882 | tgtgcca...... ccgtct ...ctagcg..... agggcggcc ......ccggggagctgttttt | | | | | 2578 | C A T V S S E G G P G E L F F |
| 11.01 | TRBV11-3*01 | TRBJ2-5*01 | TRBD1*01 | 883 | tgtgcagca...... acttatggcct .....gggg. aaagcaa ...........tacttc | | | | | 2579 | C A S N L W P G E R Q Y F |
| 11.02 | TRBV11-3*01 | TRBJ2-1*01 | TRBD2*01 | 884 | tgtgccagcag...... aattct ggga........ ....tacaatgagcagttcttc | | | | | 2580 | C A S R I L G Y N E Q F F |
| 11.03 | TRBV11-2*01 | TRBJ2-1*01 | TRBD2*01 | 885 | tgtgccagcag....... ac ........cgggg. ......tacaatgagcagttcttc | | | | | 2581 | C A S R P G Y N E Q F F |
| 11.04 | TRBV11-2*01 | TRBJ1-1*01 | TRBD2*01 | 886 | tgtgccagcagcgtt.. tg ......adcg....... cactgaagcttcttt | | | | | 2582 | C A S S F E R T E A F F |

Figure 1-33

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 11.05 | TRBV11-2*01 | TRBJ2-1*01 | TRBD2*01 | 887 | tgtgccagcagctt... | cggt | .....gggg... | tg ....tacaatgagcagttcttc | | 2583 | C A S S F G G V Y N E Q F F |
| 11.06 | TRBV11-2*01 | TRBJ2-7*01 | TRBD1*01 | 888 | tgtgccagcagctt... | c | .....gggc | ag ....tacgagcagttcttc | | 2584 | C A S S F G G Q Y E Q Y F |
| 11.07 | TRBV11-3*01 | TRBJ2-1*01 | | 889 | tgtgccagcagct... | tagaag | | ......caatgagcagttcttc | | 2585 | C A S S F R S N E Q F F |
| 11.08 | TRBV11-2*01 | TRBJ2-2*01 | TRBD1*01 | 890 | tgtgccagcagc.... | ggccccc | ggacaggg... | at ....caccggggagctgtttt | | 2586 | C A S S G P R T G I T G E L F F |
| 11.09 | TRBV11-2*01 | TRBJ1-2*01 | TRBD1*01 | 891 | tgtgccagcagc.... | gggac.... | gggag | ctaactatgctacacctc | | 2587 | C A S S G T G A N Y G Y T F |
| 11.10 | TRBV11-2*01 | TRBJ2-4*01 | TRBD2*01 | 892 | tgtgccagcagc.... | atagt | ........cgggg..... | ....aaacattcagtactc | | 2588 | C A S S I V G G N I Q Y F |
| 11.11 | TRBV11-1*01 | TRBJ2-5*01 | TRBD1*01 | 893 | tgtgccagcagc..... | a | ....agggg... | a .......agaccccagcttc | | 2589 | C A S S K G K T Q Y F |
| 11.12 | TRBV11-2*01 | TRBJ1-6*01 | TRBD2*02 | 894 | tgtgccagcagcttag.. | ccc | ......cggga.... | agggagcatacga ........caccccctccacttc | | 2590 | C A S S L A P G R E H T T P L H F |
| 11.13 | TRBV11-2*01 | TRBJ1-1*01 | TRBD1*01 | 895 | tgtgccagcagctagc | g a | ggga....... | ......gaacactgaagcttcttt | | 2591 | C A S S L A R E N T E A F F |
| 11.14 | TRBV11-2*01 | TRBJ1-1*01 | TRBD1*01 | 896 | tgtgccagcagcttaga | cccc | ....cagg..... | ......gaacactgaagcttcttt | | 2592 | C A S S L D P Q G N T E A F F |
| 11.15 | TRBV11-2*01 | TRBJ2-3*01 | TRBD2*01 | 897 | tgtgccagcagcttaga | ct | .......cgg..... | ......gcacagatacgcagtattt | | 2593 | C A S S L D S G T D T Q Y F |
| 11.16 | TRBV11-2*01 | TRBJ1-5*01 | | 898 | tgtgccagcagcttaga t tacatg......... | | | cagcccccagcattt | | 2594 | C A S S L D Y M Q P Q H F |
| 11.17 | TRBV11-2*01 | TRBJ2-7*01 | TRBD2*01 | 899 | tgtgccagcagctag | ggcc | .......gcgg... | ta ..tcctacgagcagtactc | | 2595 | C A S S L E A A V S Y E Q Y F |
| 11.18 | TRBV11-2*01 | TRBJ2-1*01 | TRBD1*01 | 900 | tgtgccagcagctt...... | ........gggggc | ccgcgga | accaagagaccagtactc | | 2596 | C A S S L G A R G N Q E T Q Y F |
| 11.19 | TRBV11-2*01 | TRBJ2-7*01 | TRBD2*01 | 901 | tgtgccagcagcttag... | g | gggactagc..... | cga ....tacgagcagtactc | | 2597 | C A S S L G G L A R Y E Q Y F |
| 11.20 | TRBV11-3*01 | TRBJ2-3*01 | TRBD2*01 | 902 | tgtgccagcagc..... | ctc | .ggactagc..... | tg ...cagatacgcagtattt | | 2598 | C A S S L G L A A D T Q Y F |
| 11.21 | TRBV11-2*01 | TRBJ1-1*01 | TRBD1*01 | 903 | tgtgccagcagc..... | ctttt | ...acaggg..... | tgg .......tgaagcttcttt | | 2599 | C A S S L L Q G G E A F F |
| 11.22 | TRBV11-2*01 | TRBJ2-2*01 | TRBD1*01 | 904 | tgtgccagcagcta.. | c gggacag..... | | gaacaccgggagctgttttt | | 2600 | C A S S L R D R N T G E L F F |
| 11.23 | TRBV11-2*01 | TRBJ2-1*01 | TRBD2*02 | 905 | tgtgccagcagctag.. | ttgggacacc | .gactagcgggag... | agg ......caatgagcagttcttc | | 2601 | C A S S L V G T P T S G R G N E Q F F |
| 11.24 | TRBV11-2*01 | TRBJ2-1*01 | TRBD1*01 | 906 | tgtgccagcagctag.. | tcccagtc | ....caggggc | tat.....caatgagcagttcttc | | 2602 | C A S S L V P V Q G A I N E Q F F |
| 11.25 | TRBV11-2*01 | TRBJ2-7*01 | TRBD1*01 | 907 | tgtgccagcagc..... | at | ......ggggg. | tt tcctacgagcagtactc | | 2603 | C A S S M G V S Y E Q Y F |
| 11.26 | TRBV11-2*01 | TRBJ2-5*01 | TRBD1*01 | 908 | tgtgccagcagc..... | ccc | ggggagc..... | cctggt ccaagagaccagtactc | | 2604 | C A S S P G T A W V Q E T Q Y F |
| 11.27 | TRBV11-1*01 | TRBJ2-7*01 | TRBD2*02 | 909 | tgtgccagcagc..... | cga ..actagcgggag... | | tttcg ....acgagcagtactc | | 2605 | C A S S R T S G S F D E Q Y F |
| 11.28 | TRBV11-2*01 | TRBJ2-7*01 | TRBD1*01 | 910 | tgtgccagcagct.... | ccgc | .ggacag....... | tccagg .........gcagtactc | | 2606 | C A S S A D S P G Q Y F |
| 11.29 | TRBV11-1*01 | TRBJ2-1*01 | TRBD1*01 | 911 | tgtgccagcagct..... | cc | gggactagcg....... | cg ....tacaatgagcagttcttc | | 2607 | C A S S G T S A Y N E Q F F |
| 11.30 | TRBV11-3*01 | TRBJ2-1*01 | TRBD1*01 | 912 | tgtgccagcagct..... | cccgt | ......gggc | ccccgtaggtttgg......tgagcagttcttc | | 2608 | C A S S P V G P R R F G E Q F F |
| 11.31 | TRBV11-2*01 | TRBJ2-5*01 | TRBD2*02 | 913 | tgtgccacagct.... | cccctg | ....ctagcgggag... | tttt ccaagagaccagtactc | | 2609 | C A S S P W L A G V F Q E T Q Y F |
| 11.32 | TRBV11-2*01 | TRBJ2-1*01 | TRBD2*01 | 914 | tgtgccagcagc..... | acag cc | gggactag......... | agtg .......aatgagcagttcttc | | 2610 | C A S S T A G T R V N E Q F F |

Figure 1-34

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 11.33 | TRBV11-2*01 | TRBJ2-2*01 | TRBD1*01 | 915 | tgtgccagcagc | accgtccggcacgcgca | gacag | cgaacaccgggagctgtttt | | 2611 | C A S S T V R H A Q T A N T G E L F F |
| 11.34 | TRBV11-2*01 | TRBJ2-2*01 | TRBD1*01 | 916 | tgtgccagcagc | gt | tagc | cct | accgggagctgtttt | 2612 | C A S S V S P T G E L F F |
| 11.35 | TRBV11-2*01 | TRBJ2-3*01 | TRBD2*02 | 917 | tgtgccagcagct | | ggaggg gcg gcaacgatacgcagtacttc | | | 2613 | C A S S W R G G T D T Q Y F |
| 11.36 | TRBV11-2*01 | TRBJ2-5*01 | TRBD2*02 | 918 | tgtgccagcagct | at | gagg cctct | caagagaccagtacttc | | 2614 | C A S S Y E A S Q E T Q Y F |
| 11.37 | TRBV11-2*01 | TRBJ2-2*01 | TRBD2*01 | 919 | tgtgccagca | ccgttggcctac | cgggg | agcc | gtttt | 2615 | C A S T V G P T G E P F F |
| 12.01 | TRBV12-5*01 | TRBJ2-2*01 | TRBD2*01 | 920 | tgtgctagtg | ctttgggg | ctagcgg | cgg | accgggagctgtttt | 2616 | C A S A L G A S G R T G E L F F |
| 12.02 | TRBV12-4*01 | TRBJ1-1*01 | TRBD1*01 | 921 | tgtgccagc | gacag | actatgag | cactgaagcttctt | | 2617 | C A S D R T M S T E A F F |
| 12.03 | TRBV12-5*01 | TRBJ1-1*01 | TRBD1*01 | 922 | tgtg | cagc gacag | tcccc tgaacactgaagcttctt | | | 2618 | C A S D S P L N T E A F F |
| 12.04 | TRBV12-4*01 | TRBJ1-1*01 | TRBD1*01 | 923 | tgtgccagc | gacag | tact a tgaacactgaagcttctt | | | 2619 | C A S D S T M N T E A F F |
| 12.05 | TRBV12-4*01 | TRBJ2-1*01 | TRBD2*02 | 924 | tgtgccagc | gaaagtt | ctagcgggag | tga | ctacaatgagcagttcttc | 2620 | C A S E S S S G S D Y N E Q F F |
| 12.06 | TRBV12-4*01 | TRBJ2-1*01 | TRBD2*01 | 925 | tgtgccagc | ttcca | cgggg | tgcta | lacaatgagcagttcttc | 2621 | C A S F H G V L Y N E Q F F |
| 12.07 | TRBV12-4*01 | TRBJ2-1*01 | TRBD1*01 | 926 | tgtgccagc | gga gacag | tttaagg | | gagcagttcttc | 2622 | C A S G D S L R E Q F F |
| 12.08 | TRBV12-5*01 | TRBJ2-7*01 | | 927 | tgtgctagtagtggttgg | caaccaatc | cctacgagcagtacttc | | | 2623 | C A S G L A T N P Y E Q Y F |
| 12.09 | TRBV12-5*01 | TRBJ2-2*01 | TRBD1*01 | 928 | tgtgctagtagtggttggt ggct | ggggagctgtttt | | | | 2624 | C A S G L V A G E L F F |
| 12.10 | TRBV12-5*01 | TRBJ2-7*01 | TRBD1*01 | 929 | tgtgctagtagtggttggt t | caggg | aagtta | ctacgagcagtacttc | | 2625 | C A S G L V Q G S Y Y E Q Y F |
| 12.11 | TRBV12-4*01 | TRBJ1-2*01 | TRBD1*01 | 930 | tgtgccagc | ggc caggg | tag | ctatggctacacttc | | 2626 | C A S G Q G S Y G Y T F |
| 12.12 | TRBV12-4*01 | TRBJ2-7*01 | TRBD1*01 | 931 | tgtgccagc | gg caggg | aaaatgg | cgagcagtacttc | | 2627 | C A S G R E N G E Q Y F |
| 12.13 | TRBV12-4*01 | TRBJ2-5*01 | TRBD1*01 | 932 | tgtgccagca | aatcttttt | cagg ct | caagagaccagtacttc | | 2628 | C A S K S F F Q A Q E T Q Y F |
| 12.14 | TRBV12-3*01 | TRBJ2-7*01 | TRBD1*01 | 933 | tgtgccag | tctttattc | cagg | ctcccccct | cgagcagtacttc | 2629 | C A S L L F Q A P P V E Q Y F |
| 12.15 | TRBV12-3*01 | TRBJ2-3*01 | TRBD1*01 | 934 | tgtgccagca | acgaagaa | agggt | cagatacgcagtacttc | | 2630 | C A S N E E R A D T Q Y F |
| 12.16 | TRBV12-3*01 | TRBJ1-5*01 | TRBD1*01 | 935 | tgtgccagcag | gggacaggggc | tttg | cagcccagcattctt | | 2631 | C A S R G Q G A L Q P Q H F |
| 12.17 | TRBV12-4*01 | TRBJ2-1*01 | TRBD1*01 | 936 | tgtgccagcag | g gggacaggg | at | aatgagcagttctt | | 2632 | C A S R G T G D N E Q F F |
| 12.18 | TRBV12-4*01 | TRBJ2-1*01 | TRBD2*01 | 937 | tgtgccagcag | acccaagtt | tagcg | accccgggccaa | acaatgagcagttcttc | 2633 | C A S R P K F S D P G P N N E Q F F |
| 12.19 | TRBV12-3*01 | TRBJ1-1*01 | TRBD1*01 | 938 | tgtgccagcag | atccct c gggaca | ccactct | caatgagcagttcttc | | 2634 | C A S R S L G T P R L N E Q F F |
| 12.20 | TRBV12-4*01 | TRBJ2-4*01 | TRBD1*01 | 939 | tgtgccagcag | cgcco ggacag | t agccaaaaacattcagtacttc | | | 2635 | C A S S A R T V A K N I Q Y F |
| 12.21 | TRBV12-3*01 | TRBJ1-1*01 | TRBD1*01 | 940 | tgtgccagcagttt | cgc gggac | c | cactgaagcttctt | | 2636 | C A S S F A G P T E A F F |
| 12.22 | TRBV12-4*01 | TRBJ1-2*01 | TRBD1*01 | 941 | tgtgccagcagttt | t | ggggg aatcg | atgctacacctc | | 2637 | C A S S F G G I D G Y T F |

Figure 1-35

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 12.23 | TRBV12-4*01 | TRBJ2-1*01 | TRBD2*02 | 942 | tgtgccagcagttt... | ct ...tagcaggag. | cccg | ......caatgagcagttcttc | | 2638 | C A S S F L A G A G N E Q F F |
| 12.24 | TRBV12-3*01 | TRBJ2-1*01 | TRBD2*01 | 943 | tgtgccagcagttt... | tctcc ...ctagcg...... | ccctttggg... | atgagcagttcttc | | 2639 | C A S S F L P S A L W D E Q F |
| 12.25 | TRBV12-3*01 | TRBJ1-2*01 | TRBD1*01 | 944 | tgtgccagcagttt... | taggatcga ..gacaggg... | agglac... | ...ggctacaccttc | | 2640 | C A S S F R I E T G R Y G Y T F |
| 12.26 | TRBV12-4*01 | TRBJ2-5*01 | TRBD2*02 | 945 | tgtgccagcagttt... | ttctcgaggcggtgttggag... | gcggag.. accaag | ......actlc | | 2641 | C A S S F S R G G V G R R E T Q D F |
| 12.27 | TRBV12-3*01 | TRBJ1-2*01 | | 946 | tgtgccagcagttt... | ctcgacctgttcg g ctaactatggctacaccttc | | | | 2642 | C A S S F S T C S A N Y G Y T F |
| 12.28 | TRBV12-3*01 | TRBJ1-2*01 | TRBD1*01 | 947 | tgtgccagcag..... | cata ..acagg.... | agc | ...clatggctacaccttc | | 2643 | C A S S I T G A Y G Y T F |
| 12.29 | TRBV12-4*01 | TRBJ2-5*01 | TRBD1*01 | 948 | tgtgccagcag..... | caa ..ggacaggg.. | aag ..ccaagagaccagtactlc | | | 2644 | C A S S K D R G S Q E T Q Y F |
| 12.30 | TRBV12-3*01 | TRBJ2-1*01 | TRBD2*01 | 949 | tgtgccagcagttt... | g ......gcgg...... | ...cctacaatgagcagttcttc | | | 2645 | C A S S L A A Y N E Q F F |
| 12.31 | TRBV12-4*0 | TRBJ1-1*01 | TRBD1*01 | 950 | tgtgccagcagttag..... | ..aggggggc gcc ggg. | ..cactgaagcttcttt | | | 2646 | C A S S L E G A P G T E A F F |
| 12.32 | TRBV12-4*01 | TRBJ1-2*01 | TRBD1*01 | 951 | tgtgccagcagttag.. aact ..gacagg... | ......cccctc. | ......ggctacaccttc | | | 2647 | C A S S L E L T G P L G Y T F |
| 12.33 | TRBV12-4*01 | TRBJ1-5*01 | | 952 | tgtgccagcagttag. aa ...aatcagcccagcattt | | | | | 2648 | C A S S L E N Q P Q H F |
| 12.34 | TRBV12-3*01 | TRBJ2-7*01 | TRBD1*01 | 953 | tgtgccagcagtta... | ttctggctcccc.... ..gaca... | | ......agcagtactlc | | 2649 | C A S S L F W A P P D K Q Y F |
| 12.35 | TRBV12-3*01 | TRBJ2-7*01 | TRBD1*01 | 954 | tgtgccagcagtta... | ttct ........gggc | tcccccgt... | ..cgagcagtactlc | | 2650 | C A S S L F W A P P V E Q Y F |
| 12.36 | TRBV12-3*01 | TRBJ2-7*01 | TRBD2*01 | 955 | tgtgccagcagtta... | ttct ........gggg... | tcccccgtca... | ......agcagtactlc | | 2651 | C A S S L F W G P P V K Q Y F |
| 12.37 | TRBV12-4*01 | TRBJ2-5*01 | | 956 | tgtgccagcagttag. g ...agagaccagtactlc | | | | | 2652 | C A S S L G E T Q Y F |
| 12.38 | TRBV12-3*01 | TRBJ1-1*01 | | 957 | tgtgccagcagttt... | g ......ggggc ag ... | ...tgaagcttttt | | | 2653 | C A S S L G G S E A F F |
| 12.39 | TRBV12-4*01 | TRBJ2-1*01 | TRBD1*01 | 958 | tgtgccagcagtttag. ggt cc gggac... | ggccttggg ... | ......caatgagcagttcttc | | | 2654 | C A S S L G S G T A L G N E Q F F |
| 12.40 | TRBV12-3*01 | TRBJ1-1*01 | TRBD1*01 | 959 | tgtgccagcagttag... | g ....cag..... | cc tgaacactgaagctttctt | | | 2655 | C A S S L G S L N T E A F F |
| 12.41 | TRBV12-4*01 | TRBJ1-2*01 | TRBD2*02 | 960 | tgtgccagcagttag.. ggactagcgggag... | atggaatgaa ... | ......cagttcttc | | | 2656 | C A S S L G T S G R W N E Q F F |
| 12.42 | TRBV12-4*01 | TRBJ1-2*01 | TRBD1*01 | 961 | tgtgccagcagtta.. aatccct ...cagggg. | acct ...clatggctacaccttc | | | | 2657 | C A S S L N P S G D L Y G Y T F |
| 12.43 | TRBV12-3*01 | TRBJ2-7*01 | TRBD2*01 | 962 | tgtgccagcagtta. to ......ccggg... | aatt ..ctacgagcagtactlc | | | | 2658 | C A S S L S G E F Y E Q Y F |
| 12.44 | TRBV12-4*01 | TRBJ2-1*01 | TRBD2*02 | 963 | tgtgccagcagtta. tca ......ggagg. ta ..acgagcagtactlc | | | | | 2659 | C A S S L S G G N E Q Y F |
| 12.45 | TRBV12-4*01 | TRBJ2-1*01 | TRBD2*01 | 964 | tgtgccagcagtta. agtata ...agggggggg to ... | ......gagcagttcttc | | | | 2660 | C A S S L S I S G G V E Q F F |
| 12.46 | TRBV12-3*01 | TRBJ2-5*01 | TRBD2*02 | 965 | tgtgccagcagtta... | ac .....ccgga... | tcg accaagagaccagtactlc | | | 2661 | C A S S L T G I D Q E T Q Y F |
| 12.47 | TRBV12-3*01 | TRBJ2-5*01 | TRBD2*01 | 966 | tgtgccagcagtt... | gaccto .......ccggg... | ttggg ...gagaccagtactlc | | | 2662 | C A S S L T S G V G E T Q Y F |
| 12.48 | TRBV12-4*01 | TRBJ2-1*01 | TRBD2*01 | 967 | tgtgccagcagtta... | ..actacgg.... | ..ctacaatgagcagttcttc | | | 2663 | C A S S L T S G Y N E Q F F |
| 12.49 | TRBV12-4*01 | TRBJ2-1*01 | TRBD2*01 | 968 | tgtgccagcagtta. tg ......gcggggg. cgaa ......aatgagcagttcttc | | | | | 2664 | C A S S L V A G G E N E Q F F |
| 12.50 | TRBV12-4*01 | TRBJ2-7*01 | TRBD2*02 | 969 | tgtgccagcagtttag. t .......gggaggg a ...cctacgagcagtactlc | | | | | 2665 | C A S S L V G G T Y E Q Y F |

Figure 1-36

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 12.51 | TRBV12-3*01 | TRBJ2-1*01 | TRBD2*02 | 970 | tgtgccagcagt | ctgta | tagcgggagg | c | atgacagttcttc | 2666 | C A S S L Y S G R H E Q F F |
| 12.52 | TRBV12-4*01 | TRBJ2-2*01 | | 971 | tgtgccagcagt | cccg | ccggggagctgttttt | | | 2667 | C A S S P A G E L F F |
| 12.53 | TRBV12-4*01 | TRBJ2-1*01 | TRBD2*01 | 972 | tgtgccagcagt | cccatt | actag | agctcctg | acaatgagcagttcttc | 2668 | C A S S P I T R A P D N E Q F F |
| 12.54 | TRBV12-4*01 | TRBJ2-7*01 | TRBD1*01 | 973 | tgtgccagcag | ccct c | gggacaggg | tttt | tacgagcagtactc | 2669 | C A S S P R D R V F Y E Q Y F |
| 12.55 | TRBV12-4*01 | TRBJ2-3*01 | TRBD2*01 | 974 | tgtgccagcag | ccccc | ggactagcgg | tagaggg | acagatacgcagtatttt | 2670 | C A S S P R T S G R G T D T Q Y F |
| 12.56 | TRBV12-4*01 | TRBJ2-1*01 | TRBD2*01 | 975 | tgtgccagcag | cc | ctacgcgggg | at | tacaatgagcagttcttc | 2671 | C A S S P S G D Y N E Q F F |
| 12.57 | TRBV12-3*01 | TRBJ2-2*01 | TRBD1*01 | 976 | tgtgccagcagt | ccc | acaggg | | ccggggagctgtttt | 2672 | C A S S P T G A G E L F F |
| 12.58 | TRBV12-4*01 | TRBJ2-3*01 | TRBD1*01 | 977 | tgtgccagcag | cc | ggacagg | t | cagatacgcagtattt | 2673 | C A S S R T G S D T Q Y F |
| 12.59 | TRBV12-4*01 | TRBJ2-7*01 | TRBD1*01 | 978 | tgtgccagcagtt | c | gggc g gcg g ctcctacgagcagtactc | | | 2674 | C A S S G G G S Y E Q Y F |
| 12.60 | TRBV12-4*01 | TRBJ1-5*01 | TRBD1*01 | 979 | tgtgccagcagtt | ca | ggacagg | gcaatcagcccagcatttt | | 2675 | C A S S G Q G N Q P Q H F |
| 12.61 | TRBV12-4*01 | TRBJ2-7*01 | | 980 | tgtgccagcagtt | ctattgatgaatt | | | ctacgagcagtactc | 2676 | C A S S S I D G F Y E Q Y F |
| 12.62 | TRBV12-3*01 | TRBJ1-2*01 | TRBD1*01 | 981 | tgtgccagcagtt | ccccgatctatcga | ggacag | ct | taactatgctacacctc | 2677 | C A S S P I Y R G Q L N Y G Y T F |
| 12.63 | TRBV12-4*01 | TRBJ2-7*01 | TRBD1*01 | 982 | tgtgccagcagt | a cc gggac | cccact | ctacgagcagtactc | | 2678 | C A S S T G T P L Y E Q Y F |
| 12.64 | TRBV12-4*01 | TRBJ2-2*01 | TRBD2*02 | 983 | tgtgccagcagt | ac | actagcgggag | ttctc | acaccgggagctgttttt | 2679 | C A S S T L A G G S H T G E L F F |
| 12.65 | TRBV12-3*01 | TRBJ2-7*01 | TRBD2*01 | 984 | tgtgccagcagt | gtg | gcg | | tcctacgagcagttcttc | 2680 | C A S S V A S Y N E Q F F |
| 12.66 | TRBV12-4*01 | TRBJ1-1*01 | TRBD1*01 | 985 | tgtgccagcagtt | gggacctacacaggg aggttaggtg | | | gctttcttt | 2681 | C A S S W D L T G E G R V A F F |
| 12.67 | TRBV12-4*01 | TRBJ2-1*01 | TRBD2*02 | 986 | tgtgccagcagtt | ggactagcgggag | ctcggg | ctacaatgagcagttcttc | | 2682 | C A S S W T S G S S G Y N E Q F F |
| 12.68 | TRBV12-3*01 | TRBJ2-3*01 | TRBD2*02 | 987 | tgtgccagca | cgt | ctacgggaggg | atcg | agatacgcagtatttt | 2683 | C A S T S S G R D R D T Q Y F |
| 12.69 | TRBV12-3*01 | TRBJ2-5*01 | TRBD2*01 | 988 | tgtgcca | cctttgtaccca | cgggg | ttggg | gagaccagtacttc | 2684 | C A T L C T H G V G E T Q Y F |
| 12.70 | TRBV12-3*01 | TRBJ2-3*01 | TRBD2*01 | 989 | tgtg | gcatgagttgggggaatgaa | agcggggggcggggggatactct | | tattt | 2685 | C G M S S G E W K R G G R G D T S Y F |
| 13.01 | TRBV13*01 | TRBJ1-6*01 | TRBD1*01 | 990 | tgtgccagcag | acttacg gggac | cta | ctataattcaccctccactt | | 2686 | C A S R L T G T Y Y N S P L H F |
| 13.02 | TRBV13*01 | TRBJ2-1*01 | TRBD2*01 | 991 | tgtgccagcagctt | cgggg | agaggg | ctcctacaatgagcagttcttc | | 2687 | C A S S F G G E G S Y N E Q F F |
| 13.03 | TRBV13*01 | TRBJ2-2*01 | TRBD1*01 | 992 | tgtgccagcagctt | caggg | ctgtctactagga | | gagctgttttt | 2688 | C A S S F R A G L L G E L F F |
| 13.04 | TRBV13*01 | TRBJ2-5*01 | TRBD2*02 | 993 | tgtgccagcagctt | tagcgggag | tcagttataagaa | | agaccagtacttc | 2689 | C A S S F S G S Q F I R K T Q Y F |
| 13.05 | TRBV13*01 | TRBJ2-2*01 | TRBD2*01 | 994 | tgtgccagcagc | cac | ggactagcgggg | ct | caccggggagctgttttt | 2690 | C A S S H G L A G L T G E L F F |
| 13.06 | TRBV13*01 | TRBJ2-5*01 | TRBD1*01 | 995 | tgtgccagcagc | atccaaa | gggac | cag | gagaccagtactc | 2691 | C A S S I Q R D Q E T Q Y F |
| 13.07 | TRBV13*01 | TRBJ2-1*01 | TRBD2*01 | 996 | tgtgccagcagctag | ctg | ctacgggg | ccggc | gcagttcttc | 2692 | C A S S L A A S G P A Q F F |

Figure 1-37

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 13.08 | TRBV13*01 | TRBJ2-7*01 | TRBD2*02 | 997 | tgtgccagcagcttag | cgc | gcggag | aatcc | acgagcagtacttc | 2693 | C A S S L A R G R I H E Q Y F |
| 13.09 | TRBV13*01 | TRBJ2-7*01 | TRBD1*01 | 998 | tgtgccagcagcttag | a | aggg | ttgg | acgagcagtacttc | 2694 | C A S S L E G L D E Q Y F |
| 13.10 | TRBV13*01 | TRBJ2-1*01 | | 999 | tgtgccagcagcttagg | gggtg | | atgagcagttcttc | | 2695 | C A S S L G G D E Q F F |
| 13.11 | TRBV13*01 | TRBJ2-1*01 | TRBD2*01 | 1000 | tgtgccagcagcttagg | cc | ggactagcggg | cccctagg | atgagcagttcttc | 2696 | C A S S L G R T S G P P R D E Q F F |
| 13.12 | TRBV13*01 | TRBJ2-5*01 | TRBD2*01 | 1001 | tgtgccagcagcttagg | ggttggtgtcgat | ggg | | gagaccagtacttc | 2697 | C A S S L G V G V D G E T Q Y F |
| 13.13 | TRBV13*01 | TRBJ2-7*01 | TRBD2*01 | 1002 | tgtgccagcagcttagg | tta | cggg | tcaa | cctacgagcagtacttc | 2698 | C A S S L G Y G S T Y E Q Y F |
| 13.14 | TRBV13*01 | TRBJ2-7*01 | TRBD2*01 | 1003 | tgtgccagcagc | ctc | cgggg | | gagcagtacttc | 2699 | C A S S L R G E Q Y F |
| 13.15 | TRBV13*01 | TRBJ1-1*01 | TRBD2*01 | 1004 | tgtgccagcagcttag | tgct | gact | c | ctttcttt | 2700 | C A S S L V L T P F F |
| 13.16 | TRBV13*01 | TRBJ1-3*01 | TRBD1*01 | 1005 | tgtgccagcagcttag | t | gaca | ccg | ggaaacaccatatattt | 2701 | C A S S L V T P G N T I Y F |
| 13.17 | TRBV13*01 | TRBJ2-7*01 | TRBD2*01 | 1006 | tgtgccagcagctta | tg | gcgt | aa | ctctacgagcagtacttc | 2702 | C A S S L W R N S Y E Q Y F |
| 13.18 | TRBV13*01 | TRBJ1-6*01 | TRBD1*01 | 1007 | tgtgccagcagc | aa ccc | gggacagcag | ac | tcaccctcacttt | 2703 | C A S S N P G Q G D S P L H F |
| 13.19 | TRBV13*01 | TRBJ2-5*01 | TRBD1*01 | 1008 | tgtgccagcagc | cca c | gggacag | t | caagagaccagtacttc | 2704 | C A S S P R D S Q E T Q Y F |
| 13.20 | TRBV13*01 | TRBJ2-2*01 | TRBD1*01 | 1009 | tgtgccagcagc | cag | tgg | | accgggagctgtttt | 2705 | C A S S Q W T G E L F F |
| 13.21 | TRBV13*01 | TRBJ1-3*01 | TRBD1*01 | 1010 | tgtgccagcagc | cga | gga | ttcg | acaccatatattt | 2706 | C A S S R G F D T I Y F |
| 13.22 | TRBV13*01 | TRBJ2-3*01 | TRBD2*02 | 1011 | tgtgccagcagct | ctgataacccct | tagcaggag | aa | acagatacgcagtattt | 2707 | C A S S D N P L A G E T D T Q Y F |
| 13.23 | TRBV13*01 | TRBJ2-3*01 | TRBD2*01 | 1012 | tgtgccagcagct | cagacc | ggactag | tcatc | gcacagatacgcagtattc | 2708 | C A S S S D R T S H R T D T Q Y F |
| 13.24 | TRBV13*01 | TRBJ1-5*01 | TRBD2*02 | 1013 | tgtgccagcagct | ccggc | gaggg | | tcagcccccagcattt | 2709 | C A S S G E G Q P Q H F |
| 13.25 | TRBV13*01 | TRBJ2-3*01 | TRBD2*02 | 1014 | tgtgccagcagct | cccctttc | gaggg | aagg | gatacgcagtactlc | 2710 | C A S S S P F E G R D T Q Y F |
| 13.26 | TRBV13*01 | TRBJ2-7*01 | TRBD1*01 | 1015 | tgtgccagcagct | ccc | gggacagggg | aa | cctacgagcagtacttc | 2711 | C A S S S R D R G T Y E Q Y F |
| 13.27 | TRBV13*01 | TRBJ2-3*01 | TRBD1*01 | 1016 | tgtgccagcagct | c | cagggg | gccc | gcacagatacgcagtattt | 2712 | C A S S S R G A R T D T Q Y F |
| 14.01 | TRBV14*01 | TRBJ2-3*01 | TRBD1*01 | 1017 | tgtgcc | ccagccactccc | cagggg | aacgcac | tatttt | 2713 | C A P S H S P G G T H Y F |
| 14.02 | TRBV14*01 | TRBJ2-7*01 | TRBD1*01 | 1018 | tgtgccagcag | ggaacca | gggacagg | caaa | gagcagtacttc | 2714 | C A S R E P G T G K E Q Y F |
| 14.03 | TRBV14*01 | TRBJ2-1*01 | TRBD2*01 | 1019 | tgtgccagcag | gattt | caggggg | acta | aatgagcagttcttc | 2715 | C A S R I S G G L N E Q F F |
| 14.04 | TRBV14*01 | TRBJ2-3*01 | TRBD2*01 | 1020 | tgtgccagcagcca | cga cc | gggacta | cctttctggg | acagatacgcagtattt | 2716 | C A S S H D R D Y L S G T D T Q Y F |
| 14.05 | TRBV14*01 | TRBJ2-1*01 | TRBD2*01 | 1021 | tgtgccagcagc | tt | actagcggg | ctcctacaatgagcagttcttc | | 2717 | C A S S L L A G S Y N E Q F F |
| 14.06 | TRBV14*01 | TRBJ2-7*01 | | 1022 | tgtgccagcagccaaga tc | cctttcgtgtg g | ctcctacgagcagtacttc | | | 2718 | C A S S Q D P F R G G S Y E Q Y F |
| 14.07 | TRBV14*01 | TRBJ1-1*01 | TRBD2*01 | 1023 | tgtgccagcagccaaga | taggg | tagc | | gcagttcttc | 2719 | C A S S Q D R V A Q F F |

Figure 1-38

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 14.08 | TRBV14*01 | TRBJ2-1*01 | TRBD2*01 | 1024 | tgtgccagcagccaaga | ttacac | gactagc | agac | acaatgagcagttcttc | 2720 | C A S S Q D Y T T S R H N E Q F F |
| 14.09 | TRBV14*01 | TRBJ2-2*01 | TRBD2*01 | 1025 | tgtgccagcagccaaaga | agggg | agccgg | acccgaagggg | caccggggagctgtttt | 2721 | C A S S Q E G E R T R R G T G E L F F |
| 14.10 | TRBV14*01 | TRBJ2-5*01 | TRBD2*01 | 1026 | tgtgccagcagccaaga | gacc | ctagcggg | ttggt | accaagagaccagtactc | 2722 | C A S S Q E T L A G W Y Q E T Q Y F |
| 14.11 | TRBV14*01 | TRBJ2-5*01 | TRBD1*01 | 1027 | tgtgccagcagccaaga | at | ggggg | caaggagaccagtactc | | 2723 | C A S S Q E W G G A R T E A F F |
| 14.12 | TRBV14*01 | TRBJ1-1*01 | TRBD1*01 | 1028 | tgtgccagcagccaag | | ggc tcg | cactgaagcttcttt | | 2724 | C A S S Q G A R T E A F F |
| 14.13 | TRBV14*01 | TRBJ2-3*01 | TRBD2*02 | 1029 | tgtgccagcagccaag | gtgcc | agcgggaggg | cc aagg | gcacagatacgcagtattt | 2725 | C A S S Q G A S G R A K G T D T Q Y F |
| 14.14 | TRBV14*01 | TRBJ2-7*01 | TRBD2*02 | 1030 | tgtgccagcagcca | gggc | ctagcggag | ttac | ctcctacgagcagtactc | 2726 | C A S S Q G L A G V T S Y E Q Y F |
| 14.15 | TRBV14*01 | TRBJ2-7*01 | TRBD2*01 | 1031 | tgtgccagcagcagg | gc | cggg | taaa | gagcagtactc | 2727 | C A S S Q G R G K E Q Y F |
| 14.16 | TRBV14*01 | TRBJ2-2*01 | TRBD1*01 | 1032 | tgtgccagcagccaa | ccaactc | gacaggg | ac | cgaacaccgggagctgttttt | 2728 | C A S S Q P T R Q G P N T G E L F F |
| 14.17 | TRBV14*01 | TRBJ2-3*01 | TRBD1*01 | 1033 | tgtgccagcagcca | gtccc | cagggg | a | acgcagtattt | 2729 | C A S S Q S P G G T Q Y F |
| 14.18 | TRBV14*01 | TRBJ2-5*01 | TRBD2*01 | 1034 | tgtgccagc | te | gactagcgg | cc | accaagagaccagtactc | 2730 | C A S S T S G H Q E T Q Y F |
| 15.01 | TRBV15*01 | TRBJ2-5*01 | TRBD1*01 | 1035 | tgtgcca | t | acagggg | acctc | agagaccagtactc | 2731 | C A I Q G T S E T Q Y F |
| 15.02 | TRBV15*01 | TRBJ2-1*01 | TRBD2*01 | 1036 | tgtgccacc | ggac | ctgagccgtagtcg | | atgagcagttcttc | 2732 | C A T G P E R V V D E Q F F |
| 15.03 | TRBV15*02 | TRBJ2-1*01 | | 1037 | tgtg | ccaccgaaagcctaaacgaaacc | gag ctcctacaatgagcagtcttc | | | 2733 | C A T R K P N E P S S Y N E Q F F |
| 15.04 | TRBV15*02 | TRBJ2-1*01 | TRBD2*01 | 1038 | tgtg | ccaccagattaaaag | gcgg | | ctacaatgagcagttcttc | 2734 | C A T R L K G G Y N E Q F F |
| 15.05 | TRBV15*01 | TRBJ2-5*01 | TRBD2*02 | 1039 | tgtgccaccagc | gctcat | ggagg | | agagaccagtactc | 2735 | C A T S A H G G E T Q Y F |
| 15.06 | TRBV15*01 | TRBJ2-2*01 | TRBD1*01 | 1040 | tgtgccaccagc | gacga | gggacaggggc | gcg | caccggggagctgttttt | 2736 | C A T S D E G Q G A R T G E L F F |
| 15.07 | TRBV15*01 | TRBJ2-1*01 | TRBD2*02 | 1041 | tgtgccaccagca | ggactagcggga | ag | | gagcagttctc | 2737 | C A T S G L A G E E Q F F |
| 15.08 | TRBV15*01 | TRBJ2-2*01 | TRBD2*01 | 1042 | tgtgccaccagca | tagcaggtaccatgaacac | cgggg | agca | gttttt | 2738 | C A T S I A G T M N T G E Q F F |
| 15.09 | TRBV15*01 | TRBJ2-5*01 | TRBD2*01 | 1043 | tgtgccaccagca | tagtc | gcggg | cgagaacaattt | cttc | 2739 | C A T S I V A G E N N F F |
| 15.10 | TRBV15*02 | TRBJ2-1*01 | TRBD1*01 | 1044 | tgtg | ccaccagcaaagattac | acagg | ctcctacaatgagcagttcttc | | 2740 | C A T S K D Y T G S Y N E Q F F |
| 15.11 | TRBV15*01 | TRBJ2-1*01 | TRBD2*01 | 1045 | tgtg | ccaccagtcta | actagcggg | | tacaatgagcagttcttc | 2741 | C A T S L T S G Y N E Q F F |
| 15.12 | TRBV15*01 | TRBJ2-5*01 | TRBD2*01 | 1046 | tgtgccaccagca | accatg | gcgg | | agagaccagtactc | 2742 | C A T S N H G G E T Q Y F |
| 15.13 | TRBV15*01 | TRBJ2-7*01 | TRBD2*02 | 1047 | tgtgccaccagc | cccg | gcgggag | tctgag | ccgagcagtactc | 2743 | C A T S P G G S L S E Q Y F |
| 15.14 | TRBV15*01 | TRBJ2-5*01 | TRBD1*01 | 1048 | tgtgccaccag | cctc gggaca | ccgtacaagagaccaa | tacttc | | 2744 | C A T S P R D T V Q E T Q Y F |
| 15.15 | TRBV15*01 | TRBJ2-7*01 | TRBD2*01 | 1049 | tgtgccaccacag | g | gcgg | ccggg | tacgcagtactc | 2745 | C A T S R A A G Y E Q Y F |
| 15.16 | TRBV15*02 | TRBJ1-5*01 | TRBD1*01 | 1050 | tgtg | ccaccagcagag | cagggg | c | caatcagcccccagcagttt | 2746 | C A T S R A G A N Q P Q H F |

Figure 1-39

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 15.17 | TRBV15*02 | TRBJ2-1*01 | TRBD1*01 | 1051 | tgtg....... | ccaccagcagagcaa | .ggacagg... | cctt ....... | aatgagcagttcttc | 2747 | C A T S R A R T G L N E Q F F |
| 15.18 | TRBV15*02 | TRBJ2-7*01 | TRBD1*01 | 1052 | tgtg....... | ccaccagcagagatgcc | .ggacag...... | ............ | tacgagcagtactc | 2748 | C A T S R D A G Q Y E Q Y F |
| 15.19 | TRBV15*02 | TRBJ2-7*01 | TRBD2*02 | 1053 | tgtg....... | ccaccagcagagagat | gggactagcaggagg | ..... | tacgagcagtactc | 2749 | C A T S R D G T S G R Y E Q Y F |
| 15.20 | TRBV15*02 | TRBJ1-5*01 | | 1054 | tgtg....... | ccaccagcagagatcacgcagcttcttg | .........gcccccagcattt | | | 2750 | C A T S R D H A A S S W P Q H F |
| 15.21 | TRBV15*02 | TRBJ2-3*01 | TRBD2*02 | 1055 | tgtg....... | ccaccagcagagagatc | ..ctagcggaggg | ...cagatacgcagtatttt | | 2751 | C A T S R D P S G R A D T Q Y F |
| 15.22 | TRBV15*02 | TRBJ2-5*01 | TRBD1*01 | 1056 | tgtg....... | ccaccagcagagatcccag | ....cagg.... | cgaatt ...gagaccagtactc | | 2752 | C A T S R D P S R R I E T Q Y F |
| 15.23 | TRBV15*02 | TRBJ2-1*01 | TRBD1*01 | 1057 | tgtg....... | ccaccagcagca | gggacagggg.... | cg ....acaatgagcagttcttc | | 2753 | C A T S R D R G D N E Q F F |
| 15.24 | TRBV15*01 | TRBJ2-6*01 | TRBD1*01 | 1058 | tgtgccaccagcagcag... | gga ...acaggg... | ctctgggccaacgtcctgacttc | | | 2754 | C A T S R E Q Q S G A N V L T F |
| 15.25 | TRBV15*02 | TRBJ2-3*01 | TRBD1*01 | 1059 | tgtg....... | ccaccagcagagaaa cc | gggacagggg. | at ...cagatacgcagtattttt | | 2755 | C A T S R E T G T G G S D T Q Y F |
| 15.26 | TRBV15*02 | TRBJ1-1*01 | TRBD1*01 | 1060 | tgtg....... | ccaccagcagagagt | .....ggggg. taggaag | ...cactgaagcttcttt | | 2756 | C A T S R E V G V G S T E A F F |
| 15.27 | TRBV15*02 | TRBJ2-7*01 | TRBD2*02 | 1061 | tgtg....... | ccaccagcagaggagct | ..actagcgggag... | catc ....ggagcagtactc | | 2757 | C A T S R G E L L A G A S E Q Y F |
| 15.28 | TRBV15*02 | TRBJ2-5*01 | TRBD2*01 | 1062 | tgtg....... | ccaccagcagagggaaa | .........ggggggg. | .aagagaccagtactc | | 2758 | C A T S R G K G G E E T Q Y F |
| 15.29 | TRBV15*02 | TRBJ2-7*01 | TRBD1*01 | 1063 | tgtg....... | ccaccagcag | gggacagggggc g aga | ......gagcagtactc | | 2759 | C A T S R G Q G A R E Q Y F |
| 15.30 | TRBV15*02 | TRBJ2-1*01 | TRBD1*01 | 1064 | tgtg....... | ccaccagcag | gggacag.... | ctt ag ctcctacaatgagcagttcttc | | 2760 | C A T S R G Q L S S Y N E Q F F |
| 15.31 | TRBV15*01 | TRBJ1-5*01 | TRBD2*02 | 1065 | tgtgccaccagcagag. | .......ggagg gagagag | ....tcagcccagcatt | | | 2761 | C A T S R G R G E S Q P Q H F |
| 15.32 | TRBV15*01 | TRBJ2-3*01 | TRBD2*02 | 1066 | tgtgccaccagcagag. | .gtaca | ......gggagg. agaggg | ..acagatacgcagtatttt | | 2762 | C A T S R G T G R R G T D T Q Y F |
| 15.33 | TRBV15*01 | TRBJ2-1*01 | TRBD2*01 | 1067 | tgtgccaccagcagag. | ..ggactagcg... | c ........ | ......caatgagcagttcttc | | 2763 | C A T S R G T S A N E Q F F |
| 15.34 | TRBV15*01 | TRBJ2-7*01 | TRBD2*01 | 1068 | tgtg | ccaccagcagagcgt. | ..ctagcgg..... | atttc ctcctacgagcagtactc | | 2764 | C A T S R R L A D S S Y E Q Y F |
| 15.35 | TRBV15*02 | TRBJ2-7*01 | TRBD1*01 | 1069 | tgtg....... | ccaccagtagaa ..ggacag..... | ctc ..cctacgagcagtactc | | | 2765 | C A T S R R T A P Y E Q Y F |
| 15.36 | TRBV15*02 | TRBJ1-1*01 | TRBD2*02 | 1070 | tgtg....... | ccaccagcagcagatcat c | gggacag.... | tgg ...tacgagcagtactc | | 2766 | C A T S R S S G Q W Y E Q Y F |
| 15.37 | TRBV15*02 | TRBJ2-2*02 | TRBD2*01 | 1071 | tgtg....... | ccaccagcagagtttcc | ........ggag. | a ......tgaagcttcttt | | 2767 | C A T S R V S G D E A F F |
| 15.38 | TRBV15*02 | TRBJ2-5*01 | TRBD2*01 | 1072 | tgtgccaccag..... | tcggt .......ggggggg t | ....gagaccagtactc | | | 2768 | C A T S R W G G E T Q Y F |
| 15.39 | TRBV15*02 | TRBJ1-6*01 | TRBD2*02 | 1073 | tgtg....... | ccaccagccgatac | ...cggaag. agc. | ....aattcaccctccacttt | | 2769 | C A T S R Y R E S N S P L H F |
| 15.40 | TRBV15*01 | TRBJ2-3*01 | TRBD2*01 | 1074 | tgtgccaccagcag.. | cgcagca ...act........ | agcacagatacgcagtatttt | | | 2770 | C A T S S A A T S T D T Q Y F |
| 15.41 | TRBV15*02 | TRBJ2-7*01 | TRBD1*01 | 1075 | tgtg....... | ccaccagcagaca..... | ......tacgagcagtactc | | | 2771 | C A T S S F G T Q Y E Q Y F |
| 15.42 | TRBV15*02 | TRBJ2-5*01 | TRBD2*01 | 1076 | tgtg....... | ccaccagcagcca | ........cgggggg. | .agagaccagtactc | | 2772 | C A T S S H G G E T Q Y F |
| 15.43 | TRBV15*01 | TRBJ2-5*01 | TRBD1*01 | 1077 | tgtgccaccac...... | gtcatccacgg | ....cagggg ....... | gagaccagtactc | | 2773 | C A T S S T A G E T Q Y F |

Figure 1-40

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 15.44 | TRBV15*01 | TRBJ2-5*01 | TRBD2*01 | 1078 | tgtgccacagca... | ccgtc ......gcggg... | c ...gagaccagtactc | | | 2774 | C A T S T V A G E T Q Y F |
| 18.01 | TRBV18*01 | TRBJ2-5*01 | TRBD2*02 | 1079 | tgtgccagctcacc... c | ........gagg. tgag. | ccaaggagaccagtactc | | | 2775 | C A S S P E V S Q E T Q Y F |
| 18.02 | TRBV18*01 | TRBJ1-1*01 | TRBD1*01 | 1080 | tgtgccagctc... | ccc .....ggggc agg | gaaacactgaagcttctt | | | 2776 | C A S S P G A G N T E A F F |
| 18.03 | TRBV18*01 | TRBJ1-3*01 | TRBD1*01 | 1081 | tgtgccagctcacc... c | .......gggc agtcaggagagt...tgaaacaccatatattt | | | | 2777 | C A S S P G Q S G E F G N T I Y F |
| 18.04 | TRBV18*01 | TRBJ1-5*01 | TRBD1*01 | 1082 | tgtgccagctcacca... | ggg. tcggg ....tcagcccagcattt | | | | 2778 | C A S S P G S G Q P Q H F |
| 18.05 | TRBV18*01 | TRBJ1-3*01 | TRBD1*01 | 1083 | tgtgccagctcacc... | tccc ..gacagg.... agaa ..ctgaaacaccatatattt | | | | 2779 | C A S S P P D R R T G N T I Y F |
| 18.06 | TRBV18*01 | TRBJ1-6*01 | TRBD1*01 | 1084 | tgtgccagctcaccacc | ggt .......ggc ggcattagaa .......tcacccctccacttt | | | | 2780 | C A S S P P V A A L E S P L H F |
| 18.07 | TRBV18*01 | TRBJ2-1*01 | TRBD2*01 | 1085 | tgtgccagctcaccac. | gggac............. ggggc ......caatgagcagttcttc | | | | 2781 | C A S S P R D G A N E Q F F |
| 18.08 | TRBV18*01 | TRBJ2-6*01 | TRBD1*01 | 1086 | tgtgccagctcacc... | ggt ...acagggggc ctctggggccaacgtcctgactc | | | | 2782 | C A S S P V Q G A S G A N V L T F |
| 18.09 | TRBV18*01 | TRBJ2-2*01 | TRBD1*01 | 1087 | tgtgccagctcac... | aa .ggacaggg... ctc ...caccgggagctcttt | | | | 2783 | C A S S Q G G S T G E L F F |
| 18.10 | TRBV18*01 | TRBJ2-7*01 | TRBD1*01 | 1088 | tgtgccagctc...... | gcgtacc ......gggc ccgaatctc ..cctacgagcagtacttc | | | | 2784 | C A S S R T G P E S P Y E Q Y F |
| 18.11 | TRBV18*01 | TRBJ2-2*01 | TRBD2*01 | 1089 | tgtgccagctc...... | cc ..ggacta........ cgaacaccgggagagctgttt | | | | 2785 | C A S S R T T N T G E L F F |
| 19.01 | TRBV19*01 | TRBJ2-3*01 | TRBD1*01 | 1090 | tgtgccagt........ | gctgggggtcgg ....ctagcgg........ tgag ....agatacgcagtatt | | | | 2786 | C A S A G G R L A V R D T Q Y F |
| 19.02 | TRBV19*01 | TRBJ2-1*01 | TRBD1*01 | 1091 | tgtgccagt...... | cgaa ..gac....... caagt ...agatacgcagtattt | | | | 2787 | C A S E D Q V D T Q Y F |
| 19.03 | TRBV19*01 | TRBJ1-3*01 | TRBD1*01 | 1092 | tgtgccag....... | c ..ggacag.... aaaac ctctgaaacaccatatattt | | | | 2788 | C A S G Q K T S G N T I Y F |
| 19.04 | TRBV19*01 | TRBJ1-2*01 | TRBD2*01 | 1093 | tgtgccagt...... | gggt ........ cggg........ tggctacacctc | | | | 2789 | C A S G S G G Y T F |
| 19.05 | TRBV19*01 | TRBJ2-7*01 | TRBD1*01 | 1094 | tgtgccagt...... | gggacagg... ac ..cctacgagcagtactc | | | | 2790 | C A S G T G P Y E Q Y F |
| 19.06 | TRBV19*01 | TRBJ1-1*01 | TRBD1*01 | 1095 | tgtgccagt....... | catgg ....caggg... taggg ......actgaagcttctt | | | | 2791 | C A S H G R V G T E A F F |
| 19.07 | TRBV19*01 | TRBJ1-5*01 | TRBD1*01 | 1096 | tgtgccagta..... | t ...acaggggc tggg agcaatcagcccagcattt | | | | 2792 | C A S I Q G A G S N Q P Q H F |
| 19.08 | TRBV19*01 | TRBJ2-1*01 | TRBD2*02 | 1097 | tgtgccagt....... | ctagcggggagg c tt...... aatgagcagttcttc | | | | 2793 | C A S L A G G L N E Q F F |
| 19.09 | TRBV19*01 | TRBJ1-1*01 | TRBD1*01 | 1098 | tgtgccagta..... | tgattcctc ..gacaggggc cggg .....ctgaagcttctt | | | | 2794 | C A S M I P S T G G R A E A F F |
| 19.10 | TRBV19*01 | TRBJ2-1*01 | TRBD2*01 | 1099 | tgtgcc.......... | tccca gggactagc....... ag g ctcctacaatgagcagttctc | | | | 2795 | C A S Q G L A G S Y N E Q F F |
| 19.11 | TRBV19*01 | TRBJ2-7*01 | TRBD2*01 | 1100 | tgtgccag....... | c ........cgggg... aga ctcctacgagcagtactc | | | | 2796 | C A S R G D S Y E Q Y F |
| 19.12 | TRBV19*01 | TRBJ2-2*01 | | 1101 | tgtgccagtag..... | acactgcta ....accgggggagctgttt | | | | 2797 | C A S R H W L T G E L F F |
| 19.13 | TRBV19*01 | TRBJ2-1*01 | TRBD1*01 | 1102 | tgtgccagt........ | cgct ...caggg... cc ....caccgggggagctgttttt | | | | 2798 | C A S R S G P T G E L F F |
| 19.14 | TRBV19*01 | TRBJ2-7*01 | TRBD2*01 | 1103 | tgtgccagtag..... | gt ...ctagcggggg.. aacct ...ctacgagcagtactc | | | | 2799 | C A S R S S G G N L Y E Q Y F |
| 19.15 | TRBV19*01 | TRBJ1-5*01 | TRBD2*01 | 1104 | tgtgccag........ | c ........cggg... tagcagcata ...caatcagcccagcattt | | | | 2800 | C A S R V A A Y N Q P Q H F |

Figure 1-41

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 19.16 | TRBV19*01 | TRBJ2-1*01 | TRBD2*02 | 1105 | tgtgccagt... | cgag ... | tagcggaagg | c ...cctacaatgagcagttcttc | | 2801 | C A S R V A G G P Y N E Q F F |
| 19.17 | TRBV19*01 | TRBJ1-2*01 | TRBD1*01 | 1106 | tgtgccagtag... | cg cc | gggac... | ggcg ... | tatggctacacctc | 2802 | C A S S A G T A Y G Y T F |
| 19.18 | TRBV19*01 | TRBJ2-2*01 | TRBD2*01 | 1107 | tgtgccagtagt... | gccct ... | actagc... | ccct ... | gggagctgttttt | 2803 | C A S S A L L A P G E L F F |
| 19.19 | TRBV19*01 | TRBJ2-1*01 | TRBD2*02 | 1108 | tgtgccagtact... | gc ... | gactagcgggag.. | tggaa ... | ctacaatgagcagttcttc | 2804 | C A S S A T S G G N Y N E Q F F |
| 19.20 | TRBV19*01 | TRBJ2-2*01 | TRBD2*02 | 1109 | tgtgccagtag... | cttc ... | actagcgggag.. | tatatggg ... | ccgggagctgttttt | 2805 | C A S S F T S G S I W A G E L F F |
| 19.21 | TRBV19*01 | TRBJ2-3*01 | TRBD2*02 | 1110 | tgtgccagtag... | c | ggactagcggga... | tcctcccggg ... | cagatacgcagtattt | 2806 | C A S S G L A G S S R A D T Q Y F |
| 19.22 | TRBV19*01 | TRBJ2-3*01 | TRBD2*01 | 1111 | tgtgccagtag... | c | ggacta... | tcggatcctcccggcagatacgcat ... lattt | | 2807 | C A S S G L S G S S R A D T H Y F |
| 19.23 | TRBV19*01 | TRBJ2-2*01 | TRBD1*01 | 1112 | tgtgccagtagt... | ggaa ... | gacaggg... | aaa | gaacaccgggagctgttttt | 2808 | C A S S G R Q G K N T G E L F F |
| 19.24 | TRBV19*01 | TRBJ1-1*01 | TRBD1*01 | 1113 | tgtgccagtagtatag... | c | ggac... | cga ... | gaagctttctt | 2809 | C A S S I A D R E A F F |
| 19.25 | TRBV19*01 | TRBJ2-1*01 | TRBD2*01 | 1114 | tgtgccagtagtatag... | cggg... | t | ... | tacaatgagcagttcttc | 2810 | C A S S I A G Y N E Q F F |
| 19.26 | TRBV19*01 | TRBJ2-1*01 | TRBD2*01 | 1115 | tgtgccagtagtatag... | ctgt | gggacta... | aatgagcagttcttc | | 2811 | C A S S I A V G L N E Q F F |
| 19.27 | TRBV19*01 | TRBJ2-7*01 | TRBD2*02 | 1116 | tgtgccagtagtataga | tggcgg ... | agcaggg... | cgt ...ctacgagcagttcttc | | 2812 | C A S S I D G G A G V Y E Q Y F |
| 19.28 | TRBV19*01 | TRBJ2-1*01 | TRBD1*01 | 1117 | tgtgccagtagtat... | c | gaca... | aacc ... | caatgagcagttcttc | 2813 | C A S S I D K P N E Q F F |
| 19.29 | TRBV19*01 | TRBJ1-5*01 | TRBD1*01 | 1118 | tgtgccagtagtataga | ctc | ggac... | ct | ...caatcagcccagcattt | 2814 | C A S S I D S D L N Q P Q H F |
| 19.30 | TRBV19*01 | TRBJ2-1*01 | TRBD2*01 | 1119 | tgtgccagtagtataga | c | ...actagcgggag.. | ctcctacaatgagcagttcttc | | 2815 | C A S S I D T S G G S Y N E Q F F |
| 19.31 | TRBV19*01 | TRBJ2-5*01 | TRBD1*01 | 1120 | tgtgccagtagtataga | tt | ggacaggg... | tatttg ... | gagaccgagttactc | 2816 | C A S S I D W T G Y L E T Q Y F |
| 19.32 | TRBV19*01 | TRBJ2-7*01 | | 1121 | tgtgccagtagtat... | cttcttttg | g | ctcctacgagcagttcttc | | 2817 | C A S S I F F G S Y E Q Y F |
| 19.33 | TRBV19*01 | TRBJ2-7*01 | TRBD1*01 | 1122 | tgtgccagtagtat... | cttcggcg ... | cttcgggac... | agc... | agc... | actc | 2818 | C A S S I F G E Q H F |
| 19.34 | TRBV19*01 | TRBJ2-2*01 | TRBD1*01 | 1123 | tgtgccagtagtat... | tttt | gggaca... | agtt ...acacggggagctgttttt | | 2819 | C A S S I F G T S Y T G E L F F |
| 19.35 | TRBV19*01 | TRBJ2-7*01 | TRBD2*01 | 1124 | tgtgccagtagtatag... | gtg ... | ctagcggg... | tctttg ... | gagcagttcttc | 2820 | C A S S I G A S G S L E Q F F |
| 19.36 | TRBV19*01 | TRBJ2-3*01 | TRBD2*02 | 1125 | tgtgccagtagtatag... | g | gggactagcgggag.. | ... | cagatacgcagtattt | 2821 | C A S S I G G L A G A D T Q Y F |
| 19.37 | TRBV19*01 | TRBJ1-5*01 | TRBD1*01 | 1126 | tgtgccagtagtat... | ggggc | acctacg ... | gcaatcagcccagcattt | | 2822 | C A S S I G G T Y G N Q P Q H F |
| 19.38 | TRBV19*01 | TRBJ2-4*01 | TRBD1*01 | 1127 | tgtgccagtagtat... | ggcac ...acagg... | cgga ct agccaaaaacattcagttcttc | | | 2823 | C A S S I G H T G G L A K N I Q Y F |
| 19.39 | TRBV19*01 | TRBJ2-1*01 | TRBD1*01 | 1128 | tgtgccagtagtat... | t | ... | gggc agt ctctacaatgagcagttcttc | | 2824 | C A S S I G Q V S Y N E Q F F |
| 19.40 | TRBV19*01 | TRBJ1-2*01 | TRBD2*01 | 1129 | tgtgccagtagtatag... | ggt ... | cgggggg... | clattt ... | tatgctacacctc | 2825 | C A S S I G S G G Y F Y G Y T F |
| 19.41 | TRBV19*01 | TRBJ2-7*01 | TRBD1*01 | 1130 | tgtgccagtagtat... | c | gggacacgg... | tcctacgagcagttcttc | | 2826 | C A S S I G T G S Y E Q Y F |
| 19.42 | TRBV19*01 | TRBJ1-2*01 | | 1131 | tgtgccagtagtat... | cgg ...ctatgctacacctc | | | | 2827 | C A S S I G Y G Y T F |
| 19.43 | TRBV19*01 | TRBJ2-1*01 | TRBD2*01 | 1132 | tgtgccagtagtat... | tatttcggg | cc | ggac... | gct ...tacaatgagcagttcttc | 2828 | C A S S I I S G R D A Y N E Q F F |

Figure 1-42

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 19.44 | TRBV19*01 | TRBJ1-1*01 | TRBD1*01 | 1133 | tgtgccagtagtat... | taa...acaggggc | cggg | a | tgaacactgaagctttctt | 2829 | C A S S I K Q G A G M N T E A F F |
| 19.45 | TRBV19*01 | TRBJ1-2*01 | | 1134 | tgtgccagtagtat... | cctttt | | ......caatgagcagttcttc | | 2830 | C A S S I L F N E Q F F |
| 19.46 | TRBV19*01 | TRBJ2-1*01 | TRBD2*01 | 1135 | tgtgccagtagtat... | ctt...actagcg... | cg | ...tacaatgagcagttcttc | | 2831 | C A S S I L A A Y N E Q F F |
| 19.47 | TRBV19*01 | TRBJ2-1*01 | TRBD2*01 | 1136 | tgtgccagtagtat... | cttgtt | ggg... | to | ...acaatgagcagttcttc | 2832 | C A S S I L L G H N E Q F F |
| 19.48 | TRBV19*01 | TRBJ1-5*01 | | 1137 | tgtgccagtagtat... | ta | a | tagcaatcagcccagcatttt | | 2833 | C A S S I N S N Q P Q H F |
| 19.49 | TRBV19*01 | TRBJ2-5*01 | TRBD1*01 | 1138 | tgtgccagtagtata... | a | gggacag... | ...ccaagagaccccagtactc | | 2834 | C A S S I R D S Q E T Q Y F |
| 19.50 | TRBV19*01 | TRBJ1-5*01 | TRBD1*01 | 1139 | tgtgccagtagtat... | ct cc | gggacagg... | tct | ...aatcagcccagcatttt | 2835 | C A S S I S G T G S N Q P Q H F |
| 19.51 | TRBV19*01 | TRBJ2-7*01 | TRBD1*01 | 1140 | tgtgccagtagtata... | tcca | gggacagg... | cgcga | ......gagcagtactc | 2836 | C A S S I S R D R A R E Q Y F |
| 19.52 | TRBV19*01 | TRBJ2-7*01 | TRBD2*01 | 1141 | tgtgccagtag.tataacc... | agcgggg... | aacct | ...tacgagcagtactc | | 2837 | C A S S I T S G E P Y E Q Y F |
| 19.53 | TRBV19*01 | TRBJ1-5*01 | | 1142 | tgtgccagtagtatag.ttct..caatcagcccagcatttt | | | | | 2838 | C A S S I V L N Q P Q H F |
| 19.54 | TRBV19*01 | TRBJ2-7*01 | TRBD1*01 | 1143 | tgtgccagtagtat... | cgtcgta..gacag.... | tta | ...ctacgagcagtactc | | 2839 | C A S S I V V D S Y Y E Q Y F |
| 19.55 | TRBV19*01 | TRBJ1-5*01 | TRBD2*01 | 1144 | tgtgccagtagtat... | tt | ......gggggg | gggtacccaccccccaggt | ......tttt | 2840 | C A S S I W G G G T H P Q V F |
| 19.56 | TRBV19*01 | TRBJ2-7*01 | | 1145 | tgtgccagtagtat...ctgccctgccg...acgagcagtactc | | | | | 2841 | C A S S I W P A D E Q Y F |
| 19.57 | TRBV19*01 | TRBJ2-2*01 | TRBD1*01 | 1146 | tgtgccagtagt... | ...ctagcg... | tccgg | ......cggggagctgtttt | | 2842 | C A S S L A S G G E L F F |
| 19.58 | TRBV19*01 | TRBJ2-7*01 | TRBD2*01 | 1147 | tgtgccagtagt... | ctcct | ...cggggg... | a | .tcctacgagcagtactc | 2843 | C A S S L L G G S Y E Q Y F |
| 19.59 | TRBV19*01 | TRBJ2-7*01 | TRBD1*01 | 1148 | tgtgccagtagt... | ctacgatc... | caggg... | ag | ...tacgagcagtactc | 2844 | C A S S L R S R E Y E Q Y F |
| 19.60 | TRBV19*01 | TRBJ1-5*01 | TRBD1*01 | 1149 | tgtgccagtagt... | ggac... | caggc... | | cagcccagcatt | 2845 | C A S S M D P G Q P Q H F |
| 19.61 | TRBV19*01 | TRBJ1-5*01 | TRBD1*01 | 1150 | tgtgccagtagt... | gggat... | ggggg... | | agcccagcatt | 2846 | C A S S M G M G E P Q H F |
| 19.62 | TRBV19*01 | TRBJ2-3*01 | TRBD1*01 | 1151 | tgtgccagtagt... | gcttc | ...cagg... | | acagatacgcagtatttt | 2847 | C A S S M L P G T D T Q Y F |
| 19.63 | TRBV19*01 | TRBJ2-1*01 | TRBD2*01 | 1152 | tgtgccagtagtat... | ...gactagcggggg... | a | ag ctcctacaatgagcagttcttc | | 2848 | C A S S M T S G G S S Y N E Q F F |
| 19.64 | TRBV19*01 | TRBJ2-1*01 | TRBD2*01 | 1153 | tgtgccagtagtat... | ggtacgtctccgg | oggact... | ...ttga | ....acaatgagcagttcttc | 2849 | C A S S M V R L R G T L N N E Q F F |
| 19.65 | TRBV19*01 | TRBJ2-1*01 | | 1154 | tgtgccagtagtat... g | | | ...tacaatgagcagttcttc | | 2850 | C A S S M Y N E Q F F |
| 19.66 | TRBV19*01 | TRBJ2-1*01 | TRBD2*02 | 1155 | tgtgccagtagta... | atgct | ...ctagcgga... | cct | ...tacaatgagcagttcttc | 2851 | C A S S N A L A G P Y N E Q F F |
| 19.67 | TRBV19*01 | TRBJ2-1*01 | TRBD2*01 | 1156 | tgtgccagtagta... | a | ......cgggg... | cgatatgg | ......aatgagcagttcttc | 2852 | C A S S N G A I W N E Q F F |
| 19.68 | TRBV19*01 | TRBJ1-2*01 | TRBD1*01 | 1157 | tgtgccagtagt... | ...ccggca cc | gggacagggg... | aaag | ...atgctacacctc | 2853 | C A S S P A P G Q G K D G Y T F |
| 19.69 | TRBV19*01 | TRBJ2-1*01 | TRBD2*01 | 1158 | tgtgccagtagt... | cca | ggact... | caaaacggg | ........tgagcagttcttc | 2854 | C A S S P G L K T G E Q F F |
| 19.70 | TRBV19*01 | TRBJ1-5*01 | TRBD1*01 | 1159 | tgtgccagtag... | ccctata | gggacaggg... | aagt | ...tcagcccagcatttt | 2855 | C A S S P I G T G E V Q P Q H F |
| 19.71 | TRBV19*01 | TRBJ2-3*01 | TRBD2*01 | 1160 | tgtgccagtag...ccccc | ......cggggg | aggccag | ......gatacgcagtatttt | | 2856 | C A S S P P G G G Q D T Q Y F |

Figure 1-43

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 19.72 | TRBV19*01 | TRBJ2-1*01 | TRBD1*01 | 1161 | tgtgccagtagt | cccac | ggaca | ca ag ctcctacaatgagcagttcttc | | 2857 | C A S S P T D T S S Y N E Q F F |
| 19.73 | TRBV19*01 | TRBJ2-4*01 | TRBD1*01 | 1162 | tgtgccagtagt | ccctatc | gacagggg | agg | acattgactactc | 2858 | C A S S P Y R Q G E D I Q Y F |
| 19.74 | TRBV19*01 | TRBJ1-5*01 | TRBD1*01 | 1163 | tgtgccagtag | c | cagggg | tttacc | agcaatcagcccagcattt | 2859 | C A S S Q G F T S N Q P Q H F |
| 19.75 | TRBV19*01 | TRBJ1-6*01 | TRBD1*01 | 1164 | tgtgccag | cagtcag | caggg | cgg | taattcaccctccacttt | 2860 | C A S S Q Q G G N S P L H F |
| 19.76 | TRBV19*01 | TRBJ1-4*01 | TRBD1*01 | 1165 | tgtgccagtagt | ca | gacag | caactaatgaaaaactgttttt | | 2861 | C A S S Q T A T N E K L F F |
| 19.77 | TRBV19*01 | TRBJ2-3*01 | TRBD1*01 | 1166 | tgtgccagtagt | caaac | ggggc | g | gatacgcagtattt | 2862 | C A S S Q T G A D T Q Y F |
| 19.78 | TRBV19*01 | TRBJ2-7*01 | TRBD1*01 | 1167 | tgtgccagtag | cca | gacagggg | | ctacgagcagtactc | 2863 | C A S S Q T G G Y E Q Y F |
| 19.79 | TRBV19*01 | TRBJ2-3*01 | TRBD2*01 | 1168 | tgtgccagtag | cc | gggac | cctgggat | agatacgcagtattt | 2864 | C A S S R D P S G I D T Q Y F |
| 19.80 | TRBV19*01 | TRBJ2-7*01 | TRBD2*01 | 1169 | tgtgccagtagt | c | grcg | tttcagca | acgagcagtactc | 2865 | C A S S R G F S N E Q Y F |
| 19.81 | TRBV19*01 | TRBJ2-3*01 | TRBD2*01 | 1170 | tgtgccagtagt | c | gactaccg | attg | gcacagatacgcagtattt | 2866 | C A S S R L A I G T D T Q Y F |
| 19.82 | TRBV19*01 | TRBJ1-4*01 | TRBD1*01 | 1171 | tgtgccagtagt | tccgccgagg | aggg | cgtgggg | gaaaaactgttttt | 2867 | C A S S A E E G V G E K L F F |
| 19.83 | TRBV19*01 | TRBJ1-1*01 | TRBD1*01 | 1172 | tgtgccagtagt | tcgg | cagggg | gtcgag | cactgaagcttcttt | 2868 | C A S S A G G W S T E A F F |
| 19.84 | TRBV19*01 | TRBJ2-1*01 | TRBD1*01 | 1173 | tgtgccagtagt | tccgagtgtcgg | gggacagggggc | tacgcggcc | cctacaatgagcagttcttc | 2869 | C A S S E V W G D R G L A G P Y N E Q F F |
| 19.85 | TRBV19*01 | TRBJ2-7*01 | TRBD1*01 | 1174 | tgtgccagtagt | tcc | gacagg | tgag | ctacgagcagtactc | 2870 | C A S S R Q V S Y N E Q F F |
| 19.86 | TRBV19*01 | TRBJ2-7*01 | TRBD1*01 | 1175 | tgtgccagtagt | tcctcgt | cggacaggg | ta | tacaatgagcagttctc | 2871 | C A S S W D R V Y N E Q F F |
| 19.87 | TRBV19*01 | TRBJ2-2*01 | TRBD2*01 | 1176 | tgtgccagtagta | | cgg | | ccgggagctgtttt | 2872 | C A S S T A G E L F F |
| 19.88 | TRBV19*01 | TRBJ2-7*01 | TRBD2*01 | 1177 | tgtgccagtagta | c | agccgg | ttg | cctacgagcagtactc | 2873 | C A S S T A V A Y E Q Y F |
| 19.89 | TRBV19*01 | TRBJ2-2*01 | TRBD2*01 | 1178 | tgtgccagtagta | c | gggactacgcggag | tccgcg | ccggggagctgttttt | 2874 | C A S S T G L A G V R A G E L F F |
| 19.90 | TRBV19*01 | TRBJ2-1*01 | TRBD2*02 | 1179 | tgtgccagtagta | cccatgaa | ggactacgcggaggg | c aaggg | atgagcagttcttc | 2875 | C A S S T H E G L A G G G D E Q F F |
| 19.91 | TRBV19*01 | TRBJ2-2*01 | TRBD2*02 | 1180 | tgtgccagtagta | caaacgccgatgacct | caccgggagctgtttt | | | 2876 | C A S S T N A D D L T G E L F F |
| 19.92 | TRBV19*01 | TRBJ1-1*01 | TRBD1*01 | 1181 | tgtgccagtagt | gt gggacagggg | cgg | actgaagcttcttt | | | 2877 | C A S S V G Q G R T E A F F |
| 19.93 | TRBV19*01 | TRBJ2-7*01 | TRBD2*01 | 1182 | tgtgccagtagta | gtcc gggac | | ggaggta | cctacgagcagtactc | 2878 | C A S S V R D G G T Y E Q Y F |
| 19.94 | TRBV19*01 | TRBJ2-7*02 | TRBD2*02 | 1183 | tgtgccagta | caaa | cggga | tt | aacaccgggagctgttttt | 2879 | C A S T N G I N T G E L F F |
| 19.95 | TRBV19*01 | TRBJ2-2*01 | TRBD2*01 | 1184 | tgtgccagta | ctccgggagag gggactag | tcgt | accgggagctgtttt | | 2880 | C A S T P G E G T S R T G E L F F |
| 19.96 | TRBV19*01 | TRBJ2-7*01 | TRBD2*02 | 1185 | tgtgccagt | gttca | gggagg | cgagcagtg | ctc | 2881 | C A S V Q Q G E Q C F |
| 19.97 | TRBV19*01 | TRBJ2-7*01 | TRBD2*02 | 1186 | tgtgccagt | gttca | gggagg | cgagcagtactc | | 2882 | C A S V Q Q G E Q Y F |
| 19.98 | TRBV19*01 | TRBJ2-1*01 | TRBD2*01 | 1187 | tgtgccagt | tacggcccctgag | agcg | ag | ctacaatgagcagttcttc | 2883 | C A S Y G P W R A S Y N E Q F F |

Figure 1-44

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 19.99 | TRBV19*01 | TRBJ2-2*01 |  | 1188 | tgtgcca... | ctaagg... | ccgggagctgtttt |  |  | 2884 | C A T K A G E L F F |
| 20.001 | TRBV21-1*01 | TRBJ1-6*01 |  | 1189 | tgtgccagcagcaaa.. | tcccgagag | ...aattcaccctccactt |  |  | 2885 | C A S S K S R E N S P L H F |
| 20.002 | TRBV20-1*01 | TRBJ2-7*01 | TRBD1*01 | 1190 | tgcagtgct... | g ccc gggaca... | aactgccctactctgggt | ...tacgagcagtactc |  | 2886 | C S A A R D K L P L L W G Y E Q Y F |
| 20.003 | TRBV20-1*01 | TRBJ2-2*01 | TRBD1*01 | 1191 | tgcagtgct... | gacg | ...caggggc g | cgaacacgggagctgtttt |  | 2887 | C S A D A G G A N T G E L F F |
| 20.004 | TRBV20-1*01 | TRBJ2-1*01 | TRBD2*01 | 1192 | tgcagtgc... | ggataa ..gactag... | t ... | tacaatgagcagttcttc |  | 2888 | C S A D K T S Y N E Q F F |
| 20.005 | TRBV20-1*01 | TRBJ1-1*01 | TRBD1*01 | 1193 | tgcagtgc... | c ..gacagg... | aac | ...ctgaagcttcttt |  | 2889 | C S A D R E P E A F F |
| 20.006 | TRBV20-1*01 | TRBJ2-2*01 | TRBD1*01 | 1194 | tgcagtgct... | gac ...acaggggc g | cgaacacgggagctgtttt |  |  | 2890 | C S A D T G G A N T G E L F F |
| 20.007 | TRBV20-1*01 | TRBJ2-1*01 | TRBD2*01 | 1195 | tgcagtgc... | agac ...actacg... | tccc | ctcctacaatgagcagttcttc |  | 2891 | C S A D T S V P S Y N E Q F F |
| 20.008 | TRBV20-1*01 | TRBJ2-7*01 | TRBD1*01 | 1196 | tgcagtgct... | gaga cc gggaca..... | tctat | ......cgagcagtactc |  | 2892 | C S A E T G T S I E Q Y F |
| 20.009 | TRBV20-1*01 | TRBJ2-3*01 | TRBD2*02 | 1197 | tgcagtgct... | tttcccc | ...cgggagg.. cgggg .ccaagagaccagtactc | gatacgcagtattt |  | 2893 | C S A F P P G G P S D T Q Y F |
| 20.010 | TRBV20-1*01 | TRBJ2-5*01 | TRBD2*01 | 1198 | tgcagtgct... | gg ... | agcggggg... cggg ..ccaagagaccagtactc |  |  | 2894 | C S A G A G A G Q E T Q Y F |
| 20.011 | TRBV20-1*01 | TRBJ1-1*01 | TRBD1*01 | 1199 | tgcagtgct... | gggggt | gggacaggggc taaaggg.. | actgaagcttcttt |  | 2895 | C S A G G W D R G L K G T E A F F |
| 20.012 | TRBV20-1*01 | TRBJ2-3*01 | TRBD2*01 | 1200 | tgcagtgct... | gggattatgtac ..gactagc... | agca | agcacagatacgcagtattt |  | 2896 | C S A G I I V R L A A S T D T Q Y F |
| 20.013 | TRBV20-1*01 | TRBJ2-5*01 | TRBD1*01 | 1201 | tgcagtgc... | a ..ggacagggg.. gta | ...aagagaccagtactc |  |  | 2897 | C S A G Q Q G K E T Q Y F |
| 20.014 | TRBV20-1*01 | TRBJ1-5*01 | TRBD1*01 | 1202 | tgcagtgct... | cacgggg ...caggggg.. | agaggg | ....tcagcccccagcattt |  | 2898 | C S A H A A G G E G Q P Q H F |
| 20.015 | TRBV20-1*01 | TRBJ2-3*01 | TRBD2*02 | 1203 | tgcagtgcta... | ttg ...ctacgcggaggg cc ggcc.. | cagatacgcagtattt |  |  | 2899 | C S A I A S G R A G P D T Q Y F |
| 20.016 | TRBV20-1*01 | TRBJ2-7*01 | TRBD2*02 | 1204 | tgcagtgcta... | tc ... | gaggg c tcaggatgga | ....acgagcagtactc |  | 2900 | C S A I E G S G W N E Q Y F |
| 20.017 | TRBV20-1*01 | TRBJ2-5*01 | TRBD1*01 | 1205 | tgcagtgc... | gatacgg ...cagggggc cac | ....gagaccagtactc |  |  | 2901 | C S A I R A G G H E T Q Y F |
| 20.018 | TRBV20-1*01 | TRBJ2-3*01 | TRBD2*01 | 1206 | tgcagtgcta... | tcc ..ggactagcgggg.. | tgga | ....agatacgcagtattt |  | 2902 | C S A I R T S G V G D T Q Y F |
| 20.019 | TRBV20-1*01 | TRBJ2-6*01 | TRBD1*01 | 1207 | tgcagtgcta... | ttact cc gggaca.... | ccg | ctctggggccaacgtcctgacttc |  | 2903 | C S A I T P G H R S G A N V L T F |
| 20.020 | TRBV20-1*01 | TRBJ2-7*01 | TRBD1*01 | 1208 | tgcagtgc... | cctgg gggacagg... | acggga | ...tacgagcagtactc |  | 2904 | C S A L G D R T G Y E Q Y F |
| 20.021 | TRBV20-1*01 | TRBJ2-2*01 | TRBD2*02 | 1209 | tgcagtgc... | cctggggga ...actagcggga... | ttggc.. | ......gagcagttcttc |  | 2905 | C S A L G E L A G V G E Q F F |
| 20.022 | TRBV20-1*01 | TRBJ2-1*01 | TRBD1*01 | 1210 | tgcagtgc... | ctttt cc gggac... | gcctc | ..acaatgagcagttcttc |  | 2906 | C S A L S G T P H N E Q F F |
| 20.023 | TRBV20-1*01 | TRBJ1-2*01 | TRBD1*01 | 1211 | tgcagtgc... | cctcgtt ggga... | tcc | ...........acacctc |  | 2907 | C S A L V G I H T F |
| 20.024 | TRBV20-1*01 | TRBJ1-2*01 | TRBD1*01 | 1212 | tgcagtgcta... | atcct ...caggg...... | ctatgctacacctc |  |  | 2908 | C S A N P Q G Y G Y T F |
| 20.025 | TRBV20-1*01 | TRBJ1-1*01 | TRBD2*02 | 1213 | tgcagtgc... | caattc gggactagcggga... | aca | ......aatgagcagttcttc |  | 2909 | C S A N S G L A G T N E Q F F |
| 20.026 | TRBV20-1*01 | TRBJ2-5*01 | TRBD2*02 | 1214 | tgcagtgcta... | actctatg... | agcgggag.. t | ....gagaccagtactc |  | 2910 | C S A N S M S G S E T Q Y F |

Figure 1-45

| clone # | V name | J name | D name | SEQ ID NO: | V-REGION | N1 | D-REGION | (P) | N2 | J-REGION | SEQ ID NO: | CDR3 amino acid |
|---|---|---|---|---|---|---|---|---|---|---|---|---|
| 20.027 | TRBV20-1*01 | TRBJ2-1*01 | TRBD2*01 | 1215 | tgcagtgct | ccagcctc | actagcg | tccaacggg | g | ctcctacaatgagcagttcttc | 2911 | C S A P A S L A S Q R G S Y N E Q F F |
| 20.028 | TRBV20-1*01 | TRBJ1-5*01 | TRBD1*01 | 1216 | tgcagtgc | cccggga | gggacag | atcta | | aatcagcccagcattt | 2912 | C S A P G G T D L N Q P Q H F |
| 20.029 | TRBV20-1*01 | TRBJ2-2*01 | TRBD2*02 | 1217 | tgcagtgct | cctcttatc | cggaggg | ac | cggggagctgttttt | | 2913 | C S A P L I R E G P G E L F F |
| 20.030 | TRBV20-1*01 | TRBJ2-7*01 | TRBD1*01 | 1218 | tgcagtgct | ccgaacctaa | acagggg | gat | tacgagcagtactc | | 2914 | C S A P N L N R G D Y E Q Y F |
| 20.031 | TRBV20-1*02 | TRBJ1-5*01 | TRBD1*01 | 1219 | tgcagtgct ccgaacactgg | gggacagggg | cgttgg | agcaatcagcccagcatttt | | | 2915 | C S A P N T G G G R W S N Q P Q H F |
| 20.032 | TRBV20-1*01 | TRBJ2-7*01 | TRBD1*01 | 1220 | tgcagtgc | cccgac | ccggg | atgccagcaga | | agtactc | 2916 | C S A P T G D A S E K Y F |
| 20.033 | TRBV20-1*01 | TRBJ2-3*01 | TRBD2*02 | 1221 | tgcagtgc | ccctggg | ctagcgggag | cggggg | | acgcagtattt | 2917 | C S A P W A S G G S R G T Q Y F |
| 20.034 | TRBV20-1*01 | TRBJ1-4*01 | TRBD1*01 | 1222 | tgcagtgctagag | cccac | ggaca | tag | taatgaaaaactgtttt | | 2918 | C S A R A H G H S N E K L F F |
| 20.035 | TRBV20-1*01 | TRBJ2-7*01 | TRBD2*02 | 1223 | tgcagtgctagag | c | actagcgggag | ag | | tacgagcagtactc | 2919 | C S A R A L A G E Y E Q Y F |
| 20.036 | TRBV20-1*01 | TRBJ1-5*01 | TRBD2*01 | 1224 | tgcagtgctagag | cccta | gggggg | gtcagccccaa | | cattt | 2920 | C S A R A L G G G Q P Q H F |
| 20.037 | TRBV20-1*01 | TRBJ2-1*01 | TRBD1*01 | 1225 | tgcagtgctagaga | t ga c | gggactagc | c | acaatgagcagttcttc | | 2921 | C S A R D D G T S H N E Q F F |
| 20.038 | TRBV20-1*01 | TRBJ1-1*01 | TRBD1*01 | 1226 | tgcagtgctagaga | tgataagggg | | cggggg | | atgagcagttcttc | 2922 | C S A R D D D K G P G D E Q F F |
| 20.039 | TRBV20-1*01 | TRBJ2-7*01 | TRBD1*01 | 1227 | tgcagtgctagaga t ga | gggact | | cctg | tcctacgagcagtactc | | 2923 | C S A R D E G L L S Y E Q Y F |
| 20.040 | TRBV20-1*01 | TRBJ2-1*01 | TRBD2*02 | 1228 | tgcagtgctagaga | tgag | gttgag | aga | ctacaatgagcagttcttc | | 2924 | C S A R D E G R D Y N E Q F F |
| 20.041 | TRBV20-1*01 | TRBJ2-1*01 | TRBD2*02 | 1229 | tgcagtgctagaga t ttcg | gccggag | aaggc | ctcctacaatgagcagttcttc | | | 2925 | C S A R D F G G G R R A S Y N E Q F F |
| 20.042 | TRBV20-1*01 | TRBJ2-1*01 | | 1230 | tgcagtgctagaga t ttaacctcgtc | | | | caatgagcagttctc | | 2926 | C S A R D F T S S N E Q F F |
| 20.043 | TRBV20-1*01 | TRBJ1-2*01 | TRBD1*01 | 1231 | tgcagtgctagaga t ggga | | | ta | tacaatgagcagttcttc | | 2927 | C S A R D G I Y N E Q F F |
| 20.044 | TRBV20-1*01 | TRBJ2-2*01 | | 1232 | tgcagtgctagaga cgga | | | | aacaccgggagctgttttt | | 2928 | C S A R D G N T G E L F F |
| 20.045 | TRBV20-1*01 | TRBJ2-2*02 | TRBD2*02 | 1233 | tgcagtgctagaga t ggg | agcgga | t | gaacaccgggagctgttttt | | | 2929 | C S A R D G S G M N T G E L F F |
| 20.046 | TRBV20-1*01 | TRBJ1-2*01 | TRBD1*01 | 1234 | tgcagtgctag | gga c gggacagg | | a | atgctacacttc | | 2930 | C S A R D G T G N G Y T F |
| 20.047 | TRBV20-1*01 | TRBJ1-5*01 | TRBD1*01 | 1235 | tgcagtgc | aagaga c gggaca | | cattatagcaatcagcccagcatttt | | | 2931 | C S A R D G T H Y S N Q P Q H F |
| 20.048 | TRBV20-1*01 | TRBJ2-1*01 | TRBD2*02 | 1236 | tgcagtgctagaga | tcac | ctagcggg | tgcctt | caatgagcagttcttc | | 2932 | C S A R D H L A G A F N E Q F F |
| 20.049 | TRBV20-1*01 | TRBJ2-3*01 | TRBD2*01 | 1237 | tgcagtgctagaga tct | cggggg | tttaa | agatacgcagtattt | | | 2933 | C S A R D L G G F K D T Q Y F |
| 20.050 | TRBV20-1*01 | TRBJ2-2*01 | TRBD1*01 | 1238 | tgcagtgctagaga tct | gggg | | | accgggagctgttttt | | 2934 | C S A R D L G T G E L F F |
| 20.051 | TRBV20-1*01 | TRBJ1-4*01 | | 1239 | tgcagtgctagaga tct tggc | | | actaatgaaaaactgtttt | | | 2935 | C S A R D L G T N E K L F F |
| 20.052 | TRBV20-1*01 | TRBJ1-4*01 | TRBD1*01 | 1240 | tgcagtgctag | ggaca | acatag | caactaatgaaaaactgtttt | | | 2936 | C S A R D N I A T N E K L F F |
| 20.053 | TRBV20-1*01 | TRBJ2-2*01 | TRBD2*01 | 1241 | tgcagtgct cgaagccc | agcgg | | cgaaccgggagctgttttt | | | 2937 | C S A R D P A A N T G E L F F |
| 20.054 | TRBV20-1*02 | TRBJ2-7*01 | TRBD1*01 | 1242 | tgcagtgct cgagaccc | gacagg | ct | ctacgagcagtactc | | | 2938 | C S A R D P D R L Y E Q Y F |

Figure 1-46

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 20.055 | TRBV20-1*01 | TRBJ2-1*01 | TRBD2*02 | 1243 | tgcagtgctagaga | tcccggg | ...ctagcggga... | agggaatgggtgag | ..........gcagttcttc | 2939 | C S A R D P G L A G R E W V R Q F F |
| 20.056 | TRBV20-1*01 | TRBJ2-1*01 | TRBD2*01 | 1244 | tgcagtgctagaga | tc cgactgcga | c gggactagcgg.... | a  ...ctacaatgagcagttcttc | | 2940 | C S A R D P T A T G L A D Y N E Q F F |
| 20.057 | TRBV20-1*06 | TRBJ2-7*01 | TRBD2*02 | 1245 | tgcagtgct | ag agatccatatgc | ...actagcgggga... | at ..ctacgagcagtactc | | 2941 | C S A R D P Y A L A G I Y E Q Y F |
| 20.058 | TRBV20-1*01 | TRBJ2-7*01 | TRBD1*01 | 1246 | tgcagtgctagaga | cca ..gacaggg.. | attttgtgaa.......... | cagtactc | | 2942 | C S A R D Q T G I F G E Q Y F |
| 20.059 | TRBV20-1*01 | TRBJ2-3*01 | TRBD1*01 | 1247 | tgcagtgctagaa | taggga ....agggg. | agaggt ....agatacgcag | | | 2943 | C S A R D R E G G E V D T Q Y F |
| 20.060 | TRBV20-1*01 | TRBJ2-7*01 | TRBD1*01 | 1248 | tgcagtgctagaga | ....cagg.... | cctca ctcctacgagcagtactc | | | 2944 | C S A R D R P H S Y E Q Y F |
| 20.061 | TRBV20-1*01 | TRBJ1-2*01 | TRBD1*01 | 1249 | tgcagtgctagaa | tc gg .....agggggc | ...actatgctacacctc | | | 2945 | C S A R D R R G H Y G Y T F |
| 20.062 | TRBV20-1*01 | TRBJ1-5*01 | TRBD1*01 | 1250 | tgcagtgctagaga | tcg ....cagg..... | cgtat ..caatcagcccagcattt | | | 2946 | C S A R D R R R I N Q P Q H F |
| 20.063 | TRBV20-1*02 | TRBJ2-7*01 | TRBD2*02 | 1251 | tgcagtgct ag agatc | .......ggag.. | ctcctacgagcagtactc | | | 2947 | C S A R D R S S Y E Q Y F |
| 20.064 | TRBV20-1*01 | TRBJ2-7*01 | TRBD2*01 | 1252 | tgcagtgctagaa | .......tagcgggg... | ccg ..cctacgagcagtactc | | | 2948 | C S A R D S G A A Y E Q Y F |
| 20.065 | TRBV20-1*01 | TRBJ1-5*01 | | 1253 | tgcagtgctagaga | t accccctcgg | ..gcaatcagcccagcattt | | | 2949 | C S A R D T P S G N Q P Q H F |
| 20.066 | TRBV20-1*01 | TRBJ2-5*01 | TRBD2*02 | 1254 | tgcagtgctagaa | t gtt ....ctagcggga... | aagatg ......gagacccagtactc | | | 2950 | C S A R D V L A G K M E T Q Y F |
| 20.067 | TRBV20-1*01 | TRBJ2-7*01 | TRBD1*01 | 1255 | tgcagtgctagaga | t t gggacag... | ctcctacgagcagtactc | | | 2951 | C S A R D W D S S Y E Q Y F |
| 20.068 | TRBV20-1*01 | TRBJ2-3*01 | TRBD1*01 | 1256 | tgcagtgctagaa | ag gggacaggg.. | atacg ......gatacgcagtattt | | | 2952 | C S A R E G D R D T D T Q Y F |
| 20.069 | TRBV20-1*01 | TRBJ2-7*01 | TRBD1*01 | 1257 | tgcagtgctagaa | ..gacaggg.. | ta ..ctacgagcagtactc | | | 2953 | C S A R E T G Y Y E Q Y F |
| 20.070 | TRBV20-1*01 | TRBJ2-5*01 | TRBD2*02 | 1258 | tgcagtgctag... | gtt....tagcgggagg | cc accagatg..caagagaccagtactc | | | 2954 | C S A R F S G R A T Q M Q E T Q Y F |
| 20.071 | TRBV20-1*01 | TRBJ2-5*01 | TRBD1*01 | 1259 | tgcagtgct.... | cga ....gggc g g | cttggt accaagagaccagtactc | | | 2955 | C S A R G A A W Y Q E T Q Y F |
| 20.072 | TRBV20-1*01 | TRBJ1-1*01 | TRBD2*02 | 1260 | tgcagtgctagag. | g ...agcaggag.. | tacc ......caatgagcagttcttc | | | 2956 | C S A R G A G V P N E Q F F |
| 20.073 | TRBV20-1*01 | TRBJ1-6*0 | TRBD1*01 | 1261 | tgcagtgctagag. | g ........agggg | ........taattcaccctcact | | | 2957 | C S A R G G G N S P L H F |
| 20.074 | TRBV20-1*01 | TRBJ2-3*01 | TRBD1*01 | 1262 | tgcagtgctagag. | gggggt ....tagcggg... | c .gcacagatacgcagtattt | | | 2958 | C S A R G G V S G R T D T Q Y F |
| 20.075 | TRBV20-1*01 | TRBJ2-7*01 | TRBD2*02 | 1263 | tgcagtgctag... | gggta .....agcggga... | ...ctacgagcagtactc | | | 2959 | C S A R G K R D Y E Q Y F |
| 20.076 | TRBV20-1*01 | TRBJ2-7*01 | TRBD1*01 | 1264 | tgcagtgctag... | ........gggggc | tccggacga ctcctacgagcagtactc | | | 2960 | C S A R G L R D D S Y E Q Y F |
| 20.077 | TRBV20-1*01 | TRBJ2-7*01 | TRBD2*01 | 1265 | tgcagtgctagag. | gcat ggacta..... | tct ctcctacgagcagtactc | | | 2961 | C S A R G M D Y L S Y E Q Y F |
| 20.078 | TRBV20-1*01 | TRBJ2-7*01 | TRBD2*01 | 1266 | tgcagtgctag.... | gggtc ...ctagcg..... | tt tcctacgagcagtactc | | | 2962 | C S A R G P S V S Y E Q Y F |
| 20.079 | TRBV20-1*01 | TRBJ2-7*01 | TRBD1*01 | 1267 | tgcagtgctag.... | ..gacag... | tgggct ag ctcctacgagcagtactc | | | 2963 | C S A R G Q W A S S Y E Q Y F |
| 20.080 | TRBV20-1*02 | TRBJ2-7*01 | TRBD1*01 | 1268 | tgcagtgct ag a | gggacag.... | cggag ...tacgagcagtactc | | | 2964 | C S A R G T A E Y E Q Y F |
| 20.081 | TRBV20-1*01 | TRBJ2-5*01 | TRBD1*01 | 1269 | tgcagtc..... | aa ..gaca...... | cacgagctt ..ccaagagaccagtactc | | | 2965 | C S A R H T S F Q E T Q Y F |
| 20.082 | TRBV20-1*01 | TRBJ2-7*01 | TRBD2*01 | 1270 | tgcagtgctaga. | a .....tagcggg... | cgtcg ...cctacgagcagtactc | | | 2966 | C S A R I A G V A Y E Q Y F |

Figure 1-47

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 20.083 | TRBV20-1*01 | TRBJ1-1*01 | TRBD2*02 | 1271 | tgaagtgctaga.. | atcctttt | .......gaagg.. | ......tgaagcttcttt | | 2967 | C S A R I L L E G E A F F |
| 20.084 | TRBV20-1*01 | TRBJ2-3*01 | TRBD2*02 | 1272 | tgcagtgctaga.. | aagctgggtattgag | ......gatacgcagtattt | | | 2968 | C S A R K L G I E D T Q Y F |
| 20.085 | TRBV20-1*01 | TRBJ2-2*01 | TRBD2*02 | 1273 | tgcagtgctaga.. | ...ctacgcggaag.. | ....acaccgggagctgttttt | | | 2969 | C S A R L A G D T G E L F F |
| 20.086 | TRBV20-1*01 | TRBJ2-1*01 | TRBD2*01 | 1274 | tgcagtgctag.. | gctcg | ....agcgggggg.. | .....acaatgagcagtcttc | | 2970 | C S A R L E R G D N E Q F F |
| 20.087 | TRBV20-1*01 | TRBJ2-7*01 | TRBD1*01 | 1275 | tgcagtgc.. | ....ccgtttga | gggaca.. | ......cctacgagcagtactc | | 2971 | C S A R L R D T Y E Q Y F |
| 20.088 | TRBV20-1*06 | TRBJ2-2*01 | TRBD2*02 | 1276 | tgcagtgc.. | gagaat | gggactagccggaag.. | ..acaccgggagctgttttt | | 2972 | C S A R M G L A G D T G E L F F |
| 20.089 | TRBV20-1*01 | TRBJ2-1*01 | TRBD1*01 | 1277 | tgcagtgc.. | ....ccgcaatgggagccc | ......ggggc c | .....caatgagcagtcttc | | 2973 | C S A R N G E P G P N E Q F F |
| 20.090 | TRBV20-1*01 | TRBJ2-1*01 | TRBD2*01 | 1278 | tgcagtgctaga.. | aa cc | gggac.. | ...........ggggg ..cctacaatgagcagtcttc | | 2974 | C S A R N R D G A Y N E Q F F |
| 20.091 | TRBV20-1*01 | TRBJ2-7*01 | TRBD2*01 | 1279 | tgcagtgc.. | ....ccggc | ......cggggg.. | .......ctacgagcagtactc | | 2975 | C S A R P G G Y E Q Y F |
| 20.092 | TRBV20-1*01 | TRBJ1-5*01 | TRBD1*01 | 1280 | tgcagtgctaga.. | ....caggg.. | tttag..gcaatcagcccagcattt | | | 2976 | C S A R Q G L G N Q P Q H F |
| 20.093 | TRBV20-1*01 | TRBJ2-3*01 | TRBD2*02 | 1281 | tgcagtgc.. | ....ccgaag.. | .....agcgggag.. | .....cagatacgcagtattt | | 2977 | C S A R R A G A D T Q Y F |
| 20.094 | TRBV20-1*01 | TRBJ2-7*01 | TRBD1*01 | 1282 | tgcagtgct.. | cgac ..gacaggg.. | atccgct ..tacgagcagtactc | | | 2978 | C S A R R Q G S A Y E Q Y F |
| 20.095 | TRBV20-1*01 | TRBJ2-7*01 | TRBD2*01 | 1283 | tgcagtgctag.. | gagta ..gga.. | .........cctacgagcagtactc | | | 2979 | C S A R S R T Y E Q Y F |
| 20.096 | TRBV20-1*01 | TRBJ1-5*01 | TRBD1*01 | 1284 | tgcagtgc.. | .....cagg.. | accgactgatattgg | ........agccccagcattt | | 2980 | C S A R T R L I L E P Q H F |
| 20.097 | TRBV20-1*01 | TRBJ2-1*01 | TRBD1*01 | 1285 | tgcagtgc.. | ......cc | ggactagccgggg.. | ....at | ......aatgagcagttcttc | 2981 | C S A R T S G D N E Q F F |
| 20.098 | TRBV20-1*01 | TRBJ2-7*01 | TRBD2*02 | 1286 | tgcagtgctaga.. | acc | ......agcgggag.. | aggactggggg.. | .....cgagcagtactc | 2982 | C S A R T S G R G L G G E Q Y F |
| 20.099 | TRBV20-1*01 | TRBJ2-1*01 | TRBD2*02 | 1287 | tgcagtgc.. | ......aa | ggactagccgggagg.. | ttaaatcccg.. | ......atgagcagttcttc | 2983 | C S A R T S G R L N P D E Q F F |
| 20.100 | TRBV20-1*01 | TRBJ2-1*01 | TRBD1*01 | 1288 | tcg | ....cagggg.. | ccgggagt | ....cagatacgcagtattt | | 2984 | C S A R V A G A G E S D T Q Y F |
| 20.101 | TRBV20-1*01 | TRBJ2-3*01 | TRBD1*01 | 1289 | tgcagtgctagag.. | tcct ..gga.. | .......... t | .....tacgagcagtactc | | 2985 | C S A R V L D Y E Q Y F |
| 20.102 | TRBV20-1*01 | TRBJ2-7*01 | TRBD1*01 | 1290 | tgcagtgctagag.. | ta cc gggacag.. | ......aa ..ctacgagcagtactc | | | 2986 | C S A R V P G Q N Y E Q Y F |
| 20.103 | TRBV20-1*01 | TRBJ2-7*01 | TRBD1*01 | 1291 | tgcagtgctagag.. | tccctccaga ..gacaggg.. | acttaca ..cctacgagcagtactc | | | 2987 | C S A R V P P E T G T Y T Y E Q Y F |
| 20.104 | TRBV20-1*01 | TRBJ2-5*01 | TRBD2*01 | 1292 | tgcagtgctag.. | ggtc | ....cgggagg.. cg | .....gagaccagtactc | | 2988 | C S A R V R E A E T Q Y F |
| 20.105 | TRBV20-1*01 | TRBJ2-1*01 | TRBD2*02 | 1293 | tgcagtgctag.. | tt | ......cgggaggg cc tcag | .....caatgagcagtcttc | | 2989 | C S A R V R E G L S N E Q F F |
| 20.106 | TRBV20-1*01 | TRBJ2-7*01 | TRBD1*01 | 1294 | tgcagtgctag.. | tgc ..ggacaggg.. | ttctgtcg ...cgagcagtactc | | | 2990 | C S A R V A D R G S G R E Q Y F |
| 20.107 | TRBV20-1*01 | TRBJ2-1*01 | TRBD2*01 | 1295 | tgcagtgctag.. | cgc | ........cgggg.. | .......tgagcagttcttc | | 2991 | C S A S A G G E Q F F |
| 20.108 | TRBV20-1*01 | TRBJ1-5*01 | TRBD2*01 | 1296 | tgcagtgctag.. | ....t | .......gcgggggg accggtcatcat.. | ......cccagcatttt | | 2992 | C S A S A G G T G H H P Q H F |
| 20.109 | TRBV20-1*01 | TRBJ1-5*01 | TRBD2*01 | 1297 | tgcagtgctag.. | ....t | .......gcgggggg accggtcatcaaccccagtt | ......ttt | | 2993 | C S A S A G G T G H Q P Q F F |
| 20.110 | TRBV20-1*01 | TRBJ1-5*01 | TRBD2*01 | 1298 | tgcagtgctag.. | .....t | .......gcgggggg accggtc.. | .....atcagcccagcatttt | | 2994 | C S A S A G G T G H Q P Q H F |

Figure 1-48

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 20.111 | TRBV20-1*01 | TRBJ2-7*01 | TRBD2*01 | 1299 | tgcagtgctag... | tg ccc | gggac......... | ggatta. | cctacgagcagttcttc | 2995 | C S A S A R D G F T Y E Q Y F |
| 20.112 | TRBV20-1*01 | TRBJ2-3*01 | TRBD2*02 | 1300 | tgcagtgctag... | tgat .. | ctagcgggag..... | aaac... | cacagataccgcagttcttc | 2996 | C S A S D L A G E T T D T Q Y F |
| 20.113 | TRBV20-1*01 | TRBJ2-7*01 | TRBD2*01 | 1301 | tgcagtgct.... | t ....... | cggggg.. cagggataagctcctacgagcagttcttc | | | 2997 | C S A S G A G I S S Y E Q Y F |
| 20.114 | TRBV20-1*01 | TRBJ2-4*01 | TRBD1*01 | 1302 | tgcagtgctag... | cggt ... | ggggc aggtcat ..ccaaaaacattcagttactc | | | 2998 | C S A S G G A G S S K N I Q Y F |
| 20.115 | TRBV20-1*01 | TRBJ2-1*01 | TRBD2*02 | 1303 | tgcagtgctag.. | tgg | gggactagcgggagg. | aagta ..cctacaatgagcagttcttc | | 2999 | C S A S G G L A G G S T Y N E Q F F |
| 20.116 | TRBV20-1*01 | TRBJ2-7*01 | TRBD2*01 | 1304 | tgcagtgctag... | c ..ggactagcgg..... | a | ctcctacgagcagtactc | | 3000 | C S A S G L A D S Y E Q Y F |
| 20.117 | TRBV20-1*01 | TRBJ2-5*01 | TRBD2*02 | 1305 | tgcagtgctag.. | t ........ | gggag.. t ..caagagacccagtactc | | | 3001 | C S A S G S Q E T Q Y F |
| 20.118 | TRBV20-1*01 | TRBJ1-1*01 | TRBD1*01 | 1306 | tgcagtgc...... | ct cc gggacagggg.. tttctgg | | ......... agcttctt | | 3002 | C S A S G T G V S G A F F |
| 20.119 | TRBV20-1*01 | TRBJ2-7*01 | TRBD2*01 | 1307 | tgcagtgctag... | tcatggatc....... | cggg... | ttca..cctacgagcagtactc | | 3003 | C S A S H G S G F T Y E Q Y F |
| 20.120 | TRBV20-1*01 | TRBJ2-1*01 | TRBD1*01 | 1308 | tgcagtgc...... | ctcaaagtc........ | gggc tatccaccag ... | tgagcagcttctt | | 3004 | C S A S K S G Y P P S E Q F F |
| 20.121 | TRBV20-1*01 | TRBJ1-1*01 | TRBD1*01 | 1309 | tgcagtgctag... | cc ...cagggg.. ttgggg ... | acactgaagcttcttt | | | 3005 | C S A S P G V G D T E A F F |
| 20.122 | TRBV20-1*01 | TRBJ1-2*01 | TRBD2*02 | 1310 | tgcagtgc....... | atccctaacgatgactgg .... | aggg.. cgtttgg ..... | tggctacacctc | | 3006 | C S A S P N D D W R A F G G Y T F |
| 20.123 | TRBV20-1*01 | TRBJ1-1*01 | TRBD1*01 | 1311 | tgcagtgctag.. | tccca ....... | ggaaggg gt tgaacactgaagcttcttt | | | 3007 | C S A S P R E G L N T E A F F |
| 20.124 | TRBV20-1*01 | TRBJ2-1*01 | TRBD1*01 | 1312 | tgcagtgct ag tccctggcga tcctacaatgagcagttcttc | | | | | 3008 | C S A S P W R S Y N E Q F F |
| 20.125 | TRBV20-1*01 | TRBJ2-3*01 | TRBD1*01 | 1313 | tgcagtgctag... | cagg.... | aagtgactc agcacagataccgcagtatttt | | | 3009 | C S A S R K V L S T D T Q Y F |
| 20.126 | TRBV20-1*01 | TRBJ1-5*01 | TRBD1*01 | 1314 | tgcagtgctag... | tagt..gacag.... ttactt tagcaatcagcccccagcatttt | | | | 3010 | C S A S S D S Y F S N Q P Q H F |
| 20.127 | TRBV20-1*01 | TRBJ2-1*01 | TRBD2*02 | 1315 | tgcagtgctag... | tacaattgt gggactagcgggag.. cat ....... atgagcagttcttc | | | | 3011 | C S A S T I V G L A G A Y E Q F F |
| 20.128 | TRBV20-1*01 | TRBJ2-3*01 | TRBD2*01 | 1316 | tgcagtgc...... | ctcgaccc...gactacgcggggg.. acagatacc......... cagtatttt | | | | 3012 | C S A S T P T S G G T D T Q Y F |
| 20.129 | TRBV20-1*01 | TRBJ2-7*01 | TRBD1*01 | 1317 | tgcagtgc...... | cagcactcaccgtg ... ggggg ttag ....acgagcagtactc | | | | 3013 | C S A S T S P V G G L D E Q Y F |
| 20.130 | TRBV20-1*01 | TRBJ2-5*01 | TRBD2*02 | 1318 | tgcagtgct a cagaaa cc gggactagcgggag. ttggaagagcctgtg ...gagaccccagtact | | | | | 3014 | C S A T E T G T S G S W E E P V E T Q Y F |
| 20.131 | TRBV20-1*01 | TRBJ1-6*02 | TRBD2*01 | 1319 | tgcagtgcta... | c ...... | cggggg.... aa ag | ctcctataattcaccccctccactt | | 3015 | C S A T G E S S Y N S P L H F |
| 20.132 | TRBV20-1*01 | TRBJ2-1*01 | TRBD1*01 | 1320 | tgcagtgc...... | c ...acaggg... actcttaggcg ....... atgagcagttcttc | | | | 3016 | C S A T G T L S D E Q F F |
| 20.133 | TRBV20-1*01 | TRBJ2-1*01 | TRBD2*01 | 1321 | tgcagtgcta... | ccc .......cggggggg cc gagctcctacaatgagcagttcttc | | | | 3017 | C S A T P G G P S S Y N E Q F F |
| 20.134 | TRBV20-1*01 | TRBJ2-7*01 | TRBD1*01 | 1322 | tgcagtgc...... | aaccaccacatcgac....acagg.... tcc ..cctacgagcagtactc | | | | 3018 | C S A T P T S T Q V P Y E Q Y F |
| 20.135 | TRBV20-1*01 | TRBJ2-7*01 | TRBD1*01 | 1323 | tgcagtgcta... | cccaacga .. tcctacgagcagtactc | | | | 3019 | C S A T Q R S Y E Q Y F |
| 20.136 | TRBV20-1*01 | TRBJ2-7*01 | TRBD2*01 | 1324 | tgcagtgcta... | cctccgggacga ...... | cggggg. | ..cctacgagcagtactc | | 3020 | C S A T S G T T G A Y E Q Y F |
| 20.137 | TRBV20-1*01 | TRBJ2-7*01 | TRBD1*01 | 1325 | tgcagtgc...... | aaccagcccctaggagcc ...ctag........ aggatagg ....... gagcagtactc | | | | 3021 | C S A T S P L G A L E D R E Q Y F |
| 20.138 | TRBV20-1*01 | TRBJ2-7*01 | TRBD1*01 | 1326 | tgcagtgc...... | aac ...gacta........ agcccc ... acgagcagtactc | | | | 3022 | C S A T T K P H E Q Y F |

Figure 1-49

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 20.139 | TRBV20-1*01 | TRBJ2-5*01 | TRBD2*01 | 1327 | tgcagtgct | gtgggct | ggggg | aagagacccagtactc | | 3023 | C S A V G L E E T Q Y F |
| 20.140 | TRBV20-1*01 | TRBJ2-1*01 | TRBD1*01 | 1328 | tgcagtgc | ctggggccat | caggggc cggacatgc | | tgagcagttcttc | 3024 | C S A W G H Q G A G H A E Q F F |
| 20.141 | TRBV20-1*01 | TRBJ2-1*01 | TRBD1*01 | 1329 | tgcagtgc | gtggaga gggacaggggc | cctactagtcgc | | gagcagttcttc | 3025 | C S A W R G T G G P T S R E Q F F |
| 20.142 | TRBV20-1*01 | TRBJ2-7*01 | TRBD2*02 | 1330 | tgcagt | tgtgaggggaga gggagactagcgggaggg ag | cgagcagtactc | | | 3026 | C S C E G E G L A G G S E Q Y F |
| 20.143 | TRBV20-1*01 | TRBJ2-5*01 | | 1331 | tgcagtg | accccagcag | agagacccagtactc | | | 3027 | C S D P S R E T Q Y F |
| 20.144 | TRBV20-1*01 | TRBJ2-5*01 | TRBD2*01 | 1332 | tgcagtg | g | agcgggg | aggcgtact caagagaccagtactc | | 3028 | C S G A G R R T Q E T Q Y F |
| 20.145 | TRBV20-1*01 | TRBJ2-5*01 | TRBD1*01 | 1333 | tgcagtg | gaaggagc | caggg cctccg | agagacccagtactc | | 3029 | C S G R S Q G L R E T Q Y F |
| 20.146 | TRBV20-1*02 | TRBJ2-1*01 | TRBD1*01 | 1334 | tgcagt | tccct gggac | gaaa ctacaatgagcagttctc | | | 3030 | C S S L G R N Y N E Q F F |
| 20.147 | TRBV20-1*01 | TRBJ2-7*01 | TRBD2*02 | 1335 | tgcag | cacaccaggg | gcgggagg ttca | gagcagtactc | | 3031 | C S S T P G A G G S E Q Y F |
| 20.148 | TRBV20-1*01 | TRBJ2-4*01 | TRBD1*01 | 1336 | tgcagtg | tctatcaccctcctcatttgt | aaacattcagtactc | | | 3032 | C S V L S P S S F V N I Q Y F |
| 20.149 | TRBV20-1*01 | TRBJ2-1*01 | | 1337 | tgca | ctaccaaggctaagctt | caggg | tgagcagttcttc | | 3033 | C T T K A K L Q G E Q F F |
| 23.01 | TRBV23-1*01 | TRBJ1-2*01 | TRBD2*01 | 1338 | tgcgccagcag | cttcaataattccaagt | cgggggg c ga | ggctacaccttc | | 3034 | C A S S F N N S R S G G R G Y T F |
| 23.02 | TRBV23-1*01 | TRBJ2-7*01 | TRBD1*01 | 1339 | tgcgccagcagtca | tcc gggacag | ccgatca | cctacgagcagtactc | | 3035 | C A S S H P G Q P I T Y E Q Y F |
| 23.03 | TRBV23-1*01 | TRBJ2-1*01 | TRBD1*01 | 1340 | tgcgccagcagt | tca ggacaggggc | ca | actgaagcagttcttt | | 3036 | C A S S H Q D R G P T E A F F |
| 23.04 | TRBV23-1*01 | TRBJ2-4*01 | TRBD2*01 | 1341 | tgcgccagcag | ccctc | cggggg tacg | agccaaaaacattcagtactc | | 3037 | C A S S P P P G V R A K N I Q Y F |
| 23.05 | TRBV23-1*01 | TRBJ2-6*01 | TRBD1*01 | 1342 | tgcgccagcagtcaa | c ggacag | aa tctgggccaacgtcctgacttc | | | 3038 | C A S S Q R T E S G A N V L T F |
| 23.06 | TRBV23-1*01 | TRBJ2-2*01 | TRBD2*02 | 1343 | tgcgccagcagtcaatc ga ccttc | actagcgggag tcatactact | ggggagctgttttt | | | 3039 | C A S S Q S T F T S G S H T T G E L F F |
| 24.01 | TRBV24-1*01 | TRBJ2-2*01 | TRBD2*02 | 1344 | tgtgccac | ggtgatcccga | agggcagaaa | aacaccggggagctgttttt | | 3040 | C A T G D P E G Q K N T G E L F F |
| 24.02 | TRBV24-1*01 | TRBJ2-7*01 | TRBD2*01 | 1345 | tgtgccacc | ggtagt ggga | acgagcagtactc | | | 3041 | C A T G S G N E Q Y F |
| 24.03 | TRBV24-1*01 | TRBJ2-1*01 | TRBD2*02 | 1346 | tgtgccacca | tatcc | agcgggag ctctacaagatgagcagttctc | | | 3042 | C A T I S S G S S Y N E Q F F |
| 24.04 | TRBV24-1*01 | TRBJ1-1*01 | TRBD1*01 | 1347 | tgtgccacca | tg gggacaggggg | tgaagctttcttt | | | 3043 | C A T M G T G G E A F F |
| 24.05 | TRBV24-1*01 | TRBJ2-1*01 | TRBD1*01 | 1348 | tgtgccacca | t gacagtg | aatgagcagttcttc | | | 3044 | C A T M T G N E Q F F |
| 24.06 | TRBV24-1*01 | TRBJ2-2*01 | TRBD2*02 | 1349 | tgtgccaccag | gacga | tagcggggag acc cctacaatgagcagtttttt | | | 3045 | C A T R T I A G D P Y N E Q F F |
| 24.07 | TRBV24-1*01 | TRBJ2-1*01 | TRBD2*01 | 1350 | tgtgccaccagtg | cggggg | ccggggagctgtttt | | | 3046 | C A T S A G A G E L F F |
| 24.08 | TRBV24-1*01 | TRBJ2-5*01 | TRBD2*01 | 1351 | tgtgccaccagtg | ccc | cggggggg tacggc | gagacccagtactc | | 3047 | C A T S A P G G Y G E T Q Y F |
| 24.09 | TRBV24-1*01 | TRBJ2-1*01 | TRBD1*01 | 1352 | tgtgccaccagtgatt | caggg | agac | gagcagttcttc | | 3048 | C A T S D F R G D E Q F F |
| 24.10 | TRBV24-1*01 | TRBJ2-2*01 | TRBD1*01 | 1353 | tgtgccaccagtgattt | tc ggacagggg | at | accgggggagctgttttt | | 3049 | C A T S D F R T G D T G E L F F |

Figure 1-50

| clone # | V name | J name | D name | SEQ ID NO: | V-REGION N1 D-REGION (P) N2 J-REGION | SEQ ID NO: | CDR3 amino acid |
|---|---|---|---|---|---|---|---|
| 24.11 | TRBV24-1*01 | TRBJ2-5*01 | TRBD1*01 | 1354 | tgtgccaccagtga....cct..ggacag...taga..caagggaccagtactc | 3050 | C A T S D L D S R Q E T Q Y F |
| 24.12 | TRBV24-1*01 | TRBJ1-3*01 | TRBD1*01 | 1355 | tgtgccaccagtgattg..ccgg.....agggg..tcgaa...tggaacaccatatattt | 3051 | C A T S D L P E G S N G N T I Y F |
| 24.13 | TRBV24-1*01 | TRBJ1-5*01 | TRBD1*01 | 1356 | tgtgccaccagtgatt...acaggg..ag....ataagcccagcattt | 3052 | C A T S D L Q G D Q P Q H F |
| 24.14 | TRBV24-1*01 | TRBJ2-2*01 | TRBD2*02 | 1357 | tgtgccaccagtgatttg ca g....ctagcgggagg..ttctgac.........gagctgtttt | 3053 | C A T S D L Q L A G G S D E L F F |
| 24.15 | TRBV24-1*01 | TRBJ2-3*01 | | 1358 | tgtgccaccagtgatttg tcg agcacagatacgcagtatt | 3054 | C A T S D L S S T D T Q Y F |
| 24.16 | TRBV24-1*01 | TRBJ2-3*01 | TRBD1*01 | 1359 | tgtgccaccagtgat....ct..gacaggg....ct..agcacagatacgcagtatt | 3055 | C A T S D L T G A S T D T Q Y F |
| 24.17 | TRBV24-1*01 | TRBJ1-1*01 | TRBD2*02 | 1360 | tgtgccaccagtgatttg acaccc........ggaggg.....actgaagctttctt | 3056 | C A T S D L T P G G T E A F |
| 24.18 | TRBV24-1*01 | TRBJ2-1*01 | TRBD1*01 | 1361 | tgtgccaccagtgatttg t......gggg..tgg......tgagcagttcttc | 3057 | C A T S D L W G G E Q F F |
| 24.19 | TRBV24-1*01 | TRBJ2-2*01 | TRBD1*01 | 1362 | tgtgccaccagtgat...cccgaa.....gggc agaaa..aacacggggagctgtttt | 3058 | C A T S D P E G Q K N T G E L F F |
| 24.20 | TRBV24-1*01 | TRBJ2-5*01 | TRBD2*01 | 1363 | tgtgccaccagtgat..ccacc........cggggg..cag...acacggggagctgagctgtttt | 3059 | C A T S D P P R G A D T G E L F F |
| 24.21 | TRBV24-1*01 | TRBJ2-5*01 | TRBD1*01 | 1364 | tgtgccaccagtga...ccctaggg....caggggg...tggt.......ccagtacttc | 3060 | C A T S D P R A G V V Q Y F |
| 24.22 | TRBV24-1*01 | TRBJ2-1*01 | TRBD2*01 | 1365 | tgtgccaccagtga...cccatc......cggggg..agt......tgagcagttcttc | 3061 | C A T S D P S G G V E Q F F |
| 24.23 | TRBV24-1*01 | TRBJ2-4*01 | | 1366 | tgtgccaccagtga.....ccctatctacccggcct..gccaaaaacattcagtacttc | 3062 | C A T S D P Y L P G L A K N I Q Y F |
| 24.24 | TRBV24-1*01 | TRBJ2-1*01 | TRBD1*01 | 1367 | tgtgccaccagtga.....cca..acaggg....t..tcctacaatgagcagttcttc | 3063 | C A T S D Q Q G S Y N E Q F F |
| 24.25 | TRBV24-1*01 | TRBJ2-2*01 | TRBD2*01 | 1368 | tgtgccaccagtga...cca..gactagcgggg...tt....accgggagctgtttt | 3064 | C A T S D Q T S G V T G E L F F |
| 24.26 | TRBV24-1*01 | TRBJ2-3*01 | TRBD2*01 | 1369 | tgtgccacc........tccgatcggc..ggact......agcacagatacgcagtatt | 3065 | C A T S D R R T S T D T Q Y F |
| 24.27 | TRBV24-1*01 | TRBJ2-1*01 | TRBD2*01 | 1370 | tgtgccaccagtgatt..c......cggggg..aggaaatacaactgagcat..........ttcttc | 3066 | C A T S D S G G R K Y T E H F F |
| 24.28 | TRBV24-1*01 | TRBJ2-3*01 | TRBD2*02 | 1371 | tgtgccaccagtga.....ctcaggcat...gaggg agcc..cacagatacgcagtatt | 3067 | C A T S D S G M R E P T D T Q Y F |
| 24.29 | TRBV24-1*01 | TRBJ2-7*01 | TRBD2*01 | 1372 | tgtgccaccagtgatt..cgcatcaa.....agc........c.....acgagcagttcttc | 3068 | C A T S D S H Q S H E Q Y F |
| 24.30 | TRBV24-1*01 | TRBJ2-1*01 | TRBD2*02 | 1373 | tgtgccaccagtgatt......ctagcgggag..agaa....tacaatgagcagttcttc | 3069 | C A T S D S S G R E Y N E Q F F |
| 24.31 | TRBV24-1*01 | TRBJ2-3*01 | TRBD2*01 | 1374 | tgtgccaccagtgat...accgagagctt..gaca......aatacc...........cagtattt | 3070 | C A T S D T E S L T N T Q Y F |
| 24.32 | TRBV24-1*01 | TRBJ2-2*01 | TRBD1*01 | 1375 | tgtgccaccagtga.....ggga....agggg..tacgt.......cgggagctgtttt | 3071 | C A T S E G R G Y V G E L F F |
| 24.33 | TRBV24-1*01 | TRBJ2-1*01 | TRBD1*01 | 1376 | tgtgccaccagtga...acgagaaat gggacag..... ac ....caatgagcagttcttc | 3072 | C A T S E R E M G Q T N E Q F F |
| 24.34 | TRBV24-1*01 | TRBJ2-7*01 | TRBD1*01 | 1377 | tgtgccaccagtga....ac..ggacag....cgactc...acgagcagtactc | 3073 | C A T S E R T A T H E Q Y F |
| 24.35 | TRBV24-1*01 | TRBJ2-3*01 | TRBD2*02 | 1378 | tgtgccaccag......cttcaggaccct..........gaggg aa......atacccagtattt | 3074 | C A T S F R T P E G N T Q Y F |
| 24.36 | TRBV24-1*01 | TRBJ1-1*01 | TRBD2*02 | 1379 | tgtgccaccagtg...........gggagg ttgcg......actgaagctttctt | 3075 | C A T S G E V A T E A F F |
| 24.37 | TRBV24-1*01 | TRBJ2-2*01 | TRBD1*01 | 1380 | tgtgccaccagt......ccc..ggacaggggc g gt...caccgggagctgtttt | 3076 | C A T S P G Q G A V T G E L F F |

Figure 1-51

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 24.38 | TRBV24-1*01 | TRBJ2-1*01 | TRBD2*01 | 1381 | tgtgccacca | cc | gcagggg | actata | acaatgagcagttcttc | 3077 | C A T T A G D Y N N E Q F F |
| 25.001 | TRBV25-1*01 | TRBJ1-1*01 | TRBD2*01 | 1382 | tgtgccagc | gccg | tagc | tg | tgaacactgaagcttcttt | 3078 | C A S A V A V N T E A F F |
| 25.002 | TRBV25-1*01 | TRBJ2-2*01 | TRBD2*01 | 1383 | tgtgccagc | ga | actagc | cgt | cgggagctgttttt | 3079 | C A S E L A V G E L F F |
| 25.003 | TRBV25-1*01 | TRBJ2-3*01 | TRBD1*01 | 1384 | tgtgccagc | | ggacaggg | actgag | gcagtatttt | 3080 | C A S G Q G V R Q Y F |
| 25.004 | TRBV25-1*01 | TRBJ2-2*01 | TRBD1*01 | 1385 | tgtgccagc | cggat | tattt | ccgggagctgttttt | | 3081 | C A S R M G Y S G E L F F |
| 25.005 | TRBV25-1*01 | TRBJ2-7*01 | TRBD1*01 | 1386 | tgtgccagcagtg | cc | caggggg | agct | ctacgagcagtactc | 3082 | C A S S A Q G E L Y E Q Y F |
| 25.006 | TRBV25-1*01 | TRBJ2-1*01 | TRBD1*01 | 1387 | tgtgccagcagtg | c | gacag | agttg | atgagcagttcttc | 3083 | C A S S A T E F D E Q F F |
| 25.007 | TRBV25-1*01 | TRBJ2-5*01 | TRBD2*02 | 1388 | tgtgccagcagtga | ggcc | gcgggaggg | gtagg | agagaccagtactc | 3084 | C A S S E A A G G V G E T Q Y F |
| 25.008 | TRBV25-1*01 | TRBJ1-2*01 | TRBD1*01 | 1389 | tgtgccagcagtga | gacag | ttggc | atgctcacctc | | 3085 | C A S S E T V G H G Y T F |
| 25.009 | TRBV25-1*01 | TRBJ2-1*01 | TRBD1*01 | 1390 | tgtgccagcagtgaata | cga | ggac | gc gag ctctacaatgagcagttcttc | | 3086 | C A S S E Y E D A S S Y N E Q F F |
| 25.010 | TRBV25-1*01 | TRBJ2-3*01 | | 1391 | tgtgccagcagtgaata ta | aggctccgaaagcacaagat | | gatacgcagtattt | | 3087 | C A S S E Y K A P K A Q D D T Q Y F |
| 25.011 | TRBV25-1*01 | TRBJ2-3*01 | TRBD1*01 | 1392 | tgtgccagcagtgaata | ctctt | ggc | gcacagatacgcagtattti | | 3088 | C A S S E Y S W R T D T Q F F |
| 25.012 | TRBV25-1*01 | TRBJ2-1*01 | TRBD2*02 | 1393 | tgtgccagcagt | tt | tagcgggag | t | tacaatgagcagttcttc | 3089 | C A S S F S G G S Y N E Q F F |
| 25.013 | TRBV25-1*01 | TRBJ2-7*01 | TRBD1*01 | 1394 | tgtgccagcagt | ct | agggg | | ctacgagcagtactc | 3090 | C A S S L G G Y E Q Y F |
| 25.014 | TRBV25-1*01 | TRBJ2-7*01 | TRBD1*01 | 1395 | tgtgccagcagtg | t | agggg | | acgagcagtactc | 3091 | C A S S V G D E Q Y F |
| 25.015 | TRBV25-1*01 | TRBJ2-3*01 | TRBD2*01 | 1396 | tgtgccag | taccat | ggggg | | agatacgcagtactc | 3092 | C A S T P G D T Q Y F |
| 25.016 | TRBV25-1*01 | TRBJ2-1*01 | TRBD1*01 | 1397 | tgtgccagca | ccc | cggg | | agatacgcagtactc | 3093 | C A S T M G D E Q F F |
| 25.017 | TRBV25-1*01 | TRBJ2-1*01 | TRBD2*01 | 1398 | tgtgccagc | c | gact | cttcttaggaatgcat | aatgagcagttcttc | 3094 | C A S R L F L G C H N E Q F F |
| 27.001 | TRBV27*01 | TRBJ1-1*01 | | 1399 | tgtgcc | gccagaatcatccatctccatacaatgatcac | | | ttcttc | 3095 | C A A R I H P S P Y N D H F F |
| 27.002 | TRBV27*01 | TRBJ2-7*01 | TRBD1*01 | 1400 | tgtgcc | gccagatt | acaggggc | aaattacgagg | agtactc | 3096 | C A A R L Q G A N Y E E Y F |
| 27.003 | TRBV27*01 | TRBJ1-1*01 | TRBD2*01 | 1401 | tgtgcc | cag | caggggg | ccgctcctgtgc | acactgaagcttcttt | 3097 | C A Q Q G P L L W H T E A F F |
| 27.004 | TRBV27*01 | TRBJ1-1*01 | TRBD2*02 | 1402 | tgtgccag | tgaaag | gcgggagg | cctccgtcg | cctacaatgagcagttcttc | 3098 | C A S E R R E A S V A Y N E Q F F |
| 27.005 | TRBV27*01 | TRBJ1-1*01 | TRBD1*01 | 1403 | tgtgccag | ttcccggg | ggggc | cg | acactgaagcttcttt | 3099 | C A S F P G G A D T E A F F |
| 27.006 | TRBV27*01 | TRBJ2-3*01 | | 1404 | tgtgccagc | ggccacggcctac | ct agcacagatacgcagtatttt | | | 3100 | C A S G H G L P S T D T Q Y F |
| 27.007 | TRBV27*01 | TRBJ2-7*01 | TRBD2*01 | 1405 | tgtgccagc | gggttacggggcct | ctag | t | gagcagtactc | 3101 | C A S G L R A S S E Q Y F |
| 27.008 | TRBV27*01 | TRBJ2-7*01 | | 1406 | tgtgccagc | ggctggaagct | gcagtactc | | | 3102 | C A S G W K L Q Y F |
| 27.009 | TRBV27*01 | TRBJ2-7*01 | TRBD1*01 | 1407 | tgtgccagca | a | gacagg | aa | cctacgagcagtactc | 3103 | C A S K T G T Y E Q Y F |

Figure 1-52

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 27.010 | TRBV27*01 | TRBJ2-7*01 | TRBD2*01 | 1408 | tgtgccagca | aggt | ggg | tcctc | cctacgagcagtacttc | 3104 | C A S K V G P P Y E Q Y F |
| 27.011 | TRBV27*01 | TRBJ2-5*01 | TRBD2*02 | 1409 | tgtgccagc | tta | ggagg | tcccccgg | agagaccagtacttc | 3105 | C A S L G G P P P G E T Q Y F |
| 27.012 | TRBV27*01 | TRBJ2-3*01 | TRBD2*01 | 1410 | tgtgccagca | atctaggaacatt | cgggg | attccga | tattt | 3106 | C A S N L G T F G D S R Y F |
| 27.013 | TRBV27*01 | TRBJ2-4*01 | TRBD2*01 | 1411 | tgtgccagcag | ggatcaa | gggggg | | acattcagtacttc | 3107 | C A S R D Q G G D I Q Y F |
| 27.014 | TRBV27*01 | TRBJ2-7*01 | TRBD1*01 | 1412 | tgtgccagc | c | gggacagg | accgacgagg | cgagtacttc | 3108 | C A S R D R T D E G Q Y F |
| 27.015 | TRBV27*01 | TRBJ2-2*01 | TRBD2*01 | 1413 | tgtgccagcag | | ggggg | t ggggagctgttttt | | 3109 | C A S R G G G E L F F |
| 27.016 | TRBV27*01 | TRBJ2-1*01 | TRBD1*01 | 1414 | tgtgccagcag | aat | acag | ccatctcca | tacaatgagcagttcttc | 3110 | C A S R I Q P S P Y N E Q F F |
| 27.017 | TRBV27*01 | TRBJ1-2*01 | TRBD1*01 | 1415 | tgtgccagcag | aaa | gaca | cgtcgg | tatgctacacctc | 3111 | C A S R K T R R Y G Y T F |
| 27.018 | TRBV27*01 | TRBJ2-7*01 | TRBD2*02 | 1416 | tgtgccagc | c | gactagcgggag | tca | acgagcagtacttc | 3112 | C A S R L A G V N E Q Y F |
| 27.019 | TRBV27*01 | TRBJ2-7*01 | TRBD2*02 | 1417 | tgtgccagc | cggctct | tagcgggag | cctacgagcagtacttc | | 3113 | C A S R L L A G A Y E Q Y F |
| 27.020 | TRBV27*01 | TRBJ2-7*01 | TRBD2*02 | 1418 | tgtgccagcag | aac | cgggag | cctcgg | cgagcagtacttc | 3114 | C A S R T G S L G E Q Y F |
| 27.021 | TRBV27*01 | TRBJ2-1*01 | TRBD1*01 | 1419 | tgtgccagcag | | gacaaggg | tcgtg | aatgagcagttcttc | 3115 | C A S R T G V V N E Q F F |
| 27.022 | TRBV27*01 | TRBJ2-1*01 | TRBD1*01 | 1420 | tgtgccagcag | aacatc | gaca | tctccataccatgac | cagttcttc | 3116 | C A S R T S T S P Y H D Q F F |
| 27.023 | TRBV27*01 | TRBJ1-5*01 | TRBD1*01 | 1421 | tgtgccagcagt | gatgcc | cagg | tatcg | aatcagcccagcattt | 3117 | C A S S D G Q V S N Q P Q H F |
| 27.024 | TRBV27*01 | TRBJ1-2*01 | TRBD1*01 | 1422 | tgtgccagcagt | gaccgtcc | ggggg | tag | atgctacacctc | 3118 | C A S S D R P G V D G Y T F |
| 27.025 | TRBV27*01 | TRBJ1-2*01 | TRBD1*01 | 1423 | tgtgccagcagttt | c | ggaacaggg | a | tatggctacacctc | 3119 | C A S S F G Q G Y G Y T F |
| 27.026 | TRBV27*01 | TRBJ1-1*01 | TRBD2*02 | 1424 | tgtgccagcagttt | t | gggag | aggg | actgaagctttctt | 3120 | C A S S F G R G T E A F F |
| 27.027 | TRBV27*01 | TRBJ2-7*01 | TRBD2*01 | 1425 | tgtgccagcagttt | c gggactagcg | | t ctcctacgagcagtacttc | | 3121 | C A S S F G T S V S Y E Q Y F |
| 27.028 | TRBV27*01 | TRBJ1-2*01 | TRBD1*01 | 1426 | tgtgccagcagttt | ttt | gggg | a taactatggctacacctc | | 3122 | C A S S F L G D N Y G Y T F |
| 27.029 | TRBV27*01 | TRBJ1-5*01 | TRBD2*01 | 1427 | tgtgccagcagttt | ccc gggacaggg | | t | tacaatgagcccagcattc | 3123 | C A S S F P G Q G Y N E Q F F |
| 27.030 | TRBV27*01 | TRBJ1-2*01 | | 1428 | tgtgccagcagttt | ctccgacg | | | acaatgagcagttcttc | 3124 | C A S S F S D D N E Q F F |
| 27.031 | TRBV27*01 | TRBJ2-1*01 | TRBD1*01 | 1429 | tgtgccagcagttt | c | acaggg | ttc | atgagcagttctt | 3125 | C A S S F T G V H E Q F F |
| 27.032 | TRBV27*01 | TRBJ2-1*01 | TRBD1*01 | 1430 | tgtgccagcagttt | cactct c gggacagggg | ga | acgagcagtacttc | | 3126 | C A S S F T L G T G G N E Q Y F |
| 27.033 | TRBV27*01 | TRBJ1-5*01 | TRBD1*01 | 1431 | tgtgccagcagttt | lgt gacaggggc | | cagcccagcattt | | 3127 | C A S S F V T G G Q P Q H F |
| 27.034 | TRBV27*01 | TRBJ2-7*01 | TRBD2*01 | 1432 | tgtgccagc | tcc ggactag | a | ctacgagcagtacttc | | 3128 | C A S S G L D Y E Q Y F |
| 27.035 | TRBV27*01 | TRBJ2-7*01 | TRBD1*01 | 1433 | tgtgccagcagt | ggctact | cagggg | acgagcagtacttc | | 3129 | C A S S G Y S G D E Q Y F |
| 27.036 | TRBV27*01 | TRBJ2-1*01 | TRBD1*01 | 1434 | tgtgccagcag | ccatt ggacagggg | agtc | cgagcagttcttc | | 3130 | C A S S H W T G E S E Q Y F |
| 27.037 | TRBV27*01 | TRBJ2-5*01 | TRBD1*01 | 1435 | tgtgccagcagt | at c gggacaggggg | gcca | caagagaccagtacttc | | 3131 | C A S S I G T G G P Q E T Q Y F |

Figure 1-53

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 27.038 | TRBV27*01 | TRBJ2-5*01 | TRBD2*01 | 1436 | tgtgccagcag | cattaggaggg | gcgggggg | gagacccagtactlc | | 3132 | C A S S I R R G G E T Q Y F |
| 27.039 | TRBV27*01 | TRBJ2-1*01 | TRBD2*02 | 1437 | tgtgccagcagt | at | tagcggaggg gg | aatgagcagttctlc | | 3133 | C A S S I S G R G N E Q F F |
| 27.040 | TRBV27*01 | TRBJ2-7*01 | TRBD1*01 | 1438 | tgtgccagcagtta. g | caggggg | ctacgagcagtactlc | | | 3134 | C A S S L A G G Y E Q Y F |
| 27.041 | TRBV27*01 | TRBJ2-5*01 | TRBD2*01 | 1439 | tgtgccagcagt | ctcgcc ggactacgg | agatgg | gagacccagtactlc | | 3135 | C A S S L A G L A R W E T Q Y F |
| 27.042 | TRBV27*01 | TRBJ2-1*01 | TRBD2*02 | 1440 | tgtgccagcagtta. | gagga | agcgggag. tcgcgagg | aatgagcagttctlc | | 3136 | C A S S L E E A G V A R N E Q F F |
| 27.043 | TRBV27*01 | TRBJ2-1*01 | TRBD2*01 | 1441 | tgtgccagcagttat. tt | gcggg | ctctacaatgagcagttcttc | | | 3137 | C A S S L F A G S Y N E Q F F |
| 27.044 | TRBV27*01 | TRBJ2-1*01 | | 1442 | tgtgccagcagtttat. tcgat | | aatgagcagttcttc | | | 3138 | C A S S L F D N E Q F F |
| 27.045 | TRBV27*01 | TRBJ2-1*01 | TRBD1*01 | 1443 | tgtgccagcagtttat. ttggag | cagggg. gggg | aatgagcagttcttc | | | 3139 | C A S S L F G A G G G N E Q F F |
| 27.046 | TRBV27*01 | TRBJ2-2*01 | | 1444 | tgtgccagcagtttat. tcttgt | ccgggagctgttttt | | | | 3140 | C A S S L F L S G E L F F |
| 27.047 | TRBV27*01 | TRBJ2-1*01 | | 1445 | tgtgccagcagttat. t | caggggg. tt | atgagcagttcttc | | | 3141 | C A S S L F R G Y E Q F F |
| 27.048 | TRBV27*01 | TRBJ2-3*01 | TRBD2*01 | 1446 | tgtgccagcagttat. tttctccaggagtgggt | actagcg | ttgaagggg | agatacgcagtatttt | | 3142 | C A S S L F S P G V G T S V G R G D T Q Y F |
| 27.049 | TRBV27*01 | TRBJ2-4*01 | TRBD1*01 | 1447 | tgtgccagcagtta. | ggggc cctttatgaaaacattcat | tactlc | | | 3143 | C A S S L G A L Y E N I H Y F |
| 27.050 | TRBV27*01 | TRBJ2-2*01 | TRBD1*01 | 1448 | tgtgccagcagtta. | ggggc. caccgggagctgttttt | | | | 3144 | C A S S L G A T G E L F F |
| 27.051 | TRBV27*01 | TRBJ2-3*01 | | 1449 | tgtgccagcagtta. ggcttt | cacagatacgcagtattt | | | | 3145 | C A S S L G F T D T Q Y F |
| 27.052 | TRBV27*01 | TRBJ2-7*01 | TRBD2*01 | 1450 | tgtgccagcagtta. | ggg tcagtcacg | ggcagtacttc | | | 3146 | C A S S L G S V T E Q Y F |
| 27.053 | TRBV27*01 | TRBJ2-7*01 | TRBD2*02 | 1451 | tgtgccagcagtta. gat | tagcggga. a | ctacgagcagtactlc | | | 3147 | C A S S L I S G N Y E Q Y F |
| 27.054 | TRBV27*01 | TRBJ2-7*01 | TRBD1*01 | 1452 | tgtgccagcagtta. aa ggacaggggg. a | tcctacgagcagtactlc | | | | 3148 | C A S S L K D R G S Y E Q Y F |
| 27.055 | TRBV27*01 | TRBJ2-1*01 | TRBD2*02 | 1453 | tgtgccagcagttt. gctctctttcg | gcgggaggcgcggag | atgagcagttcttc | | | 3149 | C A S S L L S F G G R A G D E Q F F |
| 27.056 | TRBV27*01 | TRBJ2-1*01 | TRBD2*02 | 1454 | tgtgccagcagtt. gctctctttcg | gcgggaggcgcgga | aatgagcagttcttc | | | 3150 | C A S S L L S F G G R A G N E Q F F |
| 27.057 | TRBV27*01 | TRBJ2-5*01 | | 1455 | tgtgccagcagtta. aaccgaa | aagagacccagtactlc | | | | 3151 | C A S S L N R K E T Q Y F |
| 27.058 | TRBV27*01 | TRBJ1-5*01 | TRBD1*01 | 1456 | tgtgccagcagtttt. g | cagg. ct | aatcagcccacagcatttt | | | 3152 | C A S S L Q A N Q P Q H F |
| 27.059 | TRBV27*01 | TRBJ2-7*01 | TRBD1*01 | 1457 | tgtgccagcagt. ctc | caggggg. acacca | cctacgagcagtactlc | | | 3153 | C A S S L Q G D T T Y E Q Y F |
| 27.060 | TRBV27*01 | TRBJ2-7*01 | | 1458 | tgtgccagcagtta. agagctcctc ctcctacgagcagtactlc | | | | | 3154 | C A S S L R A P S S Y E Q Y F |
| 27.061 | TRBV27*01 | TRBJ2-7*01 | TRBD1*01 | 1459 | tgtgccagcagtta. aggg | aatcg | tacgagcagtactlc | | | 3155 | C A S S L R E S Y E Q Y F |
| 27.062 | TRBV27*01 | TRBJ2-3*01 | TRBD2*02 | 1460 | tgtgccagcagtta. a | gaggg gc | cacagatacgcagtatttt | | | 3156 | C A S S L R G A T D T Q Y F |
| 27.063 | TRBV27*01 | TRBJ1-2*01 | TRBD1*01 | 1461 | tgtgccagcagttatc g g | cagggggc | ggctacacctlc | | | 3157 | C A S S L S A G G G Y T F |
| 27.064 | TRBV27*01 | TRBJ1-1*01 | TRBD1*01 | 1462 | tgtgccagcagttatc c | gacagggggc gc ag | caatgagcagttcttc | | | 3158 | C A S S L S D R G R S N E Q F F |
| 27.065 | TRBV27*01 | TRBJ2-6*01 | | 1463 | tgtgccagcagtt. g tctggggccaacctgcactlc | | | | | 3159 | C A S S L S G A N V L T F |

Figure 1-54

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 27.066 | TRBV27*01 | TRBJ2-7*01 | TRBD2*01 | 1464 | tgtgccagcag..... | ccta ..... | agcgggg.. ca | ..cc | tacgagcagtactc | 3160 | C A S S L S G G T Y E Q Y F |
| 27.067 | TRBV27*01 | TRBJ2-1*01 | TRBD2*02 | 1465 | tgtgccagcagtta.. | agtctggt | ....ctagcggga... at | ....... | tgagcagttcttc | 3161 | C A S S L S L G L A G I E Q F F |
| 27.068 | TRBV27*01 | TRBJ2-1*01 | TRBD2*01 | 1466 | tgtgccagcagttatc | ccttta | gga.......... | atg.. | acaatgagcagttcttc | 3162 | C A S S L L G N D N E Q F F |
| 27.069 | TRBV27*01 | TRBJ2-3*01 | TRBD2*02 | 1467 | tgtgccagcagtttat | o gc | ..ctagcgggag.. ttcaa | ..... | ataccgagcagtattt | 3163 | C A S S L P S G S S N T Q Y F |
| 27.070 | TRBV27*01 | TRBJ2-1*01 | TRBD1*01 | 1468 | tgtgccagcagttta.. | ag | ...cagggg.. actcct | ..... | caatgagcagttcttc | 3164 | C A S S L S R G L L N E Q F F |
| 27.071 | TRBV27*01 | TRBJ2-7*01 | TRBD2*02 | 1469 | tgtgccagcagttatc | ......... | gaggg gctccct | ... | ctacgagcagtactc | 3165 | C A S S L S R G S L Y E Q Y F |
| 27.072 | TRBV27*01 | TRBJ1-1*01 | TRBD1*01 | 1470 | tgtgccagcagttatc | aa | ggacagg.. tctag | ..... | tgaagcttctt | 3166 | C A S S L S R T G S S E A F F |
| 27.073 | TRBV27*01 | TRBJ1-1*01 | | 1471 | tgtgccagcagttta.. | agctctcccct | .... | caatgagcagttcttc | | 3167 | C A S S L S S P L N E Q F F |
| 27.074 | TRBV27*01 | TRBJ2-1*01 | TRBD1*01 | 1472 | tgtgccagcagttat | ct | ....gggg. tcacccaa | ...... | aatgagcagttcttc | 3168 | C A S S L S W G S P Q N E Q F F |
| 27.075 | TRBV27*01 | TRBJ2-1*01 | TRBD1*02 | 1473 | tgtgccagcagt..... | ctaccta | ......gaggg tac. | ........ | gagcagttcttc | 3169 | C A S S L T L G G Y E Q F F |
| 27.076 | TRBV27*01 | TRBJ2-7*01 | TRBD2*02 | 1474 | tgtgccagcagtta.. | ....actagcggga... ca | .. | tacgagcagtactc | | 3170 | C A S S L T S G T Y E Q Y F |
| 27.077 | TRBV27*01 | TRBJ2-7*01 | TRBD2*01 | 1475 | tgtgccagcagtta.. | gttagc | ....ctagcgggag.. ag | ... | tacgagcagtactc | 3171 | C A S S L V S L A G E Y E Q Y F |
| 27.078 | TRBV27*01 | TRBJ2-3*01 | TRBD1*01 | 1476 | tgtgccagcagttat | gggac | ......ggaaccatg | .gataccgagtattt | | 3172 | C A S S L W D G T M D T Q Y F |
| 27.079 | TRBV27*01 | TRBJ2-6*01 | TRBD1*01 | 1477 | tgtgccagcagttat | ......... | ggggag ..ctggggccaacctcctgacttc | | | 3173 | C A S S L W G A G A N V L T F |
| 27.080 | TRBV27*01 | TRBJ1-4*01 | TRBD1*01 | 1478 | tgtgccagcagttat | accc | ...acagg... | ........ | aaaactgtttt | 3174 | C A S S L Y P Q G K L F F |
| 27.081 | TRBV27*01 | TRBJ2-7*01 | TRBD1*01 | 1479 | tgtgccagcagt..... | ctatact | ..cagggggc tcagg | ...... | cgagcagtactc | 3175 | C A S S L Y S G G G G E Q Y F |
| 27.082 | TRBV27*01 | TRBJ2-1*01 | TRBD2*01 | 1480 | tgtgccagcag..... | cct | .gacag.. | tctct | ..ctacaatgagcagttcttc | 3176 | C A S S P D S L L Y N E Q F F |
| 27.083 | TRBV27*01 | TRBJ2-2*01 | | 1481 | tgtgccagcag..... | cccattcttgtcgcgagctgta | ........ | | ...tttt | 3177 | C A S S P F L S G E L Y F |
| 27.084 | TRBV27*01 | TRBJ2-1*01 | TRBD2*02 | 1482 | tgtgccagcag..... | ccctggg | ....ctagcgggag... t | ... | tacaatgagcagttcttc | 3178 | C A S S P G A S G S Y N E Q F F |
| 27.085 | TRBV27*01 | TRBJ2-7*01 | TRBD1*01 | 1483 | tgtgccagcagt..... | cc | gggacaggg... agg | ..ctacgagcagtactc | | 3179 | C A S S P G Q G G Y E Q Y F |
| 27.086 | TRBV27*01 | TRBJ2-7*01 | TRBD2*01 | 1484 | tgtgccagcagt..... | ccc | gggact......... | gccgc | .....cgagcagtactc | 3180 | C A S S P G T A A E Q Y F |
| 27.087 | TRBV27*01 | TRBJ2-1*01 | TRBD1*01 | 1485 | tgtgccagcagt..... | ccg | gggacagggggc ta | ...ctacaatgagcagttcttc | | 3181 | C A S S P G T G G Y Y N E Q F F |
| 27.088 | TRBV27*01 | TRBJ1-3*01 | TRBD1*01 | 1486 | tgtgccagcag..... | cccc | gggac....... gattga | ctctgaaacaccatatttt | | 3182 | C A S S P G T I D S G N T I Y F |
| 27.089 | TRBV27*01 | TRBJ2-3*01 | TRBD1*01 | 1487 | tgtgccagcagt..... | cccaccc | ..gacagg... tctg | ....cagatacgcagtatttt | | 3183 | C A S S P H P T G S A D T Q Y F |
| 27.090 | TRBV27*01 | TRBJ1-2*01 | TRBD1*01 | 1488 | tgtgccagcagt..... | ccccctga | ..gacag...... cgggag | ........ | atggctacaccttc | 3184 | C A S S P L E T A G D G Y T F |
| 27.091 | TRBV27*01 | TRBJ1-2*01 | TRBD1*01 | 1489 | tgtgccagcag..... | cccctcaagacag c ggga.... | g | ... | atggctacaccttc | 3185 | C A S S P L K T A G D G Y T F |
| 27.092 | TRBV27*01 | TRBJ2-3*01 | TRBD2*01 | 1490 | tgtgccagcag..... | cccac | .....cgggg... aag | ....... | acgcagtatttt | 3186 | C A S S P P G K T Q Y F |
| 27.093 | TRBV27*01 | TRBJ2-7*01 | TRBD2*02 | 1491 | Vtgtgccagcagt..... | cccgggg | .....agcgggaggg c | ..cc | tacgagcagtactc | 3187 | C A S S P R G A G G P Y E Q Y F |

Figure 1-55

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 27.094 | TRBV27*01 | TRBJ1-6*01 | TRBD1*01 | 1492 | tgtgccagcagt.. | ccaaggggtt.cc | ggaaca...... | agtc...... | aattcacccctcacttt | 3188 | C A S S P R V P G Q V N S P L H F |
| 27.095 | TRBV27*01 | TRBJ1-1*01 | TRBD1*01 | 1493 | tgtgccagcagt.. | ccatc..gacaggg..ccc | ...ctgaagcttcttt | | | 3189 | C A S S P S T G A P E A F F |
| 27.096 | TRBV27*01 | TRBJ1-5*01 | TRBD1*01 | 1494 | tgtgccagcagt.. | ccctc..gacaggggc ag | ...tcagcccagcattt | | | 3190 | C A S S P S T G G S Q P Q H F |
| 27.097 | TRBV27*01 | TRBJ2-7*01 | TRBD1*01 | 1495 | tgtgccagcagt.. | cccaccg...caggggc | cgaa......acgagcagtacttc | | | 3191 | C A S S P T A G G R N E Q Y F |
| 27.098 | TRBV27*01 | TRBJ2-2*01 | | 1496 | tgtgccagcagt.. | ccct..acaccggggagctgttttt | | | | 3192 | C A S S P Y T G E L F F |
| 27.099 | TRBV27*01 | TRBJ2-7*01 | TRBD1*01 | 1497 | tgtgccagcagt.. | cagacct cc gggacag.... ca | .tacgagcagtacttc | | | 3193 | C A S S Q T S G T A Y E Q Y F |
| 27.100 | TRBV27*01 | TRBJ1-2*01 | TRBD2*01 | 1498 | tgtgccagcagt.. | ag......agcgg......ca | ..aactatggctacacctc | | | 3194 | C A S S R A A N Y G Y T F |
| 27.101 | TRBV27*01 | TRBJ2-5*01 | TRBD2*01 | 1499 | tgtgccagcagt.. | cg......agcgg...... | atcc ..ccaagagaccagtacttc | | | 3195 | C A S S R A D P Q E T Q Y F |
| 27.102 | TRBV27*01 | TRBJ2-2*01 | TRBD2*02 | 1500 | tgtgccagcagt.. | cgag ......gggag.. t | ......ccggggagctgttttt | | | 3196 | C A S S R G E S G E L F F |
| 27.103 | TRBV27*01 | TRBJ2-7*01 | TRBD1*01 | 1501 | tgtgccagcag.. | cc..gacagggg..ata | ..cctacgagcagtacttc | | | 3197 | C A S S R Q G D T Y E Q Y F |
| 27.104 | TRBV27*01 | TRBJ2-3*01 | TRBD2*01 | 1502 | tgtgccagcagt.. | cagatg....ctagc...... | tgggga...acagatacgcagtatttt | | | 3198 | C A S S D A S W G T D T Q Y F |
| 27.105 | TRBV27*01 | TRBJ2-7*01 | TRBD1*01 | 1503 | tgtgccagcagt.. | caga gggacag.....cga | ..cctacgagcagtacttc | | | 3199 | C A S S E C Q A T Y E Q Y F |
| 27.106 | TRBV27*01 | TRBJ1-2*01 | TRBD1*01 | 1504 | tgtgccagcagt.. | ctttc..gacag...... | ctatggctacacctc | | | 3200 | C A S S F D S Y G Y T F |
| 27.107 | TRBV27*01 | TRBJ2-1*01 | | 1505 | tgtgccagcagt.. | ccggtggcct ....caatgagcagttcttc | | | | 3201 | C A S S G G L N E Q F F |
| 27.108 | TRBV27*01 | TRBJ1-1*01 | TRBD1*01 | 1506 | tgtgccagcagt.. | ccgg......caagg.... tt | ...cactgaagcttcttt | | | 3202 | C A S S G R F T E A F F |
| 27.109 | TRBV27*01 | TRBJ1-1*01 | | 1507 | tgtgccagcagt.. | ccctccctata ......tgaagcttcttt | | | | 3203 | C A S S L P L Y E A F F |
| 27.110 | TRBV27*01 | TRBJ2-1*01 | TRBD2*02 | 1508 | tgtgccagcagt.. | cccaagga ccc gggactagccggag.. tt | ...tacaatgagcagttcttc | | | 3204 | C A S S Q D P G L A G V Y N E Q F F |
| 27.111 | TRBV27*01 | TRBJ1-5*01 | TRBD1*01 | 1509 | tgtgccagcagt.. | caacc ..ggacaggg.. a | ...aatcagcccagcattt | | | 3205 | C A S S T G Q G N Q P Q H F |
| 27.112 | TRBV27*01 | TRBJ2-7*01 | TRBD2*01 | 1510 | tgtgccagcagt.. | cctggga ......taqcgg.... a | ag ctctacgagcagtacttc | | | 3206 | C A S S W D S G S S Y E Q Y F |
| 27.113 | TRBV27*01 | TRBJ2-7*01 | TRBD1*01 | 1511 | tgtgccagcagt.. | cat ggga............ | ctcctacgagcagtacttc | | | 3207 | C A S S W D S Y E Q Y F |
| 27.114 | TRBV27*01 | TRBJ2-7*01 | TRBD2*01 | 1512 | tgtgccagcagt.. | cat ..acaggg.. agtc | ..cctacgagcagtacttc | | | 3208 | C A S S Y R G G P Y E Q Y F |
| 27.115 | TRBV27*01 | TRBJ1-2*01 | | 1513 | tgtgccagcagt.. | acagg.... actg ....tatggctacacctc | | | | 3209 | C A S S T G L Y G Y T F |
| 27.116 | TRBV27*01 | TRBJ2-2*01 | TRBD2*02 | 1514 | tgtgccagcagt..... | ac ......cggga.. t | ..gaacacacggggagctgttttt | | | 3210 | C A S S T G M N T G E L F F |
| 27.117 | TRBV27*01 | TRBJ1-5*01 | TRBD1*01 | 1515 | tgtgccagcagt.. | accc ..acaggggg | gggaatagcgtgatg..gcaatcagcccagcatttt | | | 3211 | C A S S T H R G G N S V D G N Q P Q H F |
| 27.118 | TRBV27*01 | TRBJ2-2*01 | TRBD1*01 | 1516 | tgtgccagcagt.. | gtaagac.. ..ggggc | caaaa ..aacaccggggagctgttttt | | | 3212 | C A S S V R R G P K N T G E L F F |
| 27.119 | TRBV27*01 | TRBJ1-5*01 | TRBD1*01 | 1517 | tgtgccagcagt.. | gggacagggg.. agttc | ...tcagcccagcattt | | | 3213 | C A S S W D R G G S Q P Q H F |
| 27.120 | TRBV27*01 | TRBJ2-2*01 | TRBD1*01 | 1518 | tgtgccagcagt.. | ggggt ......agggg...... | ..caccggggagctgttttt | | | 3214 | C A S S W G R G T G E L F F |
| 27.121 | TRBV27*01 | TRBJ2-3*01 | TRBD2*01 | 1519 | tgtgccagcagt.. | ggcagaaa ......cggg.... | .gcacagatacgcagtatttt | | | 3215 | C A S S W Q K R G T D T Q Y F |

Figure 1-56

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 27.122 | TRBV27*01 | TRBJ2-1*01 | TRBD2*02 | 1520 | tgtgccagcag | ct | ggactagcgggaggg | tag | atgagcagttcttc | 3216 | C A S S W T S G R V D E Q F F |
| 27.123 | TRBV27*01 | TRBJ2-1*01 | TRBD2*01 | 1521 | tgtgccagcagtt | acttc | gcggg | aatgagcagttcttc | | 3217 | C A S S Y F R G N E Q F F |
| 27.124 | TRBV27*01 | TRBJ2-7*01 | TRBD2*02 | 1522 | tgtgccagcagtt | accta | aggg tac | cgagcagtactc | | 3218 | C A S S Y L K G T E Q Y F |
| 27.125 | TRBV27*01 | TRBJ2-2*01 | | 1523 | tgtgccagca | ctgacg | | ccggggagctgtttt | | 3219 | C A S T D A G E L F F |
| 27.126 | TRBV27*01 | TRBJ2-3*01 | TRBD2*02 | 1524 | tgtgccagca | cc | ggag | gcacagatacgcagtattt | | 3220 | C A S T G G T D T Q Y F |
| 27.127 | TRBV27*01 | TRBJ2-2*01 | TRBD2*01 | 1525 | tgtgccagca | ca | agcgggggg | accggggagctgtttt | | 3221 | C A S T S G G T G E L F F |
| 27.128 | TRBV27*01 | TRBJ2-1*01 | TRBD1*01 | 1526 | tgtgcca | ccagaat | acag | ccatctccatacaatgagcac | ttcttc | 3222 | C A T R I Q P S P Y N E H F F |
| 27.129 | TRBV27*01 | TRBJ2-1*01 | TRBD1*01 | 1527 | tgtgcca | cca | ggacaggg | tcgtgaatgagcat | ttcttc | 3223 | C A T R T G V V N E H F F |
| 27.130 | TRBV27*01 | TRBJ2-1*01 | TRBD1*01 | 1528 | tgtgcca | ccagtccg | gggacaggggc tactacaatgac | cagtcttc | | 3224 | C A T S P G T G G Y Y N D Q F F |
| 28.01 | TRBV28*01 | TRBJ1-1*01 | TRBD1*01 | 1529 | tgtgcc | tgctgttttggc | ggac | ctgaac | ctttcttt | 3225 | C A C C F G G P E P F F |
| 28.02 | TRBV28*01 | TRBJ2-2*01 | TRBD1*01 | 1530 | tgtgcc | tgcttct | ggggc g ggc | agctgtttt | | 3226 | C A C F W G G Q L F F |
| 28.03 | TRBV28*01 | TRBJ2-5*01 | TRBD2*01 | 1531 | tgtgcc | tgccagcctcc | gga | agtctctc | agagacccagtacttc | 3227 | C A C Q P P E G L S E T Q Y F |
| 28.04 | TRBV28*01 | TRBJ2-3*01 | TRBD2*01 | 1532 | tgtgcca | tca ggactagcg | | gcacagatacgcagtattt | | 3228 | C A I R T S G T D T Q Y F |
| 28.05 | TRBV28*01 | TRBJ2-7*01 | TRBD2*02 | 1533 | tgtgcca | ataaac | agcagga | ccgttaccagcaga | actc | 3229 | C A N K Q R D R Y Q Q N F |
| 28.06 | TRBV28*01 | TRBJ2-1*01 | | 1534 | tgtgccagc | gcctcaaa | ctacaatgagcagttcttc | | | 3230 | C A S A S N Y N E Q F F |
| 28.07 | TRBV28*01 | TRBJ1-1*01 | TRBD1*01 | 1535 | tgtgccagc | ga | gggc cgga | gaacactgaagctttcttt | | 3231 | C A S E G P E N T E A F F |
| 28.08 | TRBV28*01 | TRBJ1-3*01 | TRBD1*01 | 1536 | tgtgccagc | ttaccogcgctgg | cag | cctctgaaacaccatatttt | | 3232 | C A S F T R V A A S G N T I Y F |
| 28.09 | TRBV28*01 | TRBJ2-7*01 | TRBD1*01 | 1537 | tgtgccagc | ggttccggggaacctcctgtgt | ggggg a | ctacgagcagtactc | | 3233 | C A S G S G E P P V V G D Y E Q Y F |
| 28.10 | TRBV28*01 | TRBJ2-5*01 | TRBD1*01 | 1538 | tgtgccagca | agctgggacgg | caggggg att | gagaccagtacttc | | 3234 | C A S K L G R Q G I E T Q Y F |
| 28.11 | TRBV28*01 | TRBJ2-3*01 | TRBD2*02 | 1539 | tgtgccagca | agca | agcgggagg aatcg | gcacagatacgcagtatttt | | 3235 | C A S K Q A G G I G T D T Q Y F |
| 28.12 | TRBV28*01 | TRBJ2-1*01 | TRBD2*01 | 1540 | tgtgccag | tttggccttggggtggc | ggactagccgg | tac | caatgagcagttcttc | 3236 | C A S L A L G W R T S G T N E Q F F |
| 28.13 | TRBV28*01 | TRBJ2-1*01 | TRBD2*02 | 1541 | tgtgccagca | tgg | ctagccgga | agg | atgagcagttcttc | 3237 | C A S M A S G K D E Q F F |
| 28.14 | TRBV28*01 | TRBJ2-1*01 | TRBD1*01 | 1542 | tgtgccagca | ataga | ggacag | tccttggg | gagcagttcttc | 3238 | C A S N R G Q S F G E Q Y F |
| 28.15 | TRBV28*01 | TRBJ2-7*01 | TRBD2*01 | 1543 | tgtgccagc | caatcc | gggactagccgg | ag | acgagcagtactc | 3239 | C A S Q S G T S G D E Q Y F |
| 28.16 | TRBV28*01 | TRBJ2-7*01 | TRBD1*01 | 1544 | tgtgccagcag | ggct | acaggg | tctgaaaaccatatttt | | 3240 | C A S R A T G S G N T I Y F |
| 28.17 | TRBV28*01 | TRBJ2-7*01 | TRBD1*01 | 1545 | tgtgccagcag | gggaa cc gggacag | ccatcc | acgacgagtactc | | 3241 | C A S R G T G T A I H E Q Y F |
| 28.18 | TRBV28*01 | TRBJ2-7*01 | TRBD1*01 | 1546 | tgtgccagcag | gatt | gacaggg | cc ag ctcctacgagcagtactc | | 3242 | C A S R I D R A S S Y E Q Y F |

Figure 1-57

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 28.19 | TRBV28*01 | TRBJ2-1*01 | TRBD1*01 | 1547 | tgtgccagcag | aatc | gacag | ctcctacaatgagcagttcttc | | 3243 | C A S R I D S S Y N E Q F F |
| 28.20 | TRBV28*01 | TRBJ1-2*01 | TRBD1*01 | 1548 | tgtgccagcag | accacc | caggg | cgg | ctatgctacacctc | 3244 | C A S R P P Q G G Y G Y T F |
| 28.21 | TRBV28*01 | TRBJ2-5*01 | TRBD1*01 | 1549 | tgtgccagcag | gaggat | ggacagg | cagattgct | gagaccagtactc | 3245 | C A S R R M D R Q I A E T Q Y F |
| 28.22 | TRBV28*01 | TRBJ2-1*01 | TRBD2*01 | 1550 | tgtgccagcag | gtcct | cggg | tatgg | atgagcagttcttc | 3246 | C A S R S S G M D E Q F F |
| 28.23 | TRBV28*01 | TRBJ1-1*01 | TRBD2*02 | 1551 | tgtgccagcag | aacac | agcgggagg | caa | acaatgagcagttcttc | 3247 | C A S R T Q R E A N N E Q F F |
| 28.24 | TRBV28*01 | TRBJ2-2*01 | TRBD1*01 | 1552 | tgtgccagc | cgctactt | cc gggacagg | | ccgggagctgtttt | 3248 | C A S R Y F R D R A G E L F F |
| 28.25 | TRBV28*01 | TRBJ2-3*01 | TRBD1*01 | 1553 | tgtgccagcagt | gaaaggaaa | c gggaca | aactaca | cacagatacgcagtattt | 3249 | C A S S E R K R D K L H T D T Q Y F |
| 28.26 | TRBV28*01 | TRBJ1-1*01 | TRBD1*01 | 1554 | tgtgccagcagttt | c | gacag | ct | tgaacactgaagcttc | 3250 | C A S S F D S L N T E A F F |
| 28.27 | TRBV28*01 | TRBJ2-7*01 | TRBD1*01 | 1555 | tgtgccagcagttt | tttt | ggacaggggc | ca | acgagcagtactc | 3251 | C A S S F F G Q G A N E Q Y F |
| 28.28 | TRBV28*01 | TRBJ2-1*01 | TRBD2*02 | 1556 | tgtgccagcagttt | t | ggaggg | | gagcagttcttc | 3252 | C A S S F G G E Q F F |
| 28.29 | TRBV28*01 | TRBJ2-7*01 | | 1557 | tgtgccagcagttt | | tggcatcctga | | cctacgagcagtactc | 3253 | C A S S F G I L T Y E Q Y F |
| 28.30 | TRBV28*01 | TRBJ2-1*01 | TRBD2*02 | 1558 | tgtgccagcagttt | ct | tagcggaggg | tcagg | caatgagcagttcttc | 3254 | C A S S F L A G G S G N E Q F F |
| 28.31 | TRBV28*01 | TRBJ1-2*01 | TRBD1*01 | 1559 | tgtgccagcagttt | taatt | caggg | | aactatgctacacctc | 3255 | C A S S F N S G N Y G Y T F |
| 28.32 | TRBV28*01 | TRBJ2-7*01 | TRBD1*01 | 1560 | tgtgccagcagt | cca | gggacaggggc | actttcg | cctacgagcagtactc | 3256 | C A S S F Q G G A L F A Y E Q Y F |
| 28.33 | TRBV28*01 | TRBJ1-1*01 | TRBD1*01 | 1561 | tgtgccagcagttt | ccaa | acagggg | c g gg | actgaagcttctt | 3257 | C A S S F Q T G G T E A F F |
| 28.34 | TRBV28*01 | TRBJ2-3*01 | | 1562 | tgtgccagcagttt | ttcgcgtacgc | gcacagatacgcagtatttt | | | 3258 | C A S S F S R T R T D T Q Y F |
| 28.35 | TRBV28*01 | TRBJ2-1*01 | TRBD2*01 | 1563 | tgtgccagcagttt | ctggcgct | cggggg | | aatgagcagttcttc | 3259 | C A S S F W R S G N E Q F F |
| 28.36 | TRBV28*01 | TRBJ2-7*01 | TRBD1*01 | 1564 | tgtgccagcag | tt cc gggacaggggg | | ctacgagcagtactc | | 3260 | C A S S G T G G Y E Q Y F |
| 28.37 | TRBV28*01 | TRBJ2-7*01 | TRBD1*01 | 1565 | tgtgccagcagt | ata | gacaggg | aagtgcg | ctacgagcagtactc | 3261 | C A S S I D R E V R Y E Q Y F |
| 28.38 | TRBV28*01 | TRBJ2-1*01 | TRBD2*01 | 1566 | tgtgccagcagt | a | tag | aa | gagcagttcttc | 3262 | C A S S I E E Q F F |
| 28.39 | TRBV28*01 | TRBJ2-7*01 | | 1567 | tgtgccagcagtta | gctcgccaga | acgagcagtactc | | | 3263 | C A S S L A R Q N E Q Y F |
| 28.40 | TRBV28*01 | TRBJ2-5*01 | TRBD1*01 | 1568 | tgtgccagcagt | ct ggacagg | cccgaa | aagagaccagtactc | | 3264 | C A S S L D R A R K E T Q Y F |
| 28.41 | TRBV28*01 | TRBJ1-2*01 | | 1569 | tgtgccagcagtta | gagccattgg | atgcctacacctc | | | 3265 | C A S S L E P L D G Y T F |
| 28.42 | TRBV28*01 | TRBJ2-2*01 | TRBD2*02 | 1570 | tgtgccagcagt | ct | ggagg tgtgg | | ggggagctgtttt | 3266 | C A S S L E V W G E L F F |
| 28.43 | TRBV28*01 | TRBJ2-1*01 | TRBD2*02 | 1571 | tgtgccagcagtta | ggga | tagcggagg | ct | atgagcagttcttc | 3267 | C A S S L G I A G G Y E Q F F |
| 28.44 | TRBV28*01 | TRBJ2-5*01 | | 1572 | tgtgccagcagtta | gcccg | agagaccagtactc | | | 3268 | C A S S L G R E T Q Y F |
| 28.45 | TRBV28*01 | TRBJ2-1*01 | TRBD1*01 | 1573 | tgtgccagcagtta | gg | gggacaggg | acg | tacaatgagcagttcttc | 3269 | C A S S L G T G T Y N E Q F F |
| 28.46 | TRBV28*01 | TRBJ2-7*01 | TRBD2*01 | 1574 | tgtgccagcagtta | gg | cta | t | tcctacgagcagtactc | 3270 | C A S S L G Y S Y E Q Y F |

Figure 1-58

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 28.47 | TRBV28*01 | TRBJ2-7*01 | TRBD2*02 | 1575 | tgtgccagcagt... | cttaaaaa... | gggag... | aaat... | ctacgagcagtactlc | 3271 | C A S S L K K G E I Y E Q Y F |
| 28.48 | TRBV28*01 | TRBJ2-7*01 | TRBD2*01 | 1576 | tgtgccagcagtt... | g ...ctag... | acct | ...cgagcagtacttc | | 3272 | C A S S L L L D L E Q Y F |
| 28.49 | TRBV28*01 | TRBJ2-7*01 | TRBD2*02 | 1577 | tgtgccagcagtt... | gttggt | ...aggg ctgtg . | tcctacgagcagtacttc | | 3273 | C A S S L L G R A V S Y E Q Y F |
| 28.50 | TRBV28*01 | TRBJ2-6*01 | TRBD2*01 | 1578 | tgtgccagcagtta.. | ctaca ...... | tagcg...... c | ctctggggccaacgtcctgacttc | | 3274 | C A S S L L H S A S G A N V L T F |
| 28.51 | TRBV28*01 | TRBJ2-7*01 | TRBD2*01 | 1579 | tgtgccagcagtta.. | claaggacc... | agcagggg... | ...tacgagcagtacttc | | 3275 | C A S S L L R D Q R G Y E Q Y F |
| 28.52 | TRBV28*01 | TRBJ1-2*01 | | 1580 | tgtgccagcagtta.. | aacatgt ...ctatggctacacctc | | | | 3276 | C A S S L N M V Y G Y T F |
| 28.53 | TRBV28*01 | TRBJ2-2*01 | | 1581 | tgtgccagcagt..... | ct . gaacaccgggagctgttttt | | | | 3277 | C A S S L N T G E L F F |
| 28.54 | TRBV28*01 | TRBJ1-2*01 | TRBD2*02 | 1582 | tgtgccagcagtta.. | c ........ cggga... a | ........ gctacacctc | | | 3278 | C A S S L P G S Y T F |
| 28.55 | TRBV28*01 | TRBJ1-1*01 | TRBD1*01 | 1583 | tgtgccagcag...... | cctccaa gggacaggg... | tgg .. | .actgaagcttctt | | 3279 | C A S S L Q G T G W T E A F F |
| 28.56 | TRBV28*01 | TRBJ2-7*01 | TRBD1*01 | 1584 | tgtgccagcagtta.. | cagggg... | tacc .. | cctacgagcagtacttc | | 3280 | C A S S L Q G Y P Y E Q Y F |
| 28.57 | TRBV28*01 | TRBJ2-3*01 | TRBD1*01 | 1585 | tgtgccagcagtttat. | ctat ... gggg. t | ...cagatacgcagtattt | | | 3281 | C A S S L M G S D T Q Y F |
| 28.58 | TRBV28*01 | TRBJ2-3*01 | | 1586 | tgtgccagcagtta.. | ...acagatacgcagtattt | | | | 3282 | C A S S L T D T Q Y F |
| 28.59 | TRBV28*01 | TRBJ2-3*01 | TRBD2*01 | 1587 | tgtgccagcagtta.. | ...actacgcgggg... | atact ct | agcacagatacgcagtattt | | 3283 | C A S S L T S G G Y S S T D T Q Y F |
| 28.60 | TRBV28*01 | TRBJ2-7*01 | TRBD2*02 | 1588 | tgtgccagcagtta.. | gtg ...gcggag.. | aacct .. | ..tacgagcagtactlc | | 3284 | C A S S L V A G E P Y E Q Y F |
| 28.61 | TRBV28*01 | TRBJ2-7*01 | | 1589 | tgtgccagcagtta.. | gtcttgtt ...tacgagcagtacttc | | | | 3285 | C A S S L V L V Y E Q Y F |
| 28.62 | TRBV28*01 | TRBJ2-3*01 | TRBD1*01 | 1590 | tgtgccagcagtttatg | .......ggc | agcacagatacgcagtattt | | | 3286 | C A S S L W G S T D T Q Y F |
| 28.63 | TRBV28*01 | TRBJ2-7*01 | TRBD1*01 | 1591 | tgtgccagcagtttatg g | gggaca..... | cta ...tacgagcagtactlc | | | 3287 | C A S S L W G T L Y E Q Y F |
| 28.64 | TRBV28*01 | TRBJ2-1*01 | TRBD1*01 | 1592 | tgtgccagcagt..... | at . gacaggg... | acctt .. | ..caatgagcagttcttc | | 3288 | C A S S M T G T F N E Q F F |
| 28.65 | TRBV28*01 | TRBJ1-5*01 | TRBD1*01 | 1593 | tgtgccagcagt..... | c ... caggg... | atcgacct | ..caatcagcccagcatt | | 3289 | C A S S P G I D L N Q P Q H F |
| 28.66 | TRBV28*01 | TRBJ2-7*01 | TRBD2*01 | 1594 | tgtgccagcag...... | ccc gggactagcg..... | ac . | ......cgagcagtacttc | | 3290 | C A S S P G L A T E Q Y F |
| 28.67 | TRBV28*01 | TRBJ2-7*01 | TRBD2*02 | 1595 | tgtgccagcag...... | cccatgggggg ...ctagcgggag.. t | ...ctacgagcagtactlc | | | 3291 | C A S S P M G G L A G V Y E Q Y F |
| 28.68 | TRBV28*01 | TRBJ1-6*01 | TRBD1*01 | 1596 | tgtgccagcag...... | cccaccg... | agggg... | taattcaccctccactt | | 3292 | C A S S P P G G G N S P L H F |
| 28.69 | TRBV28*01 | TRBJ1-1*01 | TRBD1*01 | 1597 | tgtgccagcagt..... | cca ccc gggacagggg.. | ttctagg... | cactgaagcttcttt | | 3293 | C A S S P P G T G V L G T E A F F |
| 28.70 | TRBV28*01 | TRBJ1-2*01 | TRBD1*01 | 1598 | tgtgccagcagt..... | cccaga gggaca.. | tt . | ...ctatgctacacctc | | 3294 | C A S S P R G T F Y G Y T F |
| 28.71 | TRBV28*01 | TRBJ2-5*01 | TRBD1*01 | 1599 | tgtgccagcagt..... | ccct cc gggacaggg.. | ttg . | ....gagaccagtactlc | | 3295 | C A S S P S G T G L E T Q Y F |
| 28.72 | TRBV28*01 | TRBJ2-7*01 | TRBD1*01 | 1600 | tgtgccagcagt..... | cc ..gacagg... | tcttt . | ......cgagcagtacttc | | 3296 | C A S S P T G S F E Q Y F |
| 28.73 | TRBV28*01 | TRBJ1-2*01 | TRBD1*01 | 1601 | tgtgccagcag...... | cccta cc gggaca..... | aaaa . | ...atggctacacctc | | 3297 | C A S S P T G T K N G Y T F |
| 28.74 | TRBV28*01 | TRBJ2-7*01 | TRBD1*01 | 1602 | tgtgccagcag...... | cca ..gacaggg... | cgg . | ..cctacgagcagtacttc | | 3298 | C A S S Q T G A A Y E Q Y F |

Figure 1-59

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 28.75 | TRBV28*01 | TRBJ2-2*01 | TRBJ2-2*01 | 1603 | tgtgccagcag | cc | gcggggg | agagg | acacgggagctgttttt | 3299 | C A S S R G G E D T G E L F F |
| 28.76 | TRBV28*01 | TRBJ2-1*01 | TRBD2*01 | 1604 | tgtgccagcag | cagaa | tagcg | atatg | aatgagcagttcttc | 3300 | C A S S R I A D M N E Q F F |
| 28.77 | TRBV28*01 | TRBJ2-5*01 | TRBD2*02 | 1605 | tgtgccagcag | cagatt | gcggga | acgggg | agagaccccagtactc | 3301 | C A S S R L R E R G E T Q Y F |
| 28.78 | TRBV28*01 | TRBJ1-5*01 | TRBD1*01 | 1606 | tgtgccagcag | cte | ggacaggg | taagg | aatcagcccagcattt | 3302 | C A S S D R V R N Q P Q H F |
| 28.79 | TRBV28*01 | TRBJ2-7*01 | TRBD1*01 | 1607 | tgtgccagcagtt | caata | gggacag | | cctacgagcagtactc | 3303 | C A S S I G T A Y E Q Y F |
| 28.80 | TRBV28*01 | TRBJ2-3*01 | TRBD1*01 | 1608 | tgtgccagcagtt | cct cc | gggaca | caaaa | cacagatacgcagtatttt | 3304 | C A S S S G T Q N T D T Q Y F |
| 28.81 | TRBV28*01 | TRBJ1-4*01 | TRBD1*01 | 1609 | tgtgccagcag | ctc | gacaggg | ttttcc | gaaaaactgttttt | 3305 | C A S S S T G F S E K L F F |
| 28.82 | TRBV28*01 | TRBJ2-3*01 | TRBD2*01 | 1610 | tgtgccagcagtt | cct | ggactagcg | aga | cacagatacgcagtattt | 3306 | C A S S S W T S G D T D T Q Y F |
| 28.83 | TRBV28*01 | TRBJ2-1*01 | TRBD2*02 | 1611 | tgtgccagcagt | | acggtccag | | aatgagcagttcttc | 3307 | C A S S T V Q N E Q F F |
| 28.84 | TRBV28*01 | TRBJ2-1*01 | TRBD2*01 | 1612 | tgtgccagcagt | gggact | | tc ag ctcctacaatgagcagttcttc | | 3308 | C A S S W D F S S Y N E Q F F |
| 28.85 | TRBV28*01 | TRBJ2-7*01 | TRBD2*01 | 1613 | tgtgccagcagt | | gggggg aaag | | gagcagtactc | 3309 | C A S S W G G K E Q Y F |
| 28.86 | TRBV28*01 | TRBJ2-7*01 | TRBD1*01 | 1614 | tgtgccagcagtt | g | gggacagg | tttc | cgagcagtactc | 3310 | C A S S W G Q V S E Q Y F |
| 28.87 | TRBV28*01 | TRBJ2-7*01 | TRBD2*02 | 1615 | tgtgccagcagtt | at | ctagccggga | | cctacgagcagtactc | 3311 | C A S S Y L A G A Y E Q Y F |
| 28.88 | TRBV28*01 | TRBJ2-7*01 | TRBD2*02 | 1616 | tgtgccagca | ccgat | ggactagcgggag | | cctacgagcagtactc | 3312 | C A S T D G L A G A Y E Q Y F |
| 28.89 | TRBV28*01 | TRBJ1-1*01 | TRBD1*01 | 1617 | tgtgccagca | cgata | acag | a | gaacactgaagcttctt | 3313 | C A S T I T E N T E A F F |
| 28.90 | TRBV28*01 | TRBJ2-7*01 | TRBD2*02 | 1618 | tgtgccagca | cottgggc | ctagcggga | cccc | cctacgagcagtactc | 3314 | C A S T L G L A G P P Y E Q Y F |
| 28.91 | TRBV28*01 | TRBJ2-7*01 | TRBD2*01 | 1619 | tgtgcca | ccaggttcatg | gcggg | tccaaccc | acgagcagtactc | 3315 | C A T R F M A G P T H E Q Y F |
| 28.92 | TRBV28*01 | TRBJ2-2*01 | TRBD2*02 | 1620 | tgtgcca | ccagtgatccga | | aggg cagaaa | aacaccgggagctgtttt | 3316 | C A T S D P E G Q K N T G E L F F |
| 28.93 | TRBV28*01 | TRBJ2-3*01 | TRBD2*02 | 1621 | tgtgcca | ccagtcg | tagccggag | cttg | acagatacgcagtatttt | 3317 | C A T S R S G S L T D T Q Y F |
| 29.01 | TRBV29-1*01 | TRBJ1-4*01 | TRBD1*01 | 1622 | tgcagcg | ct gggacagg | tggc | actaatgaaaaactgtttt | | 3318 | C S A G T G G T N E K L F F |
| 29.02 | TRBV29-1*03 | TRBJ2-7*01 | TRBD1*01 | 1623 | tgcagcgc | cc | gacaggg | agcg | cctacgagcagtactc | 3319 | C S A R Q G S A Y E Q Y F |
| 29.03 | TRBV29-1*03 | TRBJ2-1*01 | TRBD2*01 | 1624 | tgcagcg | gggagggcagtc | gactagcgggg | ttcg | atgagcagttctc | 3320 | C S G E G R S T S G G F D E Q F F |
| 29.04 | TRBV29-1*03 | TRBJ2-5*01 | TRBD2*02 | 1625 | tgcagc | acaa | gactagcgggag | agcg | ccaagagaccagtactc | 3321 | C S T R L A G E R Q E T Q Y F |
| 29.05 | TRBV29-1*01 | TRBJ2-4*01 | TRBD2*01 | 1626 | tgcagcgt | cgct | gact | ctattgagccaaaaacattcagtactc | | 3322 | C S V A D S I G A K N I Q Y F |
| 29.06 | TRBV29-1*03 | TRBJ2-7*01 | TRBD2*02 | 1627 | tgcagcg | tcg | ctagcggga | ccgg | ctacgagcagtactc | 3323 | C S V A S G T G Y E Q Y F |
| 29.07 | TRBV29-1*03 | TRBJ2-5*01 | TRBD2*01 | 1628 | tgcagcg | ttgatccgacgggt | | cgggg | ccaagagaccagtactc | 3324 | C S V D P T G R G Q E T Q Y F |
| 29.08 | TRBV29-1*03 | TRBJ2-4*01 | TRBD1*01 | 1629 | tgcagcg | t ggacaggg | cg | aaaacattcagtactc | | 3325 | C S V D R G E N I Q Y F |

Figure 1-60

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 29.09 | TRBV29-1*01 | TRBJ1-1*01 | TRBD1*01 | 1630 | tgcagcgt...... | a ...gacag..... | .gaacactgaagcttcatt | | | 3326 | C S V D R N T E A F F |
| 29.10 | TRBV29-1*03 | TRBJ2-1*01 | TRBD1*01 2 | 1631 | tgcagcg..... | ttgattct .....agggg. | ctcctacaatgagcagttcttc | | | 3327 | C S V D S R G S Y N E Q F F |
| 29.11 | TRBV29-1*03 | TRBJ2-3*01 | TRBD1*01 | 1632 | tgcagcg..... | ttgacgtc ..cagtag..... | ccgt ...acagatacgcagtatttt | | | 3328 | C S V D V Q G R T D T Q Y F |
| 29.12 | TRBV29-1*01 | TRBJ2-1*01 | TRBD1*01 | 1633 | tgcagcgttgaag. | cagtca .ggac....... cct | ........gttcttc | | | 3329 | C S V E A V R T L F F |
| 29.13 | TRBV29-1*01 | TRBJ2-2*01 | TRBD2*01 | 1634 | tgcagcgttgaag. | cgtggg ......agcgggg..... | gaacacgggagctgttttt | | | 3330 | C S V E A W E R G N T G E L F F |
| 29.14 | TRBV29-1*03 | TRBJ2-2*01 | TRBD2*02 | 1635 | tgcagcg..... | ttgaagatcga ........ | ggaggt t cgaacaccgggagctgttttt | | | 3331 | C S V E D G G G S N T G E L F F |
| 29.15 | TRBV29-1*03 | TRBJ2-5*01 | TRBD2*01 | 1636 | tgcagcg..... | ttgaagaccc ....ctagccg..... | aagt ...agagaccagtacttc | | | 3332 | C S V E D P L A E V E T Q Y F |
| 29.16 | TRBV29-1*03 | TRBJ1-2*01 | TRBD1*01 | 1637 | tgcagcg..... | ttgaagatcc ..acaggg..... | .aactatgctacacctc | | | 3333 | C S V E D P Q G N Y G Y T F |
| 29.17 | TRBV29-1*03 | TRBJ2-3*01 | TRBD2*01 | 1638 | tgcagcg..... | ttgaagactggga ....lagccg..... | aaccgccg ...cagatacgcagtatttt | | | 3334 | C S V E D W D S G T A A D T Q Y F |
| 29.18 | TRBV29-1*01 | TRBJ2-7*01 | TRBD1*01 | 1639 | tgcagcgttgaaga | a ...aca....... aa | ...ctacgagcagttc | | | 3335 | C S V E E T N Y E Q Y F |
| 29.19 | TRBV29-1*01 | TRBJ2-1*01 | TRBD1*01 | 1640 | tgcagcg..... | tcg ....agggg. ag..... | .gagcagttcttc | | | 3336 | C S V E G E E Q F F |
| 29.20 | TRBV29-1*01 | TRBJ2-6*01 | TRBD2*01 | 1641 | tgcagcgttgaag. | gaaat ggg....... | .ggggccaacgtcctgacttc | | | 3337 | C S V E G N C G A N V L T F |
| 29.21 | TRBV29-1*03 | TRBJ1-3*01 | TRBD1*01 | 1642 | tgcagcg..... | ttga .......ggggc gcc ta | ...ggaaacaccatatttt | | | 3338 | C S V E G R L G N T I Y F |
| 29.22 | TRBV29-1*01 | TRBJ2-1*01 | TRBD2*02 | 1643 | tgcagcgttgaag. | g ....tagcgggag. aa | ...cctacaatgagcagttc | | | 3339 | C S V E G S G R T Y N E Q F F |
| 29.23 | TRBV29-1*03 | TRBJ2-5*01 | TRBD1*01 | 1644 | tgcagcgttgaag. | ggacagt .ggacaggg..... | aagcgtgg ......gagacccagtacttc | | | 3340 | C S V E G T V D R E A W E T Q Y F |
| 29.24 | TRBV29-1*01 | TRBJ2-7*01 | TRBD2*01 | 1645 | tgcagcg..... | ttga ....acta....... ttca | ...acgagcagtacttc | | | 3341 | C S V E L F N E Q Y F |
| 29.25 | TRBV29-1*01 | TRBJ2-7*01 | TRBD2*01 | 1646 | tgcagcg..... | tta ........gggggg | ...cctacgagcagtacttc | | | 3342 | C S V E L G G A Y E Q Y F |
| 29.26 | TRBV29-1*03 | TRBJ2-1*01 | TRBD2*02 | 1647 | tgcagcgttgaa.. | ...actagccggagg. tt | .......caatgagcagttc | | | 3343 | C S V E T S G R F N E Q F F |
| 29.27 | TRBV29-1*01 | TRBJ2-5*01 | TRBD2*01 | 1648 | tgcagcgttga.. | ggtg ....gcgggggg. cggg | .....gagacccagtacttc | | | 3344 | C S V E V A G G G E T Q Y F |
| 29.28 | TRBV29-1*03 | TRBJ1-2*01 | | 1649 | tgcagcg..... | ttgaagttttggg taactatgctacacctc | | | | 3345 | C S V E V L G N Y G Y T F |
| 29.29 | TRBV29-1*01 | TRBJ2-1*01 | TRBD2*02 | 1650 | tgcagcgttgaa.. | tggtct .........gaggg gca ctcctacaatgagcagttc | | | | 3346 | C S V E W S E G H S Y N E Q F F |
| 29.30 | TRBV29-1*03 | TRBJ1-4*01 | TRBD1*01 | 1651 | tgcagcg..... | ttgagct ....ggggc ..actaatgaaaaactgttttt | | | | 3347 | C S V G A G G T N E K L F F |
| 29.31 | TRBV29-1*03 | TRBJ2-7*01 | TRBD1*01 | 1652 | tgcagcg..... | ttgattt ....agggg ..aaccga ...tacgagcagtacttc | | | | 3348 | C S V G F R G T G Y E Q Y F |
| 29.32 | TRBV29-1*01 | TRBJ1-2*01 | TRBD2*01 | 1653 | tgcagcgttg..... | ..ggggg. tcgtt ..ctatgctacacctc | | | | 3349 | C S V G G S F Y G Y T F |
| 29.33 | TRBV29-1*01 | TRBJ1-2*01 | TRBD2*01 | 1654 | tgcagcgttg..... | gga ........ tcgtttcgaa .....ggctacacctc | | | | 3350 | C S V G I V S E G Y T F |
| 29.34 | TRBV29-1*01 | TRBJ2-7*01 | | 1655 | tgcagcgt.......... c gggacta............cctacgagcagtactc | | | | | 3351 | C S V G T T Y E Q Y F |
| 29.35 | TRBV29-1*03 | TRBJ1-2*01 | TRBD1*01 | 1656 | tgcagcg..... | tgaa ..gacaggg..... aata ......gctacacctc | | | | 3352 | C S V K T G N S Y T F |
| 29.36 | TRBV29-1*03 | TRBJ2-1*01 | TRBD1*01 | 1657 | tgcagcg..... | ttctcggt ..acag..... aatca ag ctcctacaatgagcagttc | | | | 3353 | C S V L G T E S S Y N E Q F F |

Figure 1-61

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 29.37 | TRBV29-1*01 | TRBJ2-2*01 | TRBD2*01 | 1658 | tgcagcgtt... | ccccggtt | ggg... | ...cggggagctgttttt | | 3354 | C S V P R L G G E L F F |
| 29.38 | TRBV29-1*01 | TRBJ2-7*01 | TRBD2*01 | 1659 | tgcagcg... | taca | ggacta... | ...ctacgagcagtacttc | | 3355 | C S V Q D Y Y E Q Y F |
| 29.39 | TRBV29-1*03 | TRBJ2-2*01 | TRBD2*01 | 1660 | tgcagcg... | ...ttcaa | ...agcgg... | tt | .acaccgggagctgttttt | 3356 | C S V Q S G Y T G E L F F |
| 29.40 | TRBV29-1*03 | TRBJ2-7*01 | TRBD1*01 | 1661 | tgcagcg... | teac | ggac... | gtcagtt | ctcctacgagcagtacttc | 3357 | C S V T D V Q F S Y E Q Y F |
| 29.41 | TRBV29-1*03 | TRBJ2-3*01 | TRBD1*01 | 1662 | tgcagcg... | tgttg | gggacag... | ctt | ..cacagatacgcagtattt | 3358 | C S V V G D S F T D T Q Y F |
| 29.42 | TRBV29-1*03 | TRBJ2-7*01 | | 1663 | tgcagcg... | | tgttagttgcg | | .cctacgagcagttcttc | 3359 | C S V V S G A Y E Q Y F |
| 29.43 | TRBV29-1*01 | TRBJ2-7*01 | TRBD2*01 | 1664 | tgcagcgtt... | t | ......ggggggg | gggaag | ...ctacgagcagtacttc | 3360 | C S V W G G G S Y E Q F F |
| 30.01 | TRBV30*01 | TRBJ2-1*01 | TRBD2*01 | 1665 | tgtgcctg... | cc | gggact... | cgggg | ......aatgagcagttcttc | 3361 | C A C R D S G N E Q F F |
| 30.02 | TRBV30*01 | TRBJ2-7*01 | TRBD1*01 | 1666 | tgtgcc... | | cgaggct... | ggggg | .aacg....acgagcagtacttc | 3362 | C A R G W G N D E Q Y F |
| 30.03 | TRBV30*01 | TRBJ2-1*01 | | 1667 | tgtgcctgg... | gacgga | .....tacaatgagcagttcttc | | | 3363 | C A W D G Y N E Q F F |
| 30.04 | TRBV30*01 | TRBJ2-3*01 | TRBJ2-3*01 | 1668 | tgtgcctg... | ...ggc | tt | ...agatacgcagtattt | | 3364 | C A W G L D T Q Y F |
| 30.05 | TRBV30*01 | TRBJ2-3*01 | TRBD1*01 | 1669 | tgtgcctg... | ...ggc | ttaa | ...atacgcagtattt | | 3365 | C A W G L N T Q Y F |
| 30.06 | TRBV30*01 | TRBJ2-7*01 | TRBD1*01 | 1670 | tgtgcctga... | aatt | .gacaggg... | ct | ..ctacgagcagtacttc | 3366 | C A W K L T G L Y E Q Y F |
| 30.07 | TRBV30*01 | TRBJ2-5*01 | TRBD2*02 | 1671 | tgtgcctga... | atgtaca | ...agcggga... | a | ...aagagacccagttcttc | 3367 | C A W N V Q A G K E T Q Y F |
| 30.08 | TRBV30*01 | TRBJ2-1*01 | TRBD1*01 | 1672 | tgtgcctgag... | ag | cc | gggacaggggg... | tg | ......aatgagcagttcttc | 3368 | C A W R A G T G V N E Q F F |
| 30.09 | TRBV30*01 | TRBJ2-7*01 | TRBD2*01 | 1673 | tgtgcctgag... | aaaa | ....tagcggg... | | gagcagtacttc | 3369 | C A W R N S G E Q Y F |
| 30.10 | TRBV30*01 | TRBJ2-1*01 | TRBD2*01 | 1674 | tgtgcctgag... | aactct | ...tagcgggg... | cg | ...tacaatgagcagttcttc | 3370 | C A W R T L S G A Y N E Q F F |
| 30.11 | TRBV30*01 | TRBJ1-1*01 | TRBD1*01 | 1675 | tgtgcctgagtg. | ca | .gaca... | tgaacactgaagcttcttt | | 3371 | C A W S A D M N T E A F F |
| 30.12 | TRBV30*01 | TRBJ2-5*01 | TRBD1*01 | 1676 | tgtgcctgag... | cgacgt | ggga... | ......agaccccagtactc | | 3372 | C A W S D G G K T Q Y F |
| 30.13 | TRBV30*01 | TRBJ2-1*01 | | 1677 | tgtgcctgagtg. | aagglaacc | ....atgagcagttcttc | | | 3373 | C A W S E G N H E Q Y F |
| 30.14 | TRBV30*01 | TRBJ2-3*01 | TRBD1*01 | 1678 | tgtgcctgagtg. | gggacag... | attcca | ....agatacgcagtattt | | 3374 | C A W S G D R F Q D T Q Y F |
| 30.15 | TRBV30*01 | TRBJ2-1*01 | TRBD2*01 | 1679 | tgtgcctgagtg. | ga | ...actag... | ctcaatgagcagttcttc | | 3375 | C A W S G T S Y N E Q F F |
| 30.16 | TRBV30*01 | TRBJ2-7*01 | | 1680 | tgtgcctgagtg. | g | ...ctacgagcagtacttc | | | 3376 | C A W S G Y E Q Y F |
| 30.17 | TRBV30*01 | TRBJ2-7*01 | TRBD1*01 | 1681 | tgtgcctgagt. | aaaa | cc | gggacaggg... | .....acgagcagtacttc | 3377 | C A W S K T G T G D E Q Y F |
| 30.18 | TRBV30*01 | TRBJ2-1*01 | TRBD2*02 | 1682 | tgtgcctggagt. | cct | ...actagcgggaagg | .......aatgagcagttcttc | | 3378 | C A W S P T S G R N E Q F F |
| 30.19 | TRBV30*01 | TRBJ2-3*01 | TRBD1*01 | 1683 | tgtgcctgag... | cc | gggacag... | tg | .gcacagatacgcagtattt | 3379 | C A W S R D S G T D T Q Y F |
| 30.20 | TRBV30*01 | TRBJ2-7*01 | TRBD2*01 | 1684 | tgtgcctgagt. | agttttcgg | gggactagcggg... | t | .tcctacgagcagtacttc | 3380 | C A W S S F G G L A G S Y E Q Y F |

Figure 1-62

| clone # | V name | J name | D name | SEQ ID NO: | V-REGION | N1 | D-REGION | (P) N2 | J-REGION | SEQ ID NO: | CDR3 amino acid |
|---|---|---|---|---|---|---|---|---|---|---|---|
| 30.21 | TRBV30*01 | TRBJ1-1*01 | TRBD1*01 | 1685 | tgtgcctggagt. | ...acaggggc gcg | | ...actgaagcttcttt | | 3381 | C A W S T G G A T E A F F |
| 30.22 | TRBV30*01 | TRBJ2-1*01 | TRBD1*01 | 1686 | tgtgcctggagtgt a | gggacaggggg. | att | ....... tgagcagttcttc | | 3382 | C A W S V G T G G F E Q F F |
| 30.23 | TRBV30*01 | TRBJ2-5*01 | TRBD2*02 | 1687 | tgtgcctggagtgt aca | ......agcggga. | .....aaagagaccat | ........tacttc | | 3383 | C A W S V Q A G K E T H Y F |
| 30.24 | TRBV30*01 | TRBJ2-5*01 | TRBD2*02 | 1688 | tgtgcctggagtgt aca | ......agcggga... a | ...aagagaccagtactc | | | 3384 | C A W S V Q A G K E T Q Y F |
| 30.25 | TRBV30*01 | TRBJ1-2*01 | TRBD2*02 | 1689 | tgtgcctggagtgt aca | agggtatt | ......gggagg. tcc | ..actatgctacaccttc | | 3385 | C A W S V Q G Y W E V H Y G Y T |
| 30.26 | TRBV30*05 | TRBJ2-7*01 | TRBD2*02 | 1690 | gtgtcctgg... agtgtacaac | .......cggga... | aaagaaaccct | ...........tacttc | | 3386 | C A W S V Q P G K E T P Y F |
| 30.27 | TRBV30*01 | TRBJ2-1*01 | TRBD2*01 | 1691 | tgtgcctggagtgt acaa | ....agcggg... tccc | .......atgacagttcttc | | | 3387 | C A W S V Q S G S H E Q F F |
| 30.28 | TRBV30*05 | TRBJ2-7*01 | | 1692 | tgtgcctgg... agtgtatcggtgaagcct | ......cgagcagtacttc | | | | 3388 | C A W S V S V S L E Q Y F |
| 30.29 | TRBV30*01 | TRBJ2-2*01 | TRBD2*02 | 1693 | tgtgcctggagtgt aa | ........cggga... ttcccacc | .. caccggggaagctgttttt | | | 3389 | C A W S V T G F P P T G E L F F |
| 30.30 | TRBV30*01 | TRBJ1-2*01 | TRBD1*01 | 1694 | tgtgcctggagtgt agt | .....gggg. gggggaatgttacc | ..........cctc | | | 3390 | C A W S V V G G G N G Y P F |
| 30.31 | TRBV30*02 | TRBJ1-1*01 | | 1695 | tgtgcctgg..... gtataccgcgcagct | ..aacactgaagcttcttt | | | | 3391 | C A W V Y R A A N T E A F F |
| 30.32 | TRBV30*01 | TRBJ2-5*01 | TRBD1*01 | 1696 | tgt............cctccgg ...caggggcg gccc gggagggccg | ....gagaccagtacttc | | | | 3392 | C P S G R G R P G G P E T Q Y F |

CANCER ANTIGEN-SPECIFIC T-CELL RECEPTOR GENE, PEPTIDE ENCODED BY THE GENE, AND USE OF THEM

SEQUENCE LISTING

The instant application contains a Sequence Listing which has been submitted electronically in ASCII format and is hereby incorporated by reference in its entirety. Said ASCII copy, created on Feb. 14, 2017, is named 05273 0120-02000 SL.txt. and is 582,500 bytes in size.

TECHNICAL FIELD

The present invention relates to a polynucleotide contained in the gene for a cancer antigen-specific T-cell receptor, and the peptide encoded by the polynucleotide, and to cancer tests, e.g., diagnosis, prognosis, or treatment monitoring using the same, cancer therapy, and the like.

BACKGROUND ART

Cancer treatments include extirpation of cancer by surgical operation, radiotherapy, treatment with anti-cancer medication, and immunotherapy. Among these treatments, immunotherapy in particular has drawn attention in recent years because it is a treatment more selective and specific against cancer with least side effects. Inter alia, attempts have been extensively made to treat cancer and leukemia by targeting WT1 protein, which is abundantly present in many types of cancer cells and leukemia cells. In order to study the mechanism of the WT1-targeted anti-cancer therapy and to further increase the effect of the therapy, it is necessary to identify the nucleotide sequences of the T-cell receptor (TCR) genes of WT1-specific cytotoxic T-cells (CTL) and the amino acid sequences of the receptor peptides encoded by the nucleotide sequences. However, up to the present date, little is known about the sequences of those receptor genes and the receptor peptides, let alone that no effective use of them has been described, although a number of researches have been conducted (see, e.g., non-patent documents 1-5).

Non-Patent Document 1: Valmori D. et al., J. Immunol. 168: 4231-4240, 2002
Non-Patent Document 2: Dietrich P.Y. et al., Cancer Res. 61: 2047-2054, 2001
Non-Patent Document 3: Coulie P.G. et al., Proc. Natl. Acad. Sci. U.S.A. 98: 10290-10295, 2001
Non-Patent Document 4: Godelaine D. et al. J. Immunol. 171: 4893-4897, 2003
Non-Patent Document 5: Mandruzzato S. et al., J. Immunol. 169: 4017-4024, 2002

SUMMARY OF THE INVENTION

An object of the present invention was to reveal the amino acid sequences of T-cell receptors (TCRs) of WT1-specific cytotoxic T-cells (CTLs) for WT1 protein, and the nucleotide sequences of the genes encoding them, in particular, the amino acid and nucleotide sequences of the CDR3 region of them, as well as to use those pieces of information in cancer tests (diagnosis, prognosis, treatment monitoring, or the like) and in cancer therapy.

DISCLOSURE OF INVENTION

Problems to be Solved by the Invention

To accomplish the above object, the present inventors have conducted extensive research and determined, for the first time, the nucleotide and amino acid sequences of CD3 of the Vβ chain of T-cell receptors (TCRs) of WT1-specific cytotoxic T-cells (CTLs) from healthy individuals and HLA-A*2402-positive patients, and have thereby completed the present invention.

Thus, the present invention provides the following:
(1) A polynucleotide having a nucleotide sequence encoding CDR3 of a Vβ chain of a T-cell receptor (TCR) of a WT1-specific cytotoxic T-cell (CTL), said polynucleotide having DNA having any of the CDR3 nucleotide sequences shown in SEQ ID Nos.: 1-1696, RNA complementary to the DNA, or a polynucleotide having a complementary sequence thereof;
(2) The polynucleotide according to (1), wherein said polynucleotide consists of a DNA comprising any of the CDR3 nucleotide sequences shown in SEQ ID Nos.: 1-1696, or an RNA complementary thereto, or complementary sequences thereof;
(3) A peptide having an amino acid sequence of CDR3 of a Vβ chain of a T-cell receptor (TCR) of a WT1-specific cytotoxic T-cell (CTL), said peptide having any of the amino acid sequences of CDR3 shown in SEQ ID Nos.: 1697-3392;
(4) The peptide according to (3) consisting of any of the amino acid sequences of CDR3 shown in SEQ ID Nos.: 1697-3392;
(5) Use of the polynucleotide of (1) or (2), or the peptide of (3) or (4) as a cancer marker;
(6) A method for diagnosing cancer in an HLA-A*2402-positive patient, which comprises assessing the clonality of a WT1-specific CTL having any of the polynucleotides of (1) or (2), or any of the peptides of (3) or (4) in a sample obtained from the patient before therapy, wherein when a WT1-specific CTL having a multiplicity of clonality is present, the patient is determined to have a possibility of having cancer;
(7) The method according to (6), wherein a higher possibility of developing cancer in the patient before therapy is determined when the clonality of a WT1-specific CTL having any of the CDR3 polynucleotides or any of the CDR3 peptides and having the clonality of 3 or more is higher, or when the types of a WT1-specific CTL having the clonality of 3 or more are more abundant;
(8) A method for testing for sensitivity of an HLA-A*2402-positive patient to WT1 peptide immunotherapy, which comprises assessing the clonality and the number of types of WT1-specific CTLs having any of the polynucleotides of (1) or (2) or any of the peptides of (3) or (4) in a sample obtained from the patient before therapy, wherein the patient is determined to have sensitivity to WT1 peptide immunotherapy when the types of WT1-specific CTLs with a multiplicity of clonality are more abundant in the patient than in a subject non-responsive to the therapy;
(9) The method according to (8), wherein a patient is determined to have higher sensitivity to WT1 peptide immunotherapy when the types of WT1-specific CTL clones with a multiplicity of clonality are more abundant, or the clonality is larger in the patient before the therapy;
(10) A method for monitoring WT1 peptide immunotherapy in an HLA-A*2402-positive patient, which comprises assessing the clonality of WT1-specific CTL clones having any of the polynucleotides of (1) or (2) or any of the peptides of (3) or (4) in a sample obtained from the patient before and after the therapy, wherein the patient is determined to have responded to WT1 peptide immunotherapy when the clonality of any of the WT1-specific CTL clones increases after the therapy compared to before the therapy;

(11) The method according to (10), wherein a patient is determined to have higher responsiveness to WT1 peptide immunotherapy when the larger becomes the increase rate in the clonality, or the more abundant become the types of clones with increased clonality after the WT1 peptide immunotherapy;
(12) An antibody against the peptide of (3) or (4);
(13) A chip comprising the polynucleotide of (1) or (2), the peptide of (3) or (4), or the antibody of (12);
(14) A primer for amplifying a CDR3 polynucleotide, which has a sequence selected from the sequences shown in SEQ ID Nos.: 3394-3421.
(15) A kit for diagnosing cancer, a kit for testing for sensitivity of a patient to WT1 peptide immunotherapy, or a kit for monitoring WT1 peptide immunotherapy, comprising means for detecting a WT1-specific CTL having the polynucleotide of (1) or (2) or the peptide of (3) or (4);
(16) A device for cancer diagnosis, a device for testing for sensitivity of a patient to WT1 peptide immunotherapy, or a device for monitoring WT1 peptide immunotherapy, comprising means for detecting a WT1-specific CTL having the polynucleotide of (1) or (2) or the peptide of (3) or (4);
(17) The kit according to (15), comprising the chip of (13) or the primer of (14);
(18) The device according to (16), wherein the chip of (13) or the primer of (14) is used in the device;
(19) A lymphocyte of an HLA-A*2402-positive cancer patient, into which a T-cell receptor gene comprising a sequence of the polynucleotide of (1) or (2) is introduced.

The present invention also provides cancer therapy using lymphocytes from HLA-A*2402-positive patients, wherein a T-cell receptor gene containing a CDR3 polynucleotide is introduced into the lymphocytes.

Further, the present invention provides an antibody raised against a CDR3 polypeptide and use thereof.

Effect of the Invention

By virtue of the present invention, the nucleotide sequences contained in the gene for the Vβ chain of T-cell receptors (TCRs) of WT1-specific cytotoxic T-cells (CTLs), and the amino acid sequences of peptides encoded by them, in particular, the nucleotide and amino acid sequences of CDR3 have been revealed, and extensive cancer tests (diagnosis, prognosis, treatment monitoring, or the like), cancer therapy, and the like are enabled using these polynucleotides and peptides.

BRIEF DESCRIPTION OF DRAWINGS

FIG. 1-1 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-2 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-3 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-4 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-5 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-6 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-7 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-8 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-9 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-10 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-11 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-12 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-13 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-14 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-15 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-16 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-17 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-18 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-19 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-20 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-21 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-22 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-23 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-24 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-25 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-26 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-27 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-28 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-29 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-30 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-31 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-32 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-33 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-34 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-35 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIG. 1-36 shows the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-REGION . . . N1 . . . D-REGION . . . (P)N2 . . . J-REGION" on the nucleotide sequence indicate the origins of each portion of the nucleotide sequence.

FIGS. 1-37 to 1-62 show the nucleotide and amino acid sequences of CDR3 of the Vβ chain of T-cell receptors (TCRs) of WT1-specific cytotoxic T-cells (CTLs) from healthy individuals and HLA-A*2402-positive patients, which sequences have been identified in the present invention. In the figure, "clone #" indicates the clone numbers, the numbers to the left of the dot indicate the family numbers of Vβ chains, and the numbers to the right of the dot indicate the reference numbers. V name, J name, and D name indicate the details of the V region, J region, and D region, respectively. The letters "V-Region . . . N1 . . . D-REGION . . . (P)N2 . . . J-REGION" on the nucleotide sequence indicate the origins of each portion of the nucleotide sequence.

In FIGS. 1-1 to 1-62, the nucleotide sequences shown under "V-REGION . . . NI . . . D-REGION . . . (P) N2 . . . J-REGION" correspond to SEQ ID NOs: 1-1696 as identified in the Sequence Listing, and the amino acid sequences shown under "CDR3 amino acid" correspond to SEQ ID NOs: 1697-3392 as identified in the Sequence Listing.

FIG. 2-1 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-2 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-3 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-4 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-5 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-6 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-7 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-8 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-9 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-10 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-11 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-12 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-13 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-14 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-15 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-16 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-17 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-18 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-19 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-20 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-21 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-22 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-23 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-24 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-25 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-26 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-27 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-28 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-29 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-30 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-31 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-32 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-33 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-34 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-35 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

FIG. 2-36 shows the clonality of each clone of the WT1-specific cytotoxic T-cells (CTLs) from healthy individuals and HLA-A*2402-positive patients identified in the present invention. In the figure, "clone #" indicates the clone numbers, the numbers to the left of the dot indicate the family numbers of Vβ chains, and the numbers to the right of the dot indicate the reference numbers; HV is healthy volunteers, AML is patients with acute myelocytic leukemia, and MDS is patients with dysmyelopoietic syndrome. The numbers added to these abbreviations are healthy volunteer numbers and patient numbers. HV is healthy volunteers, AML is patients with acute myelocytic leukemia, and MDS is patients with dysmyelopoietic syndrome. The numbers added to these abbreviations are healthy volunteer numbers and patient numbers. Res indicates patients who responded to treatment; and nonRes indicates patients who did not respond to treatment. Further, pre indicates pre-treatment, and 4 w, 8 w, 12 w, and 42 w indicate 4 weeks, 8 weeks, 12 weeks, and 42 weeks, respectively, after the treatment. Phase 1 denotes the first phase of clinical trials. PB(pre) indicates peripheral blood before treatment; and BM(pre) indicates bone marrow before treatment.

BEST MODE FOR CARRYING OUT THE INVENTION

Figures 2, 3, 4, 5, 6, 7, 8, 9, 10, 11, 12, 13, 14, 15, 16, 17, 18, 19, 20:
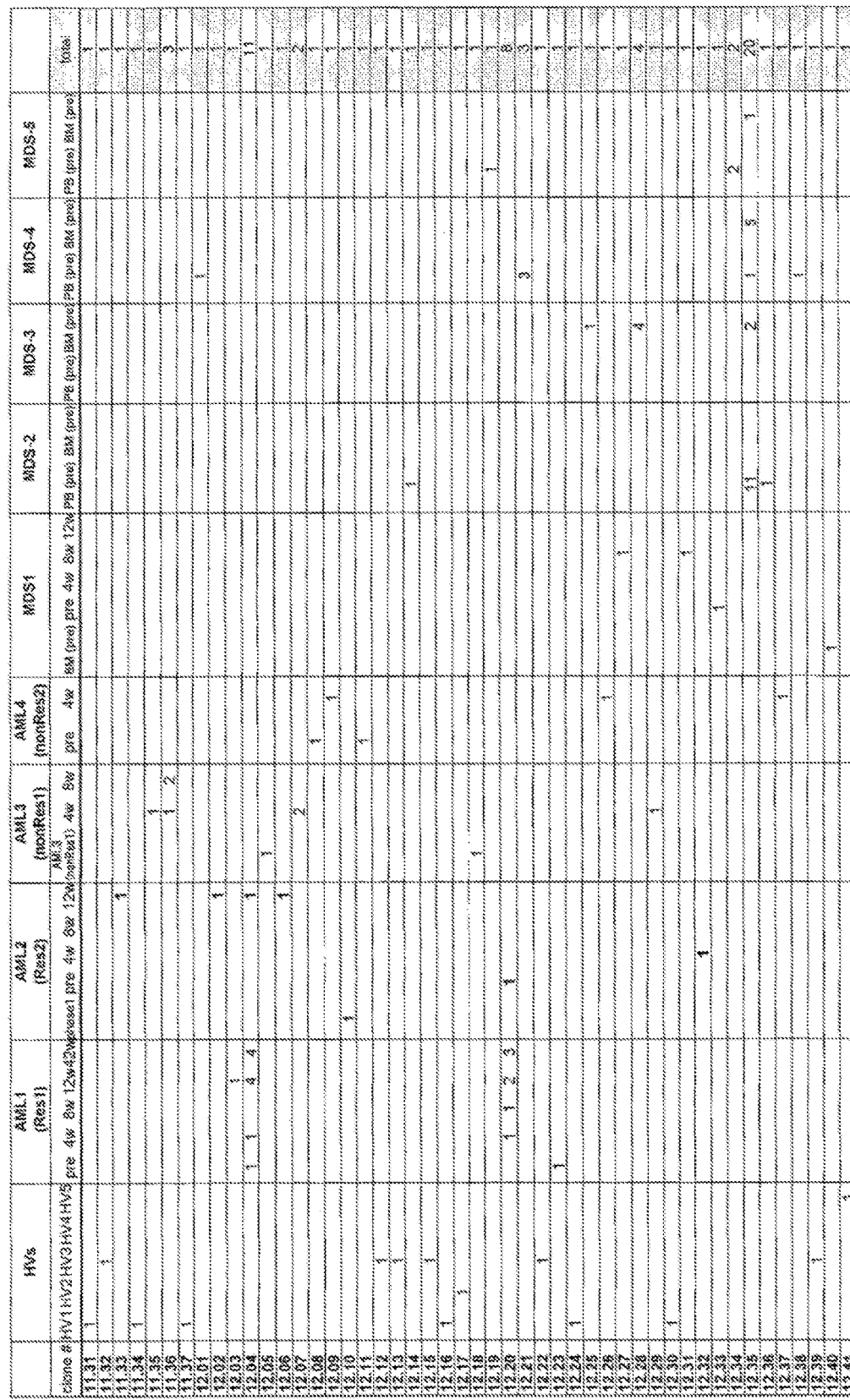

The present inventors stained the peripheral lymphocytes from cancer patients with WT1 tetramer that comprises WT1 peptide/HLA-A*2402 complexes, and separated WT1 tetramer-positive cells one by one using a FACS; cDNAs were generated from each separated cell, and the nucleotide sequences encoding CDR3 contained in the Vβ chain of T-cell receptors (hereinafter may be referred to as "TCR") of WT1-specific cytotoxic T-cells (CTLs, hereinafter may be referred to as "WT1-specific CTL") were determined by applying PCR method (FIGS. 1-1 to 1-62). From these results, the amino acid sequences of the CDR3 were also determined (FIGS. 1-1 to 1-62; SEQ ID Nos.: 1697-3392). These sequences have been determined for the first time in the present invention.

Thus, in a first aspect, the present invention provides a polynucleotide having the nucleotide sequence encoding CDR3 of the Vβ chain of T-cell receptors (TCRs) of WT1-specific cytotoxic T-cells (CTLs) obtained from healthy individuals and HLA-A*2402-positive patients, wherein the polynucleotide is DNA having any of the CDR3 nucleotide sequences shown in SEQ ID Nos.: 1-1696, RNA complementary to the DNA, or a polynucleotide having a complementary sequence thereof. As used herein, these DNA and RNA molecules and the complementary polynucleotides thereof are collectively referred to as "CDR3 polynucleotides." For example, the CDR3 polynucleotides include, in addition to the DNAs comprising the nucleotide sequences shown in SEQ ID Nos.: 1-1696, DNAs comprising these sequences. Also, for example, the CDR3 polynucleotides include, in addition to the RNAs complementary to the DNAs comprising the nucleotide sequences shown in SEQ ID Nos.: 1-1696, RNAs comprising these sequences. Further, for example, the CDR3 polynucleotides include polynucleotides having the sequences of the DNAs or RNAs, and polynucleotides complementary to the RNAs. The "CDR3 polynucleotides" include those having degenerate sequences encoding "CDR3 peptides."

In another aspect, the present invention provides peptides having the amino acid sequences of CDR3 of the Vβ chain of T-cell receptors (TCRs) of WT1-specific cytotoxic T-cells (CTLs), which CDR3 amino acid sequences being shown in any of SEQ ID Nos.: 1697-3392. As used herein, these peptides are collectively referred to as "CDR3 peptides." For example, the CDR3 peptides include, in addition to a peptide comprising any of the CDR3 amino acid sequences shown in SEQ ID Nos.: 1697-3392, peptides comprising these CDR3 amino acid sequences (such as, for example, Vβ chain peptides or a portion thereof). In addition, a peptide consisting or comprising the amino acid sequence shown in SEQ ID Nos.: 1697-3392 in which one or a few, preferably one to three, one or two, or one amino acid is substituted, added, or deleted is included in the "CDR3 peptides." However, these peptides are required to have equivalent functions to the original peptide. These CDR3 peptides are encoded by the above-mentioned CDR3 polynucleotides.

The CDR3 regions are the most diverse portions and are the most responsible parts for the specificity of antigen recognition. Thus, the sequences of the CDR3 polynucleotides and CDR3 peptides of the present invention are considered peculiar to WT1-specific CTL in HLA-A*2402-positive patients. Therefore, provided that the polynucleotide encoding the CDR3 region of the gene for the TCR Vβ chain of a certain T-cell or the peptide corresponding to the CDR3 region have the sequence of the polynucleotide or peptide of the present invention, the T-cell is considered as specific for WT1. Accordingly, the CDR3 polynucleotides and CDR3 peptides of the present invention may find use as markers for a wide variety of cancers, use in applications such as diagnosis of cancer, diagnosis of the susceptibility of patients to WT1 peptide immunotherapy, and tests for the responsiveness in the patients to WT1 peptide immunotherapy.

The CDR3 polynucleotides and CDR3 peptides of the present invention may be present in the lymphocytes of patients with any type of cancer as long as the cancer is generated from cells containing WT1. WT1 is known as a cancer antigen in a variety of cancers and hematological malignancies. Thus, the CDR3 polynucleotides and CDR3 peptides of the present invention, as well as the methods of the present invention described below, may be applied to almost all the types of cancers including, but not limited to, for example, hematologic malignancies, such as acute myelocytic leukemia, acute lymphocytic leukemia, malignant lymphoma, multiple myeloma, chronic myelocytic leukemia, myelodysplastic syndrome, and recurrence after the transplantation of hematopoietic stem cells of the same type; solid cancers, such as tongue cancer, gingival cancer, mouth floor cancer, pharyngeal cancer, larynx cancer, salivary gland cancer, and thyroid cancer; thoracic cancers, such as breast cancer, lung cancer, and thymic cancer; gastrointestinal cancers, such as colon cancer, small intestine cancer, gastric cancer, pancreatic cancer, liver cancer, bile duct cancer, gastrointestinal endocrine tumor, and gastrointestinal carcinoid; cancers of urinary and genital tract, such as renal cancer, urothelial cancer, germinoma, Wilms' tumor, prostate cancer, uterine body cancer, cervical cancer, uterine sarcoma, and ovarian malignancy; musculoskeletal malignancies, such as primary malignancy of bone (e.g., osteosarcoma and Ewing's sarcoma) and soft tissue sarcoma; and other cancers, such as skin cancer, neuroblastoma, malignant glioma (glioblastoma), primary malignant lymphoma of the central nervous system, medulloblastoma, and PNET.

When producing CDR3 polynucleotides or CDR3 peptides, conventional genetic engineering techniques and/or chemical synthetic procedures may be used. For example, CDR3 polynucleotides may be isolated from cells or chemically synthesized. CDR3 polynucleotides may also be amplified using a known method, such as PCR. Also, for example, a CDR3 polynucleotide (optionally amplified to an appropriate level using a known method) may be integrated into a suitable vector and introduced into suitable cells, or may be introduced into suitable cells by biolistic bombardment or electroporation. Then the cells into which the CDR3 polynucleotide is introduced are cultured for expression, thereby obtaining the CDR3 polynucleotide or peptide. Available vectors and cells, conditions for gene transfer, culture conditions, and methods for isolating genes and peptides are known to those skilled in the art and appropriately selected for use. Chemical synthesis may be used to produce CDR3 polynucleotides or CDR3 peptides. Methods for such chemical synthesis are known, and the methods for chemical synthesis of genes include solid-phase DNA synthesis using amidite, and the 1-4 phosphonate method; the methods for chemical synthesis of peptides include the Fmoc method.

Thus, in a further aspect, the present invention provides a method for diagnosing cancer in an HLA-A*2402-positive patient, the method including assessing the clonality of WT1-specific CTL having any of the CDR3 polynucleotides or CDR3 peptides in a sample obtained from the patient before therapy, wherein if a multiplicity of clonality are present, the patient is determined to have a possibility of cancer. As used herein, the term "clonality" refers to the frequency of detection of cells having an identical nucleotide or amino acid sequence. To examine clonality, it is general to use a cell sorter that allows identification of individual cells. The "patients" include both humans suspected to have cancer and those suffering from cancer.

The present inventors have found that it is possible to determine whether a patient develops cancer or not by examining the clonality of WT1-specific CTL having any of the CDR3 polynucleotides or CDR3 peptides in the patient. As can be seen from FIGS. 2-1 to 2-36, in the healthy individuals (HV1 to HV4), the clonality of WT1-specific CTL having any of the CDR3 polynucleotides or CDR3 peptides is 1 for almost all the clones, and 2 or 3 for rare clones; however, by contrast, all the cancer patients before therapy (AMLs (acute myelocytic leukemia) 1-4 and MDS (myelodysplastic syndrome) 1-5) have a multiplicity of clonality of the WT1-specific CTLs having any of the CDR3 polynucleotides or CDR3 peptides without exception. The number of the clonality is larger and the types of such cells are more abundant than those of the healthy individuals. The increases in clonality and in types of cells having a multiplicity of clonality in patients before therapy indicate a possibility that defense and attack against cancer cells has already been launched in the patients.

In view of these results, the possibility of cancer in a patient may be determined if a multiplicity of clonality is found in the WT1-specific CTL having any of the CDR3 polynucleotides or CDR3 peptides when examining a sample from a subject. Further, it is possible to determine that the larger the clonality of WT1-specific CTL having any of the CDR3 polynucleotides or CDR3 peptides, or the more abundant the types of WT1-specific CTLs having a multiplicity of clonality, the higher the possibility of developing cancer is in the subject before therapy. Also, in the determination method, it is possible to determine that the higher the possibility of developing cancer in the patient before therapy is when the clonality of WT1-specific CTL having any of the CDR3 polynucleotides or CDR3 peptides and having the clonality of 3 or more is larger, or the types of WT1-specific CTL having the clonality of 3 or more are more abundant.

In a further aspect, the present invention provides a method for testing for the sensitivity of an HLA-A*2402-positive patient to WT1 peptide immunotherapy, the method including assessing the clonality and the number of types of WT1-specific CTL clones having any of the polynucleotides of claim 1 or any of the peptides of claim in a sample obtained from the patient before therapy, wherein the patient is determined to have the sensitivity to WT1 peptide immunotherapy when the types of WT1-specific CTL clones with a multiplicity of clonality are more abundant in the patient than in non-responsive subjects.

WT1-specific CTLs having any of the CDR3 polynucleotides or CDR3 peptides act against cancer cells in the patients. In this process, the clones that already have a multiplicity of clonality before the therapy tend to further increase the clonality or maintain their clonality by WT1 peptide immunotherapy. It is also considered that WT1 immunotherapy is more likely to be successful when there are clones of as many types as possible, which gives increased number and types of effective WT1-specific CTL clones as a whole. More strictly speaking, the sensitivity of a patient to WT1 peptide immunotherapy may be determined as being high when the types of WT1-specific CTL clones with a multiplicity of clonality are more abundant in the patient than in non-responsive subjects.

As can be seen from FIGS. 2-1 to 2-36, the AML patients who responded to WT1 peptide immunotherapy had a larger number of the types of clones with a multiplicity of clonality than the healthy subjects and non-responsive patients before the therapy. AML1 (responder): 10 types (clonality of 58 in total); AML2 (responder): 12 types (clonality of 93 in total); AML3 (non-responder): 9 types (clonality of 27 in total); and AML4 (non-responder): 4 types (clonality of 15 in total). Healthy individuals HV1-5 had clones with a multiplicity of clonality in a range of 0 to 2 types.

In a further aspect, the present invention provides a method for monitoring WT1 peptide immunotherapy in an HLA-A*2402-positive patient, the method including assessing the clonality of WT1-specific CTL clones having any of the polynucleotides of claim 1 or any of the peptides of claim 2 in a sample obtained from the patient before and after the therapy, wherein the patient is determined to have responded to WT1 peptide immunotherapy when the clonality of any of the WT1-specific CTL clones increases after the therapy compared to before the therapy.

As can be seen from FIGS. 2-1 to 2-36, WT1-specific CTLs are observed in which the clonality increased (including the cases where the clonality increased from 0 to 1 or more) in the AML patients during the period of WT1 peptide immunotherapy. The exemplary clones exhibiting such behavior include Clones #02.28, #05.034, #05.135, #05.219, #09.65, #12.04, #13.13, #27.016, and #28.83 from AML (Pt1), and Clones #02.27, #05.035, #05.141, #05.219, #06.009, #12.04, #12.20, #15.44, #20.068, and #27.032 from AML (Pt2). The presence of clones that increases their clonality due to WT1 peptide immunotherapy indicates the responsiveness to the WT1 peptide immunotherapy. In other words, increases in the clonality suggests that the WT1 peptide immunotherapy showed its effect for a certain period of time. These increases in clonality may be transient or sustained. If the clonality of certain clones may increase only temporarily and then decrease, the clonality of other WT1-specific CTLs would increase to complement the effect. Considering the effect on cancer cells, a larger increase in the clonality is more desired. Therefore, the larger becomes the increase in the clonality or the more abundant become the types of clones with increased clonality after the WT1 peptide immunotherapy, the patient may be determined to have higher responsiveness to the WT1 peptide immunotherapy. The number and properties of cancer cells may be examined using an appropriate method depending on the type and site of the cancer.

In the method for monitoring therapy, although the clonality is compared before and after WT1 peptide immunotherapy, the time period between the before and after the therapy may be of any length. For example, it may be a few days, one week, two, three, or four weeks, or two or three months or more.

In the methods of the present invention described above, the means and methods for assessing clonality and determining the types of clones (i.e., determining the amino acid sequences of CDR3 peptides or the nucleotide sequences encoding the same) are known in the art, and those skilled in the art may conveniently carry out these operations. For example, as shown in Examples in the specification, a known sorting apparatus, such as the FACSAria system, and a method for gene amplification, such as PCR (using, for example, a primer set selected from the sequences listed in Table 1), may be used. In order to analyze the CDR3 polynucleotides or CDR peptides of the present invention in a stricter or more definite manner, one has only to confirm whether the nucleotide sequences of CDR3, IMGT, and the J and D regions in the Vβ chain gene are shown in FIGS. 1-1 to 1-62. Such confirmation is well within the ordinary skill of the art.

WT1 peptide immunotherapy is also known. For example, it may be performed on HLA-A*2402-positive patients by administering HLA-A*2402-restricted WT1 peptide in the native form (having the amino acid sequence: CMTWNQMNL) or in the modified form (having the amino acid sequence: CYTWNQMNL) via, for example, a transdermal route. In general, a single dose is in the order of µg/kg body weight to mg/kg body weight, and it may be administered at an interval of one week to a few weeks.

In a further aspect, the present invention provides a chip comprising the CDR3 polynucleotides or the polynucleotides complementary thereto; a chip comprising the CDR3 peptides; or a chip comprising antibodies against the CDR3 peptides. The chips may be in the form of microchips, microarrays, and the like. The production of the chips may be conducted according to conventional methods; for example, antibodies raised against the CDR3 polynucleotides or CDR3 peptides may be immobilized on a glass substrate. The species of the CDR3 polynucleotides or the polynucleotides complementary thereto, the CDR3 peptides, or the antibodies against the CDR3 peptides that is immobilized on the chip may be one to all; preferably, all the species are immobilized for exhaustive analysis. For example, all the polynucleotides comprising the nucleotide sequences complementary to the nucleotide sequences shown in SEQ ID Nos.: 1-1696 may be immobilized on the chip; alternatively, for example, antibodies that specifically recognize and bind to all the peptides comprising the amino acid sequences shown in SEQ ID Nos.: 1697-3392 may be immobilized on the chip. The CDR3 polynucleotides or the polynucleotides complementary thereto, the CDR3 peptides, or the antibodies against the CDR3 peptides may be placed at any position on the chip.

The chips may be used for, for example, diagnosis of cancer as described above. The samples may be affected tissues, body fluids such as blood and lymphatic fluid, or mucosal membranes. Preferably, the samples are peripheral blood. For example, when CDR3 polynucleotides are to be analyzed, the nucleic acids are extracted from the cells according to conventional methods, and a chip onto which all the species of polynucleotides comprising the nucleotide sequences complementary to the nucleotide sequences shown in SEQ ID Nos.: 1-1696 are immobilized may be used to examine the species and quantity of the hybridized DNA present in the sample. Also, for example, when CDR3 peptides are to be analyzed, a chip onto which antibodies that specifically recognize and bind to all the species of peptides comprising the amino acid sequences shown in SEQ ID Nos.: 1697-3392 are immobilized may be used to examine the species and quantity of the specifically bound peptides present in the sample.

In this regard, the present invention provides an antibody that specifically recognizes and binds to a CDR3 peptide. Preferably, such an antibody specifically recognizes and binds to any of the amino acid sequences shown in SEQ ID Nos.: 1697-3392. Methods for preparing such an antibody are known to those skilled in the art.

Typically, DNAs in the sample or DNA sequences placed on the chip are labeled so that the presence or absence, or the amount of hybridization is indicated. For example, the presence or absence, or the species of CDR3 peptides in a sample may be identified by arraying antibodies for each of the CDR3 peptides of SEQ ID Nos.: 1697-3392 on a chip and testing for their specific binding to the CDR3 peptides present in the sample. Typically, the peptides in the sample or the antibodies on the chip are labeled so that the presence or absence of the specific binding can be determined. Labels capable of indicating the presence or absence and the amount of hybridization or specific binding are known and include, for example, fluorescent labels, radioactive labels, enzyme labels, and chromophore labels. One skilled in the art may conveniently select suitable labels. The chips described above may be used to analyze a plurality of samples at the same time.

The CDR3 polynucleotides and CDR peptides of the present invention may be analyzed and identified using a known method, such as Southern blotting, Northern blotting, colony hybridization, and ELISA, as well as using the chips described above.

As described above, the CDR3 DNAs of the present invention have been identified using the primers shown in Examples, particularly, the primer sets shown in Table 1. Therefore, the present invention provides primers for amplifying CDR polynucleotides, which primers having the sequences selected from the sequences shown in SEQ ID Nos.: 3394-3421. For example, a primer set comprising the primers shown in SEQ ID Nos.: 3396-3420 may be used for amplification of a CDR3 polynucleotide.

The present invention also provides a kit for diagnosing cancer including means for detecting a WT1-specific CTL having a CDR3 polynucleotide or CDR3 peptide; a kit for testing for the sensitivity of a patient to WT1 peptide immunotherapy; or a kit for monitoring WT1 peptide immunotherapy. The present invention further provides a device for cancer diagnosis including means for detecting a WT1-specific CTL having a CDR3 polynucleotide or CDR3 peptide; a device for testing for the sensitivity of a cancer patient to WT1 peptide immunotherapy; or a device for monitoring WT1 peptide immunotherapy. A part for amplifying genes, such as a primer set, as described above, a chip as described above, or means for analyzing the information obtained from the chip may be used in the kit as a component or in the device.

In still another aspect, the present invention relates to a lymphocyte from an HLA-A*2402-positive cancer patient, which lymphocyte incorporating a T-cell receptor gene containing a sequence of a CDR3 polynucleotide. Preferably, such a lymphocyte is a peripheral blood lymphocyte into which the gene for the Vβ chain of TCR of WT1-specific CTLs comprising a CDR3 polynucleotide of the present invention, and a gene for the Vα chain of TCR of WT1-specific CTLs. In preparation of such a peripheral blood lymphocyte, a single species of the gene for the Vβ chain of TCR of WT1-specific CTLs may be used to obtain a plurality of types of peripheral blood lymphocytes, which are in turn introduced into patients. However, in view of improving the therapeutic effect, it is preferred to use a plurality of species of the gene for the Vβ chain of TCR of WT1-specific CTLs to obtain a plurality of types of peripheral blood lymphocytes, which are in turn introduced into patients. Alternatively, it is also preferred to select the nucleotide sequences of a suitable gene to be introduced depending on individual circumstances, because the therapeutically effective nucleotide sequences in the gene may differ depending on patients and cancer types.

Methods for preparing a gene to be introduced and for introducing the gene into peripheral blood lymphocytes are known in the art. For example, a gene to be introduced may be integrated into a suitable vector and then introduced into suitable cells, or may be introduced into suitable cells by biolistic bombardment or electroporation. Other conditions for gene transfer and for cell culture may be appropriately selected by those skilled in the art.

The lymphocytes into which a gene has been introduced as described above may be cultured ex vivo to obtain a large amount of WT1-specific CTLs. Then, the CTLs obtained may be introduced into a cancer patient to kill tumor cells expressing WT1, thereby performing cancer therapy. Patients preferred for introduction of the CTLs obtained are the patients from whom the peripheral blood lymphocytes were obtained.

The cancer therapy described above may be combined with other cancer therapies including anti-cancer agents and radiotherapy. The cancer therapy described above has a wide range of applications. They are exemplified above, but are not limited thereto.

In still another aspect, the present invention provides an antibody against a CDR3 peptide and a method of use thereof. Methods for preparing such an antibody are known in the art. Such an antibody may be used to detect or identify a lymphocyte having the amino acid sequence of the CDR3 peptide of the present invention or an amino acid sequence containing the above sequence in its Vβ chain in the subject sample. For example, antibodies against peptides comprising the amino acid sequences of any of SEQ ID Nos.: 1697-3392 may be used to detect or identify cancer-specific lymphocytes. These antibodies may also be used to carry out the methods of the present invention, for example, the method for diagnosing cancer.

Such an antibody may also be contacted with lymphocytes having the amino acid sequence of CDR3 of the present invention to activate them. The lymphocytes thus activated may be used to treat cancer. Preferably, lymphocytes obtained from a cancer patient are activated and, if necessary, proliferated, and the cancer therapy is conducted by returning the lymphocytes to the patient. Such an antibody may also be used to enrich the WT1-specific T-cells of interest. For example, such an antibody may be used to enrich the WT1-specific T-cells in a cancer patient, thereby assisting the cancer therapy.

In a further aspect, the present invention provides a method for identifying the position and size of a solid cancer, the method including: administering the peripheral blood lymphocytes of the present invention described above after being labeled with a detectable label, and then examining the location and quantity of the label. The label may be a known label, such as radioactive label, e.g. Tecnecium-99, and fluorescent label. Methods for labeling cells are also known. Detection of labels and quantification of signals are also known in the art; they can be performed using a radiation counter, by fluorescence assay, or by obtaining a tissue sample by biopsy.

The present invention is illustrated in greater detail below with reference to Examples, but it should be understood that the present invention is not construed as being limited thereto.

EXAMPLE 1

A. Experimental Methods and Materials Used (1) Cells

Peripheral blood samples were obtained from five healthy volunteers (HV1 to HV5) and four HLA-A*2402-positive AML patients (AML1 to AML4). Bone marrow samples and peripheral blood samples were obtained from five HLA-A*2402-positive MDS patients (MDS1 to MDS5). More specifically, peripheral blood was obtained before treatment and at weeks 4, 8, 12, and 42 of treatment from ALM1. Peripheral blood was obtained before treatment and at weeks 4, 8, 12, and 42 of treatment from ALM2. Peripheral blood was obtained before treatment and at weeks 4 and 8 of treatment from ALM3. Peripheral blood was obtained before treatment and at week 4 of treatment from ALM4. From MDS1, bone marrow and peripheral blood were obtained before treatment; and peripheral blood was obtained at weeks 4, 8, and 12 of treatment. Peripheral blood and bone marrow before treatment were collected from MDS1 to MDS5. The peripheral blood samples obtained were subjected to Ficoll-Hypaque (Pharmacia, Uppsala, Sweden) density gradient centrifugation and peripheral blood mononuclear cells (PBMCs) were separated and stored frozen at $-170°$ C. until use. The treatment on the patients was conducted using WT1 peptide immunotherapy. The amino acid sequence of the WT1 peptide used in the treatment is Cys-Tyr-Thr-Trp-Asn-Gln-Met-Asn-Leu (SEQ ID No.: 3393). This peptide was administered by intradermal injection at an interval of two weeks.

(2) Flow Cytometric Analysis and Sorting

Initially, $2×10^6$ PBMCs per sample were stained with PE-conjugated HLA-A*2402-WT1 235-243 tetramers (MBL, Tokyo, Japan) in FACS buffer (PBS containing 2% fetal bovine serum) for 30 minutes at 37° C. Subsequently, they were stained with monoclonal antibodies labeled with five different fluorescent dyes as described below for 25 minutes on ice in dark: FITC-labeled anti-CD4, CD14, CD16, CD19, and CD56, anti-CD3-PerCP, anti-CD8-APC-Cy7 (BD Bioscience, San Jose, Calif.), anti-CD45RA-APC, and anti-CCR7-PE-Cy7 (BD Pharmingen, San Diego, Calif.). The stained cells were washed twice in FACS buffer. Sorting was performed using the FACSAria system (BD Biosciences) and data analysis was performed using the FACSDiva software (BD Biosciences). As a result, single HLA-A*2402-WT1 235-243 tetramer$^+$CD3$^+$CD8$^+$ cells were obtained from the fraction of CD4⁻CD14⁻CD16⁻CD19⁻CD56⁻ cells and were defined as WT1-Tet⁺ cells.

(3) cDNA Synthesis of the TCR-β Chain from the Single Cells Sorted

To eliminate DNA contamination for RT-PCR of sufficient single cells, cDNA synthesis was carried out, and all the steps of PCR were performed in a different clean bench. Single WT1-Tet⁺ cells were sorted directly in a PCR tube containing 15 μl of a cDNA reaction mixture. The cDNA reaction mixture contained the following components in lysis buffer (1×cDNA buffer containing 0.5% Triton X-100): reverse transcriptase (SuperScript III, Invitrogen, Carlsbad, Calif.), 0.5 mM dNTPs (Invitrogen), 20 units (U) of Rnase inhibitor (Invitrogen), 100 μg/ml gelatin (Roche, Indianapolis, Ind.), 100 μg/ml tRNA (Roche), and a 200 nM primer (5'-CACCAGTGTGGCCTTTTG-3' (SEQ ID No.: 3394)) specific for the TCR-β chain constant region. After the sorting, the samples were incubated for 90 minutes at 50° C. for cDNA synthesis, and then incubated for 5 minutes at 95° C. for terminating the reaction.

(4) Semi-Nested Multiplex-PCR

Ten μl of a synthesized cDNA product obtained by the above procedure was added to 40 μl of a reaction mixture. The reaction mixture contained 1×PCR buffer, 2 mM MgCl₂, 0.25 mM dNTPs, 1.25 U DNA polymerase (Platinum Taq DNA Polymerase, Invitrogen), a 5 nM mixture of 24 different Vβ-family-specific forward primers (shown in Table 1), and 5 nM 3'-Cβ reverse primer (5'-GCTTCT-GATGGCTCAAACACAGC-3' (SEQ ID No.: 3395)). The procedure of PCR was as follows: a pre-PCR heating step at 95° C. for 2 minutes, followed by 40 cycles of a denaturing step at 95° C. for 45 seconds, an annealing step at 57° C. for 45 seconds, and an extension step at 72° C. for 50 seconds.

TABLE 1

| S2 | TRBV2 | GGTCACACAGATGGGACAGGAAGT | (SEQ ID No. 3396) |
|---|---|---|---|
| S2 | TRBV3 | CCCAGACTCCAAAATACCTGGTCA | (SEQ ID No. 3397) |
| S5 | TRBV4 | TACGCAGACACCAA<GA>ACACCTGGTCA | (SEQ ID No. 3398) |
| S1 | TRBV5 | ACAGCAAGTGAC<TAG>CTGAGATGCTC | (SEQ ID No. 3399) |
| S7 | TRBV6 | GTGTCACTCAGACCCCAAAATTCC | (SEQ ID No. 3400) |
| S4 | TRBV7-1 | GTGTGATCCAATTTCAGGTCATAC | (SEQ ID No. 3401) |
| S3 | TRBV7-3 | ATGTAACT<CT>TCAGGTGTGATCCAA | (SEQ ID No. 3402) |
| S1 | TRBV9 | ACAGCAAGTGAC<TAG>CTGAGATGCTC | (SEQ ID No. 3403) |
| S1 | TRBV10 | CCAAGACACAAGGTCACAGAGACA | (SEQ ID No. 3404) |
| S4 | TRBV11 | CAGTCTCCCAGATATAAGATTATAGAG | (SEQ ID No. 3405) |
| S4 | TRBV12 | GGTGACAGAGATGGGACAAGAAGT | (SEQ ID No. 3406) |
| S8 | TRBV13 | CTGATCAAAGAAAAGAGGGAAACAGCC | (SEQ ID No. 3407) |
| S6 | TRBV14 | ATAGAAGCTGGAGTTACTCAGTTC | (SEQ ID No. 3408) |
| S8 | TRBV15 | CAAGATACCAGGTTACCCAGTTTG | (SEQ ID No. 3409) |
| S5 | TRBV18 | TGCAGAACCCAAGACACCTGGTCA | (SEQ ID No. 3410) |
| S5 | TRBV19 | CACTCAGTCCCCAAAGTACCTGTT | (SEQ ID No. 3411) |
| S2 | TRBV20 | GAGTGCCGTTCCCTGGACTTTCAG | (SEQ ID No. 3412) |
| S6 | TRBV21 | AAGGTCACCCAGAGACCTAGACTT | (SEQ ID No. 3413) |
| S6 | TRBV23 | ACAAAGATGGATTGTACCCCCGAA | (SEQ ID No. 3414) |
| S7 | TRBV24 | GTTACCCAGACCCCAAGGAATAGG | (SEQ ID No. 3415) |
| 51 | TRBV25 | GATCACTCTGGAATGTTCTCAAACC | (SEQ ID No. 3416) |
| S3 | TRBV27 | GTGACCCAGAACCCAAGATACCTC | (SEQ ID No. 3417) |
| S2 | TRBV28 | GTAACCCAGAGCTCGAGATATCTA | (SEQ ID No. 3418) |
| S3 | TRBV29 | TCCAGTGTCAAGTCCATAGCCAAGTC | (SEQ ID No. 3419) |
| S5 | TRBV30 | GTCAGATCTCAGACTATTCATCAATGG | (SEQ ID No. 3420) |

Next, the PCR products were subjected to screening PCR. One μl of each PCR product was placed in separate 8 tubes and 24 μl of a reaction mixture was added to each of the tubes. The reaction mixture contained 1×PCR buffer, 2 mM MgCl₂, 0.2 mM dNTPs, 1.0 U of Platinum Taq DNA polymerase, one set of forward primers selected from the 8 screening sets S1 to S8, shown in Table 1, and 5'-Cβ reverse primer (5'-GGAACACGTTTTTCAGGTCCT-3' (SEQ ID No.: 3421)) (150 nM each). The procedure of PCR was as follows: a pre-PCR heating step at 95° C. for 2 minutes, followed by 35 cycles of a denaturing step at 94° C. for 45 seconds, an annealing step at 57° C. for 45 seconds, and an extension step at 72° C. for 40 seconds.

To verify positive reactions in the 8 screening PCRs, 5 µl of each screening PCR product was subjected to 2% agarose gel electrophoresis, followed by further PCR. This PCR was performed 35 cycles using 150 nM each of the Vβ-specific forward primers contained in the screening sets that were confirmed as positive. The positive reaction was verified by 2% agarose gel electrophoresis. A cell-free system was used as negative contrast, and three wells were prepared for the negative contrast in the same manner as above. The experiment was performed according to the same procedure.

(5) Determination and Analysis of the Sequences of the Complementarity-Determining Region 3 (CDR3) of TCR-β

Amplified fragments of the TCR-β gene were purified using the PCR Purification Kit (Qiagen, Valencia, Calif.). Corresponding TCR Vβ-specific forward primers were used for sequencing. The ABI PRIAM BigDye Terminator v 3.1 Cycle Sequencing kit (Applied Biosystems, Foster City, Calif., USA) was used for sequencing, and the ABI PRISM 3100 Genetic Analyzer (Applied Biosystems) was used for analysis. The sequence data on CDR3 were analyzed by comparing the sequences with those available from the website of the IMGT human TCR gene database (imgt.cines.fr).

B. Results

The sequences of the gene for the Vβ chain, the J region sequences, D region sequences, N region sequences, CDR3 nucleotide sequences, and CDR3 amino acid sequences of WT1-specific CTLs derived from healthy individuals and cancer patients (AML1 to AML4 and MDS1 to MDS5) are shown in FIGS. 1-1 to 1-62. The clonality of each WT1-specific CTL is shown in FIGS. 2-1 to 2-36. The CDR3 nucleotide sequences are shown in SEQ ID Nos.: 1-1696 (since clones #24.29 and #28.92 have the identical CDR3 nucleotide sequence, only clone #24.29 is shown in the Sequence Listing), and the CDR3 amino acid sequences are shown in SEQ ID Nos.: 1697-3392 (since clones #2.53 and #28.58 have the identical CDR3 amino acid sequence, and so do clones #24.29 and #28.92, only clones #2.53 and #24.19 are shown in the Sequence Listing). Among the AML patients, AML1 and AML2 responded to the treatment, but AML3 and AML4 did not. The response of the MDS patients to the treatment has not been determined.

As can be seen from FIGS. 2-1 to 2-36, in the healthy individuals (HV1 to HV4), the clonality of WT1-specific CTL having any of the CDR3 polynucleotides or CDR3 peptides is 1 for almost all the clones, and 2 or 3 for rare clones; however, all the cancer patients before therapy (AMLs and MDSs) have a multiplicity of clonality of the WT1-specific CTLs having any of the CDR3 polynucleotides or CDR3 peptides without exception. The number of the clonality was larger and the types of such cells were more abundant in the cancer patients than in the healthy individuals.

The increases in clonality and in types of cells having a multiplicity of clonality in patients before therapy indicate a possibility that defense and attack against cancer cells has already been launched in the patients and suggest that cancer cell are already present in the patients.

Also, as can be seen from FIGS. 2-1 to 2-36, the AML patients who responded to WT1 peptide immunotherapy had a larger number of types of clones with a multiplicity of clonality than the healthy subjects and non-responsive patients before the therapy. AML1 (responder): 10 types (clonality of 58 in total); AML2 (responder): 12 types (clonality of 93 in total); AML3 (non-responder): 9 types (clonality of 27 in total); and AML4 (non-responder): 4 types (clonality of 15 in total. Healthy individuals HV1-5 had clones with a multiplicity of clonality in a range of 0 to 2 types.

The clones that already have a multiplicity of clonality before the therapy tend to further increase the clonality or maintain their clonality by WT1 peptide immunotherapy. It is also considered that WT1 peptide immunotherapy is more likely to be successful when there are clones of as many types as possible, which gives increased number and types of effective WT1-specific CTL clones as a whole.

As can be seen from FIGS. 2-1 to 2-36, WT1-specific CTLs were observed in which the clonality increased either temporarily or continuously (including the cases where the clonality increased from 0 to 1 or more) in the AML patients during the period of WT1 peptide immunotherapy. The exemplary clones exhibiting such behavior include clones #02.28, #05.034, #05.135, #05.219, #09.65, #12.04, #13.13, #27.016, and #28.83 from AML (patient 1—a responder), and clones #02.27, #05.035, #05.141, #05.219, #06.009, #12.04, #12.20, #15.44, #20.068, and #27.032 from AML (patient 1—a non-responder). For example, from the change in the clonality of clone #02.28 from AML patient 1, it is found that the therapeutic effect was high at the onset of the treatment and at week 4.

An increase in the clonality of a certain clone indicates that the WT1 peptide immunotherapy showed its effect for a certain period of time. Even if the clonality of certain clones may increase temporarily and then decrease, the clonality of other WT1-specific CTLs would increase to complement the effect. Considering the effect on cancer cells, a larger increase in the clonality is more desired. Therefore, the larger becomes the increase in the clonality or the more abundant become the types of clones with increased clonality after the WT1 peptide immunotherapy, the responsiveness to the WT1 peptide immunotherapy is considered to have been high.

INDUSTRIAL APPLICABILITY

The present invention may provide pharmaceutical compositions useful for anti-cancer therapy, cancer test kits or reagents, reagents for cancer research, and the like. Therefore, the present invention may find use in the fields of pharmaceuticals for cancer therapy, of cancer test kits or reagents, and of cancer research.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10093977B2). An electronic copy of the "Sequence Listing" will also be available from the USPTO upon request and payment of the fee set forth in 37 CFR 1.19(b)(3).

The invention claimed is:

1. A synthesized cDNA, comprising:
   (1) a nucleotide sequence encoding the entire amino acid sequence of a complementarity determining region 3 (CDR3) of a vβ chain of a T-cell receptor (TCR) of a WT1-specific HLA-A*2402-positive cytotoxic T-cell (CTL), wherein the nucleotide sequence is selected from the group consisting of SEQ ID NOs: 1-200, or
   (2) the nucleotide sequence that is complementary to the full length of the nucleotide sequence of (1),
   wherein the cDNA further comprises a label attached to the cDNA, said label selected from fluorescent labels, radioactive labels, enzyme labels, and chromophore labels.

2. The cDNA according to claim 1, wherein said cDNA consists of:
   (1) the nucleotide sequence selected from the group consisting of SEQ ID NOs: 1-200, or
   (2) the nucleotide sequence that is complementary to the full length of the nucleotide sequence of (1): and
   the label.

3. The cDNA according to claim 1, wherein the CDR3 is identified by comparing with a human TCR gene database.

* * * * *

UNITED STATES PATENT AND TRADEMARK OFFICE
CERTIFICATE OF CORRECTION

PATENT NO.         : 10,093,977 B2
APPLICATION NO.    : 12/529701
DATED              : October 9, 2018
INVENTOR(S)        : Haruo Sugiyama Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 235 days.

Signed and Sealed this
Eighteenth Day of June, 2019

Andrei Iancu
*Director of the United States Patent and Trademark Office*